(12) United States Patent
Steineger et al.

(10) Patent No.: US 11,925,614 B2
(45) Date of Patent: Mar. 12, 2024

(54) FATTY ACID DERIVATIVES FOR TREATING NON-ALCOHOLIC STEATOHEPATITIS

(71) Applicant: BASF AS, Oslo (NO)

(72) Inventors: Hilde Hermansen Steineger, Oslo (NO); David Alan Fraser, Blommenholm (NO); Tore Skjæret, Oslo (NO)

(73) Assignee: BASF AS, Oslo (NO)

( * ) Notice: Subject to any disclaimer, the term of this patent is extended or adjusted under 35 U.S.C. 154(b) by 150 days.

(21) Appl. No.: 16/769,659

(22) PCT Filed: Dec. 5, 2018

(86) PCT No.: PCT/IB2018/001459
§ 371 (c)(1),
(2) Date: Jun. 4, 2020

(87) PCT Pub. No.: WO2019/111048
PCT Pub. Date: Jun. 13, 2019

(65) Prior Publication Data
US 2021/0177794 A1 Jun. 17, 2021

Related U.S. Application Data

(60) Provisional application No. 62/743,013, filed on Oct. 9, 2018.

(30) Foreign Application Priority Data

Dec. 6, 2017 (NO) .................................... 20171944
Dec. 6, 2017 (NO) .................................... 20171945

(51) Int. Cl.
*A61K 31/202* (2006.01)
*A61K 9/00* (2006.01)
*A61K 45/06* (2006.01)
*A61P 1/16* (2006.01)

(52) U.S. Cl.
CPC .......... *A61K 31/202* (2013.01); *A61K 9/0053* (2013.01); *A61K 45/06* (2013.01); *A61P 1/16* (2018.01)

(58) Field of Classification Search
CPC .... A61K 31/202; A61K 9/0053; A61K 45/06; A61K 31/4439; A61K 31/201; A61K 31/575; A61K 38/26; A61K 2300/00; A61K 31/616; C07C 59/58; A61P 1/16; A61P 43/00; C07K 14/205
See application file for complete search history.

(56) References Cited

U.S. PATENT DOCUMENTS

| | | | |
|---|---|---|---|
| 2,909,554 A | 10/1959 | Doerr | |
| 4,009,211 A | 2/1977 | Onopchenko et al. | |
| 4,032,564 A | 6/1977 | Henrick et al. | |
| 4,040,781 A | 8/1977 | Lamberti et al. | |
| 4,209,410 A | 6/1980 | Baldwin | |
| 4,214,088 A | 7/1980 | Abeler et al. | |
| 4,286,053 A | 8/1981 | Ishikawa et al. | |
| 4,297,268 A | 10/1981 | Abeler et al. | |
| 4,368,190 A | 1/1983 | Shen et al. | |
| 4,411,808 A | 10/1983 | Gutierrez et al. | |
| 4,444,766 A | 4/1984 | Bosies et al. | |
| 4,652,441 A | 3/1987 | Okada et al. | |
| 5,306,754 A | 4/1994 | Yamamoto et al. | |
| 5,328,953 A | 7/1994 | Lynch | |
| 5,445,832 A | 8/1995 | Orsolini et al. | |
| 5,447,820 A | 9/1995 | Hayakawa et al. | |
| 5,523,430 A | 6/1996 | Patel et al. | |
| 5,612,093 A | 3/1997 | Braig et al. | |
| 5,763,517 A | 6/1998 | Yamamoto et al. | |
| 5,770,584 A | 6/1998 | Kucera et al. | |
| 5,990,173 A | 11/1999 | Patoiseau et al. | |
| 6,060,515 A | 5/2000 | Elias et al. | |
| 6,365,628 B1 | 4/2002 | Berge | |

(Continued)

FOREIGN PATENT DOCUMENTS

| CA | 2115345 | 2/1993 |
|---|---|---|
| CA | 2667211 | 5/2008 |

(Continued)

OTHER PUBLICATIONS

Kliener et al., Histology of NAFLD and NASH in Adults and Children, Clin Liver Dis. 2016;20(2):293-312. doi:10.1016/j.cld.2015.10.011.*
Stal, Liver fibrosis in non-alcoholic fatty liver disease—diagnostic challenge with prognostic significance, World J Gastroenterol. Oct. 21, 2015; 21(39): 11077-11087.*
Siqueira et al, A Review of Pharmacological Treatments of NASH, Gastroenterol Hepatol Open Access (2015) 2(5):00058.*
Fraser, D.A. et al., "LBP-026—A structurally engineered fatty acid, icosabutate, displays optimised absorption, distribution and metabolism properties for targeting hepatic inflammation and normalises elevated liver enzymes in dyslipidemic patients," Journal of Hepatology, Abstract, p. S119 (2018).

(Continued)

*Primary Examiner* — Svetlana M Ivanova
(74) *Attorney, Agent, or Firm* — FINNEGAN, HENDERSON, FARABOW, GARRETT & DUNNER, LLP

(57) ABSTRACT

The present disclosure provides a compound for use in therapeutic and/or prophylactic treatment of non-alcoholic steatohepatitis (NASH) and/or alcoholic steatohepatitis (ASH). The compound for use according to the invention, is an unsaturated fatty acid with an oxygen incorporated in the β-position, and further comprising an α-substituent. More particularly, the invention provides a compound for use in treatment of NASH and/or ASH, and a method using this, wherein the compound is of Formula (II), wherein RI, R2, R3, X, and Y are as defined in the specification; and wherein this compound may be administered alone or in combination with an additional active agent.

30 Claims, 26 Drawing Sheets

(56) References Cited

U.S. PATENT DOCUMENTS

| | | | |
|---|---|---|---|
| 6,376,688 B1 | 4/2002 | Ferrante et al. |
| 6,511,670 B1 | 1/2003 | Maignan et al. |
| 6,624,190 B2 | 9/2003 | Khoury et al. |
| 6,723,717 B1 | 4/2004 | Youngquist et al. |
| 7,250,456 B2 | 7/2007 | Eigen et al. |
| 7,273,852 B2 | 9/2007 | Tsuji et al. |
| 7,375,135 B2 | 5/2008 | Najib-Fruchart et al. |
| 7,427,583 B2 | 9/2008 | Couillet et al. |
| 7,517,858 B1 | 4/2009 | Hostetler et al. |
| 7,902,399 B2 | 3/2011 | Berge et al. |
| 7,968,617 B2 | 6/2011 | Thalacker et al. |
| 8,173,831 B2 | 5/2012 | Milne et al. |
| 8,304,551 B2 | 11/2012 | Milne et al. |
| 8,735,436 B2 | 5/2014 | Hovland et al. |
| 8,741,966 B2 | 6/2014 | Holmeide |
| 8,759,558 B2 | 6/2014 | Holmeide et al. |
| 9,394,228 B2 | 7/2016 | Hovland et al. |
| 10,722,481 B2 | 7/2020 | Steineger |
| 11,234,948 B2 | 2/2022 | Steineger |
| 2003/0147814 A1 | 8/2003 | Scherrer et al. |
| 2004/0126424 A1 | 7/2004 | Jandacek et al. |
| 2005/0107503 A1 | 5/2005 | Couillet et al. |
| 2006/0135785 A1 | 6/2006 | Patoiseau et al. |
| 2006/0247458 A1 | 11/2006 | Yamamoto et al. |
| 2007/0060497 A1 | 3/2007 | Krahmer et al. |
| 2007/0008170 A1 | 4/2007 | Bryhn et al. |
| 2007/0167529 A1 | 7/2007 | Walton et al. |
| 2007/0254862 A1 | 11/2007 | Antel et al. |
| 2008/0161215 A1 | 7/2008 | Koshima et al. |
| 2009/0137567 A1 | 5/2009 | Perrine et al. |
| 2010/0056735 A1 | 3/2010 | Stankowiak et al. |
| 2010/0267828 A1 | 10/2010 | Holmeide et al. |
| 2010/0280109 A1 | 11/2010 | Holmeide |
| 2011/0190395 A1 | 8/2011 | Holmeide et al. |
| 2012/0122940 A1 | 5/2012 | Hovland et al. |
| 2012/0252850 A1 | 10/2012 | Milne et al. |
| 2012/0264791 A1 | 10/2012 | Milne et al. |
| 2013/0046013 A1 | 2/2013 | Hovland et al. |
| 2013/0172244 A1 | 7/2013 | Klein et al. |
| 2013/0295173 A1 | 11/2013 | Machielse et al. |
| 2013/0345269 A1 | 12/2013 | Hovland et al. |
| 2014/0221439 A1 | 8/2014 | Hovland et al. |
| 2014/0316002 A1 | 10/2014 | Holmeide et al. |
| 2016/0206585 A1 | 7/2016 | Hustvedt |
| 2018/0110747 A1 | 4/2018 | Fraser et al. |
| 2019/0314304 A1 | 10/2019 | Steineger |
| 2020/0085772 A1 | 3/2020 | Steineger |
| 2022/0280459 A1 | 9/2022 | Steineger |

FOREIGN PATENT DOCUMENTS

| | | |
|---|---|---|
| CA | 2667150 | 11/2008 |
| CN | 1248916 A | 3/2000 |
| CN | 101213281 A | 7/2008 |
| CN | 101225064 | 7/2008 |
| CN | 101213281 B | 3/2013 |
| EA | 023207 | 5/2016 |
| EP | 0 002 007 B1 | 5/1979 |
| EP | 0 050 327 | 4/1982 |
| EP | 0 175 591 | 3/1986 |
| EP | 0 399 183 | 11/1990 |
| EP | 0 463 947 | 1/1992 |
| EP | 2147910 A1 | 1/2010 |
| EP | 2 248 798 | 11/2010 |
| GB | 1038723 | 8/1966 |
| GB | 1523276 | 8/1978 |
| JP | 48-039001 B | 11/1973 |
| JP | 04-051149 | 2/1992 |
| JP | 11-180929 | 7/1999 |
| JP | 2000-344736 A | 12/2000 |
| JP | 2003-509485 | 3/2003 |
| JP | 2003-527364 T | 9/2003 |
| JP | 2012-526094 | 10/2012 |
| JP | 2014-505017 | 2/2014 |
| JP | 2018-515463 | 6/2018 |
| WO | WO 97/38688 | 10/1997 |
| WO | WO 98/32444 | 7/1998 |
| WO | WO 99/16804 | 4/1999 |
| WO | WO 00/072920 | 12/2000 |
| WO | WO 2001/021575 | 3/2001 |
| WO | WO 01/68582 | 9/2001 |
| WO | WO 01/098328 | 12/2001 |
| WO | WO 03/014073 | 2/2003 |
| WO | WO 03/063878 | 8/2003 |
| WO | WO 2005/073164 | 8/2005 |
| WO | WO 2006/025246 | 3/2006 |
| WO | WO 2006/044391 | 4/2006 |
| WO | WO 2006/094915 | 9/2006 |
| WO | WO 2006/117664 A1 | 11/2006 |
| WO | WO 2006/117668 A1 | 11/2006 |
| WO | WO 2007/116027 | 10/2007 |
| WO | WO 2008/053331 | 5/2008 |
| WO | WO 2008/053340 | 5/2008 |
| WO | WO 2008/125241 | 10/2008 |
| WO | WO 2009/056983 | 5/2009 |
| WO | WO 2009/061208 | 5/2009 |
| WO | WO 2009/147125 | 12/2009 |
| WO | WO 2009/149496 | 12/2009 |
| WO | WO 2009/156621 | 12/2009 |
| WO | WO 2010/006085 | 1/2010 |
| WO | WO 2010/008299 | 1/2010 |
| WO | WO 2010/128401 | 11/2010 |
| WO | WO 2011/089529 | 7/2011 |
| WO | WO 2012/059818 | 5/2012 |
| WO | WO 2012/059818 A1 | 5/2012 |
| WO | WO 2012/115695 | 8/2012 |
| WO | WO 2013/016531 | 1/2013 |
| WO | WO 2013/169797 | 11/2013 |
| WO | WO 2014/045293 | 3/2014 |
| WO | WO 2014/057522 | 4/2014 |
| WO | WO 2014/118097 | 8/2014 |
| WO | WO 2014/132134 A1 | 9/2014 |
| WO | WO 2014/132135 A2 | 9/2014 |
| WO | WO 2015/157697 | 10/2015 |
| WO | WO 2016/156912 | 10/2016 |
| WO | WO 2016/173923 | 11/2016 |
| WO | WO 2016/173923 A1 | 11/2016 |
| WO | WO 2019/111048 | 6/2019 |

OTHER PUBLICATIONS

Fraser, D. et al., "A Liver-Targeted Structurally Engineered Fatty Acid, Icosabutate, Potently Reduces Hepatic Pro-Fibrotic Gene Expression and Improves Glycemic Control in an Obese Diet-Induced Mouse Model of Nash," Hepatology, vol. 68, No. SI, Abstract, pp. 1002A-1003A (2018).

Fraser, D. et al., "Icosabutate, A Novel Structurally Engineered Fatty-Acid, Exhibits Potent Anti- Inflammatory and Anti-Fibrotic Effects in a Dietary Mouse Model Resembling Progressive Human Non-Alcoholic Steatohepatitis," Hepatology, vol. 68, No. SI, Abstract, pp. 749A-750A (2018).

Masterton, G.S. et al., "Review article: omega-3 fatty acids—a promising novel therapy for non-alcoholic fatty liver disease," Alimentary Pharmacology & Therapeutics, vol. 31, No. 7, pp. 679-692 (2018).

International Search Report for International Application No. PCT/IB2018/001459, dated Jun. 13, 2019.

Written Opinion for International Application No. PCT/IB2018/001459, dated Jun. 13, 2019.

2014 Therapeutic Area Partnerships meeting website; meeting dates: Nov. 19-21, 2014; Boston, MA; original website: http://www.iirusa.com/therapeuticareapartnership/home.xml; accessible via the internet archives at https://archive.org/web:https://web.archive.org/web/20141220122529/http:/www.iirusa.com/therapeuticareapartnership/home.xml (3 pages).

Ahmad, J. et al., "Reactions in Monolayers: Base-Catalyzed Ester Hydrolysis Revisited," *Langmuir* (1990) 6:1797-1799.

Arulanandan, A. et al., "Non-invasive Testing for NASH and NASH with Advanced Fibrosis: Are We There Yet?" *Current Hepatology Reports*, 2015, 14(2) 109-118.

(56) References Cited

OTHER PUBLICATIONS

Belikov, V.G., "Farmazevtit'cheskaya khimiya," Moscov, *Vyshaya shcola*, 1993, p. 43-47 (9 pages including title and copyright pages).
Berge et al., "Metabolic effects of thia fatty acids." *Current Opinion in Lipidology*. 2002; 13(3): 295-304.
Berge, S.M. et al., "Pharmaceutical Salts," *J. Pharmaceutical Sciences* (1977) 66(1):1-19.
Brain, E.G. et al., "Derivatives of 6-Aminopenicillanic Acid. Part II .* Trisubstituted Acetyl Derivatives," *J. Chemical Society*(1962) 1445-1453.
Burness, D.M. "Decarboxylation of Thetin Salts," *J. Organic Chemistry*, (1959) 24(6): 849-852.
Cao, G. Selected topics of pharmaceutical chemistry. China Medical Science Press, 1993. pp. 123-125.
Chalasani, N. et al., "The Diagnosis and Management of Nonalcoholic Fatty Liver Disease: Practice Guidance From the American Association for the Study of Liver Diseases," *Hepatology*, vol. 67, No. 1, 2018, 328-357.
Chedid, A. et al., "The Immunology of Fibrogenesis in Alcoholic Liver Disease," *Arch Pathol Lab Med*, 2004, vol. 128, 1230-1238.
Chen, et al. *Basic Drug Design*, 1st Edition (*Huazhong University of Science and Technology (HUST) Press*, 1995), pp. 162-169.
Derzhinskii, AR. et al., "Functional Sulfur-Containing Compounds. 4. Preparation of Chloro(Bromo) Alkyl Sulfones by Oxidative Halogenation of Hydroxyalkyl Sulfides and Sulfoxides with Mixtures of Hydrogen Peroxide and a Hydrohalic Acid," *Bulletin of the Academy of Sciences of the USSR* (1982) 31(5):995-1001. Translated from Russian.
English language abstract for CN 101225064.
English language abstract for EP 0 463 947.
English language abstract for JP 04-051149.
English machine translation of JP 11-180929.
English translation. Cao, G. Selected topics of pharmaceutical chemistry. China Medical Science Press, 1993. pp. 123-125.
English translation, Chen, et al. Basic Drug Design, 1st Edition (*Huazhong University of Science and Technology (HUST) Press*, 1995), p. 162-169.
English translation of JP 48-039001 B.
English translation. Silverman, R.B., The Organic Chemistry of Drug Design and Drug Action, 2$^{nd}$ Edition, 19-20, (*Chemical Industry Press*, 2008).
English Translation, Zeynalov, B.K., "Synthesis and Investigation of Esters of Alkyl Selenium Ethanols," *Azerbaijan Journal of Chemistry* (1981) 5:41-43.
Ferrell, W.J. et al., "Synthesis and Properties of $^{35}$, S, $^{14}$C and $^{3}$H Labeled S-Alkyl Glycerol Ethers and Derivatives," *Chemistry & Physics of Lipids* (1976) 16:276-284.
Ferrucci, L. et al., "Relationship of Plasma Polyunsaturated Fatty Acids to Circulating Inflammatory Markers," *J. Clin. Endocrin. & Metab*. (2006) 91(2):439-446.
Fliegner, D. et al., "Up-regulation of PPAR-gamma in myocardial infarction," *The European Journal of Heart Failure*, 10 (2008) 30-38.
Flock, S. et al., "Syntheses of Some Polyunsaturated Sulfur- and Oxygen-containing Fatty Acids Related to Eicosapentaenoic and Docosahexaenoic Acids," *Acta Chemica Scandinavica* (1999) 53:436-445.
Geleijnse, J.M. et al., "Blood Pressure Response to Fish Oil Supplementation: Metaregression Analysis of Randomized Trials," *J. Hypertension* (2002) 20(8): 1493-1499.
Goldsworthy, L.J. et al., "Some Sulphides Containing the 2-Chloroethyl Group," *J. Chemical Society* (1948) 2177-2179.
Granlund, L. et al., "Effects of Structural Changes of Fatty Acids on Lipid Accumulation in Adipocytes and Primary Hepatocytes," *Biochemica et Biophysica Acta* (2005) 1687:23-30.
Grupp, I.L. et al., "Protection Against Hypoxia-Reoxygenation in the Absence of Poly (ADP-Ribose) Synthetase in Isolated Working Hearts," *J. Mol. Cell Cardiol*. (1999) 31:297-303.
Hansen, H.H. et al., "Mouse models of nonalcoholic steatohepatitis in preclinical drug development," *Drug Discovery Today*, vol. 22, No. 11, 2017, 1707-1718.
Heckmann, B. et al., "Grignard Additions to $\alpha_1\beta$-Unsaturated Dioxolanones: Preparation of Chiral Allylic Alcohols and Protected α-Hydroxy Aldehydes," *Tetrahedron Letters* (1996) 37:1421-1424.
Hermetter, A. & Paltauf, F., "A Facile Procedure for the Synthesis of Saturated Phosphatidylcholines," *Chemistry & Physics of Lipids* (1981) 28:111-115.
Hernandez, V. A. et al., "Thiazolidinediones and Risk of Heart Failure in Patients with or at High Risk of Type 2 Diabetes Mellitus," *Am J Cardiovasc Drugs* 2011; 11(2) pp. 115-128.
Hill, A.J. & Fager, E.W., "Some α-Alkylthio Aliphatic Acids," *J. American Chemical Society* (1943) 65(12):2300-2301.
Holmeide, AK. & Skattenbol, L., "Syntheses of Some Polyunsaturated Trifluoromethyl Ketones as Potential Phospholipase $A_2$ Inhibitors," *J. Chem. Soc., Perkin Trans*. (2000) 1:2271-2276.
Hosokawa, M. et al., "Preparation of Therapeutic Phospholipids Through Porcine Pancreatic Phospholipase $A_2$-Mediated Esterification and Lipozyme-Mediated Acidolysis," *J. Am. Oil Chem. Soc*. (1995) 72(11): 1287-1291.
"ICOSABUTATE for the treatment of hypertriglyceridemia and mixed dyslipidemia," Nonconfidential Presentation distributed via e-mail by Applicant no earlier than Oct. 7, 2014 (21 pages).
"ICOSABUTATE for the treatment of hypertriglyceridemia and mixed dyslipidaemia," Presentation, Therapeutic Area Partnering meeting in Boston, MA; Nov. 21, 2014 (12 pages).
International Search Report for International Application No. PCT/IB2010/001251, dated Oct. 4, 2010.
International Search Report for International Application No. PCT/IB2011/000250, dated May 31, 2011.
International Search Report for International Application No. PCT/IB2011/002925, dated Mar. 5, 2012.
International Search Report for International Application No. PCT/IB2015/001316, dated Dec. 7, 2015 (3 pages).
International Search Report for International Application No. PCT/NO2008/000391, dated Feb. 4, 2009.
International Search Report for International Application No. PCT/NO2009/000262, dated Oct. 23, 2009.
International Search Report and Written Opinion for International Application No. PCT/EP2016/058909, dated Jun. 24, 2016 (9 pages).
International Search Report for International Application No. PCT/IB2018/001459, dated Mar. 8, 2019.
Jones, P.B. et al., "A New Class of Antituberculosis Agents," *J. Med. Chem*. (2000) 43:3304-3314.
Jordan, V.C., "Tamoxifen: A most unlikely pioneering medicine," *Nat Rev Drug Discov*, 2003: 2(3): 205-213.
Kameyama, E. et al., "Alkylcarboxymethyl Sulphoxides," *American Chemical Society Chemical Abstracts* (1971) 74(23):401.
Kasai, Y. et al., "Synthesis of Diphenylalkane Sulfonate and Its Surface Activity," *Kogyo Kagaku Zasshi* (1965) 68(11):2073-2077.
Kholodov, L.E. et al., "Klint'cheskaya farmakokinetika," Moscov, Medicina, 1985, p. 83-98, 134-138, 160, 378-380 (28 pages, including title and copyright pages).
Kim, Y. et al., "Increased Transforming Growth Factor-beta1 in Alcohol Dependence," *J Korean Med Sci*, 2009, 24, 941-944.
Lam et al., "Treatment options for nonalcoholic fatty liver disease," *Therapeutic Advances in Gastroenterology*, 3(2), 2010, 121-137.
Lamango, N.S. et al., "Inhibition Mechanism of S-Adenosylmethionine-Induced Movement Deficits by Prenylcysteine Analogs," *Pharmacology, Biochemistry, & Behavior* (2003) 76:433-442.
Larsen, L.N. et al., "α- and β-Alkyl-Substituted Eicosapentaenoic Acids: Incorporation into Phospholipids and Effects on Prostaglandin H Synthase and 5- Lipoxygenase," *Biochemical Pharmacology* (1998) 55:405-411.
Larsen, L.N. et al., "Polyunsaturated Thia- and Oxa-Fatty Acids: Incorporation into Cell-Lipids and Their Effects on Arachidonic Acid- and Eicosanoid Syntheses," *Biochimica et Biophysica Acta* (1997) 1348:346-354.
Larsen, L.N. et al., "Sulfur-Substituted and α-Methylated Fatty Acids as Peroxisome Proliferator-Activated Receptor Activators," *Lipids* (2005) 40(1):49-57.

(56) References Cited

OTHER PUBLICATIONS

Lilja-Hallberg, M. & Härröd, M., "Enzymatic Esterification of Long Polyunsaturated Fatty Acids and Lyso-Phosphatidylcholine in Isooctane and Ethanol," *Biocatalysis* (1994) 9:195-207.

Livingston, J.R. & Drogin, R., "The Synthesis and Some Surface Active Properties of Alkylthioalkyl and Alkoxyalkyl Sulfates," *The Journal of the American Oil Chemists' Society* (1965) 42:720-723.

Masson, M. et al., "Marine Lipids for Prodrugs, Soft Compounds and Other Pharmaceutical Applications," *Pharmazie* (2000) 55(3): 172-177.

Masterton, G.S., et al., "Review article: omega-3 fatty acids—a promising novel therapy for non-alcoholic fatty liver disease," *Aliment Pharmacol Ther*, 2010; 31(7): 679-692.

Matsumoto, M. et al., "Orally Administered Eicosapentaenoic Acid Reduces and Stabilizes Atherosclerotic Lesions in ApoE-Deficient Mice," *Atherosclerosis* (2008) 197:524-533.

Meyer, K.L. et al., "In Vitro Evaluation of Phosphocholine and Quaternary Ammonium Containing Lipids as Novel Anti-HIV Agents," *J. Med. Chem.* (1991) 34(4):1377-1383.

Mulder, P. et al., "Macrovesicular steatosis is associated with development of lobular inflammation and fibrosis in diet-induced non-alcoholic steatohepatitis (NASH)," *Inflammation & Cell Signaling*, 2015, vol. 2, 10 pages.

Nair, A.B., and Jacob S., "A simple practice guide for dose conversion between animals and human," *J. Basic Clin. Pharma.*, 2016;7:27-31.

Notice of Allowance in U.S. Appl. No. 12/741,890, dated Jan. 17, 2014.

Notice of Allowance in U.S. Appl. No. 13/054,212, dated Jan. 29, 2014.

Notice of Allowance in U.S. Appl. No. 13/319,101, dated Jan. 13, 2014.

Notice of Allowance in U.S. Appl. No. 13/883,405, dated Mar. 14, 2016.

Notice of Allowance in U.S. Appl. No. 16/177,108, dated Apr. 21, 2020, including Examiner Interview Summary.

Nystrom, RF. & Brown, W.G., "Reduction of Organic Compounds by Lithium Aluminum Hydride. II. Carboxylic Acids," *J. American Chemical Society* (1947) 69(10): 2548-2549.

Office Action from U.S. Appl. No. 12/741,890, dated Aug. 3, 2012.
Office Action from U.S. Appl. No. 12/741,890, dated Dec. 10, 2012.
Office Action from U.S. Appl. No. 12/741,890, dated Aug. 6, 2013.
Office Action from U.S. Appl. No. 13/054,212, dated Apr. 1, 2013.
Office Action from U.S. Appl. No. 13/054,212, dated Jul. 1, 2013.
Office Action from U.S. Appl. No. 13/319,101, dated Jan. 31, 2013.
Office Action from U.S. Appl. No. 13/319,101, dated Apr. 24, 2013.
Office Action from U.S. Appl. No. 13/319,101, dated Oct. 2, 2013.
Office Action (Restriction Requirement) for U.S. Appl. No. 13/574,132 dated Jan. 20, 2015.
Office Action dated Jul. 17, 2014, from U.S. Appl. No. 13/883,405.
Office Action dated Jan. 28, 2015, from U.S. Appl. No. 13/883,405.
Office Action (Restriction Requirement) for U.S. Appl. No. 14/263,793 dated Mar. 3, 2015.
Office Action for U.S. Appl. No. 14/263,793 dated Aug. 11, 2015.
Office Action for U.S. Appl. No. 16/177,108 dated Oct. 8, 2019.
Office Action for U.S. Appl. No. 16/532,633 dated Jun. 29, 2020.
Office Action for U.S. Appl. No. 16/532,633 dated Jan. 26, 2021.

Oh, R.C. and Lanier, J. B. "Management of Hypertriglyceridemia," *American Family Physician*, May 1, 2007, vol. 75, No. 9, pp. 1365-1371).

Okoronkwo, A.E. et al., "Synthesis of ω-Hydroxy-α-Alkyl/Aryl-γ-Organo-Selenium and γ -Organo-Tellurium: A New Class of Organochalcogen Compounds with Antinociceptive Activity," *Tetrahedron Letters* (2008) 49:3252-3256.

Parkkari, T. et al., "α-Methylated Derivatives of 2-Arachidonoyl Glycerol: Synthesis, CB1 Receptor Activity, and Enzymatic Stability," *Bioorganic. & Medicinal Chemistry Letters* (2006) 16:2437-2440.

Pitt, M.J. et al., "Synthesis of Polyunsaturated β-Oxa Fatty Acids Via Rhodium Mediated Carbenoid Insertion," *Synthesis* (1997) 11:1240-1242.

Qin, Y. et al., "Phase Ib Study of Icosabutate, a Novel Structurally Enhanced Fatty Acid, in Subjects with Hypercholesterolemia," *Circulation*; Nov. 25, 2014; 130(Suppl. 2): A11889; Originally published Nov. 14, 2014 (8 pages).

Qin, Y. et al., "Phase Ib Study of Icosabutate, a Novel Structurally Enhanced Fatty Acid, in Subjects with Hypercholesterolemia," Poster Presentation, *American Heart Association Scientific Sessions*, Chicago, IL, Nov. 17, 2014 (3 pages).

Raspé, E. et al., "Identification of Rev-erbα as a physiological repressor of apoC-III gene transcription[1]," *Journal of Lipid Research*, 2002 43: 2172-2179.

Registry Copyright 2008 ACS on STN (RN 785712-42-7, 714185-72-5, 45247-37-8).

Ringbom, T. et al., "COX-2 Inhibitory Effects of Naturally Occurring and Modified Fatty Acids," *J. Nat. Prod.* (2001) 64:745-749.

Rossmeisl, M. et al., "Prevention and Reversal of Obesity and Glucose Intolerance in Mice by DHA Derivatives," *Obesity* (2009) 17(5): 1023-1031.

Sanyal, A.J. et al., "No Significant Effects of Ethyl-Eicosapentanoic Acid on Histologic Features of Nonalcoholic Steatohepatitis in a Phase 2 Trial," *Gastroenterology* Aug. 2014, 147(2):377-384.e1. doi: 10.1053/j.gastro.2014.05.046. Epub May 9, 2014).

Schuppan, D. et al., "Liver fibrosis: Direct antifibrotic agents and targeted therapies," *Matrix Biology*, vols. 68-69, 2018, 435-451 (article in press version).

Scorletti, E. et al., "Effects of purified eicosapentaenoic & docosahexaenoic acids in Nonalcoholic fatty liver disease: Results from the WELCOME study," Hepatology 2014, Oct.;60(4): 1211-1221.

Shchepin, R. et al., "Quorum Sensing in *Candida albicans*: Probing Farnesol's Mode of Action with 40 Natural and Synthetic Farnesol Analogs," *Chemistry & Biology* (2003) 10:743-750.

Shirley, D.A. et al., "Alkylation with Long Chain p-Toluenesulfonates. IV. Alkylation of Alcohols and Amines with n-Octadecyl p-Toluenesulfonate," *J. Organic Chemistry* (1953) 18:378-381.

Silverman, R.B., The Organic Chemistry of Drug Design and Drug Action 4, 14-28 (*Academic Press* 1992).

Silverman, R.B., The Organic Chemistry of Drug Design and Drug Action, 2nd Edition, 19-20, (*Chemical Industry Press*, 2007).

Simopoulos, AP., "Essential Fatty Acids in Health and Chronic Disease," *Am. J. Clin. Nutr.* (1999) 70(Suppl): 560S-569S.

Srisiri, W. et al., "Syntheses of Polymerizable Monoacylglycerols and 1,2-Diacyl- sn-Glycerols," *J. Org. Chem.* (1996) 61(17):5911-5915.

Stahl, P.H. & Wermuth, C.G., eds., "Chapter 12: Monographs on Acids and Bases" 265-327, in *Handbook of Pharmaceutical Salts: Properties, Selection, and Use*.

Storlien, L.H. et al., "Polyunsaturated Fatty Acids, Membrane Function and Metabolic Diseases Such as Diabetes and Obesity," *Current Opinion in Clinical Nutrition & Metabolic Care* (1998) 1(6):559-563.

Supplementary European Search Report for European Patent Application No. 11 83 7647, dated Feb. 13, 2014.

Togashi, N. et al., "Antibacterial Activity of Long-Chain Fatty Alcohols Against *Staphylococcus aureus*," *Molecules* (2007) 12:139-148.

Tran, P.O.T. et al., "Inhibition of Interleukin-1β-Induced COX-2 and EP3 Gene Expression by Sodium Salicylate Enhances Pancreatic Islet B-Cell Function," *Diabetes* (2002) 51:1772-1778.

Tsotinis, A. et al., "Synthesis and Antiretroviral Evaluation of New Alkoxy and Aryloxy Phosphate Derivatives of 3'-Azido-3'-Deoxythymidine," *J. Med. Chem.* (1996) 39:3418-3422.

Tungsubutra W., et al., "Achievement of LDL-cholesterol goal with statins after an ST segment elevation myocardial infarction," *Journal Med Assoc Thai*, Feb. 2015, 98(2), pp. 129-136 (abstract only).

Udding, J. et al., "Xanthate Transfer Cyclization of Glycolic Acid-Derived Radicals. Synthesis of Five- to Eight-Membered Ring Ethers," *J. Org. Chem.* (1994) 59:6671-6682.

(56) References Cited

OTHER PUBLICATIONS

Vaagenes, H. et al., "Methylated Eicosapentaenoic Acid and Tetradecylathioacetic Acid: Effects on Fatty Acid Metabolism," *Biochem. Pharmacol.* (1999) 58:1133-1143.

Vippagunta, S.R., et al., "Crystalline solids," *Advanced Drug Delivery Reviews*, 2001; 48(1): 3-26.

Wang, P. et al., "Synthesis of Phospholipid-Inhibitor Conjugates by Enzymatic Transphosphatidylation with Phospholipase D," *J. Am. Chem. Soc.* (1993) 115:10487-10491.

Weizmann, C., et al., "The Synthesis of α-Alkoxyisobutyric Acids and Alkyl Methacrylates from Acetonechloroform," *J. Am. Chem. Soc.* (1948) 70:1153-1158.

Willumsen, N. et al., "Enhanced Hepatic Fatty Acid Oxidation and Upregulated Carnitine Palmitoyltransferase II Gene Expression by Methyl 3-Thiaoctadeca-6,9,12,15-Tetraenoate in Rats," *J. Lipid Mediators and Cell Signaling* (1997) 17:115-134.

Willumsen, N. et al., "On the Effect of 2-Deuterium- and 2-Methyl-Eicosapentaenoic Acid Derivatives on Triglycerides, Peroxisomal β-Oxidation and Platelet Aggregation in Rats," *Biochimica et Biophysica Acta* (1998) 1369:193-203.

Woodbury, D.M. & Fingl, E., "Chapter 13: Drugs Effective in the Therapy of the Epilepsies," *Basis of Therapeutics* 201-226 (5th Ed. 1975).

Written Opinion of the International Searching Authority for International Application No. PCT/IB2015/001316 (7 pages).

Xu, F., et al., "SIRT1 Mediates the Effect of GLP-1 Receptor Agonist Exenatide on Ameliorating Hepatic Steatosis," *Diabetes*, (2014) 63:3637-3646.

Zeynalov, B.K. et al., "Synthesis and Investigation of Esters of Alkyl Selenium Ethanols," *Azerbaijan Journal of Chemistry* (1981) 5:41-43.

Ban, S. et al. "Structure-based design, synthesis, and nonalcoholic steatohepatitis (NASH)-preventive effect of phenylpropanoic acid peroxisome proliferator-activated receptor (PPAR) alpha-selective agonists" *Bioorganic and Medicinal Chemistry*, (2011), vol. 19, Issue 10, pp. 3183-3191.

Eriksson J. et al. "Effects of dapagliflozin and n-3 carboxylic acids in non-alcoholic fatty liver disease in people with type 2 diabetes: a double-blind randomized placebo-controlled study" (2018), 61:1923-1334.

Francque, S. et al. "PPARalpha gene expression correlates with severity and histological treatment response in patients with non-alcoholic steatohepatitis" *Journal of Hepatology*, (2015), vol. 63, pp. 164-173.

Hsu, W.H. et al., "Monascin and ankaflavin act as natural AMPK activators with PPARalpha agonist activity to down-regulate non-alcoholic steatohepatitis in high-fat diet-fed C57BL/6 mice" *Food and Chemical Toxicology*, (2014), vol. 64, pp. 94-103.

Sanyal, A.J., et al., "No significant effects of ethyl-eicosapentanoic acid on histologic features of nonalcoholic steatohepatitis" *Gastroenterology*, Aug. 2014: 147(2):377-84.e1.doi: 10.1053/j.gastro.2014.05.046. Epub May 9, 2014.

U.S. Appl. No. 16/532,633, Notice of Allowance dated Nov. 22, 2021, (13 pages).

Wang et al., "Exendin-4 decreases liver inflammation and atherosclerosis development simultaneously by reducing macrophage infiltration," British Journal of Pharmacology, 2014, vol. 171, pp. 723-735.

Wouters, K. et al., "A central role for cholesterol metabolism and inflammation during the inhibition of non-alcoholic steatohepatitis with a synthetic PPARalpha agonist" *Chemistry and Physics of Lipids*, (2008), vol. 154, Supplement p. S56.

Yamaguchi K. et al., "Inhibiting triglyceride synthesis improves hepatic steatosis but exacerbates liver damage and fibrosis in obese mice with nonalcoholic steatohepatitis" (2007), vol. 45, No. 6, 1366-1374.

Yan J. et al., "Omega-3 poly unsaturated fatty acid supplementation and non-alcoholic fatty liver disease: a meta-analysis of randomized controlled trials" *Medicine*, (2018), 97:37, pp. 1-10.

Newsome et al., "A Placebo-Controlled Trial of Subcutaneous Semaglutide in Nonalcoholic Steatohepatitis," *N. Engl. J. Med.* 2021;384(12):1113-1124 (published Nov. 13, 2020 at NEJM.org).

Notice of Allowance in U.S. Appl. No. 16/532,633 dated Nov. 22, 2022.

Office Action for U.S. Appl. No. 17/551,673 dated May 11, 2023.

\* cited by examiner

FATTY ACID DERIVATIVES FOR TREATING NON-ALCOHOLIC STEATOHEPATITIS

This application is a national stage filing under 35 U.S.C. § 371 of International Application No. PCT/IB2018/001459, filed on Dec. 5, 2018, which claims the benefit of priority of Norwegian Patent Application No. 20171944, filed on Dec. 6, 2017; Norwegian Patent Application No. 20171945, filed on Dec. 6, 2017; and U.S. Provisional Patent Application No. 62/734,013, filed on Oct. 9, 2018. All of the foregoing applications are incorporated herein by reference in their entirety.

FIELD OF THE INVENTION

The present disclosure relates to a method of treating non-alcoholic steatohepatitis (NASH), alcoholic steatohepatitis (ASH), and other hepatic disorders characterized by fibrosis and/or hepatic inflammation in a subject in need thereof. Further, the present disclosure relates to a compound, and a composition comprising the compound, for use in treating non-alcoholic steatohepatitis (NASH), alcoholic steatohepatitis (ASH), and other hepatic disorders characterized by fibrosis and/or hepatic inflammation in a subject in need thereof. The compound for use according to the invention, is an unsaturated fatty acid with an oxygen incorporated in the R-position and further comprising an α-substituent.

BACKGROUND OF THE INVENTION

Long-chain omega-3 fatty acids, e.g. (5Z,8Z,11Z,14Z,17Z)-icosa-5,8,11,14,17-pentaenoic acid (EPA) and (4Z,7Z,10Z,13Z,16Z,19Z)-docosa-4,7,10,13,16,19-hexaenoic acid (DHA) have broad biological effects, influencing plasma lipid levels, cardiovascular and immune functions, insulin action, neuronal development, and visual function. High-dose EPA/DHA are currently prescribed for the treatment of severe hypertriglyceridemia (HTG). These effects are mediated, at least partially, by effects on fatty-acid metabolism in the liver.

The use of omega-3 compounds such as EPA and DHA to treat non-alcoholic steatohepatitis (NASH) has been suggested in the prior art. By way of example, WO 2014/057522 to Mochida relates to compositions comprising ethyl icosapentate for use in treatment or alleviation of symptoms of NASH.

Dignity Science LTD (WO2014/118097) have suggested the use of modified omega-3 compounds, such as 15-hydroxy eicosapentaenoic acid (15-OHEPA), to treat fatty liver disorders, such as non-alcoholic fatty liver disease (NAFLD) and NASH. Krisani Biosciences (WO2014/045293) have also proposed the use of modified omega-3 compounds for treating different diseases including NASH. More recently, Pronova Biopharma AS (WO2016173923 A1) proposed the use of sulphur-containing structurally modified fatty acids for the treatment of NASH.

Non-alcoholic fatty liver disease (NAFLD) and non-alcoholic steatohepatitis (NASH) are frequently used interchangeably despite the fact that NAFLD encompasses a much broader spectrum of liver disease including isolated hepatosteatosis (>5% of hepatocytes histologically). Hepatosteatosis is most likely a relatively benign disorder when not accompanied by an inflammatory response and cellular damage. However, a subgroup of NAFLD patients have liver cell injury and inflammation in addition to hepatosteatosis, a condition known as non-alcoholic steatohepatitis (NASH). NASH is virtually indistinguishable histologically from alcoholic steatohepatitis (ASH). While the simple steatosis seen in NAFLD does not correlate with increased short-term morbidity or mortality, NASH dramatically increases the risks of cirrhosis, liver failure, and hepatocellular carcinoma (HCC). Cirrhosis due to NASH is an increasingly frequent reason for liver transplantation. While the morbidity and mortality from liver causes are greatly increased in patients with NASH, they correlate even more strongly with the morbidity and mortality from cardiovascular disease.

Uniform criteria for diagnosing and staging NASH are still debated (see details in later sections). Key histologic components of NASH are steatosis, hepatocellular ballooning, and lobular inflammation; fibrosis is not part of the histologic definition of NASH. However, the degree of fibrosis on liver biopsy (stage) is predictive of the prognosis, whereas the degree of inflammation and necrosis on liver biopsy (grade) are not.

With respect to the various histological components, treatment with omega-3 fatty acids have been shown to effectively reduce hepatosteatosis in patients with NAFLD (Scorletti E, et al., Effects of purified eicosapentaenoic and docosahexanoic acids in non-alcoholic fatty liver disease: Results from the *WELCOME study, *Hepatology*, 2014 October; 60(4):1211-2 nd, if treatment is established at an early stage of the disease, this may conceivably slow progression to the latter more severe stages of the disease. However, it is questionable whether omega-3 fatty acids are sufficiently potent to treat and/or reverse NASH where pronounced histological/inflammatory changes have developed (Sanyal A J, et al; EPE-A Study Group, Gastroenterology. 2014 August; 147(2):377-84.e1).

The moderate efficacy of omega-3 fatty acids in the treatment of NASH may be secondary to their mild effects upon other pathways that underlie the pathogenesis of NASH. Research in both humans and animal models of NASH have convincingly demonstrated that there are multiple factors involved in the development of steatohepatitis and fibrosis as opposed to isolated hepatosteatosis. These include insulin resistance, oxidative stress, inflammation, gut-derived endotoxin and excessive hepatic cholesterol and bile acids. All these factors have been shown to play an important contributing role in genetically susceptible individuals and accordingly drugs targeting these pathways are being developed for the treatment of NASH.

As with NASH, alcoholic liver disease (ALD) can be grouped into histological stages representing a transition from fatty liver or simple steatosis to alcoholic hepatitis (i.e., ASH) and finally to chronic hepatitis with hepatic fibrosis or cirrhosis. Thus, although the origins of ASH and NASH may differ, the hepatic response to the respective chronic insult has many similarities, including the pro-inflammatory and pro-fibrotic cascades involving macrophage activation and cytokine production and the resultant activated stellate cells, i.e., proliferating myofibroblasts. (See, e.g., Friedman, SL; Alcoholism: Clinical and Experimental Research. 1999 May; 23(5):904-910.)

A challenge in the development of drugs targeting NASH and ASH is lack of pre-clinical models that individually represent these diseases in humans. Rodent models that may be more representative of the metabolic disturbances that typically accompany NASH, such as dyslipidemia and insulin resistance, are characterized by very mild hepatic inflammation and fibrosis. At the other end of the spectrum are chemically induced fibrosis models, e.g., carbon tetrachloride ($CCl_4$) or thioacetamide induced fibrosis, which develop more severe fibrosis but may lack translation to humans with respect to both metabolic components such as insulin resistance and obesity. Multiple pre-clinical models that address both ends of the aetiopathogenic spectrum (metabolic perturbations-inflammatory response-fibrosis) are thus needed for identification of potential NASH and ASH drugs.

Another element that is important to consider when comparing rodent versus human hepatic fibrosis is the location and functional relevance of the induced fibrosis. For example, severe fibrosis models of a shorter duration may only represent the collagen-dense large portal tracts rather than the parenchymal collagen deposits that are functionally more relevant and often represent the bulk of liver collagen. Thus, the use of combination of both biochemical (e.g. hydroxyproline) and histological (e.g. Sirius Red morphometry) assessment of fibrosis in rodent models is optimal with respect to quantity, location and functional relevance of hepatic collagen deposits.

Identifying drugs that target the fibrosis component of NASH and ASH is crucial as hepatic fibrosis can progress to cirrhosis which in turn is associated with a highly increased morbidity and mortality. It also represents the major hard endpoint in clinical studies of chronic liver diseases. For example, emerging data suggests fibrosis, rather than NASH per se, to be the most important histological predictor of both liver and non-liver related death. Additionally, cirrhosis is a strong cofactor of primary liver cancer. It is thus imperative that new drugs under development for the treatment of NASH and ASH are potent enough to prevent the development and/or reverse the progression of established fibrosis.

WO2016173923A1 of Pronova Biopharma Norge AS discloses that sulphur-containing structurally modified fatty acids like 2-ethyl-2-((5Z,8Z,11Z,14Z,17Z)-icosa-5,8,11,14, 17-pentaenylthio)butanoic acid (Compound N) may be useful in the treatment of NASH. This was based on the finding that Compound N was superior to rosiglitazone, a PPAR-gamma agonist, in preventing diet-induced hepatic fibrosis. It also indicated that Compound N prevented the influx of inflammatory cells into the liver. It was demonstrated that Compound N had efficacy in reducing fibrosis (as measured by hydroxyproline/proline ratio) in APOE*3Leiden.CETP mice. Importantly, APOE*3Leiden.CETP mice only develop a very mild hepatic fibrotic response (20-30% increase in extracellular matrix, as measured via a biochemical assay assessing hydroxyproline (HYP) content. Furthermore, in the specific model described in WO2016173923A1 (the contents of which are incorporated by reference herein), the amount of liver fibrosis as measured by Sirius Red (SR) morphometry was much lower than found in 5 previous studies using a similar experimental set-up. In those studies, around 4-5% fibrosis after 20 weeks and 7-8% after 25-30 weeks as measured by SR morphometry was found, as compared to 1.5% in the study presented in WO2016173923A1. For measurement of fibrosis, SR morphometry is more sensitive than biochemical analysis (HYP), which may underestimate more functionally relevant collagen that is mainly parenchymal, in contrast to the functionally less relevant but quantitatively prevailing portal collagen.

Thus, based on the need for potent drugs for treatment of NASH and ASH, such as to prophylactically treat or reverse hepatic fibrosis, several new studies have been made to identify compounds that may be used in treating these aspects of hepatic disease, and to confirm effect based on new assessments and better models with a higher level of fibrosis Based on the need for potent drugs for treatment of NASH and ASH, such as to prophylactically treat or reverse hepatic fibrosis, several new studies have been made to identify compounds that may be used in treating these aspects of hepatic disease, and to confirm effect based on new assessments and better models.

BRIEF SUMMARY OF THE INVENTION

The present disclosure provides a method of treatment of non-alcoholic steatohepatitis and/or alcoholic steatohepatitis in a subject in need thereof, comprising administering to the subject a pharmaceutically effective amount of a compound of Formula (II):

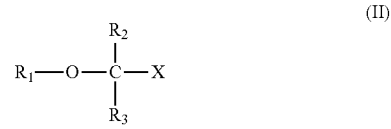

wherein $R_1$ is selected from a $C_{10}$-$C_{22}$ alkenyl having 3-6 double bonds;

$R_2$ and $R_3$ are the same or different and are selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, provided that $R_2$ and $R_3$ can be connected in order to form a cycloalkane like cyclopropane, cyclobutane, cyclopentane or cyclohexane;

X is a carboxylic acid or a derivative thereof, wherein the derivative is a carboxylate, such as a carboxylic ester; a glyceride; an anhydride; a carboxamide; a phospholipid; or a hydroxymethyl; or a prodrug thereof;

or a pharmaceutically acceptable salt, solvate, or solvate of such a salt thereof. The disclosure provides that the compound may be administered as a monotherapy or in combination with one or more additional active agents.

An equal aspect of the disclosure provides a compound of Formula (II)

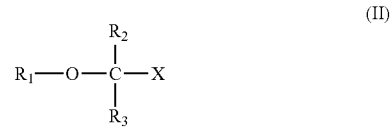

wherein $R_1$ is selected from a $C_{10}$-$C_{22}$ alkenyl having 3-6 double bonds;

$R_2$ and $R_3$ are the same or different and are selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, where $R_2$ and $R_3$ can be connected in order to form a cycloalkane like cyclopropane, cyclobutane, cyclopentane or cyclohexane;

X is a carboxylic acid or a derivative thereof, wherein the derivative is a carboxylate, such as a carboxylic ester; a glyceride; an anhydride; a carboxamide; a phospholipid; or a hydroxymethyl; or a prodrug thereof;

or a pharmaceutically acceptable salt, solvate, or solvate of such a salt thereof, for use in therapeutic and/or prophylactic treatment of non-alcoholic steatohepatitis and/or alcoholic steatohepatitis. The disclosure also provides that the compound for use may be administered as a monotherapy or in combination with one or more additional active agents.

In at least one embodiment, $R_2$ and $R_3$ are the same or different and may be selected from a group of substituents consisting of a hydrogen atom, an alkyl group, an alkoxy group, an alkenyl group; or $R_2$ and $R_3$ can be connected in order to form a cycloalkane like cyclopropane, cyclobutane, cyclopentane or cyclohexane;

X represents a carboxylic acid or a derivative thereof, wherein the derivative is a carboxylic ester, a glyceride or a phospholipid;

or a pharmaceutically acceptable salt, solvate, or solvate of such a salt thereof.

More particularly, the present disclosure relates to a method of treating non-alcoholic steatohepatitis and/or alcoholic steatohepatitis in a subject in need thereof, comprising administering to the subject a pharmaceutically effective amount of a compound of Formula (I):

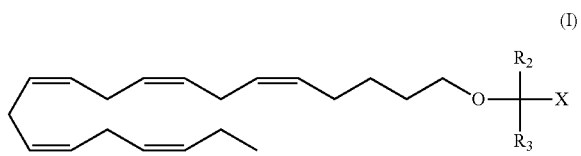

(I)

wherein $R_2$ and $R_3$ and X are defined as for Formula II.
More particularly, $R_2$ and $R_3$ are independently chosen from a hydrogen atom or linear, branched, and/or cyclic $C_1$-$C_6$ alkyl groups;

X is a carboxylic acid or a derivative thereof, wherein the derivative is a carboxylic ester, a glyceride, or a phospholipid;

or a pharmaceutically acceptable salt, solvate, or solvate of such a salt thereof.

Likewise, the present disclosure provides a compound of Formula (I):

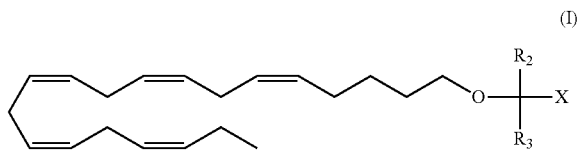

(I)

wherein $R_2$ and $R_3$ and X are defined as for Formula II.
More particularly, $R_2$ and $R_3$ are independently chosen from a hydrogen atom or linear, branched, and/or cyclic Cr $C_6$ alkyl groups;

X is a carboxylic acid or a derivative thereof, wherein the derivative is a carboxylic ester, a glyceride or a phospholipid;

or a pharmaceutically acceptable salt, solvate, or solvate of such a salt thereof, for use in treating non-alcoholic steatohepatitis.

The present disclosure also provides a method of treating non-alcoholic steatohepatitis and/or alcoholic steatohepatitis in a subject in need thereof, the method comprising administering to the subject a pharmaceutically effective amount of 2-(((5Z,8Z,11Z,14Z,17Z)-icosa-5,8,11,14,17-pentaen-1-yl)oxy)butanoic acid (Compound A):

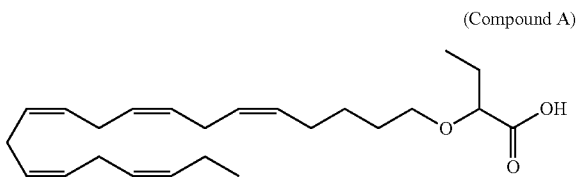 [SMILES: CC/C=C\C/C=C\C/C=C\C/C=C\C/C=C\CCCCOC(CC)C(=O)O]

(Compound A)

or a pharmaceutically acceptable salt or ester thereof.

The present disclosure also provides 2-(((5Z,8Z,11Z,14Z,17Z)-icosa-5,8,11,14,17-pentaen-1-yl)oxy)butanoic acid (Compound A) or a pharmaceutically acceptable salt or ester thereof, for use in treating non-alcoholic steatohepatitis and/or alcoholic steatohepatitis.

DETAILED DESCRIPTION

Figure 1B:
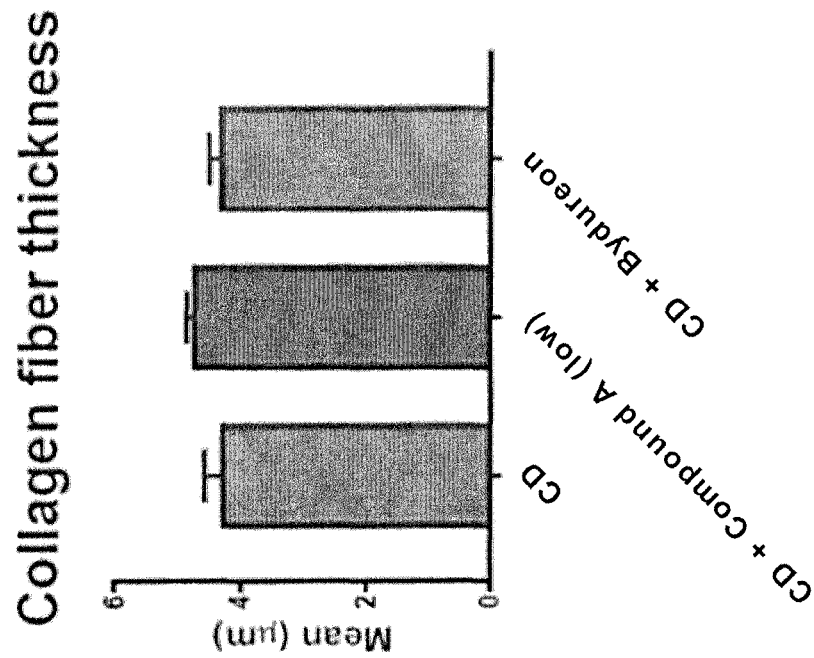
FIGS. 1A-1C depict the effect of Compound A on collagen fiber number (FIG. 1A), thickness (FIG. 1B), and length (FIG. 1C) in a CDAA/high-fat diet mouse model.

It should be noted that embodiments and features described in the context of one aspect of the present disclosure also apply to the other aspects of the invention. Particularly, the embodiments applying to the method of treating non-alcoholic steatohepatitis or alcohol steatohepatitis according to the present disclosure also apply to the aspect directed to a compound, or a composition comprising the compound, for use in treating non-alcoholic steatohepatitis or alcohol steatohepatitis, all according to the present disclosure. In some embodiments, the compound, or composition comprising the compound, is administered in combination with one or more additional active agents.

Particular aspects of the disclosure are described in greater detail below. The terms and definitions as used in the present application and as clarified herein are intended to represent the meaning within the present disclosure.

The singular forms "a," "an," and "the" include plural reference unless the context dictates otherwise.

The terms "approximately" and "about" mean to be nearly the same as a referenced number or value. As used herein, the terms "approximately" and "about" should be generally understood to encompass ±5% of a specified amount, frequency, or value.

The terms "treat," "treating," and "treatment" include any therapeutic or prophylactic application that can benefit a human or non-human mammal. Both human and veterinary treatments are within the scope of the present disclosure. Treatment may be responsive to an existing condition or it may be prophylactic, i.e., preventative.

The terms "administer," "administration," and "administering" as used herein refer to (1) providing, giving, dosing and/or prescribing by either a health practitioner or his authorized agent or under his direction a compound or composition according to the present disclosure, and (2) putting into, taking or consuming by the human patient or person himself or herself, or non-human mammal a compound or composition according to the present disclosure.

The terms "preventing and/or treating" and "therapeutic and/or prophylactic treatment of" may interchangeably be used. Typically, the compounds of Formula (I) or Formula (II) will be used for treating, i.e. therapeutic treatment of NASH or ASH. However, it is also foreseen that in some cases the compounds of Formula (I) or Formula (II) will be used for prophylactic treatment of NASH or ASH, for example in cases where a patient has one or multiple risk factors associated with NASH or ASH.

The terms "administered in combination" and "co-administration" or "coadministration" are used interchangeably and refer to administration of a (a) compound of Formula (I) or (II), or a pharmaceutically acceptable salt, solvate, or solvate of such a salt thereof; and (b) at least one additional active agent, together in a coordinated fashion. For example, the co-administration can be simultaneous administration, sequential administration, overlapping administration, interval administration, continuous administration, or a combination thereof. The mode of administration may be different for the compounds and the additional agent(s), and the co-administration includes any mode of administration, such as oral, subcutaneous, sublingual, transmucosal, parenteral, intravenous, intra-arterial, intra-peritoneal, buccal, sublingual, topical, vaginal, rectal, ophthalmic, otic, nasal, inhaled, and transdermal, or a combination thereof. Examples of the parenteral administration include but are not limited to intravenous (IV) administration, intraarterial administration, intramuscular administration, subcutaneous administration, intraosseous administration, intrathecal administration, or a combination thereof. The compound of formula (I) or (II) and the additional active agent can be independently administered, e.g. orally or parenterally. In one embodiment, the compound of Formula (I) or (II) is administered orally; and the additional active agent is administered parenterally. The parenteral administration may be conducted via injection or infusion. In some embodiments, the method and/or use of the present disclosure are directed to the therapeutic and/or prophylactic treatment of NASH or ASH using at least two different active agents, the compound of Formula (I) or (II), and an additional active agent, respectively. The at least two active agents can be seen as a "Combined product", wherein the agents are e.g. separately packed and wherein both agents are required to achieve the optimal intended effect.

The term "pharmaceutically effective amount" means an amount sufficient to achieve the desired pharmacological and/or therapeutic effects, i.e., an amount of the disclosed compound that is effective for its intended purpose. While individual subject/patient needs may vary, the determination of optimal ranges for effective amounts of the disclosed compound is within the skill of the art. Generally, the dosage regimen for treating a disease and/or condition with the compounds presently disclosed may be determined according to a variety of factors such as the type, age, weight, sex, diet, and/or medical condition of the subject/patient.

The term "pharmaceutical composition" means a compound according to the present disclosure in any form suitable for medical use.

The compounds of Formula (I) and (II) may exist in various stereoisomeric forms, including enantiomers, diastereomers, or mixtures thereof. It will be understood that the invention encompasses all optical isomers of the compounds of Formula (I) and (II) as well as mixtures thereof. Hence, compounds of Formula (I) and (II) that exist as diastereomers, racemates, and/or enantiomers are within the scope of the present disclosure.

In one aspect the compound for use according to the invention, is a compound of Formula (II)

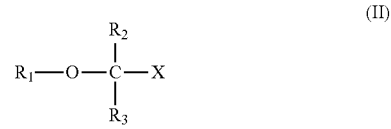
(II)

wherein $R_1$ is selected from a $C_{10}$-$C_{22}$ alkenyl having 3-6 double bonds;

$R_2$ and $R_3$ are the same or different and may be selected from a group of substituents consisting of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group, where $R_2$ and $R_3$ can be connected in order to form a cycloalkane like cyclopropane, cyclobutane, cyclopentane or cyclohexane;

X represents a carboxylic acid or a derivative thereof, wherein the derivative is a carboxylate, such as a carboxylic ester; a glyceride; an anhydride; a carboxamide; a phospholipid; or a hydroxymethyl; or a prodrug thereof;

or a pharmaceutically acceptable salt, solvate, or solvate of such a salt thereof.

In one embodiment, $R_1$ is a $C_{18}$-$C_{22}$ alkenyl having 3-6 double bonds, such as 5 or 6 double bonds, and preferably wherein one double bond is in the omega-3 position.

$R_2$ and $R_3$ are more preferably independently chosen from a hydrogen atom or linear, branched, and/or cyclic $C_1$-$C_6$ alkyl groups. In one embodiment, at least one of $R_2$ and $R_3$ is a hydrogen atom, a methyl group, an ethyl group, a n-propyl group, and an isopropyl group, a butyl group or a pentyl group.

X preferably represents a carboxylic acid or a carboxylic ester; or a pharmaceutically acceptable salt, solvate, or solvate of such a salt thereof.

The compound of Formula (II) for use may be administered as a monotherapy or in combination with one or more additional active agents.

More particularly, the present disclosure provides a method of treating non-alcoholic steatohepatitis or alcoholic steatohepatitis in a subject in need thereof, comprising administering to the subject a pharmaceutically effective amount of a compound of Formula (I):

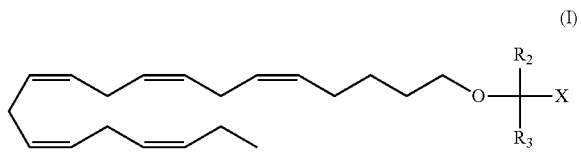

(I)

wherein $R_2$, $R_3$ and X are defined as for Formula (II).

Preferably, for compounds of Formula (I), $R_2$ and $R_3$ are independently chosen from a hydrogen atom or linear, branched, and/or cyclic $C_1$-$C_6$ alkyl groups; and X is a carboxylic acid or a carboxylic ester; or a pharmaceutically acceptable salt, solvate, or solvate of such a salt thereof.

The compound of Formula (I) may be administered as a monotherapy or in combination with one or more additional active agents.

In some embodiments, the present disclosure provides a compound of Formula (I):

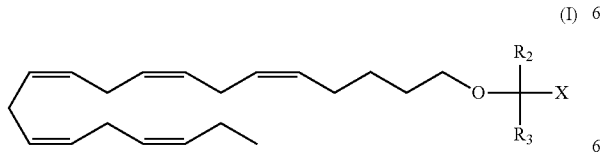

(I)

wherein $R_2$, $R_3$ and X are defined as for Formula (II), for use in treating non-alcoholic steatohepatitis or alcoholic steatohepatitis.

Preferably, for compounds of Formula (I), $R_2$ and $R_3$ are independently chosen from a hydrogen atom or linear, branched, and/or cyclic $C_1$-$C_6$ alkyl groups;

X is a carboxylic acid or a carboxylic ester; or a pharmaceutically acceptable salt, solvate, or solvate of such a salt thereof.

In those cases where $R_2$ and $R_3$ are different, the compounds of formula (I) and Formula (II) are capable of existing in stereoisomeric forms. It will be understood that the invention encompasses all optical isomers of the compounds of formula (I) and formula (II) and mixtures thereof.

In at least one embodiment, $R_2$ and $R_3$ are independently selected from the group of a hydrogen atom, a methyl group, an ethyl group, a n-propyl group, an isopropyl group, a butyl group and a pentyl group.

In at least one embodiment, $R_2$ and $R_3$ are independently selected from the group of a hydrogen atom, a methyl group, and an ethyl group.

In at least one embodiment, one of $R_2$ and $R_3$ is a hydrogen atom and the other one of $R_2$ and $R_3$ is chosen from a $C_1$-$C_3$ alkyl group. In one embodiment, one of $R_2$ and $R_3$ is a hydrogen atom and the other one of $R_2$ and $R_3$ is selected from the group of a methyl group and an ethyl group, and most preferably, one of $R_2$ and $R_3$ is a hydrogen atom and the other one is an ethyl group.

For compounds of both Formula I and Formula II, $R_2$ and $R_3$ are, in some embodiments, independently $C_1$-$C_6$ alkyl groups. In some embodiments both $R_2$ and $R_3$ are $C_1$-$C_3$ alkyl groups. In some embodiments R2 and R3 are the same or different and each are independently chosen from a methyl group, an ethyl group, an n-propyl group, or an isopropyl group. In some embodiments $R_2$ and $R_3$ are the same and are selected from a pair of methyl groups, a pair of ethyl groups, a pair of n-propyl groups or a pair of isopropyl groups. In at least one preferred embodiment $R_2$ and $R_3$ are ethyl groups. In some embodiments, one of $R_2$ and $R_3$ is a methyl group and the other one is an ethyl group. In some embodiments, one of $R_2$ and $R_3$ is an ethyl group and the other one is a n-propyl group.

In at least one embodiment, the compound is present in its various stereoisomeric forms, such as an enantiomer (R or S), a diastereomer, or mixtures thereof. In at least one embodiment, the compound is present in racemic form.

In cases where the compound according to Formula (I) is a salt of a counter-ion with at least one stereogenic center, or ester of an alcohol with at least one stereogenic center, the compound may have multiple stereocenters. In those situations, the compounds of the present disclosure may exist as diastereomers. Thus, in at least one embodiment, the compounds of the present disclosure are present as at least one diastereomer.

In at least one embodiment, the compound of the present disclosure is 2-(((5Z,8Z,11Z,14Z,17Z)-icosa-5,8,11,14,17-pentaen-1-yl)oxy)butanoic acid (Compound A):

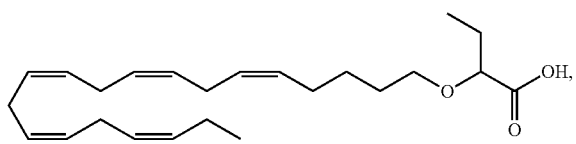

(Compound A)

In at least one embodiment, the compound of the present disclosure is 2-(((5Z,8Z,11Z,14Z,17Z)-icosa-5,8,11,14,17-pentaen-1-yl)oxy)butanoic acid (Compound A) present in its S and/or R form represented by the formulas;

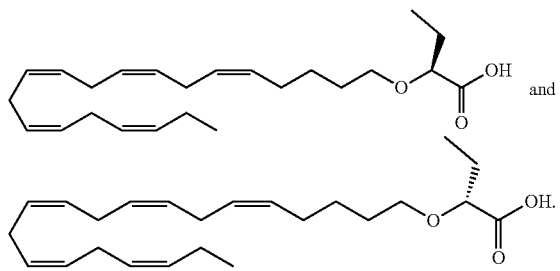

In some embodiments, 2-(((5Z,8Z,11Z,14Z,17Z)-icosa-5,8,11,14,17-pentaen-1-yl)oxy)butanoic acid (Compound A) is administered as a monotherapy. In some embodiments, 2-(((5Z,8Z,11Z,14Z,17Z)-icosa-5,8,11,14,17-pentaen-1-yl)oxy)butanoic acid (Compound A) is administered in combination with one or more additional active agents.

As previously described, multiple independent and interdependent metabolic, inflammatory and ultimately fibrotic components converge in the development of human NASH. It is likely that any successful treatment will need to address multiple aspects of NASH, preferably via upstream metabolic/inflammatory targets. However, as fibrosis development is associated with clinical outcomes, an ideal NASH therapy should target the inflammatory component and also ideally reduce or prophylactically treat both the development of fibrosis and reverse existing fibrosis. The enclosed examples show the surprising and unexpectedly potent anti-inflammatory and anti-fibrotic effects of oxygen-containing structurally modified fatty acids, such as Compound A. These findings, which were shown in multiple pre-clinical NASH models, support the use of oxygen-containing compounds of the disclosure in the therapeutic and and prophylactic treatment of NASH and ASH in human subjects.

It was surprising to find that Compound A is remarkably active in reducing or prophylactically treating the development of fibrosis and reversing hepatic fibrosis, e.g., as measured by a biochemical assay assessing hydroxyproline content in the CDAA (choline-deficient I-amino acid defined), diet-induced fibrosis mouse model (2-400% increase in extracellular matrix (ECM) vs a 20-30% increase in ECM in the milder APOE*3Leiden.CETP mouse model).

A novel finding in the CDAA-induced NASH model was further that Compound A also reduced hepatic fibrosis as measured histologically using Sirius Red morphometry (SR morphometry). In contrast to biochemical assessment of hydroxyproline (HYP) content that measures collagen in the large vessels, SR morphometry quantifies the more functionally relevant sinusoidal collagen deposits.

Given the pivotal importance of fibrosis in NASH-associated morbidity and mortality, the CDAA-induced NASH model results support the notion that oxygen-containing structurally modified fatty acids, such as Compound A, are effective for the treatment of NASH-related complications. This finding was also supported by changes in fibrosis-associated hepatic gene expression (Col1a1) and inflammatory responses (hepatic TNF-a gene expression). The significant reduction in the more functionally relevant sinusoidal collagen as measured by SR morphometry also supports the testing and use of Compound A in human NASH.

Despite the critical importance of fibrosis in clinical outcomes, regulatory approval of novel efficacious drugs for the treatment of NASH is related to resolution of NASH without worsening of fibrosis. It is also important that improvements in NAS score components are improved by novel compounds. Thus, improvements in steatosis, lobular inflammation and hepatocellular ballooning should ideally occur in addition to the desired improvement in fibrosis.

A novel finding in another NASH model, the STAM mouse model, was that in addition to improvements in steatosis and inflammation, Compound A improved hepatocellular ballooning. Hepatocellular ballooning is usually defined as cellular enlargement 1.5-2 times the normal hepatocyte diameter, with rarefied cytoplasm and has been shown to correlate with fibrosis and to be associated with liver injury.

Cellular enlargement (defined as hepatocellular hypertrophy) was also prevented by Compound A in APOE*3L.CETP double transgenic mice. The definition of hypertrophy versus ballooning relates to histological differences specific to rodent versus human hepatocytes.

In combination with the described anti-inflammatory effects, these novel findings related to hepatocellular ballooning/hypertrophy highlight the potential utility of Compound A to improve all NAS score components that in turn should contribute to a positive outcome in clinical development and subsequent regulatory approval.

It was surprising to find the efficacy of Compound A in modulating both inflammatory and fibrotic components in multiple NASH rodent models ranging in severity, as described above and as shown in the Examples.

The complex interplay of adaptive and non-adaptive immune cell recruitment, activation, differentiation and proliferation in NASH infers that reliance on any one inflammatory parameter requires concomitant measurement of fibrosis in order to interpret the functional significance of such read-outs. Thus, the anti-fibrotic effects of Compound A in the CDAA model may reinforce the clinical relevance the anti-inflammatory effects observed with oxygen-substituted structurally modified fatty-acids.

As regulatory approval of novel efficacious drugs for the treatment of NASH is dependent on resolution of NASH without worsening of fibrosis), the improvements in hepatocellular ballooning/hypertrophy observed with Compound A treatment in two distinct NASH rodent models is also an important and novel finding (ballooning/hypertrophy not measured in the CDAA mouse model).

In combination with the described anti-inflammatory effects, these novel findings related to hepatocellular ballooning/hypertrophy highlight the potential utility of Compound A to improve all NAS score components that in turn should contribute to a positive outcome in clinical development and subsequent regulatory approval.

Importantly, the ability of the compounds, such as Compound A, to improve all NAS score components and fibrosis associated with both portal tracts and parenchyma in multiple pre-clinical NASH models of differing aetiopathogenesis provides strong support for its testing in human NASH subjects.

Additionally, because a significant proportion of NASH patients also have type 2 diabetes, it is important to study the effect of delayed onset of treatment with an agent, such as Compound A, on hepatic steatosis, inflammation, and fibrosis, as well as the effect on glycemic control, in an obese diet-induced model of NASH. The anti-inflammatory, anti-fibrotic, and steatosis-reducing effects of Compound A described above was further demonstrated in an obese diet-induced NASH model (ob/ob AMLN high-fat fed mice). Compound A also had positive effects on glycemic control in this model without affecting bodyweight, unlike thiazolidinediones (e.g., pioglitazone), which adversely affect bodyweight. Further, Compound A reduced plasma levels of alanine aminotransferase (ALT) and aspartate transaminase (AST), indicating that hepatocellular injury and/or damage was reduced.

Based on these findings, the compounds of Formula (II), or preferably of Formula (I), may be administered to treat and/or reverse non-alcoholic steatohepatitis (NASH), or other hepatic disorders characterized by fibrosis, inflammation and/or hepatocellular ballooning. In some embodiments, the treatment of NASH may be prophylactic. Further, the compounds may be administered to treat at least one disease, condition or risk factor associated with NASH. In some embodiments, the treatment of at least one disease, condition, or risk factor associated with NASH may be prophylactic.

In view of the similarity in the pro-inflammatory and pro-fibrotic mechanisms between NASH and alcoholic steatohepatitis (ASH), the anti-inflammatory and anti-fibrotic effects of the disclosed compounds described herein in NASH models and in vitro experiments are thus relevant for the treatment and/or reversal of ASH, in particular, the prevention of progression and induction of regression of advanced ASH and associated fibrosis. For example, the inhibitory effects of Compound A on isolated LX-2 (human stellate) cell proliferation in vitro was independent of paracrine signaling from parenchymal cells and/or Kupffer cells, which suggests that anti-fibrotic effects of Compound A could be achieved irrespective of whether the upstreatm stimuli derive from NASH- or ASH-associated hepatic insults.

Thus, the compounds of Formula (II), or preferably of Formula (I), may be administered to treat and/or reverse ASH. In some embodiments, the treatment of ASH may be prophylactic. Further, the compounds may be administered to treat at least one disease, condition or risk factor associated with ASH. In some embodiments, the treatment of at least one disease, condition, or risk factor associated with ASH may be prophylactic.

Accordingly, the present disclosure encompasses a method of reducing or prophylactically treating the development of hepatic fibrosis and reducing existing hepatic fibrosis. By the method, the fibrosis is treated by either reducing the fibrotic area, the fibrotic content, or the severity of the fibrosis. In at least one embodiment, the method provides a decrease, such as a significant decrease, in the percentage surface area of the hepatic fibrosis. In at least one embodiment, the method provides a decrease in composite NAS score, such as a significant decrease in the NAS score. Further, the method encompasses a reduction of hepatic inflammation, such as lobular inflammation; a reduction of hepatocellular ballooning; and reduction in steatohepatitis; in addition to improving the fibrotic condition.

In some embodiments, a compound of the present disclosure reduces hepatic fibrotic area by 20%, 25%, 30%, 35%, 40%, 45%, 50%, 55%, 60%, 65%, or 70% as determined by Sirius Red morphometry. In some embodiments, a compound of the present disclosure reduces hepatic fibrotic area by 20-30%, 30-40%, 10-40%, 40-50%, 40-60%, 50-60%, 50-70%, or 60-70%. In some embodiments, a compound of the present disclosure reduces hepatic fibrosis content by 20%, 25%, 30%, 35%, or 40% as determined by hepatic hydroxyproline content. In some embodiments, a compound of the present disclosure reduces hepatic fibrosis content by 20-30%, 20-25%, 24-30%, or 30-40%, 30-35%, or 35-40%. In some embodiments, a compound of the present disclosure reduces hepatic collagen content by 20%, 25%, 30%, 35%, or 40%. In some embodiments, a compound of the present disclosure reduces hepatic collagen content by 20-30%, 20-25%, 25-30%, 30-40%, 30-35%, or 35-40%. In some embodiments, a compound of the present disclosure reduces hepatic α-SMA content area compared with pre-treatment levels by 3%.

In some embodiments, a compound of the present disclosure reduces steatosis by 40%, 45%, 50%, 55%, 60%, 65%, 70%, 75%, 80%, 85%, or 90%. In some embodiments, a compound of the present disclosure reduces steatosis by 40-50%, by 50-60%, by 60-70%, by 50-70%, by 70-80%, by 60-80%, by 70-90%, or by 80-90%. In some embodiments, a compound of the present disclosure reduces total hepatic lipid content by 20%, 25%, 30%, 35%, 40%, 45%, or 50%. In some embodiments, a compound of the present disclosure reduces total hepatic lipid content by 20-30%, by 30-40%, or by 40-50%.

In some embodiments, a compound of the present disclosure reduces hepatocellular ballooning by 30%, 35%, 40%, 45%, or 50%. In some embodiments, a compound of the present disclosure reduces hepatocellular ballooning by 30-40%, 30-35%, 35-40%, 40-50%, 40-45%, or 45-50%. In some embodiments, a compound of the present disclosure reduces hepatocellular hypertrophy by 40%, 45%, 50%, 55%, 60%, 65%, 70%, 75%, or 80%. In some embodiments, a compound of the present disclosure reduces hepatocellular hypertrophy by 40-50%, 50-60%, 60-70%, or 70-80%. In some embodiments, a compound of the present disclosure reduces NAS score by 30%, by 35%, by 40%, by 45%, by 50%, by 55%, by 60%, by 65%, or by 70%. In some embodiments, a compound of the present disclosure reduces NAS score by 30-40%, by 40-50%, by 30-50%, by 50-60%, by 60-70%, or by 50-70%.

In some embodiments, a compound of the present disclosure reduces hepatic inflammation by 20%, 30%, or 40% as determined by galectin (Gal-3) levels. In some embodiments, a compound of the present disclosure reduces hepatic inflammation by 20-30%, 20-25%, 25-30%, 30-40%, 30-35%, or 35-40%. In some embodiments, a compound of the present disclosure reduces plasma alanine aminotransferase (ALT) levels by 20%, 35%, 30%, 35%, or 40%. In some embodiments, a compound of the present disclosure reduces ALT levels by 20-30%, 20-25%, 25-30%, 30-40%, 30-35%, or 35-40%. In some embodiments, a compound of the present disclosure reduces plasma aspartate transaminase (AST) levels by 10%, 15%, or 20%. In some embodiments, a compound of the present disclosure reduces AST levels by 10-15%, by 10-20%, or by 15-20%.

In some embodiments, a compound of the present disclosure and/or treatment with a compound of the present disclosure, e.g., Compound A, improves a NAS score from a liver biopsy, MRI LiverMultiScan assessment PDFF and cT1, liver function test(s), HOMA-IR, and/or biomarker(s) of inflammation and fibrosis (including hsCRP, Pro-C3, ELF panel, and other suitable biomarkers) as compared to a control.

In some embodiments, a compound of the present disclosure and/or treatment with a compound of the present disclosure, e.g., Compound A, results in the improvement, e.g., reduction, of ballooning (e.g., score=0), e.g., with lobular inflammation score 0 or 1 and no worsening of fibrosis as compared to a control. In some embodiments, a compound of the present disclosure and/or treatment with a compound of the present disclosure, e.g., Compound A, results in a changes, e.g., improvements, from baseline in NAS score from liver biopsies, in individual histological scores for steatosis, ballooning, inflammation and fibrosis, in liver enzymes, in imaging parameters, and/or in biomarkers (including hsCRP, Pro-$C_3$, ELF panel, cytokines, and other suitable biomarkers) as compared to a control.

In some embodiments, the safety and tolerability of a compound of the present disclosure, e.g., Compound A, in patients can be assessed by monitoring adverse events in patients, monitoring laboratory values (haematology, biochemistry, and urinalysis), vital signs (blood pressure, pulse rate and temperature), hsCRP, and/or resting 12 lead ECGs as compared to a control. Pharmacokinetics of Compound A in patients can be studied, e.g., by comparison of mean trough plasma concentrations at steady state for Compound A taken at regular intervals. For example, mean trough plasma concentrations may be taken at 8 week intervals to determine the pharmacokinetics of Compound A.

Patients meeting one or more of the following criteria may show improved response to treatment with Compound A as compared to patients that do not meet the same one or more criteria: a histological diagnosis of NASH, fibrosis score 1-3 inclusive (F1 capped at 30%), PDFF >10% on MRI, compensated liver disease with the following hematologic and biochemical criteria on entry into protocol: ALT <5×ULN, AST >30, Hemoglobin >11 g/dL for females and >12 g/dL for males, White blood cell (WBC) >2.5 K/μL, Neutrophil count >1.5 K/μL, Platelets >100 K/μL, Total bilirubin <35 μmol/L (although patients with bilirubin >35 μmol/L can be included if non-conjugated bilirubin in the setting of a Gilbert syndrome), Albumin >36 g/L, International Normalized Ratio (INR)<1.4, Serum creatinine <1.3 mg/dL (men) or <1.1 (women) or estimated glomerular filtration rate ≥60 mL/min/1.73 m2, no other cause of chronic liver disease (e.g., autoimmune, primary biliary cholangitis, HBV, HCV, Wilson's, α-1-antitrypsin deficiency, hemochromatosis), and/or, if applicable, stable type 2 diabetes (defined as HgbA1c<9.5% and fasting glycemia <10 mmol/L, no changes in medication in the previous 6 months, and/or no new symptoms associated with decompensated diabetes in the previous 3 months).

Conversely, patients meeting one or more of the following criteria may not show response to treatment with Compound A as compared to patients in which the same one or more criteria is absent: a history of sustained excess alcohol ingestion, an unstable metabolic condition (e.g., as defined by a gain or loss in weight of greater than 5 kg in the last three months, diabetes with poor glycaemic control (HgbA1c>9.5%), or introduction of an antidiabetic or of an anti-obesity drug/malabsorptive or restrictive bariatric (weight loss) surgery in the past 6 months prior to screening), a history of gastrointestinal malabsorptive bariatric surgery within less than 5 years or ingestion of drugs known to produce hepatic steatosis including corticosteroids, high-dose oestrogens, methotrexate, tetracycline or amiodarone in the previous 6 months, HB antigen >0, HCV PCR >0 (patients with a history of HCV infection can be included if HCV PCR is negative for more than 3 years), or HIV infection, type 1 diabetes or a type 2 diabetes treated with insulin, diabetic ketoacidosis, fasting triglycerides >300 mg/dL, haemostasis disorders or current treatment with anticoagulants, a history of, or current cardiac dysrhythmias and/or a history of cardiovascular disease, including myocardial infarction, except in patients with well controlled hypertension, and any clinically significant ECG abnormality, and/or taking antidiabetics that are known to have activity against NASH, e.g pioglitazone, and GLP-1 receptor agonists.

Compounds of Formula (I) and Formula (II) can be prepared as described, for example, in PCT Applications WO2009/061208, WO2010/128401, WO2011/089529, WO2016/156912 and according to Examples below. In addition, Compound A can be prepared as described, for example, in PCT WO2010/128401 and WO2014/132135 and according to Example 2 below.

The Examples provided below are exemplary and one skilled in the art would understand how to apply these general methods to arrive at other compounds within the scope of Formula (I) and Formula (II). Compounds of the present disclosure may be in the form of a pharmaceutically acceptable salt or ester. For example, the compounds of Formula (I) and Formula (II) may be in the form of esters, such as a phospholipid, a glyceride or a $C_1$-$C_6$-alkyl ester. In at least one embodiment, the ester is chosen from a glyceride or a $C_1$-$C_6$-alkyl ester. In at least one embodiment, the ester is chosen from a triglyceride, a 1,2-diglyceride, a 1,3-diglyceride, a 1-monoglyceride, a 2-monoglyceride, a methyl ester, an ethyl ester, a propyl ester, an isopropyl ester, a n-butyl ester and a tert-butyl ester. In at least one embodiment, the compound of Formula (I) is present as a methyl ester, an ethyl ester, an isopropyl ester, a n-butyl ester or a tert-butyl ester, for example as a methyl ester or an ethyl ester. Typically, esters represented by Formula (I) (e.g., ethyl esters) will be hydrolyzed in the gastrointestinal tract.

Salts suitable for the present disclosure include, but are not limited to, salts of $NH^{4+}$; metal ions such as $Li^+$, $Na^+$, $K^+$, $Mg^{2+}$, or $Ca^{2+}$; a protonated primary amine such as tertbutyl ammonium, (3S,5S,7S)-adamantan-1-ammonium, 1,3-dihydroxy-2-(hydroxymethyl)propan-2-ammonium, a protonated aminopyridine (e.g., pyridine-2-ammonium); a protonated secondary amine such as diethylammonium, 2,3,4,5,6-pentahydroxy-N-methylhexan-1-ammonium, N-ethylnaphthalen-1-ammonium, a protonated tertiary amine such as 4-methylmorpholin-4-ium, a protonated quaternary amine such as 2-hydroxy-N,N,N-trimethylethan-1-aminium and a protonated guanidine such as amino((4-amino-4-carboxybutyl)amino)methaniminium or a protonated heterocycle such as 1H-imidazol-3-ium. Additional examples of suitable salts include salts of a diprotonated diamine such as ethane-1,2-diammonium or piperazine-1,4-diium. Other salts according to the present disclosure may comprise protonated Chitosan:

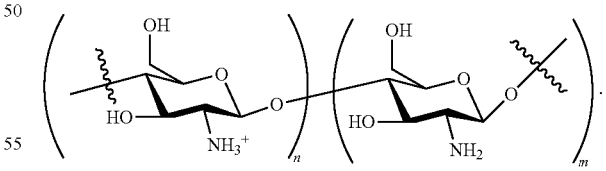

In at least embodiment, the salts are chosen from a sodium salt, a calcium salt, and a choline salt. In one embodiment the salt is a sodium salt or a calcium salt.

The present disclosure provides for a method of treating NASH or ASH in a subject in need thereof, comprising administering to the subject a pharmaceutically effective amount of a compound of Formula (I) or Formula (II). The subject may be a human or a non-human mammal. The compounds presently disclosed may be administered as a medicament, such as in a pharmaceutical composition. In one aspect, the invention provides a pharmaceutical composition comprising a compound of Formula (II), such as a compound of Formula (I), such as Compound A, for use in treating non-alcoholic steatohepatitis. The composition presently disclosed may comprise at least one compound as disclosed and optionally at least one non-active pharmaceutical ingredient, i.e., excipient. Non-active ingredients may solubilize, suspend, thicken, dilute, emulsify, stabilize, preserve, protect, color, flavor, and/or fashion active ingredients into an applicable and efficacious preparation, such that it may be safe, convenient, and/or otherwise acceptable for use. Examples of excipients include, but are not limited to, solvents, carriers, diluents, binders, fillers, sweeteners, aromas, pH modifiers, viscosity modifiers, antioxidants, extenders, humectants, disintegrating agents, solution-retarding agents, absorption accelerators, wetting agents, absorbents, lubricants, coloring agents, dispersing agents, and preservatives. Excipients may have more than one role or function or may be classified in more than one group; classifications are descriptive only and are not intended to be limiting. In some embodiments, for example, the at least one excipient may be chosen from corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose, and fatty substances such as hard fat or suitable mixtures thereof. In some embodiments, the compositions presently disclosed comprise at least one compound of Formula (II), such as one of Formula (I), and at least one pharmaceutically acceptable antioxidant, e.g., tocopherol such as alpha-tocopherol, beta-tocopherol, gamma-tocopherol, and delta-tocopherol, or mixtures thereof, BHA such as 2-tert-butyl-4-hydroxyanisole and 3-tert-butyl-4-hydroxyanisole, or mixtures thereof and BHT (3,5-di-tert-butyl-4-hydroxytoluene), or mixtures thereof.

The compositions presently disclosed may be formulated in oral administration forms, e.g., tablets or gelatin soft or hard capsules. The dosage form can be of any shape suitable for oral administration, such as spherical, oval, ellipsoidal, cube-shaped, regular, and/or irregular shaped. Conventional formulation techniques known in the art may be used to formulate the compounds according to the present disclosure. In some embodiments, the composition may be in the form of a gelatin capsule or a tablet.

A suitable daily dosage of a compound as disclosed, such as a compound of Formula (I) or a compound of Formula (II), may range from about 5 mg to about 4 g, such as from about 5 mg to about 2 g. For example, in some embodiments, the daily dose ranges from about 10 mg to about 1.5 g, from about 50 mg to about 1 g, from about 100 mg to about 1 g, from about 150 mg to about 900 mg, from about 50 mg to about 800 mg, from about 100 mg to about 800 mg, from about 100 mg to about 600 mg, from about 150 to about 550 mg, or from about 200 to about 500 mg. In at least one embodiment, the daily dose ranges from about 200 mg to about 600 mg. In at least one embodiment, the daily dose is about 50 mg, about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, or about 900 mg. The compound(s) may be administered, for example, once, twice, or three times per day.

In at least one embodiment, the compound of Formula (I) is administered in an amount ranging from about 200 mg to about 800 mg per dose. In at least one embodiment, the compound of Formula (I) is administered once per day. In at least one embodiment, the compound of Formula (I) is administered once per day at a dose of 750 mg. In some embodiments, the compound of Formula (I) is administered once per day at a dose of 600 mg. In some embodiments, the compound of Formula (I) is administered once per day at a dose of 500 mg. In some embodiments, the compound of Formula (I) is administered once per day at a dose of 300 mg. In some embodiments, the compound of Formula (I) is administered once per day at a dose of 250 mg. Preferably, the compound of Formula (I) is administered once per day at a dose of 300 mg or 600 mg.

In at least one embodiment, the compound of Formula (II) is administered in an amount ranging from about 200 mg to about 800 mg per dose. In at least one embodiment, the compound of Formula (II) is administered once per day. In at least one embodiment, the compound of Formula (II) is administered once per day at a dose of 750 mg. In some embodiments, the compound of Formula (II) is administered once per day at a dose of 600 mg. In some embodiments, the compound of Formula (II) is administered once per day at a dose of 500 mg. In some embodiments, the compound of Formula (II) is administered once per day at a dose of 300 mg. In some embodiments, the compound of Formula (II) is administered once per day at a dose of 250 mg. Preferably, the compound of Formula (II) is administered once per day at a dose of 300 mg or 600 mg.

According to the present disclosure, the compound of Formula (I) or (II) may be administered as a monotherapy or in combination with one or more additional active agents. For co-administration, the additional active agent is preferably a therapeutically active agent, such as a drug, and this preferably has a therapeutic effect on NASH or ASH, such as on one or more of the factors involved in the development and/or worsening of NASH or ASH. Preferably, the use of the combined product, i.e. the compound of Formula (I) or (II) in combination with one or more additional active agents, has a synergistic effect on preventing and/or treating of NASH or ASH. In one embodiment, the one or more additional therapeutic agents are independently selected from the group of allosteric acetyl-CoA carboxylase (ACC) inhibitors, angiotensin II receptor antagonists, angiotensin converting enzyme (ACE) inhibitors, apoptosis signal-regulating kinase-1 (ASK1) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPP IV) inhibitors, fibroblast-growth factor (FGF)-21 agonists, farnesoid X receptor (FXR) agonists, anti-CD3 mAb, galectin-3 inhibitors, glucagon-like peptide 1 (GLP1) agonists, glutathione precursors, hepatitis C virus NS3 protease inhibitors, HMG CoA reductase inhibitors, 1 Iβ-hydroxysteroid dehydrogenase (I Iβ-HSDI) inhibitors, heat shock protein (Hsp)47 inhibitors, IL-1β antagonists, IL-6 antagonists, IL-10 agonists, IL-17 antagonists, ileal sodium bile acid co-transporter inhibitors, leptin analogs, 5-lipoxygenase inhibitors, LPL gene stimulators, lysyl oxidase homolog 2 (LOXL2) inhibitors, lysophosphatidic acid 1 (LPA1) receptor antagonists, omega-3 fatty acids, PDE3 inhibitors, PDE4 inhibitors, phospholipase C (PLC) inhibitors, PPARα agonists, PPARγ agonists, PPARβ/δ agonists, recombinant human pentraxin-2 protein (PRF-1), Rho associated protein kinase 2 (ROCK2) inhibitors, semicarbazide-sensitive amine oxidase (SSAO) inhibitors, sodium glucose transporter-2 (SGLT2) inhibitors, stearoyl CoA desaturase-1 inhibitors, thyroid hormone receptor β agonists, tumor necrosis factor α (TNFα) ligand inhibitors, transglutaminase inhibitors, transglutaminase inhibitor precursors and small activating RNA (saRNA).

Particularly, in some embodiments, the one or more additional active agents are selected from the group of a Glucagon-like peptide 1 (GLP-1) agonist; a dipeptidyl peptidase inhibitor (DPP-4 antagonists) and omega-3 (n-3) fatty acids.

Glucagon-like peptide-1 receptor agonists also known as GLP-1 receptor agonists or incretin mimetics are agonists of the GLP-1 receptor. This class of drugs is typically used for the treatment of type 2 diabetes. A non-limiting example list of GLP-agonists includes: exenatide, liraglutide, lixisenatide, albiglutide, dulaglutide, taspoglutide and semaglutide.

In some embodiments, the additional active agent is a dipeptidyl peptidase inhibitor (DPP-4 antagonist). DPP-4 antagonists are a class of oral hypoglycemics that block DPP-4 (DPP-IV). They can be used to treat diabetes mellitus type 2. Glucagon increases blood glucose levels, and DPP-4 inhibitors reduce glucagon and blood glucose levels. The mechanism of DPP-4 inhibitors is to increase incretin levels (GLP-1 and GIP), which inhibit glucagon release, which in turn increases insulin secretion, decreases gastric emptying, and decreases blood glucose levels. A non-limiting example list of dipeptidyl peptidase inhibitors includes: Sitagliptin, Vildagliptin, Saxagliptin, Linagliptin, Gemigliptin, Anagliptin, Teneligliptin, Alogliptin, Trelagliptin, Omarigliptin, Evogliptin, Dutogliptin.

In some embodiments, the additional agent is an omega-3 fatty acid. When the additional active agent is an omega-3 fatty acid, the omega-3 fatty acid is typically a long chain polyunsaturated omega-3 fatty acid (LC n-3 PUFA). Preferably, this includes at least one of (all-Z omega-3)-5,8,11,14,17-eicosapentaenoic acid (EPA) and (all-Z omega-3)-4,7,10,13,16,19-docosahexaenoic acid (DHA), or derivatives thereof. The n-3 PUFAs, including the EPA and DHA, may be in different forms, and are presented in at least one of free fatty acid form; esterified form, such as C1-C4 alkyl esters, and preferably ethyl ester; phospholipids; mono/di/tri-glycerides; and salts thereof. The omega-3 fatty acid may be provided in the form of a composition, such as a composition for oral administration. Such composition may comprise at least 40%, such as at least 50%, 60%, 70% or 80% of the active omega-3 fatty acid. In some embodiments, the additional active agent is a composition comprising at least one of EPA and DHA, preferably on ethyl ester form, in a concentration of at least 70%.

In some embodiments, the one or more additional active agents are independently selected from the group of acetylsalicylic acid, alipogene tiparvovec, aramchol, atorvastatin, BI 1467335, BLX-1002, BMS-986036, BMS-986020, cenicriviroc, cobiprostone, colesevelam, emricasan, enalapril, foramulab, GFT-505, GR-MD-02, GS-0976, GS-9674, hydrochlorothiazide, icosapent ethyl ester (ethyl eicosapentaenoic acid, EPA ethyl ester), IMM-124E, IVA337, K-877, KD-025, linagliptin, liraglutide, mercaptamine, MGL-3196, ND-L02-s0201, obeticholic acid, olesox-ime, peg-ilodecakin, pioglitazone, PRM-151, PX-102, remogliflozin etabonate, selonsertib, simtuzumab, SHP-626, solithromycin, tipelukast, TRX-318, ursodeoxycholic acid, and VBY-376. The first component of the combined product, i.e. the compound of Formula (I) or (II) may be administered or formulated in any manner as described above. The second component of the combined product, the additional active agent, may be formulated as is suitable for the type of agent it is, and depends on several factors, including the mode of administration of the agent. The dose of the additional active agent depends on the type of agent selected, and it should be in accordance with the approved amounts for the specific agent. As provided in the Examples, the use of the CDAA (choline-deficient I-amino acid defined) diet-induced NASH model provides a model for both hepatic fibrosis and inflammation. As supported by the examples, the combination of a GLP-1 agonist with a compound of Formula (I) or (II), such as Compound A, has a superior effect compared with treatment with GLP-1 alone for NASH related fibrosis and inflammation. As hepatic fibrosis is largely a response to inflammatory responses, this is also supported by the demonstrated changes in inflammatory-associated hepatic gene expression (TNF-α), which demonstrate superiority of oxygen-containing structurally modified fatty acids (Compound A) in combination with a GLP-1 agonist versus a GLP-1 agonist alone. Overall the data suggest that a combination of a GLP-1 agonist (or alternatively DPP-4 antagonists) with a compound of the disclosure may achieve a synergistic effect for the treatment of both hepatic inflammation and fibrosis.

Although hepatic steatosis may be a benign condition per se, it may sensitize the liver to a "2nd hit" from other factors that induce an inflammatory response. A reduction in steatosis is therefore desirable both with respect to its contribution to NAS score and resolution of NASH as a potential 'priming' factor for other or continued hepatic insults. The novel and remarkable improvements in hepatic lipids achieved with a combination of high-dose omega-3 ethyl-esters and a low dose of an oxygen-containing structurally modified fatty acid (Compound A) strongly suggest a synergistic effect is achieved, especially as neither compound achieved a significant reduction in hepatic triglycerides (TG) alone in ApoE*3L-CETP transgenic mice.

Remarkably, Compound A, at a fraction of the dose of the omega-3 ethyl esters, significantly up- or down-regulated >1094 gene expression probes in the liver of APOE*3.CETP transgenic mice versus <10 for the omega-3 ethyl esters (data not shown). Without being bound by theory, this diverging effect upon the hepatic transcriptome may suggest that the synergistic effect observed is secondary to targeting different pathways rather than an accumulative dose effect. The significant effects upon hepatic cholesterol content may also have positive effects upon inflammatory responses relevant to the pathogenesis of NASH and ASH. Overall the data in APOE*3.CETP mice support the combination of omega-3 PUFA formulations, such as EPA ethyl esters, and an oxygen containing structurally modified fatty acid ac-cording to Formula (I) or (II) as a potent therapy for reduction of hepatic steatosis, and hence treatment of NASH and/or ASH.

The compounds of Formula (II), or preferably of Formula (I), may be administered as a monotherapy or in combination with at least one additional active agent to treat and/or reverse non-alcoholic steatohepatitis (NASH) or alcoholic steatohepatitis (ASH). In some embodiments, the at least one additional active agent is a GLP-1 agonist. Additionally, based on the findings in the APOE*3.CETP transgenic mice, the compounds of Formula (II), or preferably of Formula (I), may be adaministered in combination with at least one additional active agent to therapeutically and/or prophylactically treat and/or reverse hepatic steatosis (triglycerides and/or cholesterol content). In some embodiments, the at least one additional active agent is an omega-3 fatty acid, such as an omega 3 PUFA ethyl ester.

The above examples highlight the potential of the oxygen-containing structurally modified fatty acids to be combined with a number of other active agents for the treatment of NASH and/or ASH. These combinations may not only improve efficacy related outcomes versus monotherapy but may also improve safety. As an example of the latter, Compound A has been demonstrated to significantly reduce CETP expression in APOE*3.CETP mice and to improve lipid profiles in both rodents and humans. This may be advantageous for a combination with obeticholic acid (an FXR agonist) that, in contrast to Compound A, increases CETP expression and worsens lipid profiles in both APOE*3.CETP mice and in humans.

The present inventors have found that compounds of Formula (I), such as 2-(((5Z,8Z,11Z,14Z,17Z)-icosa-5,8,11,14,17-pentaen-1-yl)oxy)butanoic acid, have remarkably good pharmaceutical activity. Surprisingly, the compounds of Formula (I) presently disclosed exhibit improved biological activity compared to to a glucagon-like peptide 1 receptor (GLP-1R) agonist, for treating NASH associated hepatic fibrosis and inflammation. The compounds of Formula (I) also exhibit possibly synergistic effects when administered in combination with additional active agents.

EXAMPLES

The present disclosure may be further described by the following non-limiting examples, in which standard techniques known to the skilled chemist and techniques analogous to those described in these examples may be used where appropriate. It is understood that the skilled artisan will envision additional embodiments consistent with the disclosure provided herein.

Unless otherwise stated, reactions were carried out at room temperature, typically in the range between 18-25° C. with solvents of HPLC grade under anhydrous conditions. Evaporations were carried out by rotary evaporation in vacuo. Column chromatography was performed by the flash procedure on silica gel 40-63 μm (Merck) or by an Armen Spotflash using the pre-packed silica gel columns "Mini-VarioFlash", "SuperVarioFlash", "SuperVarioPrep" or "EasyVarioPrep" (Merck). Nuclear magnetic resonance (NMR) shift values were recorded on a Bruker Avance DPX 200 or 300 instrument with peak multiplicities described as follows: s, singlet; d, doublet; dd, double doublet; t, triplet; q, quartet; p, pentet; m, multiplett; br, broad. The mass spectra were recorded with a LC/MS spectrometer. Separation was performed using an Agilent 1100 series module on an Eclipse XDB-C18 2.1×150 mm column with gradient elution. As eluent were used a gradient of 5-95% acetonitrile in buffers containing 0.01% trifluoroacetic acid or 0.005% sodium formate. The mass spectra were recorded with a G1956A mass spectrometer (electrospray, 3000 V) switching positive and negative ionization mode. Reported yields are illustrative and do not necessarily represent the maximum yield attainable.

Preparation of Compounds

Example 1: Preparation of tert-butyl 2-((5Z,8Z,11Z,14Z,17Z)-icosa-5,8,11,14,17-pentaen-1-yloxy)butanoate

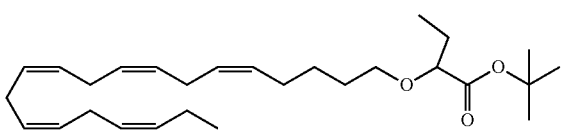 [SMILES: CC/C=C\C/C=C\C/C=C\C/C=C\C/C=C\CCCCOC(CC)C(=O)OC(C)(C)C]

Tetrabutylammonium chloride (0.55 g, 1.98 mmol) was added to a solution of (5Z,8Z,11Z,14Z,17Z)-icosa-5,8,11,14,17-pentaen-1-ol, (3.50 g, 12.1 mmol) in toluene (35 mL) at room temperature under nitrogen. An aqueous solution of sodium hydroxide (50% (w/w), 11.7 mL) was added under vigorous stirring at room temperature, followed by t-butyl 2-bromobutyrate (5.41 g, 24.3 mmol). The resulting mixture was heated to 50° C. and additional tbutyl 2-bromobutyrate was added after 1.5 hours (2.70 g, 12.1 mmol), 3.5 hours (2.70 g, 12.1 mmol) and 4.5 hours (2.70 g, 12.1 mmol) and stirred for 12 hours in total. After cooling to room temperature, ice water (25 mL) was added and the resulting two phases were separated. The organic phase was washed with a mixture of NaOH (5%) and brine, dried (MgSO$_4$), filtered and concentrated. The residue was purified by flash chromatography on silica gel using increasingly polar mixtures of heptane and ethyl acetate (100:0→95:5) as eluent. Concentration of the appropriate fractions afforded 1.87 g (36% yield) of the title compound as an oil. $^1$H NMR (300 MHz, CDCl3): δ 0.85-1.10 (m, 6H), 1.35-1.54 (m, 11H), 1.53-1.87 (m, 4H), 1.96-2.26 (m, 4H), 2.70-3.02 (m, 8H), 3.31 (dt, 1H), 3.51-3.67 (m, 2H), 5.10-5.58 (m, 10H).

Example 2: Preparation of 2-((5Z,8Z,11Z,14Z,17Z)-icosa-5,8,11,14,17-pentaenyloxy)butanoic acid (Compound A)

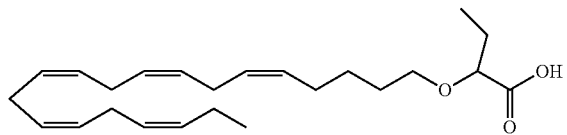 [SMILES: CC/C=C\C/C=C\C/C=C\C/C=C\C/C=C\CCCCOC(CC)C(=O)O]

tert-Butyl 2-((5Z,8Z,11Z,14Z,17Z)-icosa-5,8,11,14,17-pentaen-1-yloxy)butanoate (19.6 g, 45.5 mmol) was dissolved in dichloromethane (200 mL) and placed under nitrogen. Trifluoroacetic acid (50 mL) was added and the reaction mixture was stirred at room temperature for one hour. Water was added and the aqueous phase was extracted twice with dichloromethane. The combined organic extract was washed with brine, dried (Na$_2$SO$_4$), filtered and concentrated. The residue was subjected to flash chromatography on silica gel using increasingly polar mixtures of heptane, ethyl acetate and formic acid (90:10:1→80:20:1) as eluent. Concentration of the appropriate fractions afforded 12.1 g (71% yield) of the title compound as an oil. $^1$H-NMR (300 MHz, CDCl$_3$): δ 0.90-1.00 (m, 6H), 1.50 (m, 2H), 1.70 (m, 2H), 1.80 (m, 2H), 2.10 (m, 4H), 2.80-2.90 (m, 8H), 3.50 (m, 1H), 3.60 (m, 1H), 3.75 (t, 1H), 5.30-5.50 (m, 10H); MS (electrospray): 373.2 [M–H]$^-$.

Example 3: Preparation of Calcium 2-(((5Z,8Z,11Z,14Z,17Z)-icosa-5,8,11,14,17-pentaen-1-yl)oxy)butanoate

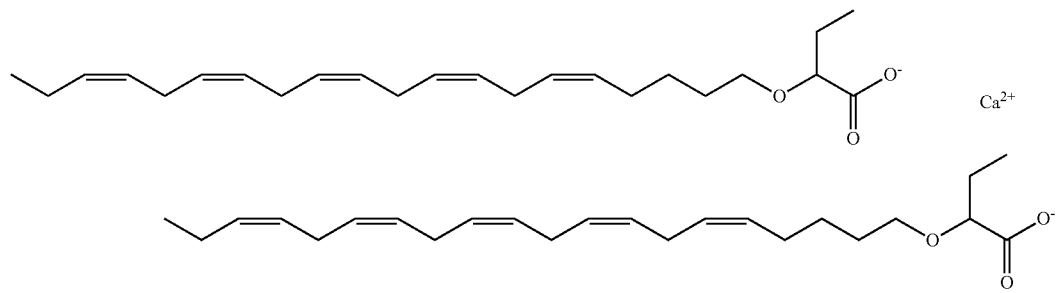

2-(((5Z,8Z,11Z,14Z,17Z)-Icosa-5,8,11,14,17-pentaen-1-yl)oxy)butanoic acid (1.87 g, 4.99 mmol, 93%) was mixed with $CaCO_3$ (0.25 g, 2.50 mmol). Water (1 ml) was added and the mixture was stirred with mechanical stirring at RT for 1 hour. $CO_2$ develops. Dense and homogeneous pasta was formed. With stirring, acetone (7 ml) was added. A solid materiel separates. The solid materiel was filtered of and dried over nitrogen sealed and stored in the fridge at 4° C. Yield: 1.86 grams (95%). The solid was not further characterized by analytical or spectroscopic methods, but a few experiments indicating that the calcium salt has formed was performed:
- The solid materiel melts on a hot plate below 100° C. No sharp melting point was determined
- The material do not liberate $CO_2$ on addition of acid, but "dissolves" and precipitates as an oil

Example 4: Preparation of Sodium 2-(((5Z,8Z,11Z,14Z,17Z)-icosa-5,8,11,14,17-pentaen-1-yl)oxy)butanoate

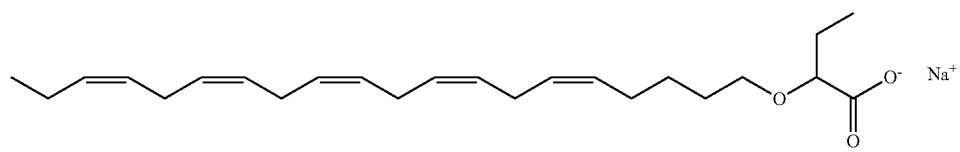 [SMILES: CC/C=C\C/C=C\C/C=C\C/C=C\C/C=C\CCCCOC(CC)C(=O)[O-] ; [Na+]]

2-(((5Z,8Z,11Z,14Z,17Z)-Icosa-5,8,11,14,17-pentaen-1-yl)oxy)butanoic acid (1.87 g, 4.99 mmol, 93%) was mixed with $NaHCO_3$ (0.420 g, 5.00 mmol). Water (1 ml) was added and the mixture was stirred with mechanical stirring at RT for 1 hour. $CO_2$ develops, and a thick homogeneous pasta was formed. With stirring, ethanol (7 ml) was added to the reaction flask. The sodium salt formed from 2-(((5Z,8Z,11Z,14Z,17Z)-icosa-5,8,11,14,17-pentaen-1-yl)oxy)butanoic acid goes into solution upon addition of ethanol (7 ml). Small amounts of unreacted $NaHCO_3$ was filtered of and the solution was evaporated to dryness. The crude slightly viscous oil was evaporated two times with 96% ethanol to remove traces of water.

Example 5: Preparation of 2-hydroxy-N,N,N-trimethylethan-1-aminium 2-(((5Z,8Z,11Z,14Z,17Z)-icosa-5,8,11,14,17-pentaen-1-yl)oxy)butanoate

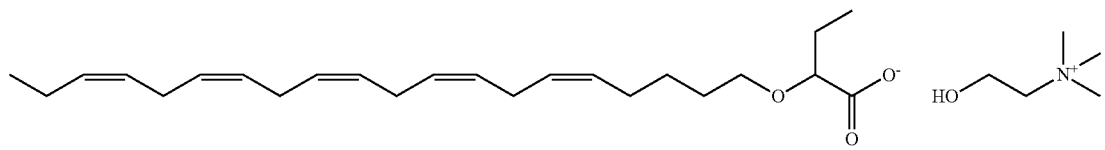

Choline hydroxide (327.7 µL) in water was pipetted into a scintillation vial with ca. 2.5 mL MTBE and 7.5 mL of n-Heptane. Within a nitrogen chamber, 2-(((5Z,8Z,11Z,14Z,17Z)-icosa-5,8,11,14,17-pentaen-1-yl)oxy)butanoic acid (500 mg, 95.8%) was transferred into the vial. Within a nitrogen chamber ca.1.0 mL of water was added to the vial slowly and under stirring. The vial was then sealed. The reaction mixture was stirred for ca. 30 minutes. The formed 2-(((5Z,8Z,11Z,14Z,17Z)-icosa-5,8,11,14,17-pentaen-1-yl)oxy)butanoic acid choline salt was a rigid, gel-like material which was filtered on a Buchner funnel. The wet material on the filter was washed 3 times using 1 mL of MTBE. The washed material appeared as a rigid gel-like solid.

Example 6: Preparation of (4S,5R)-3-((S)-2-((5Z,8Z,11Z,14Z,17Z)-icosa-5,8,11,14,17-pentaenyloxy)butanoyl)-4-methyl-5-phenyloxazolidin-2-one and (4S,5R)-3-((R)-2-((5Z,8Z,11Z,14Z,17Z)-icosa-5,8,11,14,17-pentaenyloxy)butanoyl)-4-methyl-5-phenyloxazolidin-2-one

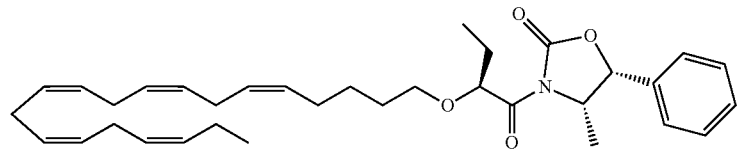

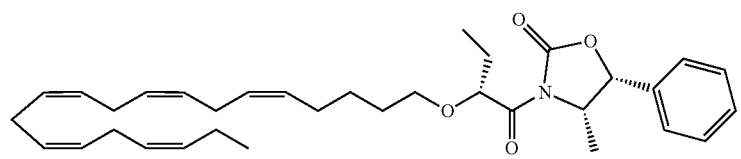

DMAP (1.10 g, 8.90 mmol) and DCC (1.90 g, 9.30 mmol) were added to a mixture of 2-((5Z,8Z,11Z,14Z,17Z)-icosa-5,8,11,14,17-pentaenyloxy)butanoic acid (3.20 g, 8.50 mmol) in dry dichloromethane (100 mL) held at 0° C. under nitrogen. The resulting mixture was stirred at 0° C. for 20 minutes. (4S,5R)-4-methyl-5-phenyloxazolidin-2-one (1.50 g, 8.50 mmol) was added and the resulting turbid mixture was stirred at ambient temperature for five days. The mixture was filtrated and concentrated under reduced pressure to give a crude product containing the desired product as a mixture of two diastereomers. The residue was purified by flash chromatography on silica gel using 15% ethyl acetate in heptane as eluent. The two diastereomers were separated and the appropriate fractions were concentrated. (4S,5R)-3-((S)-2-((5Z,8Z,11Z,14Z,17Z)-icosa-5,8,11,14,17-pentaenyloxy)butanoyl)-4-methyl-5-phenyloxazolidin-2-one eluted first and was obtained in 1.1 g (40% yield) as an oil. (4S,5R)-3-((R)-2-((5Z,8Z,11Z,14Z,17Z)-icosa-5,8,11,14,17-pentaenyloxy)butanoyl)-4-methyl-5-phenyloxazolidin-2-one was obtained in 0.95 g (34% yield) as an oil.

(4S,5R)-3-((S)-2-((5Z,8Z,11Z,14Z,17Z)-icosa-5,8,11,14,17-pentaenyloxy)butanoyl)-4-methyl-5-phenyloxazolidin-2-one (E1): $^1$H-NMR (300 MHz, CDCl$_3$): δ 0.90 (d, 3H), 1.00 (t, 3H), 1.07 (t, 3H), 1.45-1.57 (m, 2H), 1.62-1.76 (m, 3H), 1.85-1.95 (m, 1H), 2.05-2.15 (m, 4H), 2.87 (m, 8H), 3.39 (m, 1H), 3.57 (m, 1H), 4.85-4.92 (m, 2H), 5.30-5.45 (m, 10H), 5.75 (d, 1H), 7.32 (m, 2H), 7.43 (m, 3H).

(4S,5R)-3-((R)-2-((5Z,8Z,11Z,14Z,17Z)-icosa-5,8,11,14,17-pentaenyloxy)butanoyl)-4-methyl-5-phenyloxazolidin-2-one (E2): $^1$H-NMR (300 MHz, CDCl$_3$): δ 0.98 (d, 3H), 0.99 (t, 3H), 1.08 (t, 3H), 1.40-1.52 (m, 2H), 1.55-1.75 (m, 3H), 1.80-1.90 (m, 1H), 2.05-2.15 (m, 4H), 2.84 (m, 8H), 3.39 (m, 1H), 3.56 (m, 1H), 4.79 (pent, 1H), 4.97 (dd, 1H), 5.30-5.45 (m, 10H), 5.71 (d, 1H), 7.33 (m, 2H), 7.43 (m, 3H).

Example 7: Preparation of (S)-2-((5Z,8Z,11Z,14Z,17Z)-icosa-5,8,11,14,17-pentaenyloxy)butanoic acid

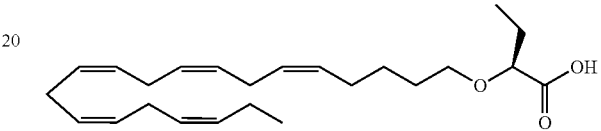

Hydrogen peroxide (35% in water, 0.75 mL, 8.54 mmol) and lithium hydroxide monohydrate (0.18 g, 4.27 mmol) was added to a solution of (4S,5R)-3-((S)-2-((5Z,8Z,11Z,14Z,17Z)-icosa-5,8,11,14,17-pentaenyloxy)butanoyl)-4-methyl-5-phenyloxazolidin-2-one (1.10 g, 2.13 mmol) in tetrahydrofuran (12 mL) and water (4 mL) held at 0° C. under nitrogen. The reaction mixture was stirred at 0° C. for 30 minutes. 10% Na$_2$SO$_3$ (aq) (30 mL) was added, the pH was adjusted to ~2 with 2M HCl and the mixture was extracted twice with heptane (30 mL). The combined organic extract was dried (Na$_2$SO$_4$), filtered and concentrated. The residue was subjected to flash chromatography on silica gel using increasingly polar mixtures of heptane and ethyl acetate (98:8→1:1) as eluent. Concentration of the appropriate fractions afforded 0.48 g (60% yield) of the title compound as an oil. $^1$HNMR (300 MHz, CDCl$_3$): δ 0.90-1.00 (m, 6H), 1.48 (m, 2H), 1.65 (m, 2H), 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electrospray): 373.3 [M−H]$^-$; [α]$_D$ −37° (c=0.104, ethanol).

Example 8: Preparation of (R)-2-(((5Z,8Z,11Z,14Z,17Z)-icosa-5,8,11,14,17-pentaenyloxy)butanoic acid

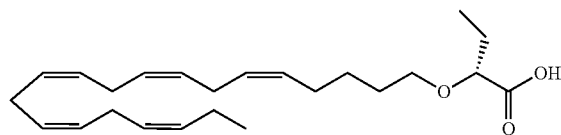 [SMILES: CC/C=C\C/C=C\C/C=C\C/C=C\C/C=C\CCCCO[C@H](CC)C(=O)O]

Hydrogen peroxide (35% in water, 0.65 mL, 7.37 mmol) and lithium hydroxide monohydrate (0.15 g, 3.69 mmol) was added to a solution of (4S,5R)-3-((R)-2-((5Z,8Z,11Z,14Z,17Z)-icosa-5,8,11,14,17-pentaenyloxy)butanoyl)-4-methyl-5-phenyloxazolidin-2-one (0.95 g, 1.84 mmol) in tetrahydrofuran (12 mL) and water (4 mL) held at 0° C. under nitrogen. The reaction mixture was stirred at 0° C. for 30 minutes. 10% $Na_2SO_3$ (aq) (30 mL) was added, the pH was adjusted to 2 with 2M HCl and the mixture was extracted twice with heptane (30 mL). The combined organic extract was dried ($Na_2SO_4$), filtered and concentrated. The residue was subjected to flash chromatography on silica gel using increasingly polar mixtures of heptane and ethyl acetate (98:8→50:50) as eluent. Concentration of the appropriate fractions afforded 0.19 g (29% yield) of the title compound as an oil. $^1$H-NMR (300 MHz, $CDCl_3$): δ 0.90-1.00 (m, 6H), 1.48 (m, 2H), 1.65 (m, 2H), 1.85 (m, 2H), 2.10 (m, 4H), 2.80-2.90 (m, 8H), 3.55 (m, 1H), 3.60 (m, 1H), 3.88 (t, 1H), 5.35-5.45 (m, 10H); MS (electrospray): 373.3 [M−H]$^-$; [α]$_D$ −31° (c=0.088, ethanol).

Example 9: Preparation of ethyl 2-(((5Z,8Z,11Z,14Z,17Z)-icosa-5,8,11,14,17-pentaen-1-yl)oxy)butanoate

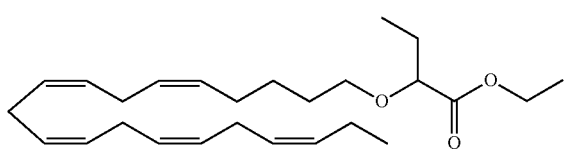 [SMILES: CC/C=C\C/C=C\C/C=C\C/C=C\C/C=C\CCCCOC(CC)C(=O)OCC]

Dicyclohexylimethanediimine (DCC) (304 mg, 1.47 mmol) and N,N-dimethylpyridin-4-amine (DMAP) (10 mg, 0.067 mmol) were added to a stirred solution of 2-(((5Z,8Z,11Z,14Z,17Z)-icosa-5,8,11,14,17-pentaen-1-yl)oxy)butanoic acid (501.3 mg, 1.335 mmol) in dichloromethane (DCM) (4 mL) at 0° C. under $N_2$-atmosphere. The mixture was stirred for 5 minutes, before ethanol (EtOH) (0.16 mL, 2.67 mmol) was added. The resulting mixture was stirred at room temperature for 20 hours. The reaction mixture was purified by flash chromatography on silica gel using increasingly mixtures of heptane and ethyl acetate (100:0→99:1) as eluent. Concentration of the appropriate fractions afforded 473 mg (88% yield) of the title compound as an oil. $^1$H NMR (300 MHz, chloroform-d) δ 0.95 (2×t, 6H), 1.37-1.48 (m, 2H), 1.54-1.79 (m, 4H), 2.01-2.10 (m, 4H), 2.77-2.84 (m, 8H), 3.27-3.34 (m, 1H), 3.53-3.60 (m, 1H), 3.69-3.73 (dd, 1H), 4.13-4.24 (m, 2H), 5.25-5.33 (m, 10H), MS (electrospray); 425.3 [M+Na]+; HRMS (electrospray): Found 425.3021 [M+Na]$^+$, calcd. for [$C_{26}H_{42}O_3$+Na]$^+$ 425.3031.

Example 10: Preparation of Isopropyl 2-(((5Z,8Z,11Z,14Z,17Z)-icosa-5,8,11,14,17-pentaen-1-yl)oxy)butanoate

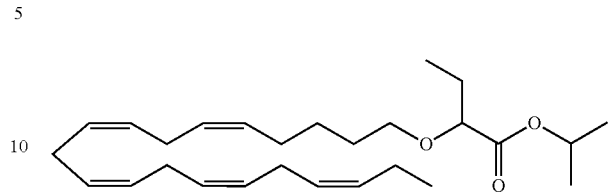

DCC (310 mg, 1.47 mmol) and DMAP (9 mg, 0.067 mmol) were added to a stirred solution of 2-(((5Z,8Z,11Z,14Z,17Z)-icosa-5,8,11,14,17-pentaen-1-yl)oxy)butanoic acid (501 mg, 1.335 mmol) in DCM (4 mL) at 0° C. under $N_2$-atmosphere. The mixture was stirred for 5 minutes, before isopropanol (iPrOH) (0.16 mL, 2.67 mmol) was added. The resulting mixture was stirred at room temperature for 20 hours. The mixture was filtered and concentrated in vacuo. The residue was added heptane (50 mL), filtered and concentrated in vacuo. The residue was purified by flash chromatography on silica gel using 1% ethyl acetate in heptane as eluent. Concentration of the appropriate fractions afforded 496 mg (89% yield) of the title compound as an oil. $^1$H NMR (300 MHz, $CDCl_3$): δ 0.97 (2×t, 6H), 1.25 (m, 6H), 1.42-1.50 (m, 2H), 1.61-1.70 (m, 2H), 1.70-1.77 (m, 2H), 2.05-2.12 (m, 4H), 2.79-2.86 (m, 8H), 3.29-3.34 (m, 1H), 3.54-3.59 (m, 1H), 3.67-3.71 (m, 1H), 5.06-5.10 (m, 1H), 5.31-5.42 (m, 10H); MS (electrospray): 439.3 [M+Na]$^+$.

Example 11: Preparation of methyl 2-(((5Z,8Z,11Z,14Z,17Z)-icosa-5,8,11,14,17-pentaen-1-yl)oxy)butanoate

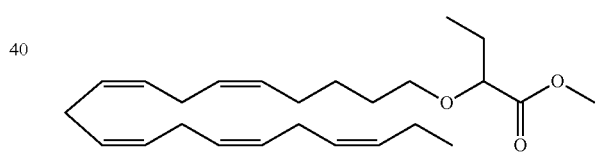

Sulphuric acid (0.049 ml, 0.918 mmol) was added to a solution of 2-(((5Z,8Z,11Z,14Z,17Z)-icosa-5,8,11,14,17-pentaen-1-yl)oxy)butanoic acid ((385 mg, 1,028 mmol) in methanol (20 ml) at room temperature under $N_2$-athmosphere and the resulting mixture was stirred at room temperature overnight. MS (electrospray): 389.3 [M+1]$^+$.

Example 12: Preparation of butyl 2-(((5Z,8Z,11Z,14Z,17Z)-icosa-5,8,11,14,17-pentaen-1-yl)oxy)butanoate

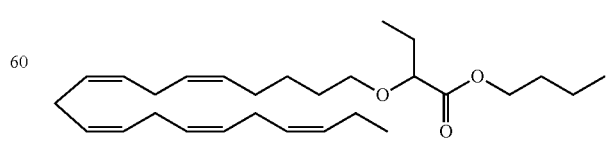

Sulphuric acid (0.049 ml, 0.918 mmol) was added to a solution of 2-(((5Z,8Z,11Z,14Z,17Z)-icosa-5,8,11,14,17-pentaen-1-yl)oxy)butanoic acid ((33 g, 88 mmol) in butan- 1-ol (400 mL, 4.37 mol) at room temperature under N₂-atmosphere and the reaction mixture was stirred for 120 hours. Heptane (400 mL) and ethyl acetate (400 mL) was added, and the solution was washed with saturated aq. NaHCO₃ (3×300 mL) and water (2×300 mL). The combined aqueous phase was extracted with heptane/ether (1:1) (2×300 mL). The combined organic phase was dried (Na₂SO₄), filtered and concentrated in vacuo. The residue was purified by flash chromatography using increasingly mixtures of heptane and ethyl acetate (99:1→96:4) as eluent. Concentration of the appropriate fractions afforded 26.3 g (67% yield) of title compound as an oil. ¹H NMR (400 MHz, CDCl3) δ 0.93-1.02 (m, 9H), 1.36-1.51 (m, 4H), 1.60-1.70 (m, 4H), 1.72-1.84 (m, 2H), 2.05-2.16 (m, 4H), 2.78-2.92 (m, 8H), 3.28-3.39 (m, 1H), 3.54-3.65 (m, 1H), 3.70-3.82 (m, 1H), 4.08-4.24 (m, 2H), 5.27-5.48 (m, 10H), MS (electrospray): 453.2 [M+Na]⁺.

Example 13: Preparation of 2,3-dihydroxypropyl 2-(((5Z,8Z,11Z,14Z,17Z)-icosa-5,8,11,14,17-pentaen-1-yl)oxy)butanoate Step a) Preparation (2,2-dimethyl-1,3-dioxolan-4-yl)methyl 2-(((5Z,8Z,11Z,14Z,17Z)-icosa-5,8,11,14,17-pentaen-1-yl)oxy)butanoate

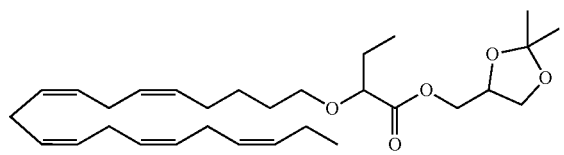 [SMILES: CC/C=C\C/C=C\C/C=C\C/C=C\C/C=C\CCCCOC(CC)C(=O)OCC1COC(C)(C)O1]

2-(((5Z,8Z,11Z,14Z,17Z)-icosa-5,8,11,14,17-pentaen-1-yl)oxy)butanoic acid (25 g, 66.7 mmol) and DMAP (8.15 g, 66.7 mmol) were added to a solution of 2,2-dimethyl-1,3-dioxolane-4-methanol (7.54 mL, 60.7 mmol) in chloroform (150 mL) under nitrogen atmosphere. A solution of DCC (13.77 g, 66.7 mmol) in chloroform (65 mL) was then added drop wise at ambient temperature. The mixture was stirred overnight and concentrated in vacuo. The residue was purified by flash chromatography on silica gel using increasingly polar mixtures of 10% ethyl acetate in heptane as eluent. Concentration of the appropriate fractions afforded 19.6 g (66% yield) of the title product as an oil. ¹H NMR (300 MHz, CDCl3) δ 0.99 (t, 6H), 1.37-1.40 (m, 3H), 1.41-1.53 (m, 5H), 1.59-1.71 (m, 2H), 1.72-1.85 (m, 2H), 2.05-2.14 (m, 4H), 2.74-2.95 (m, 8H), 3.31-3.38 (m, 1H), 3.57-3.65 (m, 1H), 3.72-3.86 (m, 2H), 4.07-4.12 (m, 1H), 4.15-4.27 (m, 2H), 4.29-4.40 (m, 1H), 5.23-5.50 (m, 10H). MS (electrospray): 511.3 [M+Na]⁺.

Step b) Preparation of 2,3-dihydroxypropyl 2-(((5Z,8Z,11Z,14Z,17Z)-icosa-5,8,11,14,17-pentaen-1-yl)oxy)butanoate

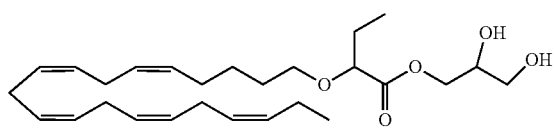 [SMILES: CC/C=C\C/C=C\C/C=C\C/C=C\C/C=C\CCCCOC(CC)C(=O)OCC(O)CO]

To a solution of (2,2-dimethyl-1,3-dioxolan-4-yl)methyl 2-(((5Z,8Z,11Z,14Z,17Z)-icosa-5,8,11,14,17-pentaen-1-yl)oxy)butanoate (27.5 g, 56.3 mmol) in dioxane (280 mL) at room temperature under nitrogen was added aq. HCl (37% (w/w), 28 mL, 341 mmol) and the mixture was stirred for 60 minutes. The mixture was then carefully poured into sat. aq. NaHCO₃ (500 mL) and extracted with EtOAc (2×300 mL). The organic phase was washed with 1M HCl (200 mL), brine (200 mL), dried (Na₂SO₄), filtered and concentrated in vacuo. The residue was purified by flash chromatography on silica gel using heptane and ethyl acetate (50:50) as eluent. Concentration of the appropriate fractions afforded 19 g of the title product as an oil, contaminated with ~10% of the isomer 1,3-dihydroxypropan-2-yl 2-(((5Z,8Z,11Z,14Z,17Z)-icosa-5,8,11,14,17-pentaen-1-yl)oxy)butanoate. The material was mixed with 1.35 gram of another batch, before further purified by preparative HPLC. An isocratic 17:83 mixture of water/acetonitrile (9:1) to acetonitrile (100%) was used as eluent. Concentration of the appropriate fractions afforded 11.3 g (38% yield) of the title product as an oil. ¹H NMR (300 MHz, CDCl3) δ 0.97-1.03 (m, 6H), 1.41-1.51 (m, 2H), 1.59-1.69 (m, 2H), 1.72-1.87 (m, 2H), 2.05-2.14 (m, 5H), 2.56 (s, 1H), 2.73-2.94 (m, 8H), 3.33-3.40 (m, 1H), 3.55-3.68 (m, 2H), 3.69-3.77 (m, 1H), 3.79-3.85 (m, 1H), 3.93-4.03 (m, 1H), 4.15-4.37 (m, 2H), 5.25-5.51 (m, 10H). MS (electrospray): 471.3 [M+Na]⁺.

Example 14: Preparation of 1,3-dihydroxypropan-2-yl 2-(((5Z,8Z,11Z,14Z,17Z)-icosa-5,8,11,14,17-pentaen-1-yl)oxy)butanoate Step a) Preparation of oxiran-2-ylmethyl 2-(((5Z,8Z,11Z,14Z,17Z)-icosa-5,8,11,14,17-pentaen-1-yl)oxy)butanoate

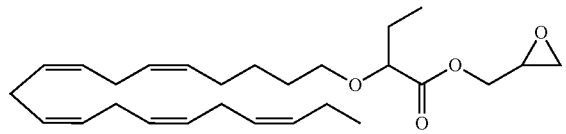

A mixture of 2-(((5Z,8Z,11Z,14Z,17Z)-icosa-5,8,11,14,17-pentaen-1-yl)oxy)butanoic acid (800 mg, 2.14 mmol), glycidol (0.17 mL, 2.56 mmol), 1-(3-dimethylaminopropyl)-3-ethylcarbodiimide hydrochloride (EDC*HCl) (491 mg, 2.56 mmol) and 4-dimethylaminopyridine (DMAP) (313 mg, 2.56 mmol) in dry DCM (7 mL) was stirred at room temperature under N₂-atmosphere. The reaction mixture was concentrated in vacuo. The residue was purified by flash chromatography on silica gel using increasingly polar mixtures of heptane and ethyl acetate (99:1→95:5) as eluent. Concentration of the appropriate fractions afforded 527 mg (57% yield) of the title product as an oil. ¹H NMR (400 MHz, CDCl3) δ 0.94-0.98 (m, 6H), 1.40-1.44 (m, 2H), 1.57-1.64 (m, 2H), 1.70-1.82 (m, 2H), 2.02-2.12 (m, 4H), 2.63 (bs, 1H), 2.78-2.84 (m, 9H), 3.20 (bs, 1H), 3.30-3.35 (m, 1H), 3.55-3.61 (m, 1H), 3.77-3.80 (m, 1H), 3.94-4.01 (m, 1H), 4.42-4.48 (m, 1H), 5.36-5.26 (m, 10H). MS (electrospray): 453.3 [M+Na]⁺.

Step b) Preparation of 2-((2-(((5Z,8Z,11Z,14Z,17Z)-icosa-5,8,11,14,17-pentaen-1-yl)oxy)butanoyl)oxy)propane-1,3-diyl bis(2,2,2-trifluoroacetate)

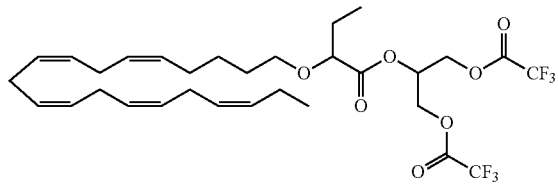 [SMILES: CC/C=C\C/C=C\C/C=C\C/C=C\C/C=C\CCCCOC(CC)C(=O)OC(COC(=O)C(F)(F)F)COC(=O)C(F)(F)F]

Trifluoroacetic anhydride (TFAA) (0.55 mL, 3.96 mmol) in dry DCM (3 mL) was added portion wise to a precooled solution of oxiran-2-ylmethyl 2-(((5Z,8Z,11Z,14Z,17Z)-icosa-5,8,11,14,17-pentaen-1-yl)oxy)butanoate (286 mg, 0.66 mmol) in dry DCM (3 mL) at −20° C. under N$_2$-atmosphere. The cooling bath was removed, and the mixture was stirred for 19 hours at ambient temperature, before reaction mixture was concentrated in vacuo pressure. The residue was dissolved in toluene (6 mL) and passed through a pad of silica (6.5 g) eluting with toluene (150 mL). Concentration in vacuo to afforded 357 mg (84% yield) of the title compound as an oil. $^1$H NMR (400 MHz, CDCl3) δ 0.95 (2×t, 6H), 1.38-1.45 (m, 2H), 1.57-1.63 (m, 2H), 1.66-1.78 (m, 2H), 2.09-2.02 (m, 4H), 2.78-2.84 (m, 8H), 3.27-3.33 (m, 1H), 3.51-3.56 (m, 1H), 3.77 (dd, 1H), 4.30-4.53 (m, 2H), 4.60-4.69 (m, 2H), 5.17-5.43 (m, 10H), 5.43-5.55 (m, 1H). MS (electrospray): 661.1 [M+Na]$^+$.

Step c) Preparation of 1,3-dihydroxypropan-2-yl 2-(((5Z,8Z,11Z,14Z,17Z)-icosa-5,8,11,14,17-pentaen-1-yl)oxy)butanoate

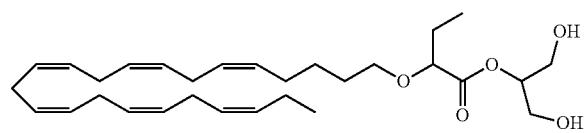 [SMILES: CC/C=C\C/C=C\C/C=C\C/C=C\C/C=C\C/C=C\CCCCOC(CC)C(=O)OC(CO)CO]

A solution of pyridine (0.4 mL, 4.95 mmol) and methanol (0.3 mL, 7.41 mmol) in pentane/DCM (2:1) (4.5 mL) was added drop wise to a solution of 2-((2-(((5Z,8Z,11Z,14Z,17Z)-icosa-5,8,11,14,17-pentaen-1-yl)oxy)butanoyl)oxy)propane-1,3-diyl bis(2,2,2-trifluoroacetate) (354 mg, 0.552 mmol) in pentane/DCM (2:1) (5 mL) cooled to −20° C. under N$_2$-atmosphere. The cooling bath was removed, and the mixture was stirred for 3 hours at room temperature, before concentrated in vacuo. The residue was purified by flash chromatography on silica gel using increasingly polar mixtures of heptane and ethyl acetate (95:5→90:10→80:20→50:50) as eluent. Concentration of the appropriate fractions afforded 223 mg of the title product as crude oil. Purification by preparative HPLC afforded 58 mg (22% yield) of the title compound as an oil. $^1$H NMR (400 MHz, CDCl3) δ 0.95 (t, 3H), 0.96 (t, 3H), 1.38-1.45 (m, 2H), 1.54-1.64 (m, 2H), 1.67-1.84 (m, 2H), 2.01-2.09 (m, 4H), 2.45 (bs, 2H), 2.83-2.77 (m, 8H), 3.36-3.30 (m, 1H), 3.60-3.55 (m, 1H), 3.84-3.78 (m, 5H), 4.98-4.93 (m, 1H), 5.65-5.09 (m, 10H). MS (electrospray): 471.1 [M+Na]$^+$.

Example 15: Preparation of 3-hydroxypropane-1,2-diyl bis(2-(((5Z,8Z,11Z,14Z,17Z)-icosa-5,8,11,14,17-pentaen-1-yl)oxy)butanoate)

Step a) Preparation of tert-butyl((2,2-dimethyl-1,3-dioxolan-4-yl)methoxy)dimethylsilane

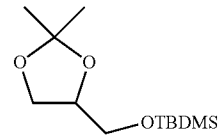 [SMILES: CC1(C)OCC(CO[Si](C)(C)C(C)(C)C)O1]

tert-Butyl-chlorodimethylsilane (14.41 g, 91 mmol) was added to a solution of (2,2-dimethyl-1,3-dioxolan-4-yl)methanol (10 g, 76 mmol) and imidazole (7.73 g, 114 mmol) in THF (100 mL) at ambient temperature under nitrogen atmosphere. The mixture was stirred for 1.5 hours, poured into water (200 mL) and extracted with tert-butyl methyl ether (2×150 mL). The phases were separated and the organic layer was washed with water (100 mL), brine (100 mL), dried (Na$_2$SO$_4$), filtered and concentrated in vacuo. The residue was purified by flash chromatography on silica gel using 3% ethyl acetate in heptane as eluent. Concentration of the appropriate fractions afforded 18 g (97% yield) of the title compound as an oil. 1H NMR (300 MHz, CDCl3) δ 0.02-0.05 (m, 6H), 0.85-0.89 (m, 9H), 1.31-1.35 (m, 3H), 1.35-1.40 (m, 3H), 3.50-3.60 (m, 1H), 3.63-3.72 (m, 1H), 3.75-3.85 (m, 1H), 3.96-4.05 (m, 1H), 4.07-4.18 (m, 1H). MS (electrospray): 229.2 [M+Na]$^+$.

Step b) Preparation of 3-((tert-butyldimethylsilyl)oxy)propane-1,2-diol

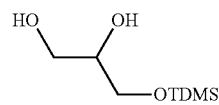

To a solution of tert-butyl((2,2-dimethyl-1,3-dioxolan-4-yl)methoxy)dimethylsilane in chloroform (60 mL) was added FeCl$_3$×6H$_2$O absorbed on silica gel (30 g, 11.9 mmol) and the mixture was stirred overnight. The mixture was filtered and concentrated in vacuo. The residue was purified by flash chromatography on silica gel using increasingly polar mixtures of heptane and ethyl acetate (50:50→25:75) as eluent. Concentration of the appropriate fractions afforded 760 mg (9% yield) of the title compound as an oil. $^1$H NMR (300 MHz, CDCl3) δ 0.09-0.12 (m, 6H). 0.91-0.95 (m, 9H), 2.11-2.17 (m, 1H), 2.60 (d, 1H), 3.57-3.85 (m, 5H). MS (electrospray): 229.2 [M+Na]$^+$.

Step c) Preparation of 3-((tert-butyldimethylsilyl)oxy)propane-1,2-diyl bis(2-(((5Z,8Z,11Z,14Z,17Z)-icosa-5,8,11,14,17-pentaen-1-yl)oxy)butanoate)

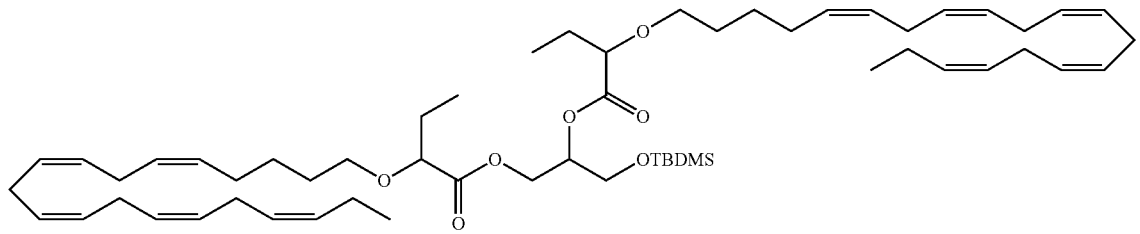 [SMILES: CC/C=C\C/C=C\C/C=C\C/C=C\C/C=C\CCCCOC(CC)C(=O)OCC(CO[Si](C)(C)C(C)(C)C)OC(=O)C(CC)OCCCC/C=C\C/C=C\C/C=C\C/C=C\C/C=C\CC]

To a solution of 3-((tert-butyldimethylsilyl)oxy)propane-1,2-diol (0.91 g, 4.41 mmol) in DMF (20 ml) under N$_2$-atmosphere at ambient temperature were added 2-(((5Z,8Z,11Z,14Z,17Z)-icosa-5,8,11,14,17-pentaen-1-yl)oxy) butanoic acid (3.47 g, 9.3 mmol), DMAP (1.13 g, 9.3 mmol), 1-(3-dimethylaminopropyl)-3-ethylcarbodiimide hydrochloride (DCI) (1.776 g, 9.26 mmol) and dry DCM (60 ml). The mixture was stirred overnight, before the reaction mixture was diluted with diethyl ether (200 mL). The mixture was washed with 1 M HCl (100 mL) and brine (100 mL), dried (Na$_2$SO$_4$), filtered and concentrated in vacuo. The residue was purified by flash chromatography on silica gel using 3% ethyl acetate in heptane as eluent. Concentration of the appropriate fractions afforded 2.26 g (56% yield) of the title compound as an oil. $^1$H NMR (300 MHz, CDCl3) δ 0.08 (s, 6H), 0.90 (d, 9H), 0.95-1.03 (m, 12H), 1.40-1.52 (m, 4H), 1.58-1.69 (m, 4H), 1.70-1.83 (m, 4H), 2.04-2.15 (m, 8H), 2.77-2.92 (m, 16H), 3.27-3.37 (m, 2H), 3.57-3.67 (m, 2H), 3.72-3.80 (m, 4H), 4.14-4.32 (m, 1H), 4.41-4.56 (m, 1H), 5.09-5.22 (m, 1H), 5.23-5.49 (m, 20H). MS (electrospray): 941.6 [M+Na]$^+$.

Step d) Preparation of 3-hydroxypropane-1,2-diyl bis(2-(((5Z,8Z,11Z,14Z,17Z)-icosa-5,8,11,14,17-pentaen-1-yl)oxy)butanoate)

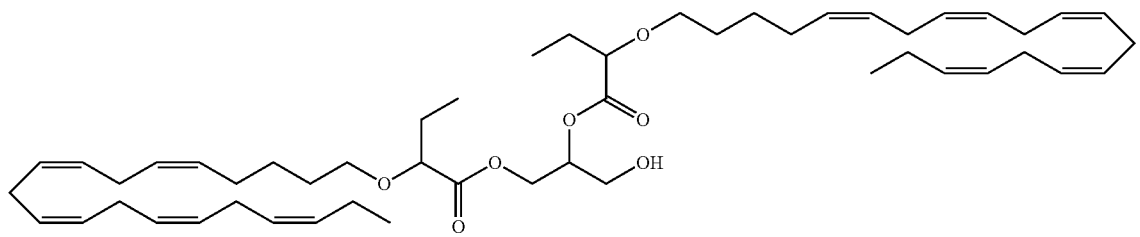 [SMILES: CC/C=C\C/C=C\C/C=C\C/C=C\C/C=C\CCCCOC(CC)C(=O)OCC(CO)OC(=O)C(CC)OCCCC/C=C\C/C=C\C/C=C\C/C=C\C/C=C\CC]

To a solution of 3-((tert-butyldimethylsilyl)oxy)propane-1,2-diyl bis(2-(((5Z,8Z,11Z,14Z,17Z)-icosa-5,8,11,14,17-pentaen-1-yl)oxy)butanoate) (2.26 g, 2.46 mmol) in dioxane (100 mL) was added aq. HCl (37% (w/w, 2 mL) and the mixture was stirred for 3 hours under nitrogen atmosphere at ambient temperature, before concentrated in vacuo. The residue was purified by flash chromatography on silica gel using 15% ethyl acetate in heptane as eluent. Concentration of the appropriate fractions afforded 0.83 g (42% yield) of the title compound as an oil. $^1$H NMR (300 MHz, CDCl3) δ 0.96-1.03 (m, 12H), 1.40-1.53 (m, 4H), 1.58-1.68 (m, 4H), 1.70-1.85 (m, 4H), 1.87-2.01 (m, 1H), 2.05-2.15 (m, 8H), 2.75-2.95 (m, 16H), 3.28-3.41 (m, 2H), 3.56-3.65 (m, 2H), 3.73-3.85 (m, 4H), 4.24-4.37 (m, 1H), 4.42-4.53 (m, 1H), 5.14-5.23 (m, 1H), 5.26-5.51 (m, 20H). MS (electrospray): 827.5 [M+Na]$^+$.

Example 16: Preparation of 2-hydroxypropane-1,3-diyl bis(2-(((5Z,8Z,11Z,14Z,17Z)-icosa-5,8,11,14,17-pentaen-1-yl)oxy)butanoate)

Step a) 2-oxopropane-1,3-diyl bis(2-(((5Z,8Z,11Z,14Z,17Z)-icosa-5,8,11,14,17-pentaen-1-yl)oxy)butanoate)

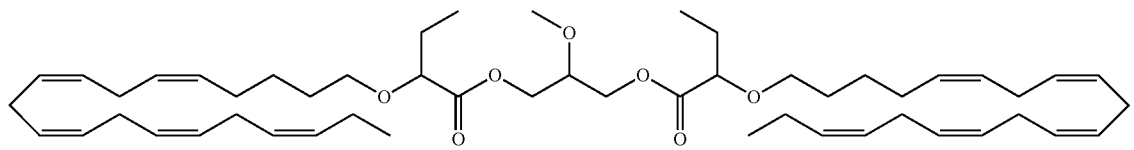 [SMILES: CC/C=C\C/C=C\C/C=C\C/C=C\C/C=C\CCCCOC(CC)C(=O)OCC(COC(=O)C(CC)OCCCC/C=C\C/C=C\C/C=C\C/C=C\C/C=C\CC)OC]

2-(((5Z,8Z,11Z,14Z,17Z)-icosa-5,8,11,14,17-pentaen-1-yl)oxy)butanoic acid (5.0 g, 13.4 mmol) and DMAP (1.63 g, 13.4 mmol) were added to a solution of 1,3-dihydroxyacetone dimer (1.145 g, 6.36 mmol) in chloroform (25 mL) under nitrogen atmosphere. A solution of DCC (2.75 g, 13.35 mmol) in chloroform (10 mL) was then added drop wise at ambient temperature. The mixture was stirred overnight at room temperature, before concentrated in vacuo. The residue was purified by flash chromatography on silica gel using increasingly polar mixtures of heptane and ethyl acetate (90:10→88:12) as eluent. Concentration of the appropriate fractions afforded 2.4 g (47% yield) of the title compound as an oil. $^1$H NMR (300 MHz, CDCl3) δ 0.97-1.06 (m, 12H). 1.38-1.53 (m, 4H), 1.57-1.73 (m, 4H), 1.73-1.96 (m, 4H), 2.03-2.17 (m, 8H), 2.76-2.92 (m, 16H), 3.35-3.42 (m, 2H), 3.63-3.70 (m, 2H), 3.89 (dd, 2H), 4.75-4.93 (m, 4H), 5.27-5.49 (m, 20H). MS (electrospray): 827.5 [M+Na]$^+$.

Step b) 2-hydroxypropane-1,3-diyl bis(2-(((5Z,8Z,11Z,14Z,17Z)-icosa-5,8,11,14,17-pentaen-1-yl)oxy)butanoate)

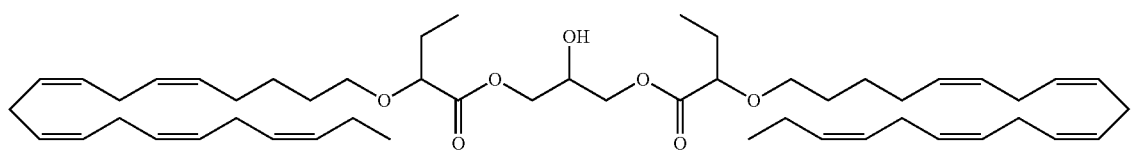 [SMILES: CC/C=C\C/C=C\C/C=C\C/C=C\C/C=C\CCCCOC(CC)C(=O)OCC(O)COC(=O)C(CC)OCCCC/C=C\C/C=C\C/C=C\C/C=C\C/C=C\CC]

NaBH$_4$ (0.336 g, 8.87 mmol) was added carefully to a solution of 2-oxopropane-1,3-diyl bis(2-(((5Z,8Z,11Z,14Z,17Z)-icosa-5,8,11,14,17-pentaen-1-yl)oxy)butanoate) (3.24 g, 4.03 mmol) in THF (55 mL) and water (4 mL) at 0° C. The mixture was stirred for 15 minutes at 0° C. Acetic acid (1 mL) was then added carefully followed by ethyl acetate (100 mL). The mixture was washed with water (100 mL), saturated aq. NaHCO$_3$ (100 mL) and brine, before dried (Na$_2$SO$_4$), filtered and concentrated in vacuo. The residue was combined with another batch of the material before purified by flash chromatography on silica gel using 15% ethyl acetate in heptane as eluent. Concentration of the appropriate fractions afforded 1.62 g (50% yield) of the title compound as an oil. $^1$H NMR (300 MHz, CDCl3) δ 0.97-1.03 (m, 12H), 1.41-1.52 (m, 4H), 1.58-1.69 (m, 6H), 1.71-1.87 (m, 4H), 2.05-2.14 (m, 8H), 2.38-2.42 (m, 1H), 2.78-2.92 (m, 16H), 3.32-3.39 (m, 2H), 3.57-3.64 (m, 2H), 3.80-3.84 (m, 2H), 4.05-4.34 (m, 5H), 5.26-5.49 (m, 20H). MS (electrospray): 827.5 [M+Na]$^+$.

Example 17: Preparation of propane-1,2,3-triyl tris (2-(((5Z,8Z,11Z,14Z,17Z)-icosa-5,8,11,14,17-pentaen-1-yl)oxy)butanoate)

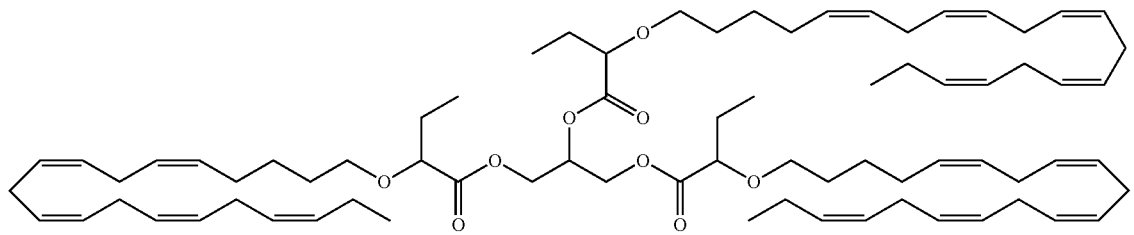 [SMILES: CC/C=C\C/C=C\C/C=C\C/C=C\C/C=C\CCCCOC(CC)C(=O)OCC(COC(=O)C(CC)OCCCC/C=C\C/C=C\C/C=C\C/C=C\C/C=C\CC)OC(=O)C(CC)OCCCC/C=C\C/C=C\C/C=C\C/C=C\C/C=C\CC]

2-(((5Z,8Z,11Z,14Z,17Z)-icosa-5,8,11,14,17-pentaen-1-yl)oxy)butanoic acid (4.0 g, 10.7 mmol), 4-dimethylaminopyridine (1.305 g, 10.7 mmol), 1-(3-dimethylaminopropyl)-3-ethylcarbodiimide hydrochloride (2.047 g, 10.7 mmol) and dry DCM (30 ml) was added to a solution of glycerol (0,173 ml, 2,373 mmol) in DMF (10 ml) under $N_2$-atmosphere at room temperature. The mixture was stirred overnight, before the reaction mixture was diluted with diethyl ether (250 mL). The mixture was washed with aq. 1 M HCl (100 mL) and brine (100 mL), before dried ($Na_2SO_4$), filtered and evaporated in vacuo. The residue was purified by flash chromatography on silica gel using 5% ethyl acetate in heptane as eluent. Concentration of the appropriate fractions afforded 2.1 g (73% yield) of the title compound as an oil. $^1$H NMR (300 MHz, CDCl3) δ 0.91-1.05 (m, 18H), 1.40-1.52 (m, 6H), 1.57-1.69 (m, 6H), 1.69-1.86 (m, 6H), 2.01-2.17 (m, 12H), 2.69-2.96 (m, 24H), 3.27-3.38 (m, 3H), 3.53-3.67 (m, 3H), 3.73-3.81 (m, 3H), 4.17-4.27 (m, 2H), 4.37-4.54 (m, 2H), 5.28-5.47 (m, 30H). MS (electrospray): 1183.8 [M+Na]$^+$.

Example 18: Preparation of tert-butyl 2-((2-((5Z,8Z,11Z,14Z,17Z)-icosa-5,8,11,14,17-pentaen-1-yloxy)butanoyl)oxy)benzoate

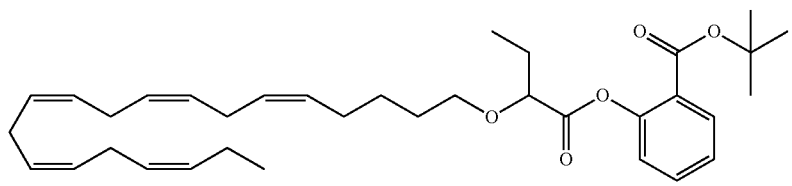 [SMILES: CC/C=C\C/C=C\C/C=C\C/C=C\C/C=C\CCCCOC(CC)C(=O)Oc1ccccc1C(=O)OC(C)(C)C]

1-Ethyl-3-(3-dimethylaminopropyl) carbodiimide (EDC) (316 mg, 1.65 mmol) and 4-dimethylaminopyridine (DMAP) (20 mg, 0.15 mmol) were added to a solution of 2-((5Z,8Z,11Z,14Z,17Z)-icosa-5,8,11,14,17-pentaen-1-yloxy)butanoic acid (561 mg, 1.5 mmol) in DCM (10 mL) and the reaction mixture was stirred for 10 minutes. tert-Butyl 2-hydroxybenzoate (291 mg, 1.5 mmol) was added and the mixture was stirred for 3 hours. Brine was added and the resulting two phases were separated. The aqueous phase was extracted with DCM, and the combined organic phases were dried ($Na_2SO_4$), filtered and concentrated in vacuo. The residue was purified by flash chromatography using a mixture of 5% EtOAc in heptane as eluent. Concentration of the appropriate fractions afforded 500 mg (61% yield) of the title compound. $^1$H NMR (300 MHz, CDCl$_3$): δ 0.98 (t, 3H), 1.11 (t, 3H), 1.13 (t, 3H), 1.45-1.75 (m, 4H), 1.56 (s, 9H), 1.90-2.20 (m, 6H), 2.80-2.90 (m, 8H), 3.45-3.60 (m, 1H), 3.80-3.90 (m, 1H), 4.05-4.15 (m, 1H), 5.25-5.50 (m, 10H), 7.06 (m, 1H), 7.28 (m, 1H), 7.52 (m, 1H), 7.89 (m, 1H). MS (ESI): 573 [M+Na]$^+$.

Example 19: Preparation of 2-((2-((5Z,8Z,11Z,14Z,17Z)-icosa-5,8,11,14,17-pentaen-1-yloxy)butanoyl)oxy)benzoic acid

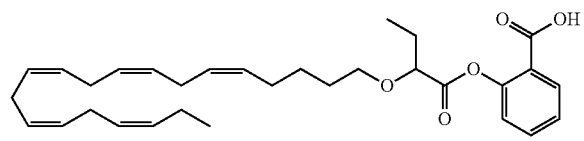

A solution of tert-butyl 2-((2-((5Z,8Z,11Z,14Z,17Z)-icosa-5,8,11,14,17-pentaen-1-yloxy)butanoyl)oxy)benzoate (500 mg, 0.9 mmol) in FA (10 mL) was stirred for 2 days. The solvent was removed under reduced pressure and the residue was subjected to flash chromatography using a gradient of 1-5% EtOAc (containing 5% FA) in heptane (also containing 5% FA) as eluent. The appropriate fractions were pooled and concentrated and the residue was purified further by a second flash chromatography using a gradient of 1-10% EtOAc in heptane as eluent. Concentration of the appropriate fractions afforded 75 mg (17% yield) of the title compound. $^1$H NMR (300 MHz, CDCl$_3$): δ 0.99 (t, 3H), 1.13 (t, 3H), 1.45-1.60 (m, 2H), 1.65-1.70 (m, 2H), 1.90-2.15 (m, 6H), 2.80-2.90 (m, 8H), 3.45-3.55 (m, 1H), 3.80-3.90 (m, 1H), 4.05-4.15 (m, 1H), 5.30-5.45 (m, 10H), 7.14 (d, 1H), 7.35-7.45 (m, 1H), 7.60-7.70 (m, 1H), 8.10-8.15 (m, 1H). MS (ESI): 517 [M+Na]$^+$.

Example 20: Preparation of 2-((tert-butoxycarbonyl)amino)ethyl 2-((5Z,8Z,11Z,14Z,17Z)-icosa-5,8,11,14,17-pentaen-1-yloxy)butanoate

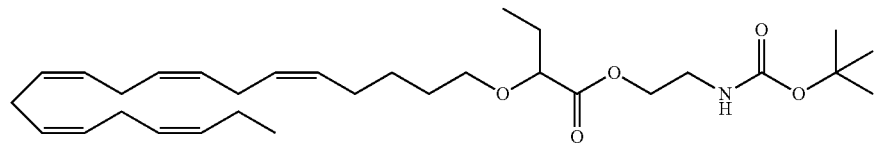 [SMILES: CC/C=C\C/C=C\C/C=C\C/C=C\C/C=C\CCCCOC(CC)C(=O)OCCNC(=O)OC(C)(C)C]

O-(7-Azabenzotriazol-1-yl)-N,N,N',N'-tetramethyluronium hexafluorophosphate (HATU) (800 mg, 2.1 mmol) and TEA (0.56 mL, 4 mmol) were added to a solution of 2-((5Z,8Z,11Z,14Z,17Z)-icosa-5,8,11,14,17-pentaen-1-yloxy)butanoic acid (748 mg, 2 mmol) in DCM (10 mL) and the reaction mixture was stirred for 20 minutes. A solution of tert-butyl N-(2-hydroxyethyl)carbamate (340 mg, 2.1 mmol) in DCM (1 mL) was added and the resulting mixture was stirred at room temperature over night. Et$_2$O (100 mL) was added and the mixture was washed with water, 1M HCl (aq), saturated NaHCO$_3$ (aq) and brine, dried (Na$_2$SO$_4$), filtered and concentrated in vacuo. The residue was purified by flash chromatography using a gradient of 10-20% EtOAc in heptane as eluent. Concentration of the appropriate fractions afforded 780 mg (76% yield) of the title compound. $^1$H NMR (300 MHz, CDCl$_3$): δ 0.98 (t, 6H), 1.40-1.55 (m, 2H), 1.45 (s, 9H), 1.60-1.85 (m, 4H), 2.05-2.20 (m, 4H), 2.75-2.90 (m, 8H), 3.30-3.45 (m, 3H), 3.55-3.65 (m, 1H), 3.75-3.80 (m, 1H), 4.20-4.25 (m, 2H), 4.76 (br s, 1H), 5.30-5.45 (m, 10H). MS (ESI): 540 [M+Na]$^+$.

Example 21: Preparation of 2-(2-acetoxybenzamido)ethyl 2-((5Z,8Z,11Z,14Z,17Z)-icosa-5,8,11,14,17-pentaen-1-yloxy)butanoate

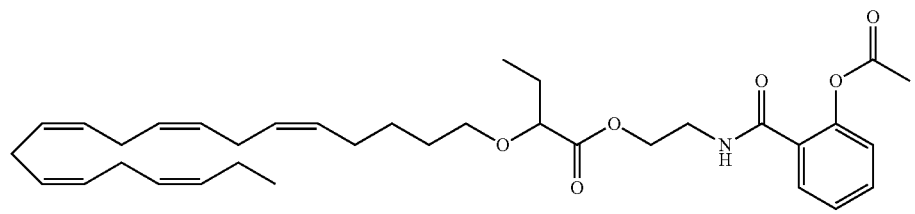 [SMILES: CC/C=C\C/C=C\C/C=C\C/C=C\C/C=C\CCCCOC(CC)C(=O)OCCNC(=O)c1ccccc1OC(C)=O]

Acetyl chloride (1 mL) was added to a solution of 2-((tert-butoxycarbonyl)amino)ethyl 2-((5Z,8Z,11Z,14Z,17Z)-icosa-5,8,11,14,17-pentaen-1-yloxy)butanoate (300 mg, 0.58 mmol) in MeOH (5 mL) at 0° C. and the reaction mixture was stirred at room temperature for 1 hour. The mixture was concentrated in vacuo to afford the HCl salt of 2-aminoethyl 2-((5Z,8Z,11Z,14Z,17Z)-icosa-5,8,11,14,17-pentaen-1-yloxy)butanoate (286 mg) as a crude product. TEA (109 µL, 0.78 mmol) was added to a solution of acetyl salicylic acid (137 mg, 0.76 mmol) in DCM (10 mL) and the mixture was cooled to 0° C. Ethyl chloroformate (75 µL, 0.78 mmol) was added drop wise and the reaction mixture was stirred for 2 hours. This solution was then added to a solution of the crude product of the HCl salt of 2-aminoethyl 2-((5Z,8Z,11Z,14Z,17Z)-icosa-5,8,11,14,17-pentaen-1-yloxy)butanoate in a mixture of DCM (10 mL) and TEA (2 mL). The resulting mixture was stirred at room temperature for 3.5 hours and then added water. The resulting two phases were separated, and the aqueous phase was extracted twice with DCM. The combined organic phases were washed with 1M HCl (aq), saturated NaHCO$_3$ (aq) and water, dried (Na$_2$SO$_4$), filtered and concentrated in vacuo. The residue was purified by flash chromatography using 20% EtOAc in heptane as eluent. Concentration of the appropriate fractions afforded 90 mg (23% yield) of the title compound. $^1$H NMR (300 MHz, CDCl$_3$): δ 0.95-1.05 (m, 6H), 1.35-1.45 (m, 2H), 1.55-1.70 (m, 2H), 1.70-1.85 (m, 2H), 2.05-2.15 (m, 4H), 2.35 (s, 3H), 2.80-2.90 (m, 8H), 3.30-3.40 (m, 1H), 3.55-3.65 (m, 1H), 3.70-3.85 (m, 3H), 4.33 (t, 2H), 5.30-5.45 (m, 10H), 6.61 (br s, 1H), 7.10-7.15 (m, 1H), 7.25-7.35 (m, 1H), 7.45-7.50 (m, 1H), 7.70-7.75 (m, 1H). MS (ESI); 602 [M+Na]$^+$.

Example 22: Preparation of 2-(2-hydroxybenzamido)ethyl 2-((5Z,8Z,11Z,14Z,17Z)-icosa-5,8,11,14,17-pentaen-1-yloxy)butanoate

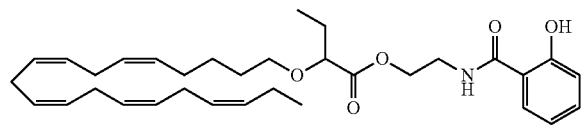 [SMILES: CC/C=C\C/C=C\C/C=C\C/C=C\C/C=C\CCCCOC(CC)C(=O)OCCNC(=O)c1ccccc1O]

Ammonia (aq, 28%, 20 drops) was added dropwise to a solution of 2-(2-acetoxybenzamido)ethyl 2-((5Z,8Z,11Z,14Z,17Z)-icosa-5,8,11,14,17-pentaen-1-yloxy)butanoate (99 mg, 0.17 mmol) in 2-propanol (9 mL) and water (3 mL) and the reaction mixture was stirred for 10 minutes. Water was added, and the resulting mixture was extracted twice with Et$_2$O. The combined organic phases were washed with brine, dried (Na$_2$SO$_4$), filtered and concentrated in vacuo. The residue was purified by flash chromatography using a gradient of 0-40% EtOAc in heptane as eluent. Concentration of the appropriate fractions afforded 33 mg (36% yield) of the title compound. $^1$H NMR (300 MHz, CDCl$_3$): δ 0.95-1.05 (m, 6H), 1.35-1.45 (m, 2H), 1.60-1.70 (m, 2H), 1.70-1.85 (m, 2H), 2.05-2.20 (m, 4H), 2.80-2.90 (m, 8H), 3.35-3.45 (m, 1H), 3.50-3.60 (m, 1H), 3.75-3.85 (m, 3H), 4.40-4.50 (m, 2H), 5.30-5.45 (m, 10H), 6.80-6.90 (m, 2H), 6.95-7.05 (m, 1H), 7.35-7.45 (m, 1H), 12.22 (s, 1H). MS (ESI): 560 [M+Na]$^+$.

Example 23: Preparation of N-benzyl-2-(((5Z,8Z,11Z,14Z,17Z)-icosa-5,8,11,14,17-pentaen-1-yl)oxy)butanamide

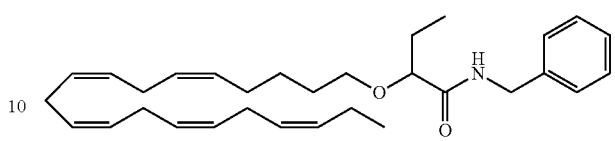

To a solution of 2-(((5Z,8Z,11Z,14Z,17Z)-icosa-5,8,11,14,17-pentaen-1-yl)oxy)butanoic acid (302.1 mg, 0.807 mmol) and o-Benzotriazol-1-yl-N,N,N',N'-tetramethyluronium tetrafluoroborate (TBTU) (285 mg, 0.888 mmol) in DCM (10 mL) at room temperature under N$_2$-atmosphere was added triethyl amine (123 µL, 0.887 mmol). After stirring for 15 minutes the mixture was added Benzylamine (97 µL, 0.887 mmol and the reaction mixture was stirred at room temperature over night. Saturated NaHCO$_3$ (25 mL) was added and the mixture was extracted with tert-butyl methyl ether (2×50 mL). The organic phases was combined, dried (Na$_2$SO$_4$), filtered and evaporated in vacuo. The residue was purified by flash chromatography on silica gel using increasingly polar mixtures of heptane and ethyl acetate (95:5→50:50) as eluent.

Concentration of the appropriate fractions afforded 0.253 g (66% yield) of the title compound as an oil. 1H NMR (400 MHz, CDCl3) d 0.97-0.90 (m, 6H), 1.41-1.35 (m, 2H), 1.59-1.52 (m, 2H), 1.75-1.68 (m, 1H), 1.86-1.80 (m, 1H), 2.09-2.03 (m, 4H), 2.82-2.77 (m, 8H), 3.44 (t, J=6.4, 2H), 3.72-3.71 (m, 1H), 4.46 (d, J=5.8, 2H), 5.36-5.28 (m, 10H), 6.83 (s, 1H), 7.26-7.24 (m, 3H), 7.33-7.30 (m, 2H).

Example 24: Preparation of 2-(((5Z,8Z,11Z,14Z,17Z)-icosa-5,8,11,14,17-pentaen-1-yl)oxy)-N,N-dimethylbutanamide

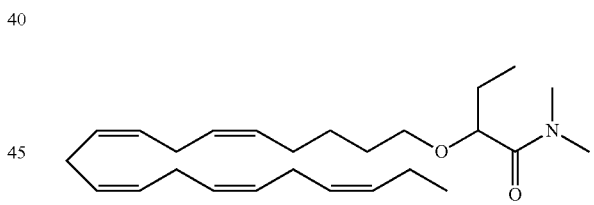

To a solution of 2-(((5Z,8Z,11Z,14Z,17Z)-icosa-5,8,11,14,17-pentaen-1-yl)oxy)butanoic acid (300.2 mg, 0.801 mmol) and o-Benzotriazol-1-yl-N,N,N',N'-tetramethyluronium tetrafluoroborate (TBTU) (286.4 mg, 0.892 mmol) in DCM (10 mL) at room temperature under N$_2$-atmosphere was added triethyl amine (123 µL, 0.884 mmol). After stirring for 15 minutes the mixture was added Dimethylamine (2.0 M in THF) (0.80 mL, 1.60 mmol) and the reaction mixture was stirred at room temperature over night. Saturated NaHCO$_3$ (25 mL) was added and the mixture was extracted with tert-butyl methyl ether (2×50 mL). The organic phases was combined, dried (Na$_2$SO$_4$), filtered and evaporated in vacuo. The residue was purified by flash chromatography on silica gel using increasingly polar mixtures of heptane and ethyl acetate (95:5→50:50) as eluent. Concentration of the appropriate fractions afforded 0.268 g (81% yield) of the title compound as an oil. 1H NMR (300 MHz, CDCl3) d 0.95 (t, 3H), 0.96 (t, 3H), 1.35-1.46 (m, 2H), 1.53-1.63 (m, 2H), 1.66-1.79 (m, 2H), 2.01-2.10 (m, 4H), 2.77-2.87 (m, 8H), 2.93 (s, 3H), 3.10 (s, 3H), 3.28 (dt, J=9.1, 6.5, 1H), 3.46 (dt, J=9.1, 6.3, 1H), 3.96 (dd, J=7.7, 6.1, 1H), 4.97-5.70 (m, 10H).

Example 25: Preparation of N-ethyl-2-(((5Z,8Z, 11Z,14Z,17Z)-icosa-5,8,11,14,17-pentaen-1-yl)oxy) butanamide

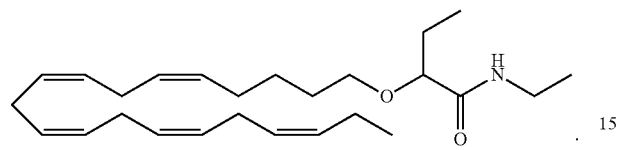

To a solution of 2-(((5Z,8Z,11Z,14Z,17Z)-icosa-5,8,11,14,17-pentaen-1-yl)oxy)butanoic acid (304.6 mg, 0.813 mmol) and o-Benzotriazol-1-yl-N,N,N',N'-tetramethyluronium tetrafluoroborate (TBTU) (286.9 mg, 0.894 mmol) in DCM (10 mL) at room temperature under N₂-atmosphere was added triethyl amine (123 μL, 0.884 mmol). After stirring for 15 minutes the mixture was added ethylamine (2.0 M in THF) (0.80 mL, 1.60 mmol) and the reaction mixture was stirred at room temperature over night. Saturated NaHCO3 (25 mL) was added and the mixture was extracted with tert-butyl methyl ether (2×50 mL). The organic phases was combined, dried (Na2SO4), filtered and evaporated in vacuo. The residue was purified by flash chromatography on silica gel using increasingly polar mixtures of heptane and ethyl acetate (95:5→50:50) as eluent. Concentration of the appropriate fractions afforded 0.186 g (56% yield) of the title compound as an oil. ¹H NMR (300 MHz, CDCl3) d 0.90 (t, 3H), 0.95 (t, 3H), 1.13 (t, 3H), 1.55-1.62 (m, 2H), 1.64-1.66 (m, 2H), 1.69-1.69 (m, 1H), 1.74-1.83 (m, 1H), 2.01-2.12 (m, 4H), 2.78-2.84 (m, 8H), 3.25-3.34 (m, 2H), 3.44 (t, 2H), 3.64 (dd, 1H), 5.50-5.13 (m, 10H), 6.50 (s, 1H).

Example 26: Preparation of tert-butyl (2-(2-(((5Z, 8Z,11Z,14Z,17Z)-icosa-5,8,11,14,17-pentaen-1-yl) oxy)butanamido)ethyl)carbamate

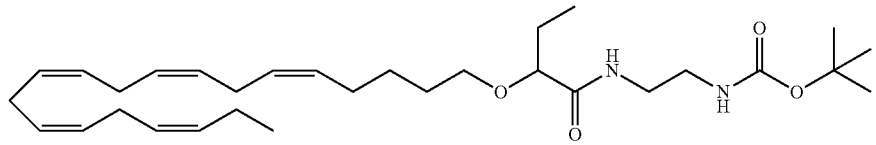 [SMILES: CC/C=C\C/C=C\C/C=C\C/C=C\C/C=C\CCCCOC(CC)C(=O)NCCNC(=O)OC(C)(C)C]

Dicyclohexylmethanediimine (DCC) (1.73 g, 8.4 mmol) and 1H-benzo[d][1,2,3]triazol-1-ol (HOBt) (1.14 g, 8.4 mmol) were added to a stirred solution of 2-(((5Z,8Z,11Z, 14Z,17Z)-icosa-5,8,11,14,17-pentaen-1-yl)oxy)butanoic acid (3.14 g, 8.4 mmol) in THF (25 mL) at 0° C. under N₂-atmosphere. The mixture was stirred for 20 minutes, before a solution of N-Boc-ethylenediamine (1.12 gram) in THF (1 mL) was added drop wise. The resulting mixture was stirred at room temperature for 1.5 hours. Diethylether (200 mL) was added and the mixture was washed with water, 1 M HCl, saturated NaHCO₃ and brine. The organic phase was dried (Na₂SO₄), filtered and concentrated in vacuo. The residue was purified by flash chromatography on silica gel using 25% ethyl acetate in heptane (added 0.5% HCOOH) as eluent.

Concentration of the appropriate fractions afforded 3.0 g (83% yield) of the title compound. ¹H NMR (300 MHz, CDCl₃): d 0.90 (t, 3H), 0.96 (t, 3H), 1.43 (s, 9H), 1.40-1.80 (m, 6H), 2.05-2.20 (m, 4H), 2.75-2.90 (m, 8H), 3.20-3.60 (m, 6H), 3.65-3.75 (m, 1H), 5.02 (br s, 1H), 5.30-5.45 (m, 10H), 7.01 (br s, 1H). MS (electrospray); 539 [M+Na]⁺

Example 27: Preparation of N-(2-aminoethyl)-2-(((5Z,8Z,11Z,14Z,17Z)-icosa-5,8,11,14,17-pentaen-1-yl)oxy)butanamide

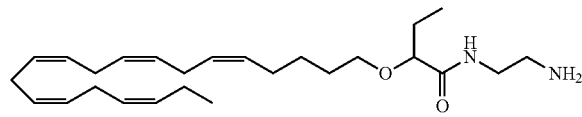 [SMILES: CC/C=C\C/C=C\C/C=C\C/C=C\C/C=C\CCCCOC(CC)C(=O)NCCN]

A solution of the tert-butyl (2-(2-(((5Z,8Z,11Z,14Z,17Z)-icosa-5,8,11,14,17-pentaen-1-yl)oxy)butanamido)ethyl)carbamate (774 mg, 1.5 mmol) in DCM (8 mL) under N₂-atmosphere at ambient temperature was added TFA (2 mL) and the reaction stirred at room temperature for 30 minutes and then concentrated in vacuo. Diethylether (50 mL) and NaOH (aq, 1M, 50 mL) was added to the residue and the mixture was stirred vigorously for 30 minutes. The phases were separated, and the organic phase was washed with brine dried (NaSO₄), filtered and concentrated in vacuo to afford 560 mg (90%) of the title compound. ¹H NMR (300 MHz, CDCl₃): d 0.85-1.05 (2×t, 6H), 1.35-1.50 (m, 2H), 1.55-1.85 (m, 4H), 2.05-2.20 (m, 4H), 2.75-2.95 (m, 8H), 3.10-3.20 (m, 1H), 3.30-3.80 (m, 6H), 4.05-4.20 (br m, 1H), 4.25-4.75 (br s, 2H), 5.30-5.50 (m, 10H). MS (electrospray); 417 [M+H]⁺, 439 [M+Na]⁺

Example 28: Preparation of N-(2-hydroxyethyl)-2-(((5Z,8Z,11Z,14Z,17Z)-icosa-5,8,11,14,17-pentaen-1-yl)oxy)butanamide

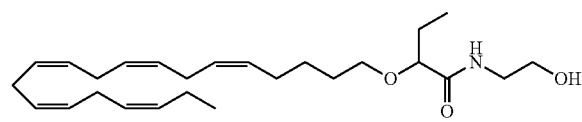 [SMILES: CC/C=C\C/C=C\C/C=C\C/C=C\C/C=C\CCCCOC(CC)C(=O)NCCO]

To a solution of 2-(((5Z,8Z,11Z,14Z,17Z)-icosa-5,8,11, 14,17-pentaen-1-yl)oxy)butanoic acid (4.5 g, 12 mmol) in DCM (100 mL) under N₂-atmosphere at room temperature was added oxalyl chloride (8.4 mL, 100 mmol) followed by 2 drops of DMF. The mixture was stirred for 30 minutes at room temperature and concentrated in vacuo. The residue was dissolved in DCM (100 mL) under N₂-atmosphere. Triethyl amine (3.34 mL, 24 mmol) was added followed by ethanolamine (1.08 mL, 18 mmol). The reaction mixture was stirred for 2 hours at room temperature. Water (300 mL) was added and the mixture was extracted twice with dichloromethane. The organic phases were combined, dried (Na₂SO₄), filtered and concentrated in vacuo. The residue was purified by flash chromatography on silica gel using increasingly polar mixtures of heptane and ethyl acetate (50:50→20:80) as eluent. Concentration of the appropriate fractions afforded 4.6 g (92% yield) of the title compound. ¹H NMR (300 MHz, CDCl₃): d 0.90-1.05 (m, 6H), 1.40-1.55 (m, 2H), 1.60-1.90 (m, 4H), 2.05-2.20 (m, 4H), 2.75-2.90 (m, 8H), 3.05 (br s, 1H), 3.40-3.55 (m, 4H), 3.70-3.80 (m, 3H), 5.30-5.45 (m, 10H), 7.04 (br s, 1H). MS (electrospray); 440 [M+Na]⁺

Example 29: Preparation of 2-(((5Z,8Z,11Z,14Z,17Z)-icosa-5,8,11,14,17-pentaen-1-yl)oxy)-N-isopropylbutanamide

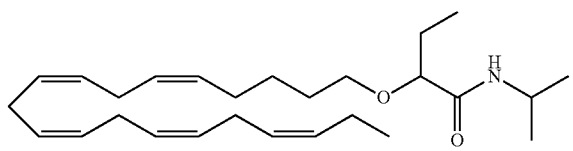 [SMILES: CC/C=C\C/C=C\C/C=C\C/C=C\C/C=C\CCCCOC(CC)C(=O)NC(C)C]

To a solution of 2-(((5Z,8Z,11Z,14Z,17Z)-icosa-5,8,11,14,17-pentaen-1-yl)oxy)butanoic acid (300 mg, 0.801 mmol) and o-Benzotriazol-1-yl-N,N,N',N'-tetramethyluronium tetrafluoroborate (TBTU) (284 mg, 0.884 mmol) in DCM (10 mL) at room temperature under N2-atmosphere was added triethyl amine (123 μL, 0.884 mmol). After stirring for 15 minutes at room temperature under N2-atmosphere Isopropylamine (76 μL, 0.884 mmol) was added and the reaction mixture was stirred at room temperature over night. Saturated NaHCO₃ (25 mL) was added and the mixture was extracted with tert-butyl methyl ether (2×50 mL). The organic phases were combined, dried (Na2SO4), filtered and evaporated in vacuo. The residue was purified by flash chromatography on silica gel using increasingly polar mixtures of heptane and ethyl acetate (95:5→50:50) as eluent. Concentration of the appropriate fractions afforded 0.207 g (59% yield) of the title compound as an oil. ¹H NMR (400 MHz, CDCl3) δ 0.83-0.93 (m, 3H), 0.95 (t, J=7.5, 3H), 1.14 (t, J=6.1, 6H), 1.39-1.47 (m, 2H), 1.56-1.73 (m, 3H), 1.73-1.83 (m, 1H), 2.02-2.11 (m, 4H), 2.80-2.84 (m, 8H), 3.43 (t, J=6.4, 2H), 3.60 (dd, J=6.6, 4.4, 1H), 4.02-4.11 (m, 1H), 5.66-5.01 (m, 10H), 6.33 (d, J=5.9, 1H).

Example 30: Preparation of 2-(((5Z,8Z,11Z,14Z,17Z)-icosa-5,8,11,14,17-pentaen-1-yl)oxy)-N-methylbutanamide

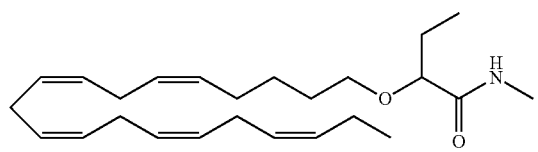 [SMILES: CC/C=C\C/C=C\C/C=C\C/C=C\C/C=C\CCCCOC(CC)C(=O)NC]

To a solution of 2-(((5Z,8Z,11Z,14Z,17Z)-icosa-5,8,11,14,17-pentaen-1-yl)oxy)butanoic acid (303.6 mg, 0.811 mmol) and o-Benzotriazol-1-yl-N,N,N',N'-tetramethyluronium tetrafluoroborate (TBTU) (285.3 mg, 0.889 mmol) in DCM (10 mL) at room temperature under N2-atmosphere was added triethyl amine (123 μL, 0.884 mmol). After stirring for 15 minutes at room temperature under N2-atmosphere Methylamine 2.0 M in THF (0.8 ml, 1,600 mmol) was added and the reaction mixture was stirred at room temperature over night. Saturated NaHCO₃ (25 mL) was added and the mixture was extracted with tert-butyl methyl ether (2×50 mL). The organic phases were combined, dried (Na2SO4), filtered and evaporated in vacuo. The residue was purified by flash chromatography on silica gel using increasingly polar mixtures of heptane and ethyl acetate (95:5→50:50) as eluent. Concentration of the appropriate fractions afforded 0.235 g (72% yield) of the title compound as an oil.

¹H NMR (300 MHz, CDCl3) δ 0.89 (t, J=7.4, 3H), 0.95 (t, J=7.5, 3H), 1.37-1.47 (m, 2H), 1.56-1.72 (m, 3H), 1.74-1.84 (m, 1H), 2.01-2.15 (m, 4H), 2.78-2.84 (m, 11H), 3.44 (t, J=6.4, 2H), 3.66 (dd, J=6.4, 4.4, 1H), 5.18-5.52 (m, 10H), 6.51 (s, 1H).

Example 31: Preparation of 2-(((5Z,8Z,11Z,14Z,17Z)-icosa-5,8,11,14,17-pentaen-1-yl)oxy)-1-(piperidin-1-yl)butan-1-one

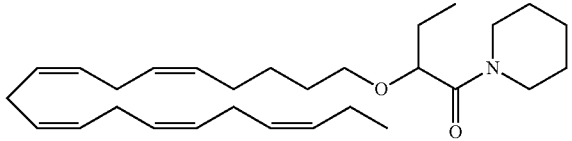 [SMILES: CC/C=C\C/C=C\C/C=C\C/C=C\C/C=C\CCCCOC(CC)C(=O)N1CCCCC1]

To a solution of 2-(((5Z,8Z,11Z,14Z,17Z)-icosa-5,8,11,14,17-pentaen-1-yl)oxy)butanoic acid (302.2 mg, 0.807 mmol) and o-Benzotriazol-1-yl-N,N,N',N'-tetramethyluronium tetrafluoroborate (TBTU) (284 mg, 0.884 mmol) in DCM (8 mL) at room temperature under N2-atmosphere was added triethyl amine (123 μL, 0.884 mmol). After stirring for 15 minutes at room temperature under N2-atmosphere piperidine (87 μL, 0.884 mmol) was added and the reaction mixture was stirred at room temperature over night. Saturated NaHCO₃ (25 mL) was added and the mixture was extracted with tert-butyl methyl ether (2×50 mL). The organic phases were combined, dried (Na2SO4), filtered and evaporated in vacuo. The residue was purified by flash chromatography on silica gel using increasingly polar mixtures of heptane and ethyl acetate (95:5→50:50) as eluent. Concentration of the appropriate fractions afforded 0.270 g (73% yield) of the title compound as an oil. ¹H NMR (400 MHz, CDCl3) d 0.93-0.98 (m, 6H) 1.37-1.46 (m, 2H), 1.51-1.62 (m, 8H), 1.66-1.77 (m, 2H), 2.02-2.09 (m, 4H), 2.77-2.83 (m, 8H), 3.30 (dt, J=9.1, 6.6, 1H), 3.47-3.52 (m, 2H), 3.54-3.62 (m, 3H), 3.95 (dd, J=7.9, 6.1, 1H), 5.02-5.65 (m, 10H).

Example 32: Preparation of 2-(((5Z,8Z,11Z,14Z,17Z)-icosa-5,8,11,14,17-pentaen-1-yl)oxy)butanamide

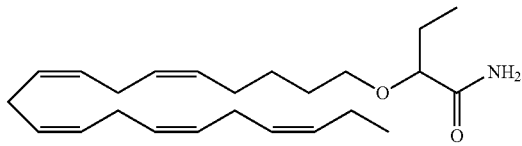 [SMILES: CC/C=C\C/C=C\C/C=C\C/C=C\C/C=C\CCCCOC(CC)C(N)=O]

To a solution of 2-(((5Z,8Z,11Z,14Z,17Z)-icosa-5,8,11,14,17-pentaen-1-yl)oxy)butanoic acid (320 g, 854 mmol) in Toluene (2500 mL) was added Oxalyl chloride (276 mL, 3.15 mol). DMF (10 mL) was then carefully added drop wise, before the mixture was stirred at ambient temperature for 1 hour and concentrated in vacuo. The residue was dissolved in DCM (750 mL) and slowly added to a stirred, cooled (0° C.) solution of Amonnia (28%, aq.) (528 mL, 6.84 mol). The mixture was stirred for 30 minutes at ambient temperature. The phases were separated and the aqueous phase was extracted with methyl tert-butyl ether (700 mL). The combined organic phase was washed with 3 M HCl (2×300 mL), sat. aq. NaHCO$_3$ (500 mL), brine (2×300 mL), dried (Na2SO4), filtered and concentrated in vacuo. The residue was purified by flash chromatography on silica gel using increasingly polar mixtures of heptane and ethyl acetate (70:30→60:40) as eluent. Concentration of the appropriate fractions afforded 249.8 gram (76% yield) of the title compound as an oil. $^1$H NMR (400 MHz, CDCl3) δ 0.87-0.92 (m, 6H), 1.32-1.46 (m, 2H), 1.52-1.59 (m, 2H), 1.62-1.79 (m, 2H), 1.97-2.06 (m, 4H), 2.68-2.85 (m, 8H), 3.34-3.51 (m, 2H), 3.60 (dd, J=6.5, 4.5, 1H), 5.18-5.42 (m, 10H), 5.61 (s, 1H), 6.42 (s, 1H).

Example 33: Preparation of N-(tert-butyl)-2-(((5Z,8Z,11Z,14Z,17Z)-icosa-5,8,11,14,17-pentaen-1-yl)oxy)butanamide

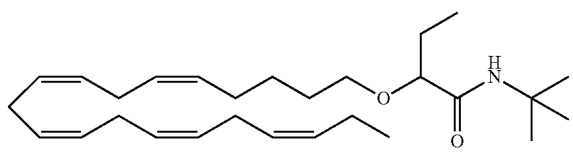 [SMILES: CC/C=C\C/C=C\C/C=C\C/C=C\C/C=C\CCCCOC(CC)C(=O)NC(C)(C)C]

To a solution of 2-(((5Z,8Z,11Z,14Z,17Z)-icosa-5,8,11,14,17-pentaen-1-yl)oxy)butanoic acid (301.3 mg, 0.804 mmol) in DCM (10 mL) at room temperature under N2-atmosphere was added o-Benzotriazol-1-yl-N,N,N',N'-tetramethyluronium tetrafluoroborate (TBTU) (285.6 mg, 0.889 mmol) followed by triethyl amine (0.123 ml, 0.885 mmol). The mixture was stirred for 15 minutes at room temperature under N2-atmosphere before 2-Amino-2-methylpropane (0.10 mL, 0.952 mmol) was added. The reaction mixture was stirred at room temperature over night. Saturated NaHCO$_3$ (25 mL) was added and the mixture was extracted with t-butyl methyl ether (2×50 mL). The combined organic phase was dried (Na2SO4), filtered and evaporated in vacuo. The residue was purified by flash chromatography on silica gel using increasingly polar mixtures of heptane and ethyl acetate (95:5→50:50) as eluent. Concentration of the appropriate fractions afforded 244.1 mg (70% yield) of the title compound as an oil. $^1$H NMR (400 MHz, CDCl3) δ 0.89 (t, J=7.4, 3H), 0.96 (t, J=7.5, 3H), 1.34 (s, 9H), 1.41-1.46 (m, 2H), 1.57-1.70 (m, 3H), 1.74-1.81 (m, 1H), 2.02-2.11 (m, 4H), 2.80-2.83 (m, 8H), 3.27-3.48 (m, 2H), 3.48-3.56 (m, 1H), 4.93-5.55 (m, 10H), 6.38 (s, 1H).

Example 34: Preparation of (R)-2-(((5Z,8Z,11Z,14Z,17Z)-icosa-5,8,11,14,17-pentaen-1-yl)oxy)-N—((R)-1-phenylethyl)butanamide

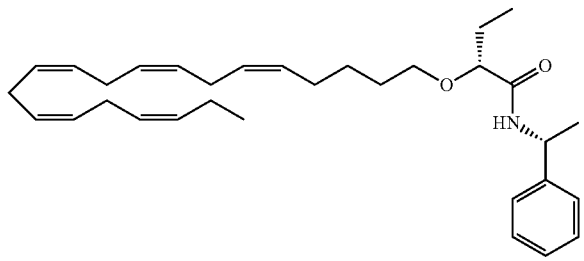 [SMILES: CC/C=C\C/C=C\C/C=C\C/C=C\C/C=C\CCCCO[C@H](CC)C(=O)N[C@H](C)c1ccccc1]

To a solution of (R)-2-(((5Z,8Z,11Z,14Z,17Z)-icosa-5,8,11,14,17-pentaen-1-yl)oxy)butanoic acid (40 mg, 0.11 mmol) and (R)-1-phenylethan-1-amine (14 μL, 0.11 mmol) in dry DMF (3 mL) at 0° C. under nitrogen was added N-methylmorpholine (14 μL, 0.13 mmol), followed by o-(Benzotriazol-1-yl)-N,N,N',N'-tetramethyluronium hexafluorophosphate (HBTU) (45 mg, 0.14 mmol). The reaction miture was stirred at room temperature under N2-atmosphere for 30 minutes. Water (10 mL) was added and the mixture extracted with heptane (10 mL). Phases were separated and the water phase was extracted with heptane (10 mL), followed by diethylether (10 mL). Organics were combined and washed with sat. aq. NH4Cl (10 mL) and brine (10 mL). The organic phase was dried (Na2SO4), filtered and evaporated in vacuo to afford the title compound (20 mg 0.042 mmol, 38% yield) as an oil.

Example 35: Preparation of (2S)-ethyl 2-(2-((5Z,8Z,11Z,14Z,17Z)-icosa-5,8,11,14,17-pentaen-1-yloxy)butanamido)-4-methylpentanoate

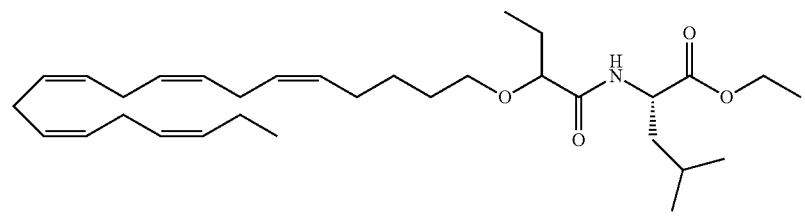 [SMILES: CC/C=C\C/C=C\C/C=C\C/C=C\C/C=C\CCCCOC(CC)C(=O)N[C@@H](CC(C)C)C(=O)OCC]

N,N'-Dicyclohexylcarbodiimide (DCC) (1.13 g, 5.5 mmol), hydroxybenzotriazole (HOBt) (0.74 g, 5.5 mmol) and triethylamine (TEA) (1.58 mL, 11.4 mmol) were added to a solution of 2-((5Z,8Z,11Z,14Z,17Z)-icosa-5,8,11,14,17-pentaen-1-yloxy)butanoic acid (1.87 g, 5.0 mmol) in tetrahydrofuran (THF) (20 mL) and the mixture was stirred for 10 minutes. L-Leucine ethyl ester hydrochloride (0.89 g, 4.6 mmol) was added and the resulting mixture was stirred for 2 hours. The mixture was concentrated in vacuo, dissolved in Et$_2$O (100 mL) and washed with 1M HCl (aq), saturated NaHCO$_3$ (aq) and brine. The organic phase was dried (Na$_2$SO$_4$), filtered and concentrated in vacuo. The residue was purified by flash chromatography using a gradient of 10-15% EtOAc in heptane as eluent. Concentration of the appropriate fractions afforded 1.88 g (80% yield) of the title compound. $^1$H NMR (300 MHz, CDCl$_3$): δ 0.90-1.05 (m, 12H), 1.25-1.35 (m, 3H), 1.45-1.85 (m, 9H), 2.05-2.20 (m, 4H), 2.80-2.90 (m, 8H), 3.40-3.70 (m, 3H), 4.18 (q, 2H), 4.55-4.70 (m, 1H), 5.30-5.45 (m, 10H), 6.80-6.95 (m, 1H). MS (ESI): 538 [M+Na]$^+$.

Example 36: Preparation of (2S)-2-(2-((5Z,8Z,11Z,14Z,17Z)-icosa-5,8,11,14,17-pentaen-1-yloxy)butanamido)-4-methylpentanoic acid

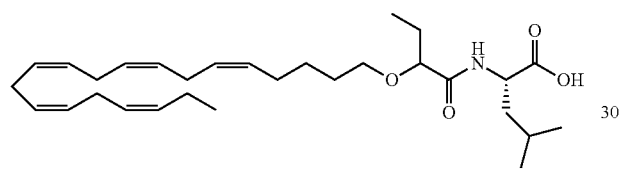

A solution of LiOH (700 mg, 29 mmol) in water (10 mL) was added to a solution of (2S)-ethyl 2-(2-((5Z,8Z,11Z,14Z,17Z)-icosa-5,8,11,14,17-pentaen-1-yloxy)butanamido)-4-methylpentanoate (1.88 g, 3.65 mmol) in EtOH (20 mL) and the reaction mixture was stirred at 40° C. for 1 hour. The mixture was cooled to ambient temperature and added 3M HCl (aq) until pH~2. The resulting mixture was extracted twice with Et$_2$O and the combined organic phases were dried (NaSO$_4$), filtered and concentrated under reduced pressure to afford 1.55 g (87% yield) of the title compound. $^1$H NMR (300 MHz, CDCl$_3$): δ 0.90-1.05 (m, 12H), 1.45-1.55 (m, 2H), 1.65-1.85 (m, 7H), 2.05-2.20 (m, 4H), 2.80-2.90 (m, 8H), 3.45-3.65 (m, 2H), 3.70-3.80 (m, 1H), 4.55-4.70 (m, 1H), 5.30-5.45 (m, 10H), 6.85-7.00 (m, 1H), 10.30 (br s, 1H). MS (ESI); 510 [M+Na]$^+$.

Example 37: Preparation of tert-butyl 2-(((2S)-2-(2-((5Z,8Z,11Z,14Z,17Z)-icosa-5,8,11,14,17-pentaen-1-yloxy)butanamido)-4-methylpentanoyl)oxy)benzoate

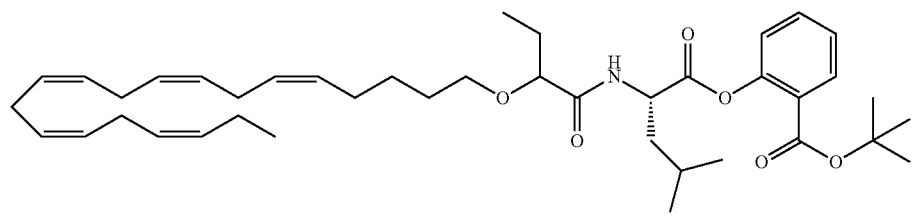 [SMILES: CC/C=C\C/C=C\C/C=C\C/C=C\C/C=C\CCCCOC(CC)C(=O)N[C@@H](CC(C)C)C(=O)Oc1ccccc1C(=O)OC(C)(C)C]

2-Hydroxy-benzoic acid tert-butyl ester (291 mg, 1.5 mmol), TEA (0.46 mL, 3.3 mmol) and O-(benzotriazol-1-yl)-N,N,N',N'-tetramethyluronium hexafluorophosphate (TBTU) (500 mg, 1.65 mmol) were added to a solution of (2S)-2-(2-((5Z,8Z,11Z,14Z,17Z)-icosa-5,8,11,14,17-pentaen-1-yloxy)butanamido)-4-methylpentanoic acid (730 mg, 1.5 mmol) in dimethylformamide (DMF) (10 mL). The reaction mixture was heated for 2 hours at 65° C., cooled to RT and added Et$_2$O (100 mL). The resulting two phases were separated and the organic phase was washed with 10% NH$_4$Cl (aq) and brine, dried (Na$_2$SO$_4$), filtered and concentrated in vacuo. The residue was purified by flash chromatography using 10% EtOAc in heptane as eluent. Concentration of the appropriate fractions afforded 404 mg (41% yield) of the title compound. $^1$H NMR (300 MHz, CDCl$_3$): δ 0.90-1.05 (m, 12H), 1.40-1.55 (m, 2H), 1.57 (s, 9H), 1.60-1.85 (m, 6H), 2.00-2.20 (m, 5H), 2.80-2.90 (m, 8H), 3.40-3.60 (m, 2H), 3.70-3.80 (m, 1H), 4.90-5.05 (m, 1H), 5.30-5.45 (m, 10H), 7.10 (d, 2H), 7.25-7.35 (m, 1H), 7.50-7.55 (m, 1H), 7.85-7.95 (m, 1H). MS (ESI): 686 [M+Na]$^+$.

Example 38: Preparation of 2-(((2S)-2-(2-((5Z,8Z,11Z,14Z,17Z)-icosa-5,8,11,14,17-pentaen-1-yloxy)butanamido)-4-methylpentanoyl)oxy)benzoic acid

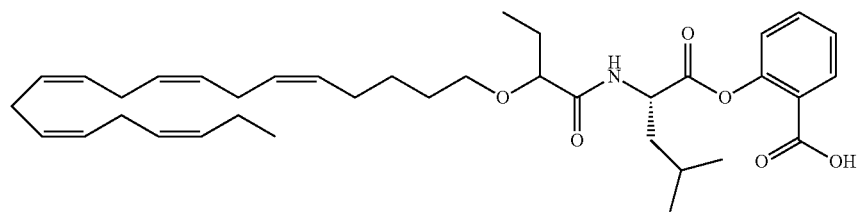 [SMILES: CC/C=C\C/C=C\C/C=C\C/C=C\C/C=C\CCCCOC(CC)C(=O)N[C@@H](CC(C)C)C(=O)Oc1ccccc1C(=O)O]

TFA (1 mL) was added to a solution of tert-butyl 2-(((2S)-2-(2-((5Z,8Z,11Z,14Z,17Z)-icosa-5,8,11,14,17-pentaen-1-yloxy)butanamido)-4-methylpentanoyl)oxy)benzoate (150 mg, 0.23 mmol) in DCM (4 mL) at 0° C. and the reaction mixture was stirred for 40 minutes. Toluene (10 mL) was added and the mixture was concentrated in vacuo. The residue was purified by flash chromatography using 13% EtOAc (containing 0.1% FA) in heptane (also containing 0.1% FA) as eluent. The appropriate fractions were concentrated and the residue (100 mg) was dissolved in Et$_2$O (50 mL). The solution was washed with saturated NaHCO$_3$(aq), dried (Na$_2$SO$_4$), filtered and concentrated in vacuo to afford 60 mg of the desired product. $^1$H NMR (300 MHz, CDCl$_3$): δ 0.85-1.05 (m, 12H), 1.35-2.15 (m, 13H), 2.75-2.90 (m, 8H), 3.40-3.60 (m, 2H), 3.70-3.80 (m, 1H), 4.85-5.05 (m, 1H), 5.30-5.45 (m, 10H), 7.0-7.20 (m, 2H), 7.25-7.40 (m, 1H), 7.50-7.65 (m, 1H), 8.00-8.15 (m, 1H). MS (ESI); 630 [M+Na]$^+$. HR-MS(ESI): calc for C$_{37}$H$_{53}$NO$_6$+Na: 630.3770, found: 630.3786.

Example 39: Preparation of tert-butyl (2-(2-((5Z,8Z,11Z,14Z,17Z)-icosa-5,8,11,14,17-pentaen-1-yloxy)butanamido)ethyl)carbamate

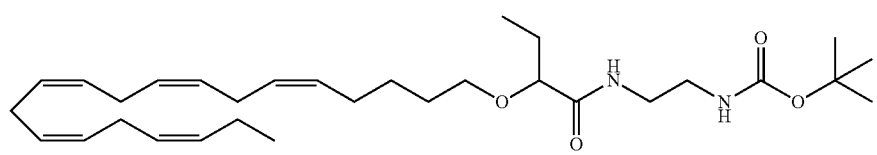

DCC (1.73 g, 8.4 mmol) and HOBt (1.14 g, 8.4 mmol) were added to a solution of 2-((5Z,8Z,11Z,14Z,17Z)-icosa-5,8,11,14,17-pentaen-1-yloxy)butanoic acid (3.14 g, 8.4 mmol) in THF (25 mL) at 0° C. and the mixture was stirred for 20 minutes. A solution of N-Boc-ethylenediamine in THF (1 mL) was added dropwise and the resulting mixture was stirred at room temperature for 1.5 hours. Et$_2$O (200 mL) was added and the mixture was washed with water, 1M HCl (aq), saturated NaHCO$_3$ (aq) and brine. The organic phase was dried (Na$_2$SO$_4$), filtered and concentrated in vacuo. The residue was purified by flash chromatography using 25% EtOAc (containing 0.5% FA) in heptane (also containing 0.5% FA) as eluent. Concentration of the appropriate fractions afforded 3.0 g (83% yield) of the title compound. $^1$H NMR (300 MHz, CDCl$_3$): δ 0.90 (t, 3H), 0.96 (t, 3H), 1.43 (s, 9H), 1.40-1.80 (m, 6H), 2.05-2.20 (m, 4H), 2.75-2.90 (m, 8H), 3.20-3.60 (m, 6H), 3.65-3.75 (m, 1H), 5.02 (br s, 1H), 5.30-5.45 (m, 10H), 7.01 (br s, 1H). MS (ESI): 539 [M+Na]$^+$.

Example 40: Preparation of 2-hydroxy-N-(2-(2-((5Z,8Z,11Z,14Z,17Z)-icosa-5,8,11,14,17-pentaen-1-yloxy)butanamido)ethyl)benzamide

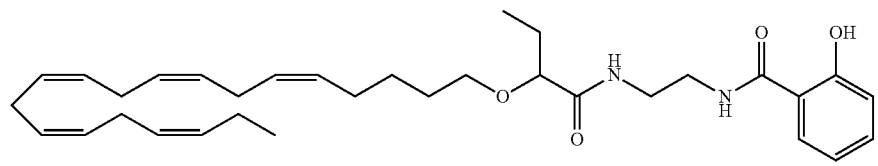 [SMILES: CC/C=C\C/C=C\C/C=C\C/C=C\C/C=C\CCCCOC(CC)C(=O)NCCNC(=O)c1ccccc1O]

TFA (2 mL) was added to a solution of tert-butyl (2-(2-((5Z,8Z,11Z,14Z,17Z)-icosa-5,8,11,14,17-pentaen-1-yloxy)butanamido)ethyl)carbamate (668 mg, 1.3 mmol) in DCM (8 mL) and the resulting mixture was stirred for 1.5 hours. The mixture was concentrated in vacuo to give the TFA salt of N-(2-aminoethyl)-2-((5Z,8Z,11Z,14Z,17Z)-icosa-5,8,11,14,17-pentaen-1-yloxy)butanamide as a crude product (800 mg, MS (ESI): 417 [M+H]$^+$, 439 [M+Na]$^+$). The residue was dissolved in DCM (10 mL) and added DCC (320 mg, 1.55 mmol), TEA (0.36 mL, 2.6 mmol) and HOBt (210 mg, 1.55 mmol). After 15 minutes, a solution of salicylic acid (214 mg, 1.55 mmol) in DCM (1 mL) was added dropwise and the resulting mixture was stirred over night. The mixture was concentrated and the residue was dissolved in Et$_2$O (100 mL), washed with water, 1M HCl (aq), saturated NaHCO$_3$ (aq) and brine. The organic phase was dried (Na$_2$SO$_4$), filtered and concentrated in vacuo. The crude oil was purified by flash chromatography using a gradient of 4-15% EtOAc (containing 5% FA) in heptane (also containing 5% FA) as eluent. Concentration of the appropriate fractions afforded 110 mg (16% yield over two steps) of the title compound. $^1$H NMR (300 MHz, CDCl$_3$): δ 0.89 (t, 3H), 0.99 (t, 3H), 1.35-1.50 (m, 2H), 1.60-1.90 (m, 4H), 2.05-2.20 (m, 4H), 2.8-2.9 (m, 8H), 3.47 (t, 2H), 3.50-3.70 (m, 4H), 3.70-3.80 (m, 1H), 5.30-5.45 (m, 10H), 6.85-6.95 (m, 1H), 6.97 (dd, 1H), 7.14 (br s, 1H), 7.35-7.45 (m, 1H), 7.48 (dd, 1H), 7.95 (br s, 1H), 12.51 (br s, 1H). MS (ESI): 537 [M+H]$^+$, 559 [M+Na]$^+$.

Example 41: Preparation of 2-(2-((5Z,8Z,11Z,14Z,17Z)-icosa-5,8,11,14,17-pentaen-1-yloxy)butanamido)ethyl 2-acetoxybenzoate

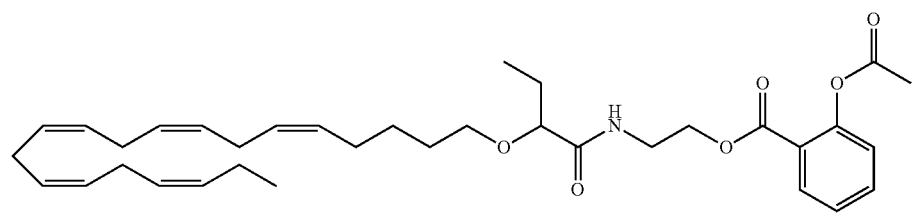 [SMILES: CC/C=C\C/C=C\C/C=C\C/C=C\C/C=C\CCCCOC(CC)C(=O)NCCOC(=O)c1ccccc1OC(C)=O]

TBTU (0.85 g, 2.64 mmol) and TEA (0.8 mL, 5.3 mmol) were added to a solution of acetylsalicylic acid (0.4 g, 2.4 mmol) in DCM (20 mL) and the mixture was stirred for 10 minutes. A solution of N-(2-hydroxyethyl)-2-((5Z,8Z,11Z,14Z,17Z)-icosa-5,8,11,14,17-pentaen-1-yloxy)butanamide (1.0 g, 1.4 mmol) in DCM (10 mL) was added and the reaction mixture was stirred at room temperature for 1 hour and then refluxed overnight. Water was added and the resulting mixture was extracted twice with DCM. The combined organic phases were dried (Na₂SO₄), filtered and concentrated in vacuo. The residue was purified by flash chromatography using a gradient of 0-20% EtOAc in heptane as eluent. Concentration of the appropriate fractions afforded 900 mg (65% yield) of the title compound. $^1$H NMR (300 MHz, CDCl₃): δ 0.85-1.00 (m, 6H), 1.35-1.50 (m, 2H), 1.50-1.85 (m, 4H), 2.00-2.20 (m, 4H), 2.37 (s, 3H), 2.75-2.90 (m, 8H), 3.40-3.55 (m, 2H), 3.55-3.75 (m, 3H), 4.15-4.45 (m, 2H), 5.30-5.50 (m, 10H), 6.80-95 (m, 1H), 7.10-7.15 (m, 1H), 7.30-7.40 (m, 1H), 7.55-7.65 (m, 1H), 8.00-8.05 (m, 1H). MS (ESI): 602 [M+Na]⁺.

Example 42: Preparation of 2-(2-((5Z,8Z,11Z,14Z,17Z)-icosa-5,8,11,14,17-pentaen-1-yloxy)butanamido)ethyl 2-hydroxybenzoate

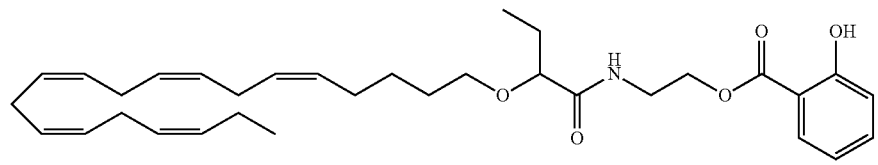 [SMILES: CC/C=C\C/C=C\C/C=C\C/C=C\C/C=C\CCCCOC(CC)C(=O)NCCOC(=O)c1ccccc1O]

Ammonia (aq, 28%, 3 mL) was added dropwise to a solution of 2-(2-((5Z,8Z,11Z,14Z,17Z)-icosa-5,8,11,14,17-pentaen-1-yloxy)butanamido)ethyl 2-acetoxybenzoate (390 mg, 0.67 mmol) in 2-propanol (27 mL) and water (9 mL) and the mixture was stirred for 10 minutes. Water was added and the resulting mixture was extracted twice with Et₂O. The combined organic phases were washed with brine, dried (Na₂SO₄), filtered and concentrated in vacuo. The residue was purified by flash chromatography using a gradient of 0-20% EtOAc in heptane as eluent. Concentration of the appropriate fractions afforded 63 mg (18% yield) of the title compound. $^1$H NMR (300 MHz, CDCl₃): δ 0.91 (t, 3H), 0.97 (t, 3H), 1.35-1.45 (m, 2H), 1.55-1.90 (m, 4H), 2.00-2.15 (m, 4H), 2.80-2.90 (m, 8H), 3.44 (t, 2H), 3.65-3.80 (m, 3H), 4.40-4.50 (m, 2H), 5.30-5.45 (m, 1 OH), 6.85-6.95 (m, 2H), 6.95-7.05 (m, 1H), 7.40-7.50 (m, 1H), 7.80-7.85 (m, 1H), 10.63 (s, 1H). MS (ESI): 560 [M+Na]⁺.

Example 43: Preparation of methyl 2-hydroxy-5-(2-((5Z,8Z,11Z,14Z,17Z)-icosa-5,8,11,14,17-pentaen-1-yloxy)butanamido)benzoate

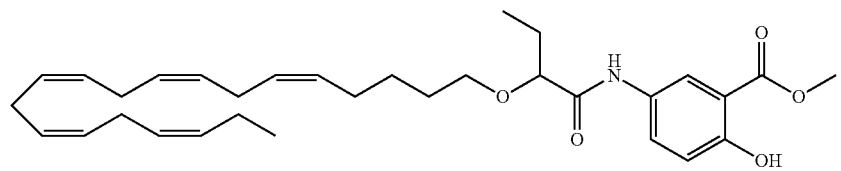 [SMILES: CC/C=C\C/C=C\C/C=C\C/C=C\C/C=C\CCCCOC(CC)C(=O)Nc1ccc(O)c(C(=O)OC)c1]

2-((5Z,8Z,11Z,14Z,17Z)-Icosa-5,8,11,14,17-pentaen-1-yloxy)butanoic acid (300 mg, 0.80 mmol), methyl 5-aminosalicylate (140 mg, 0.83 mmol) and TEA (0.22 mL, 1.60 mmol) was dissolved in MeCN (3 mL). HATU (320 mg, 0.83 mmol) was added and the reaction mixture was stirred over night. The mixture was then concentrated under reduced pressure and the residue was partitioned between Et$_2$O (30 mL) and brine (20 mL). The aqueous phase was extracted with Et$_2$O (20 mL) and the combined organic phases were washed with 2M HCl (aq, 15 mL), saturated NaHCO$_3$ (aq, 15 mL) and brine (15 mL), dried (Na$_2$SO$_4$), filtered and concentrated in vacuo. The residue was purified by flash chromatography using 5% EtOAc in heptane as eluent. Concentration of the appropriate fractions afforded 320 mg (77% yield) of the title compound. MS (ESI): 546 [M+Na]$^+$.

Example 44: Preparation of 2-hydroxy-5-(2-((5Z,8Z,11Z,14Z,17Z)-icosa-5,8,11,14,17-pentaen-1-yloxy)butanamido)benzoic acid

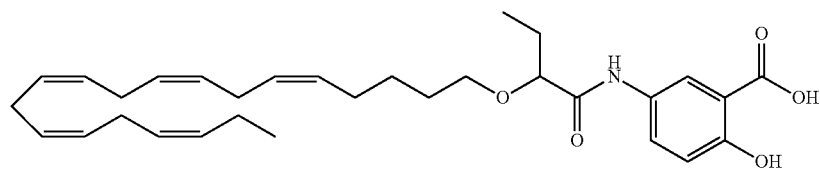 [SMILES: CC/C=C\C/C=C\C/C=C\C/C=C\C/C=C\CCCCOC(CC)C(=O)Nc1ccc(O)c(C(=O)O)c1]

2M NaOH (aq, 6 mL) was added to a solution of methyl 2-hydroxy-5-(2-((5Z,8Z,11Z,14Z,17Z)-icosa-5,8,11,14,17-pentaen-1-yloxy)butanamido)benzoate (320 mg, 0.61 mmol) in MeOH (3 mL) and the reaction mixture was heated at 50° C. over night. The mixture was cooled to ambient temperature and acidified to pH-2 with 5M HCl (aq). The resulting mixture was extracted with EtOAc and the organic phase was dried (Na$_2$SO$_4$), filtered and concentrated in vacuo. The residue was purified by flash chromatography using a gradient of 1-2% MeOH in EtOAc as eluent. Concentration of the appropriate fractions afforded 85 mg (27% yield) of the title compound. $^1$H NMR (300 MHz, CDCl$_3$): δ 0.90-1.05 (t, 3H), 1.20-1.30 (m, 1H), 1.45-1.60 (m, 2H), 1.65-1.75 (m, 2H), 1.80-1.95 (m, 2H), 2.05-2.20 (m, 4H), 2.80-2.90 (m, 8H), 3.50-3.65 (m, 2H), 3.85-3.95 (m, 1H), 5.30-5.45 (m, 10H), 6.90-7.00 (m, 1H), 7.58 (br s, 1H), 8.11 (br s, 1H), 8.40 (s, 1H). MS (ESI): 508 [M−H]$^-$.

Example 45: Preparation of (2S)-ethyl 2-(2-((5Z,8Z,11Z,14Z,17Z)-icosa-5,8,11,14,17-pentaen-1-yloxy)butanamido)-4-methylpentanoate

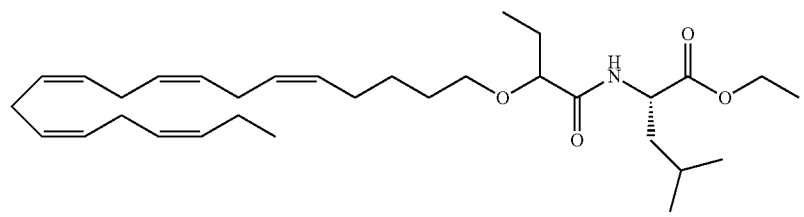 [SMILES: CC/C=C\C/C=C\C/C=C\C/C=C\C/C=C\CCCCOC(CC)C(=O)N[C@@H](CC(C)C)C(=O)OCC]

DCC (1.13 g, 5.5 mmol) and HOBt (0.74 g, 5.5 mmol) followed by TEA (1.58 mL, 11.4 mmol) were added to a solution of 2-((5Z,8Z,11Z,14Z,17Z)-icosa-5,8,11,14,17-pentaen-1-yloxy)butanoic acid (1.87 g, 5.0 mmol) in THF (20 mL) and the mixture was stirred for 10 minutes. L-Leucine ethyl ester hydrochloride (0.89 g, 4.6 mmol) was added and the resulting mixture was stirred for 2 hours. EtOAc (100 mL) was added and the mixture was washed with water, 1M HCl (aq), saturated NaHCO$_3$ (aq) and brine. The organic phase was dried (Na$_2$SO$_4$), filtered and concentrated in vacuo. The residue was purified by flash chromatography using a gradient of 10-15% EtOAc in heptane as eluent. Concentration of the appropriate fractions afforded 1.84 g (79% yield) of the title compound. $^1$H NMR (300 MHz, CDCl$_3$): δ 0.85-1.05 (m, 12H), 1.25-1.35 (m, 3H), 1.40-1.85 (m, 9H), 2.05-2.20 (m, 4H), 2.80-2.90 (m, 8H), 3.45-3.75 (m, 3H), 4.15-4.25 (m, 2H), 4.55-4.75 (m, 1H), 5.30-5.45 (m, 10H), 6.80-6.95 (m, 1H). MS (ESI): 538 [M+Na]$^+$.

Example 46: Preparation of (2S)-2-(2-((5Z,8Z,11Z,14Z,17Z)-icosa-5,8,11,14,17-pentaen-1-yloxy)butanamido)-4-methylpentanoic acid

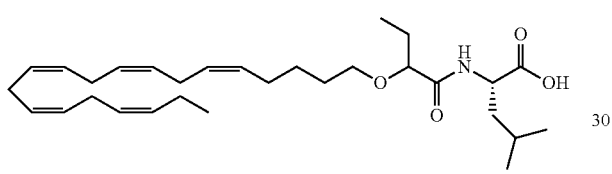

1M LiOH (aq, 28 mL) was added to a solution of (2S)-ethyl 2-(2-((5Z,8Z,11Z,14Z,17Z)-icosa-5,8,11,14,17-pentaen-1-yloxy)butanamido)-4-methylpentanoate (1.79 g, 3.5 mmol) in EtOH (50 mL) and the reaction mixture was heated to 50° C. for 2 hours. The mixture was cooled to ambient temperature and added 6M HCl (aq) to pH-2. The resulting mixture was extracted twice with Et$_2$O and the combined organic phases were dried (NaSO$_4$), filtered and concentrated under reduced pressure to afford 1.61 g (95% yield) of the title compound. $^1$H NMR (300 MHz, CDCl$_3$): δ 0.85-1.05 (m, 12H), 1.45-1.55 (m, 2H), 1.60-1.85 (m, 7H), 2.05-2.20 (m, 4H), 2.80-2.90 (m, 8H), 3.45-3.65 (m, 2H), 3.70-3.80 (m, 1H), 4.60-4.75 (m, 1H), 5.30-5.45 (m, 10H), 6.90-7.05 (m, 1H), 10.15 (br s, 1H). MS (ESI): 486 [M−H]$^-$.

Example 47: Preparation of methyl 2-hydroxy-5-((2S)-2-(2-((5Z,8Z,11Z,14Z,17Z)-icosa-5,8,11,14,17-pentaen-1-yloxy)butanamido)-4-methylpentanamido)benzoate

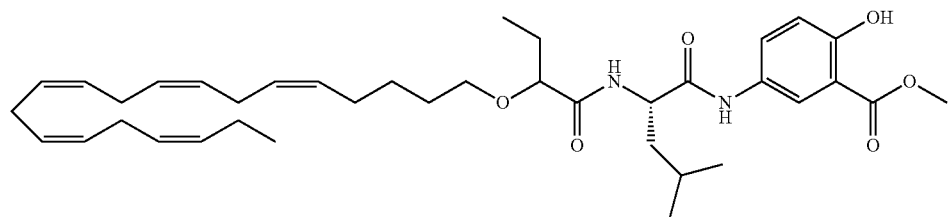 [SMILES: CC/C=C\C/C=C\C/C=C\C/C=C\C/C=C\CCCCOC(CC)C(=O)N[C@@H](CC(C)C)C(=O)Nc1ccc(O)c(C(=O)OC)c1]

DCC (248 mg, 1.2 mmol) and HOBt (163 mg, 1.2 mmol) were added to a solution of (2S)-2-(2-((5Z,8Z,11Z,14Z,17Z)-icosa-5,8,11,14,17-pentaen-1-yloxy)butanamido)-4-methylpentanoic acid (487 mg, 1.0 mmol) in THF (8 mL) at 0° C. A solution of methyl 5-amino salicylate (201 mg, 1.2 mmol) in THF (1 mL) was added dropwise and the reaction mixture was stirred at room temperature for 3 hours. Et$_2$O (100 mL) was added and the mixture was washed with water, 1M HCl (aq), saturated NaHCO$_3$ (aq) and brine. The organic phase was dried (Na$_2$SO$_4$), filtered and concentrated in vacuo. The residue was purified by flash chromatography using a gradient of 3-15% EtOAc (containing 5% FA) in heptane (also containing 5% FA) as eluent. Concentration of the appropriate fractions afforded 197 mg (31% yield) of the title compound. $^1$H NMR (300 MHz, CDCl$_3$): δ 0.85-1.05 (m, 12H), 1.40-1.50 (m, 2H), 1.60-1.90 (m, 7H), 2.05-2.20 (m, 4H), 2.80-2.90 (m, 8H), 3.45-3.55 (m, 2H), 3.75-3.80 (m, 1H), 3.94 (s, 1H), 4.55-4.65 (m, 1H), 5.30-5.45 (m, 10H), 6.90-7.00 (m, 2H), 7.45-7.50 (m, 1H), 8.00-8.10 (m, 1H), 8.66 (s, 1H), 10.59 (s, 1H). MS (ESI): 659 [M+Na]$^+$.

Example 48: Preparation of 2-hydroxy-5-((2S)-2-(2-((5Z,8Z,11Z,14Z,17Z)-icosa-5,8,11,14,17-pentaen-1-yloxy)butanamido)-4-methylpentanamido)benzoic acid

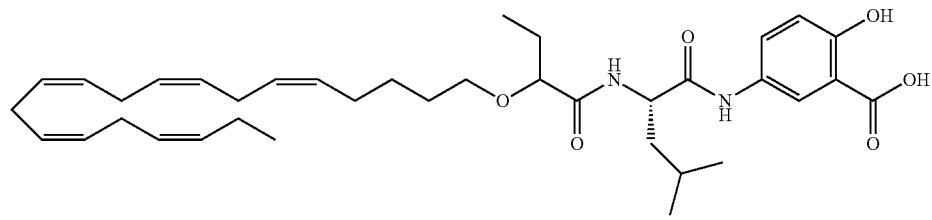 [SMILES: CC/C=C\C/C=C\C/C=C\C/C=C\C/C=C\CCCCOC(CC)C(=O)N[C@@H](CC(C)C)C(=O)Nc1ccc(O)c(C(=O)O)c1]

1M LiOH (aq, 2.5 mL) was added to a solution of methyl 2-hydroxy-5-((2S)-2-(2-((5Z,8Z,11Z,14Z,17Z)-icosa-5,8,11,14,17-pentaen-1-yloxy)butanamido)-4-methylpentanamido)benzoate (190 mg, 0.3 mmol) in MeOH (5 mL). The reaction mixture was heated at 50° C. for 5 hours and then stirred at room temperature for 3 days. The mixture was acidified with 6M HCl (aq) to pH-2 and most of the solvent was removed in vacuo. The residue was extracted twice with Et$_2$O and the combined organic phases were dried (Na$_2$SO$_4$), filtered and concentrated in vacuo. The residue was purified by flash chromatography using a gradient of 5-25% EtOAc (containing 5% FA) in heptane (also containing 5% FA) as eluent. Concentration of the appropriate fractions afforded 100 mg (54% yield) of the title compound. $^1$H NMR (300 MHz, CDCl$_3$): δ 0.90-1.05 (m, 12H), 1.40-1.50 (m, 2H), 1.60-1.90 (m, 7H), 2.05-2.20 (m, 4H), 2.80-2.90 (m, 8H), 3.45-3.60 (m, 2H), 3.80-3.90 (m, 1H), 4.60-4.75 (m, 1H), 5.30-5.45 (m, 10H), 6.89 (d, 1H), 7.24 (d, 1H), 7.70-7.90 (m, 2H), 9.02 (d, 1H), 10.37 (d, 1H). MS (ESI): 623 [M+H]$^+$.

Example 49: Preparation of methyl 2-hydroxy-5-(((2-(2-((5Z,8Z,11Z,14Z,17Z)-icosa-5,8,11,14,17-pentaen-1-yloxy)butanamido)ethoxy)carbonyl)amino)benzoate

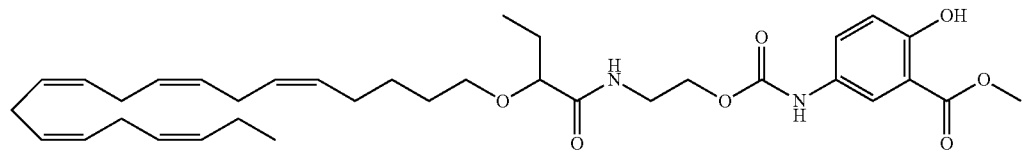 [SMILES: CC/C=C\C/C=C\C/C=C\C/C=C\C/C=C\CCCCOC(CC)C(=O)NCCOC(=O)Nc1ccc(O)c(C(=O)OC)c1]

Diphosgene (0.16 mL, 1.3 mmol) and diisopropylamine (0.16 mL, 0.96 mmol) were added to a solution of N-(2-hydroxyethyl)-2-((5Z,8Z,11Z,14Z,17Z)-icosa-5,8,11,14,17-pentaen-1-yloxy)butanamide (0.4 g, 0.96 mmol) in DCM (15 mL) at 0° C. The reaction mixture was stirred at 0° C. for 1 hour and then at room temperature for 2 hours. The mixture was concentrated under reduced pressure and the residue was suspended in THF (20 mL). The suspension was filtered and the filtrate was concentrated under reduced pressure. The residue was then suspended in Et$_2$O, filtered through a pad of silica and concentrated in vacuo to afford 0.66 g of 2-(2-((5Z,8Z,11Z,14Z,17Z)-icosa-5,8,11,14,17-pentaen-1-yloxy)butanamido)ethyl carbonochloridate as a crude product. The residue was dissolved in DCM (15 mL) and added methyl 5-aminosalicylate (0.13 g, 0.77 mmol) and TEA (0.2 mL, 1.54 mmol). The reaction mixture was stirred for 2 hours and then added water. The resulting mixture was extracted twice with DCM and the combined organic phases were dried (Na$_2$SO$_4$), filtered and concentrated in vacuo. The residue was purified by flash chromatography using a gradient of 30-50% EtOAc in heptane as eluent. Concentration of the appropriate fractions afforded 145 mg (30% yield) of the title compound. $^1$H NMR (300 MHz, CDCl$_3$): δ 0.85-1.00 (m, 6H), 1.35-1.50 (m, 2H), 1.50-1.85 (m, 4H), 2.00-2.20 (m, 4H), 2.75-2.90 (m, 8H), 3.40-3.55 (m, 2H), 3.55-3.75 (m, 3H), 3.95 (s, 3H), 4.25-4.35 (m, 2H), 5.25-5.45 (m, 1 OH), 6.68 (br s, 1H), 6.85-7.00 (m, 2H), 7.35-7.45 (m, 1H), 7.91 (br s, 1H), 10.57 (s, 1H). MS (ESI): 633 [M+Na]$^+$.

Example 50: Preparation of 2-hydroxy-5-(((2-(2-((5Z,8Z,11Z,14Z,17Z)-icosa-5,8,11,14,17-pentaen-1-yloxy)butanamido)ethoxy)carbonyl)amino)benzoic acid

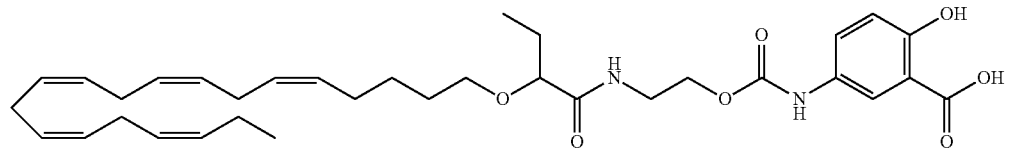 [SMILES: CC/C=C\C/C=C\C/C=C\C/C=C\C/C=C\CCCCOC(CC)C(=O)NCCOC(=O)Nc1ccc(O)c(C(=O)O)c1]

1M LiOH (aq, 1.9 mL) was added to a solution of methyl 2-hydroxy-5-(((2-(2-((5Z,8Z,11Z,14Z,17Z)-icosa-5,8,11,14,17-pentaen-1-yloxy)butanamido)ethoxy)carbonyl)amino)benzoate (145 mg, 0.24 mmol) in MeOH (20 mL) and the mixture was heated at 50° C. over night. The reaction mixture was acidified with 1M HCl (aq) to pH-2 and then extracted twice with Et$_2$O. The combined organic phases were dried (Na$_2$SO$_4$), filtered and concentrated in vacuo. The residue was purified by flash chromatography using 20% EtOAc (containing 5% FA) in heptane (also containing 5% FA) as eluent. The appropriate fractions were pooled and concentrated. The residue (46 mg) was purified further by preparative HPLC using a gradient of 30-95% MeCN in water (containing 5% MeCN and 0.01% TFA) as eluent. The appropriate fractions were pooled and concentrated and the residue was dissolved in toluene. Concentration of the solution afforded 24 mg (17% yield) of the title compound. $^1$H NMR (300 MHz, CDCl$_3$): δ 0.91-1.01 (m, 6H), 1.35-1.50 (m, 2H), 1.55-1.90 (m, 4H), 2.05-2.15 (m, 4H), 2.80-2.90 (m, 8H), 3.45-3.55 (m, 2H), 3.65-3.75 (m, 2H), 3.75-3.85 (m, 1H), 4.25-4.35 (m, 2H), 5.30-5.45 (m, 10H), 6.90-7.00 (m, 2H), 7.00-7.10 (m, 1H), 7.63 (br s, 1H), 7.83 (s, 1H), 10.43 (br s, 1H). MS (ESI): 597 [M+H]$^+$.

Example 51: Preparation of 2-((5Z,8Z,11Z,14Z,17Z)-icosa-5,8,11,14,17-pentaen-1-yloxy)-N-(2-isocyanatoethyl)butanamide

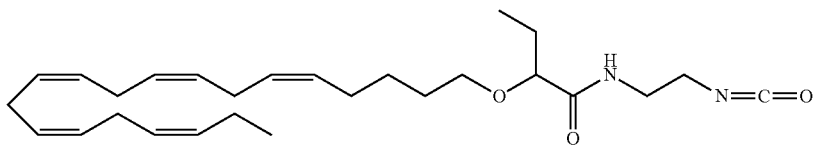 [SMILES: CC/C=C\C/C=C\C/C=C\C/C=C\C/C=C\CCCCOC(CC)C(=O)NCCN=C=O]

1,8-Bis(dimethylamino)naphthalene (577 mg, 2.7 mmol) was added to a solution of N-(2-aminoethyl)-2-((5Z,8Z,11Z,14Z,17Z)-icosa-5,8,11,14,17-pentaen-1-yloxy)butanamide (560 mg, 1.35 mmol) in DCM (10 mL) and the mixture was cooled to 0° C. Trichloromethyl chloroformate (98 µL, 0.81 mmol) was added dropwise before the cooling bath was removed and the mixture was stirred for 15 minutes. 1M HCl (aq, 30 mL) and DCM (30 mL) was added. The resulting two phases were separated and the organic phase was washed 4 times with 1M HCl (aq) and once with 1M NaOH (aq), dried (NaSO$_4$), filtered and concentrated under reduced pressure to afford 500 mg (84% yield) of the title compound as a crude product. MS (ESI): 465 [M+Na]$^+$.

Example 52: Preparation of methyl 2-hydroxy-5-(3-(2-(2-((5Z,8Z,11Z,14Z,17Z)-icosa-5,8,11,14,17-pentaen-1-yloxy)butanamido)ethyl)ureido)benzoate

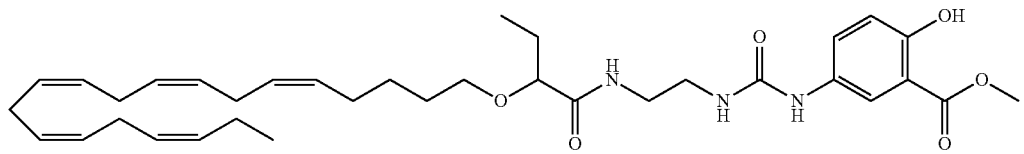 [SMILES: CC/C=C\C/C=C\C/C=C\C/C=C\C/C=C\CCCCOC(CC)C(=O)NCCNC(=O)Nc1ccc(O)c(C(=O)OC)c1]

Methyl 5-aminosalicyate (189 mg, 1.13 mmol) was added to a solution of 2-((5Z,8Z,11Z,14Z,17Z)-icosa-5,8,11,14,17-pentaen-1-yloxy)-N-(2-isocyanatoethyl)butanamide (500 mg, 1.13 mmol) in DCM (5 mL). The reaction mixture was stirred for 2 hours and then concentrated in vacuo. The residue was purified by flash chromatography using a gradient of 40-0% heptane in EtOAc as eluent. Concentration of the appropriate fractions afforded 230 mg (33% yield) of the title compound. $^1$H NMR (300 MHz, CDCl$_3$): δ 0.85-1.05 (2×t, 6H), 1.35-1.50 (m, 2H), 1.55-1.85 (m, 4H), 2.05-2.20 (m, 4H), 2.75-2.95 (m, 8H), 3.35-3.50 (m, 6H), 3.65-3.75 (m, 1H), 3.94 (s, 3H), 5.30-5.50 (m, 10H), 6.95 (d, 1H), 7.10 (br s, 1H), 7.40 (dd, 1H), 7.88 (d, 1H), 10.62 (s, 1H). MS (ESI); 632 [M+Na]$^+$.

Example 53: Preparation of 2-hydroxy-5-(3-(2-(2-((5Z,8Z,11Z,14Z,17Z)-icosa-5,8,11,14,17-pentaen-1-yloxy)butanamido)ethyl)ureido)benzoic acid

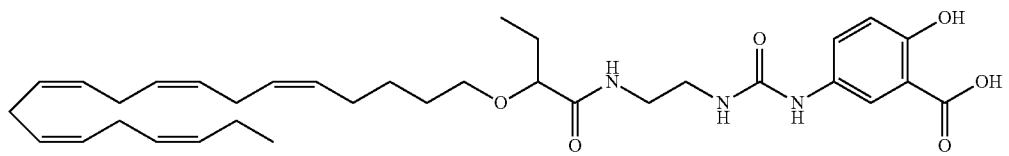 [SMILES: CC/C=C\C/C=C\C/C=C\C/C=C\C/C=C\CCCCOC(CC)C(=O)NCCNC(=O)Nc1ccc(O)c(C(=O)O)c1]

1M LiOH (aq, 2.9 mL) was added dropwise to a solution of methyl 2-hydroxy-5-(3-(2-(2-((5Z,8Z,11Z,14Z,17Z)-icosa-5,8,11,14,17-pentaen-1-yloxy)butanamido)ethyl)ureido)benzoate (220 mg, 0.36 mmol) in MeOH (10 mL) and the mixture was heated at 50° C. over night. The mixture was cooled to ambient temperature and then acidified to pH-2 with 6M HCl (aq). The resulting mixture was extracted twice with EtOAc and the combined organic phases were washed with brine, dried (NaSO$_4$), filtered and concentrated under reduced pressure. The residue was purified by flash chromatography using a gradient of 5-40% EtOAc (containing 5% FA) in heptane (also containing 5% FA) as eluent. Concentration of the appropriate fractions afforded 92 mg (43% yield) of the title compound. $^1$H NMR (300 MHz, CDCl$_3$): δ 0.91 (t, 3H), 0.98 (t, 3H), 1.40-1.50 (m, 2H), 1.60-1.90 (m, 4H), 2.05-2.20 (m, 4H), 2.80-2.90 (m, 8H), 3.40-3.60 (m, 6H), 3.75-3.80 (m, 1H), 5.30-5.45 (m, 10H), 6.90 (d, 1H), 7.25-7.35 (m, 1H), 7.45-7.55 (m, 1H), 7.80-7.95 (m, 2H), 10.56 (br s, 1H). MS (ESI): 596 [M+H]$^+$, 618 [M+Na]$^+$.

Example 54: Preparation of tert-butyl 2-((5Z,8Z,11Z,14Z,17Z)-icosa-5,8,11,14,17-pentaenyloxy)propanoate

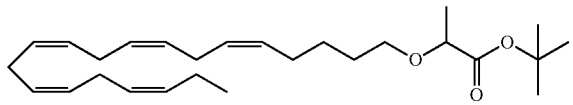 [SMILES: CC/C=C\C/C=C\C/C=C\C/C=C\C/C=C\CCCCOC(C)C(=O)OC(C)(C)C]

A mixture of (5Z,8Z,11Z,14Z,17Z)-icosa-5,8,11,14,17-pentaen-1-ol, (1.00 g, 3.47 mmol), tetrabutylammonium chloride (0.24 g, 0.87 mmol) and t-butyl 2-bromopropionate (3.62 g, 17.3 mmol) was dissolved in toluene (36 mL) and placed under nitrogen. An aqueous solution of sodium hydroxide (50%, 8 mL) was added slowly under vigorous stirring and the resulting mixture was stirred at ambient temperature for twenty hours. Water was added and the mixture was extracted three times with ether. The combined organic extract was washed with brine, dried (Na$_2$SO$_4$), filtered and concentrated. The residue was purified by flash chromatography on silica gel using 2% ethyl acetate in heptane as eluent. Concentration of the appropriate fractions afforded 1.40 g (90% yield) of the title compound as an oil. $^1$H-NMR (300 MHz, CDCl$_3$): δ 0.95 (t, 3H), 1.41 (d, 3H), 1.48 (s, 9H), 1.48-1.66 (m, 4H), 2.05 (m, 4H), 2.83 (m, 8H), 3.35 (m, 1H), 3.55 (m, 1H), 3.79 (q, 1H), 5.32-5.44 (m, 10H).

Example 55: Preparation of 2-((5Z,8Z,11Z,14Z,17Z)-icosa-5,8,11,14,17-pentaenyloxy)propanoic acid

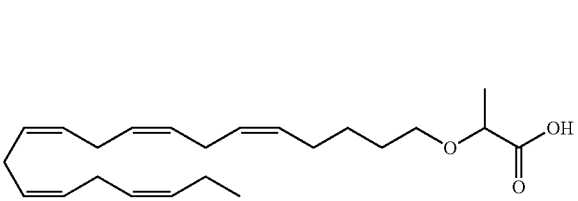 [SMILES: CC/C=C\C/C=C\C/C=C\C/C=C\C/C=C\CCCCOC(C)C(=O)O]

Trifluoroacetic acid (2 mL) was added to a solution of 2-((5Z,8Z,11Z,14Z,17Z)-icosa-5,8,11,14,17-pentaenyloxy)propanoate (1.40 g, 3.36 mmol) in dichloromethane (10 mL) held under nitrogen and the reaction mixture was stirred at room temperature for three hours. Diethyl ether (50 mL) was added and the organic phase was washed with water (30 mL), dried (Na$_2$SO$_4$) and concentrated. The residue was subjected to flash chromatography on silica gel using increasingly polar mixtures of heptane, ethyl acetate and formic acid (95:5:0.25→80:20:1) as eluent. Concentration of the appropriate fractions afforded 0.67 g of slightly impure product. This material was dissolved in heptane (15 mL), washed three times with water (5 mL), dried (Na$_2$SO$_4$), filtered and concentrated to afford 0.50 g (41% yield) of the title compound as an oil. $^1$H-NMR (300 MHz, CDCl$_3$): δ 0.99 (t, 3H), 1.40-1.48 (m, 5H), 1.67 (m, 2H), 2.09 (m, 4H), 2.80-2.60 (m, 8H), 3.53 (m, 2H), 4.01 (q, 1H), 5.31-5.47 (m, 10H); MS (electrospray): 359.2 [M−H]$^-$.

Example 56: Preparation of tert-butyl 2-((5Z,8Z,11Z,14Z,17Z)-icosa-5,8,11,14,17-pentaenyloxy)-2-methylpropanoate

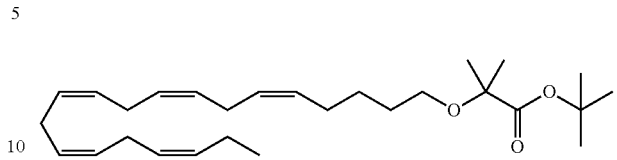

A mixture of (5Z,8Z,11Z,14Z,17Z)-icosa-5,8,11,14,17-pentaen-1-ol, (0.83 g, 3.14 mmol), tetrabutylammonium chloride (0.24 g, 0.85 mmol) and t-butyl 2-bromo isobutyrate (3.50 g, 15.7 mmol) was dissolved in toluene (15 mL) and placed under nitrogen. An aqueous solution of sodium hydroxide (50%, 5 mL) was added slowly under vigorous stirring at room temperature. The resulting mixture was heated to 60° C. and stirred for six hours. The mixture was cooled, added water and extracted three times with ether. The combined organic extract was washed with brine, dried (Na$_2$SO$_4$), filtered and concentrated. The residue was purified by flash chromatography on silica gel using a gradient of 5-10% ethyl acetate in heptane as eluent. Concentration of the appropriate fractions afforded 0.60 g (44% yield) of the title compound as an oil. MS (electrospray): 453.3 [M+Na]$^+$.

Example 57: Preparation of 2-((5Z,8Z,11Z,14Z,17Z)-icosa-5,8,11,14,17-pentaenyloxy)-2-methylpropanoic acid

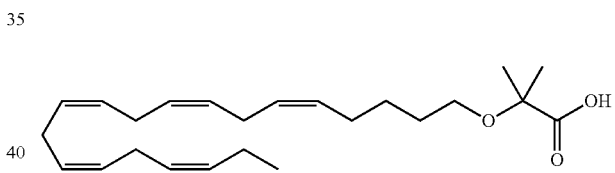

Trifluoroacetic acid (5 mL) was added to a solution of tert-butyl 2-((5Z,8Z,11Z,14Z,17Z)-icosa-5,8,11,14,17-pentaenyloxy)-2-methylpropanoate (600 mg, 1.39 mmol) in dichloromethane (20 mL) under nitrogen and the reaction mixture was stirred at room temperature for two hours. Water was added and the aqueous phase was extracted twice with dichloromethane. The combined organic extract was washed with brine, dried (Na$_2$SO$_4$), filtered and concentrated. The residue was purified by flash chromatography on silica gel using a mixture of heptane, ethyl acetate and formic acid (80:20:1) as eluent. The appropriate fractions were concentrated and the residue (135 mg) was purified further by flash chromatography on silica gel using a gradient of 5-10% of a mixture of ethyl acetate and formic acid (95:5) in heptane as eluent. Concentration of the appropriate fractions afforded 80 mg slightly impure product. This material was dissolved in heptane (5 mL), washed twice with water (5 mL), dried (Na$_2$SO$_4$) and concentrated to afford 40 mg (8% yield) of the title compound as an oil. $^1$H-NMR (300 MHz, CDCl$_3$): δ 0.99 (t, 3H), 1.47 (s, 6H), 1.64 (m, 2H), 2.07 (m, 4H), 2.81-2.88 (m, 8H), 3.46 (t, 2H), 5.29-5.44 (m, 10H); MS (electrospray): 373.3 [M−H]$^-$.

Example 58: Preparation of tert-butyl 2-ethyl-2-((5Z,8Z,11Z,14Z,17Z)-icosa-5,8,11,14,17-pentaen-1-yloxy)butanoate

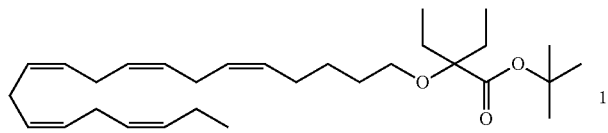

tert-Butyl 2-((5Z,8Z,11Z,14Z,17Z)-icosa-5,8,11,14,17-pentaen-1-yloxy)butanoate (480 mg, 1.11 mmol) was added dropwise over 30 minutes to a solution of lithium diisopropylamine (LDA) (2.0 M, 750 μL, 1.50 mmol) in dry tetrahydrofuran (10 mL) held at −70° C. under nitrogen. The reaction mixture was stirred for 30 minutes. Ethyl iodide (312 mg, 2.00 mmol) was added in one portion and the resulting mixture was warmed to ambient temperature during 1 hour. The reaction mixture was stirred at ambient temperature for 17 hours. The mixture was poured into saturated NH$_4$Cl (aq.) (50 mL) and extracted with heptane (2×50 mL). The combined organic phases was washed successively with brine (50 mL), 0.25 M HCl (50 mL) and brine (50 mL), dried (MgSO$_4$), filtered and concentrated. The residue was purified by flash chromatography on silica gel using increasingly polar mixtures of heptane and ethyl acetate (100:0→95:5) as eluent. Concentration of the appropriate fractions afforded 343 mg (67% yield) of the title compound as an oil. $^1$H NMR (300 MHz, CDCl$_3$): δ 0.84 (t, 6H), 0.99 (td, 3H), 1.35-1.55 (m, 11H), 1.54-1.69 (m, 2H), 1.68-1.87 (m, 4H), 1.99-2.24 (m, 4H), 2.74-2.99 (m, 8H), 3.31 (t, 2H), 5.23-5.52 (m, 10H); MS (electrospray): 401.3 [M−1]$^-$.

Example 59: Preparation of 2-ethyl-2-((5Z,8Z,11Z,14Z,17Z)-icosa-5,8,11,14,17-pentaen-1-yloxy)butanoic acid

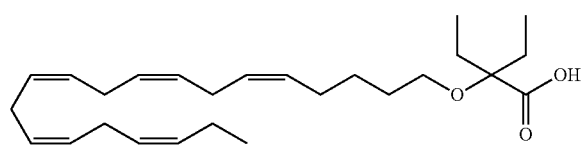 [SMILES: CC/C=C\C/C=C\C/C=C\C/C=C\C/C=C\CCCCOC(CC)(CC)C(=O)O]

A mixture of formic acid (5 ml) and tert-butyl 2-ethyl-2-((5Z,8Z,11Z,14Z,17Z)-icosa-5,8,11,14,17-pentaen-1-yloxy)butanoate (250 mg, 0.55 mmol) was stirred vigorously under nitrogen at room temperature for 4.5 hours. The formic acid was removed in vacuo. The residue was purified by flash chromatography on silica gel using increasingly polar mixtures of heptane and ethyl acetate (100:0→80:20) as eluent. Concentration of the appropriate fractions afforded 163 mg (74% yield) of the title compound as an oil. $^1$H NMR (300 MHz, CDCl$_3$): δ 0.86 (t, 6H), 0.99 (t, 3H), 1.36-1.57 (m, 2H), 1.68 (dd, 2H), 1.73-1.98 (m, 4H), 2.11 (tt, 4H), 2.70-3.01 (m, 8H), 3.39 (t, 2H), 5.20-5.56 (m, 10H). MS (electrospray): 481.4 [M+Na]$^+$.

Example 60: Preparation of tert-butyl 2-(((3Z,6Z,9Z,12Z)-pentadeca-3,6,9,12-tetraen-1-yl)oxy)butanoate Step a) (8Z,11Z,14Z,17Z)-5,6-dihydroxyicosa-8,11,14,17-tetraenoic acid

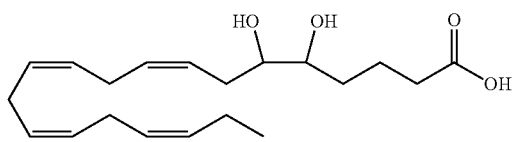 [SMILES: CC/C=C\C/C=C\C/C=C\C/C=C\CC(O)C(O)CCCC(=O)O]

A solution 6-((3Z,6Z,9Z,12Z)-1-iodopentadeca-3,6,9,12-tetraen-1-yl)tetrahydro-2H-pyran-2-one (12.5 g, 29.2 mmol) and KOH (5.73 g, 102 mmol) in a mixture of MeOH (150 mL) and Water (7.5 mL) was stirred at 60° C. under nitrogen for 4 hours. The reaction mixture was cooled to room temperature, acidified with 2 M HCl (aq.) and extracted with EtOAc (300 mL). The organic layer was washed with water (300 mL with some brine), dried (Na$_2$SO$_4$), filtered and concentrated in vacuo afforded 9.8 gram (100% yield) as an oil.

Step b) (3Z,6Z,9Z,12Z)-pentadeca-3,6,9,12-tetraen-1-ol

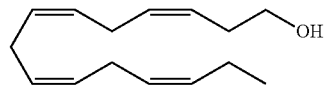 [SMILES: CC/C=C\C/C=C\C/C=C\C/C=C\CCO]

Sodium periodate (9.34 g, 43.7 mmol) was added to a solution of (8Z,11Z,14Z,17Z)-5,6-dihydroxyicosa-8,11,14,17-tetraenoic acid (9.8 g, 29.1 mmol) in THF:Water (150 mL) at 0° C. under nitrogen and stirred for 1 hour. The reaction mixture was extracted with EtOAc (300 mL). The organic layer separated and washed with diluted brine (200 mL), dried (Na$_2$SO$_4$), filtered and concentrated in vacuo. The residue was dissolved in MeOH (100 ml) and cooled to 0° C. NaBH$_4$ (3.31 g, 87 mmol) was carefully added in portions and the mixture was stirred for 30 minutes at 0° C. Water (300 mL) was added carefully and the mixture extracted with EtOAc (2'200 mL). The organic phases were combined and washed with water (200 mL), dried (Na2SO4), filtered and concentrated in vacuo. The residue was purified by flash chromatography on silica gel using 20% ethyl acetate in heptane as eluent. Concentration of the appropriate fractions afforded 4.06 g (63% yield) of the title compound as an oil.

1H NMR (400 MHz, CDCl3) δ 0.91 (t, 3H), 1.97-2.05 (m, 2H), 2.27-2.32 (m, 2H), 2.73-2.81 (m, 6H), 3.57-3.62 (m, 2H), 5.17-5.41 (m, 7H), 5.42-5.56 (m, 1H).

Step c) tert-butyl 2-(((3Z,6Z,9Z,12Z)-pentadeca-3,6,9,12-tetraen-1-yl)oxy)butanoate

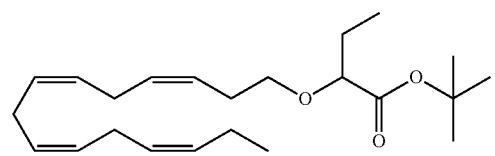 [SMILES: CC/C=C\C/C=C\C/C=C\C/C=C\CCOC(CC)C(=O)OC(C)(C)C]

Tetrabutyl ammonium chloride (0.10 g, 0.33 mmol) was added to a solution of ((3Z,6Z,9Z,12Z)-pentadeca-3,6,9,12-tetraen-1-ol (0.22 g, 1.00 mmol) in toluene (10 ml) at ambient temperature under nitrogen, followed by and t-butyl 2-bromobutyrate (1.11 g, 5.00 mmol). An aqeous solution of sodium hydroxide (50% (w/w), 4 mL) was added under vigorous stirring at room temperature. The resulting mixture was heated to 50° C. and stirred for two hours followed by stirring at ambient temperature over night. After cooling to room temperature, water was added and the aqueous phase extracted with diethylether. The phases were seprarated and water phase extracted two more times with diethylether. The organic phases were combined and washed with water followed by brine, before dried (Na$_2$SO$_4$), filtered and concentrated in vacuo. The residue was purified by flash chromatography on silica gel using 5% ethyl acetate in heptane as eluent. Concentration of the appropriate fractions afforded 0.30 g (83%) of the title compound as an oil.

Example 61: Preparation of 2-(((3Z,6Z,9Z,12Z)-pentadeca-3,6,9,12-tetraen-1-yl)oxy)butanoic acid

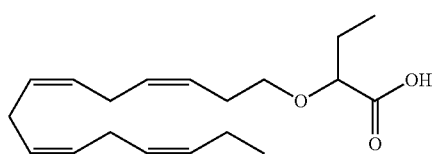 [SMILES: CC/C=C\C/C=C\C/C=C\C/C=C\CCOC(CC)C(=O)O]

Trifluoro acetic acid (2 ml) was added to a solution tert-butyl 2-(((3Z,6Z,9Z,12Z)-pentadeca-3,6,9,12-tetraen-1-yl)oxy)butanoate in dichloromethane (10 mL) under nitrogen. The reaction mixture was stirred at room temperature for one hour before water was added and the aqueous phase extracted twice with dichlormethane. The organic phases were combined and washed with brine, dried (Na$_2$SO$_4$), filtered and concentrated in vacuo. The residue was purified by flash chromatography on silica gel using 5% ethyl acetate in heptane (added 1% HCOOH) as eluent. Concentration of the appropriate fractions afforded 0.18 g (71% yield) of the title compound as an oil. $^1$H-NMR (300 MHz, CDCl$_3$): δ 0.90-1.05 (2×t, 6H), 1.75-1.90 (m, 2H), 2.05-2.15 (m, 2H), 2.30-2.50 (m, 2H), 2.85 (m, 6H), 3.60 (m, 2H), 3.85 (t, 1H), 5.25-5.60 (m, 8H).

Example 62: Preparation of 2-(((5Z,8Z,11Z,14Z,17Z)-nonadeca-5,8,11,14,17-pentaen-1-yl)oxy)butanoic acid

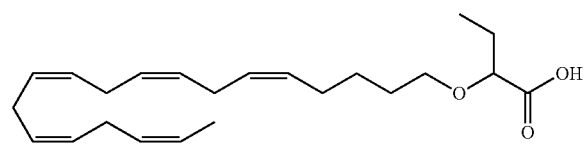 [SMILES: C/C=C\C/C=C\C/C=C\C/C=C\C/C=C\CCCCOC(CC)C(=O)O]

Step 1

A solution of deca-2,5,8-triyn-1-ol (0.94 g, 6.43 mmol) in THF (100 ml) cooled to 0° C. under nitrogen, was added to methanesulfonyl chloride (720 µL, 9.24 mmol), followed by dropwise addition of TEA (1.97 mL, 14.13 mmol) over 15 minutes. The mixture was stirred at 0° C. for 2 hours. The mixture was then poured into water:ice 1:1 (200 gram), and extracted with diethyl ether (2×100). The combined organic layer was washed with sat. (aq.) NaHCO$_3$ (200 mL), water (200 mL) and brine (200 mL), dried (Na2SO4), filtered and evaporated in vacuo to give a crude product that was further purified by dry-flash on silica gel. Fractions 1-3 were collected using heptane, fractions 4-6 using EtOAc:heptane 2.5:100, fractions 7-10 using EtOAc:heptane 5:100 and fraction 11 using EtOAc. The appropriate fractions were pooled and concentrated to give 1.07 g (4.77 mmol, 74.1% yield) of nona-2,5,7-triyn-1-yl methanesulfonate.

Step 2

To an ambient solution of ethyl magnesium bromide (4.00 mL, 12.00 mmol) diluted with dry THF (25 mL), was added portion wise a solution of propargyl alcohol (0.35 mL, 5.99 mmol) during 20 minutes. The reaction mixture was refluxed for 90 minutes, before cooled down to 0° C. during 30 minutes. A catalytic amount of bromo(dimethylsulfide) copper(I) (330 mg, 1.605 mmol) was added and the cooling bath was removed. After 15 minutes stirring, nona-2,5,7-triyn-1-yl methanesulfonate (1.05 g, 4.68 mmol) dissolved in THF (5 ml) by heating, was added dropwise over 5 minutes. The reaction mixture was heated to reflux and stirred at reflux over night. The reaction was cooled to ambient temperature and quenched by careful addition of 50 mL sat. aq. NH4Cl. The resulting mixture was transferred to a separating funnel containing diethyl ether (100 mL). The organic phase was separated and the water phase was extracted twice with diethyl ether (2×100 mL). The combined organic phase was washed with brine (50 mL) and dried (Na2SO4). The residue was concentrated in vacuo before purified by flash chromatography on silica gel. The appropriate fractions were pooled and concentrated to give 0.49 g (2.65 mmol, 56.6% yield) of dodeca-2,5,8,10-tetrayn-1-ol.

Step 3

A solution of dodeca-2,5,8,10-tetrayn-1-ol (465 mg, 2.52 mmol) in THF (30 ml) cooled to 0° C. under nitrogen, was added methanesulfonyl chloride (0.256 ml, 3.28 mmol), followed by dropwise addition of TEA (0.704 ml, 5.05 mmol) over 15 minutes. The mixture was stirred at 0° C. for 1 hours. The mixture was then poured into water:ice 1:1 (100 gram), and extracted with diethyl ether (2×100 mL). The combined organic layer was washed with sat. (aq.) NaHCO$_3$ (200 mL), water (200 mL) and brine (200 mL), dried (Na2SO4), filtered and evaporated in vacuo to give 622 mg of crude product that was further purified by dry-flash. Fractions 1-3 was collected from using heptane, fractions 4-6 using EtOAc:heptane 2.5:100, fractions 7-10 using EtOAc:heptane 5:100 and fraction 11 using EtOAc. The appropriate fractions were pooled and concentrated to give 466 mg (1.78 mmol, 70.4% yield) of trideca-2,5,8,11-tetrayn-1-yl methanesulfonate.

Step 4

To a solution/suspension of cesium carbonate (553 mg, 1.696 mmol), sodium iodide (280 mg, 1.866 mmol) and copper(I) iodide (323 mg, 1.696 mmol) in DMF (dry) (15 ml) was added ethyl hex-5-ynoate (262 mg, 1.866 mmol) in DMF (dry) (5 ml). The mixture was stirred at room temperature under nitrogen atmosphere for 40 minutes. Trideca-2,5,8,11-tetrayn-1-yl methanesulfonate (445 mg, 1.696 mmol) in DMF (dry) (5 ml) was added and the mixture was stirred at room temperature for overnight. Saturated NH4Cl (200 ml) was added and the mixture was extracted with EtOAc:Heptane (1:1, 3×150 ml). The combined organic phase was washed with brine (200 ml), dried (MgSO4), filtered and concentrated in vacuo. The residue was purification by flash chromatography on silica gel using increasingly polar mixtures of heptane and ethyl acetate as eluent, starting with a solution of 2% EtOAc in heptane. The appropriate fractions were pooled and concentrated to give 51 mg (0.166 mmol, 9.8% yield) of ethyl nonadeca-5,8,11,14,17-pentaynoate.

Step 5

A solution of ethyl nonadeca-5,8,11,14,17-pentaynoate (60 mg, 0.196 mmol) in heptane (10 ml) and toluene (15 mL) was bubbled with N2-gass before quinoline (10 µL, 0.084 mmol) and Lindlar Catalyst (50 mg, 0.023 mmol) was added under N2-atmosphere. The suspension was stirred under H2 atmosphere (1 atm) for 15 hrs. The reaction mixture was filtered through Celite and evaporated in vacuo. The crude material was purified by flash chromatography on silica gel using a mixture of 2% EtOAc in heptane as eluent. The appropriate fractions were pooled and concentrated to give (5Z,8Z,11Z,14Z,17Z)-ethyl nonadeca-5,8,11,14,17-pentaenoate (24.6 mg, 0.078 mmol, 39.7% yield) as an oil. 1H NMR (400 MHz, Chloroform-d) δ 1.27 (t, 2H), 1.59-1.70 (m, 2H), 1.72 (s, OH), 2.31 (d, 1H), 2.72-2.95 (m, 3H), 4.15 (d, 1H), 5.40 (dq, 4H).

Step 6

To a solution of (5Z,8Z,11Z,14Z,17Z)-ethyl nonadeca-5,8,11,14,17-pentaenoate (22 mg, 0.070 mmol) in tetrahydrofuran (5 ml), cooled at 0° C. was added LAH (8 mg, 0.211 mmol) in one portion. The reaction mixture was stirred 30 minutes at 0° C., before 90 minutes at ambient. Reaction mixture poured into sat. NH4Cl (aq.) (10 mL) and ice (10 g) and mixture acidified using 10% HCl (aq.) to pH ~1-2. The mixture was extracted with Et2O (25 ml) twice, and the combined organic layers were washed with water (25 mL) and brine (25 mL), before dried (MgSO4), filtered and concentrated in vacuo to afford (5Z,8Z,11Z,14Z,17Z)-nonadeca-5,8,11,14,17-pentaen-1-ol (15.5 mg, 0.056 mmol, 81% yield) as an oil.

Step 7

2-Bromobutyric acid (100 mg, 0.599 mmol) was added to a solution of (5Z,8Z,11Z,14 Z,17Z)-nonadeca-5,8,11,14,17-pentaen-1-ol (8 mg, 0.029 mmol) in tetrahydrofuran (10 ml). The mixture was cooled to 5° C., before a 17% (w/w) solution of sodium tert-butoxide (500 µl, 0.678 mmol) in tert-butyl methyl ether (30 ml) was added dropwise over 5 minutes. After 3 hours, additional sodium tert-butoxide (100 µL 0.136 mmol) was added and the reaction mixture was stirred for another 3 hours. The reaction was quenched by the addition of formic acid (0.100 ml, 2.61 mmol) and water (10 ml) and the resulting mixture was extracted with tert-butyl methyl ether (30 ml). The organic phase was washed four times with water (4×10 ml), dried (MgSO4), filtered and evaporated in vacuo. The concentrate was dissolved in Me-THF (50 ml) and wash with sat. aq. NH4Cl (20 ml) four times. The organic phase was dried (MgSO4), filtered and evaporated in vacuo to give 2-(((5Z,8Z,11Z,14Z,17Z)-nonadeca-5,8,11,14,17-pentaen-1-yl)oxy)butanoic acid (6 mg, 0.017 mmol, 57.1%) as an oil. HRMS (electrospray), [M−H]⁻: Calculated: 359.2586, found: 359.2578.

Example 63: Preparation of 2-(((6Z,9Z,12Z,15Z)-octadeca-6,9,12,15-tetraen-1-yl)oxy)butanoic acid

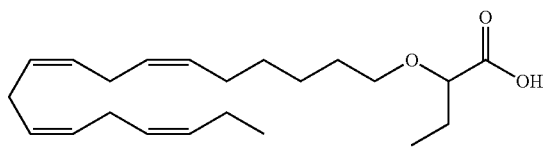 [SMILES: CC/C=C\C/C=C\C/C=C\C/C=C\CCCCCOC(CC)C(=O)O]

To a solution of (6Z,9Z,12Z,15Z)-octadeca-6,9,12,15-tetraen-1-ol (90 mg, 0.343 mmol) in toluene (3 mL) was added tetrabutylammonium hydroxide (TBAOH) (2 mg, 0.008 mmol), tert-butyl 2-bromobutanoate (190 mg, 0.819 mmol) and NaOH (50 w/w %, 1 mL) and the mixture was stirred for 3 hours at 45° C. To the reaction mixture was added more tert-butyl 2-bromobutanoate (190 mg, 0.819 mmol) and the reaction mixture was stirred for 24 hours at 45° C. The mixture was cooled to room temperature and extracted twice with Et2O (2×30 mL). The combined organic extracts were washed with water (3×25 mL) and brine (25 mL), filtered and evaporated in vacuo to give the crude product of tert-butyl 2-(((6Z,9Z,12Z,15Z)-octadeca-6,9,12,15-tetraen-1-yl)oxy)butanoate. The crude product of tert-butyl 2-(((6Z,9Z,12Z,15Z)-octadeca-6,9,12,15-tetraen-1-yl)oxy)butanoate was dissolved in formic acid (FA)(5 mL) and the resulting solution was stirred at RT for 3 h. The mixture was concentrated under vacuo at 25° C. and the residue was dissolved in EtOAc (30 mL). The solution was washed with water (4×25 mL), diluted with EtOAc (20 mL) and dried (MgSO4). The solvent was removed under vacuo and the crude product was purified by flash chromatography on silica gel using increasingly polar mixtures of heptane and acetone (1:0→5:1) as eluent. The fractions were pooled and evaporated under vacuo. The residue was dissolved in FA (5 mL) and stirred at RT for 3 h before the solvent was evaporated under vacuo. The residue was added EtOAc (30 mL), washed with water (4×25 mL), brine (25 mL), dried (MgSO4) and evaporated under vacuo. The residue was purified by preparative HPLC using 85% MeCN in water as eluent. The appropriate fractions were pooled and concentrated. The residue was dissolved in EtOAc, dried (MgSO4), filtered and concentrated under vacuo. The product was dissolved in Et2O and concentrated under vacuo to give 10 mg (8% yield) of the title compound. 1H NMR (400 MHz, CDCl3) δ 1.09-0.81 (m, 6H), 1.41 (dt, 4H), 1.67 (d, 2H), 1.97-1.74 (m, 2H), 2.10 (t, 4H), 2.84 (q, 6H), 3.55-3.42 (m, 1H), 3.65-3.54 (m, 1H), 3.88 (dd, 4.8 Hz, 1H), 5.53-5.25 (m, 8H). HRMS (electrospray), [M−H]⁻: Calculated: 347.2592, found: 347.2576.

Example 64: Preparation of 2-(((4Z,7Z,10Z,13Z,16Z)-nonadeca-4,7,10,13,16-pentaen-1-yl)oxy)butanoic acid

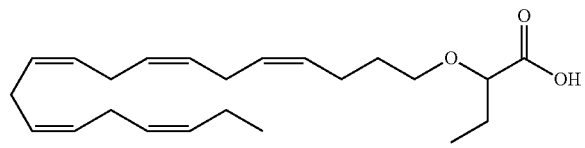 [SMILES: CC/C=C\C/C=C\C/C=C\C/C=C\C/C=C\CCCOC(CC)C(=O)O]

Step 1

To a solution of (4Z,7Z,10Z,13Z,16Z)-nonadeca-4,7,10,13,16-pentaen-1-ol (446 mg, 1.625 mmol) and tert-butyl 2-bromobutyrate (501 mg, 2.246 mmol) in toluene (5 ml) was added tetrabutylammonium hydrogen sulphate (102 mg, 0.300 mmol). Sodium hydroxide (2.5 mL, 46.9 mmol) was added under stirring, and the reaction was warmed directly to 50° C. After 1-hour, extra tert-butyl 2-bromobutyrate (533 mg, 2.389 mmol) was added, and the reaction was left for 3 more hours before being cooled under stirring overnight. Et2O (50 mL) was added and an emulation was formed. Saturated NH4Cl (aq.) (50 mL) was added and the mixture was shaken. The phases were separated, and the water phase was extracted with Et2O (50 mL). The combined organic phase was washed with 5% w/w of NaOH (aq.) (2×50 mL), dried (MgSO4), filtered and evaporated. The residue was dried on a vacuum line for 5 days, before diluted with heptane (1 mL) and purified by dry-flash using silica gel (5 gram), eluting with: 2×50 mL heptane followed by 6×50 mL of mixture of Heptane:EtOAc (95:5) in a total of 8 fractions. Fraction 3-4 collected to give tert-butyl 2-((4Z,7Z,10Z,13Z,16Z)-nonadeca-4,7,10,13,16-pentaenyloxy)butanoate (455 mg, 1.092 mmol, 67.2% yield) after evaporation. 1H NMR (300 MHz, Chloroform-d) δ 0.98 (td, 6H), 1.49 (s, 9H), 1.57-1.84 (m, 4H), 2.00-2.28 (m, 4H), 2.74-2.94 (m, 8H), 3.33 (dt, 1H), 3.50-3.70 (m, 2H), 5.24-5.50 (m, 10H).

Step 2

A mixture of tert-butyl 2-((4Z,7Z,10Z,13Z,16Z)-nonadeca-4,7,10,13,16-pentaenyloxy)butanoate (373 mg, 0.895 mmol) in HCOOH (10 mL) was stirred vigorously for 2.5 hrs. The mixture was concentrated after total 3 hours reaction time, diluted with Ethyl acetate (50 mL) and washed with water (3×50 mL) to give neutral pH in water phase. Organic phase dried (MgSO4), filtered and concentrated in vacuo. Purification by dry-flash using silica gel (8 g) and eluting with Heptane:EtoAc 90:10 (3×30 mL), followed by 80:20 (7×50 mL). Fraction 4-6 collected and concentrated in vacuo to afford 2-((4Z,7Z,10Z,13Z,16Z)-nonadeca-4,7,10,13,16-pentaenyloxy)butanoic acid (122 mg, 0.338 mmol, 37.8% yield). 1H NMR (300 MHz, Chloroform-d) δ 1.00 (td, 2.6 Hz, 6H), 1.62-1.79 (m, 2H), 1.79-1.92 (m, 2H), 1.99-2.13 (m, 2H), 2.19 (dd, 2H), 2.85 (dtd, 8H), 3.47-3.67 (m, 2H), 3.88 (dd, 1H), 5.31-5.47 (m, 10H). HRMS (electrospray), [M–H]⁻: Calculated: 359.2586, found: 359.2590.

Example 65: Preparation of 2-(((8Z,11Z,14Z)-octadeca-8,11,14,17-tetraen-1-yl)oxy)butanoic acid

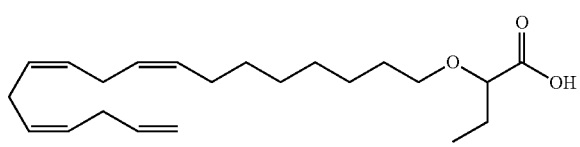

Step 1

To a solution of Cesium carbonate (2.67 g, 8.20 mmol), NaI (1.23 g, 8.20 mmol) and copper(I)iodide (1.56 g, 8.20 mmol) in DMF (20 ml) was added methyl non-8-ynoate (1.38 g, 8.20 mmol) in DMF (5 ml). The mixture was stirred at room temperature under nitrogen atmosphere for 40 minutes. Nona-8-en-2,5-diyn-1-yl methanesulfonate (1.74 g, 8.20 mmol) in DMF (5 ml) was added and the mixture was stirred at room temperature overnight. Saturated NH4Cl (200 ml) was added and the mixture was extracted with EtOAc:heptane (1:1, 3×150 ml). The combined organic phase was washed with brine (100 ml), dried (Na2SO4), filtered and concentrated in vacuo. Flash chromatography (heptane/EtOAc 92/8) afforded methyl octadeca-17-en-8,11,14-triynoate (1.43 g, 5.03 mmol, 61.3% yield) as an oil. 1H NMR (400 MHz, CDCl3) δ 5.80-5.67 (m, 1H), 5.29-5.18 (m, 1H), 5.08-4.99 (m, 1H), 3.60 (s, 3H), 3.15-3.09 (m, 2H), 3.09-3.05 (m, 2H), 2.93-2.85 (m, 2H), 2.24 (t, 2H), 2.11-2.05 (m, 2H), 1.60-1.52 (m, 2H), 1.46-1.38 (m, 2H), 1.35-1.23 (m, 4H). MS (electrospray): 307.1 [M+Na]+.

Step 2

A suspension of Lindlar Catalyst (1.063 g, 0.499 mmol) in heptane (15 ml) under N2-atmosphere was added to quinoline (0.177 ml, 1.498 mmol) and a solution of methyl octadeca-17-en-8,11,14-triynoate (1.42 g, 4.99 mmol) in heptane (5 ml). The mixture was stirred under H2 atmosphere (1 atm) overnight. The mixture was filtered and concentrated in vacuo. Flash chromatography (heptane/EtOAc 98.5/1.5) afforded (8Z,11Z,14Z)-methyl octadeca-8,11,14,17-tetraenoate (0.830 g, 2.86 mmol, 57.2% yield) as an oil. 1H NMR (400 MHz, CDCl3) δ 5.84-5.65 (m, 1H), 5.43-5.19 (m, 6H), 5.05-4.85 (m, 2H), 3.60 (s, 3H), 2.81-2.68 (m, 6H), 2.23 (t, 2H), 2.02-1.92 (m, 2H), 1.59-1.52 (m, 2H), 1.34-1.18 (m, 6H). MS (electrospray): 313.2 [M+Na]+.

Step 3

A solution of (8Z,11Z,14Z)-methyl octadeca-8,11,14,17-tetraenoate (830 mg, 2.86 mmol) in THF (2 ml) was added dropwise to a cooled (0° C.) suspension of LAH (114 mg, 3.00 mmol) in THF (10 ml) under N2-atmosphere. The mixture was stirred for 40 minutes at 0° C. and poured carefully into cold saturated NH4Cl (20 mL). The aqueous layer was acidified with HCl (2M) to pH-2. The phases were separated, and the aqueous phase was extracted with heptane (3×20 ml). The combined organic phase was washed with brine (20 mL), dried (Na2SO4), filtered and concentrated in vacuo to afford (8Z,11Z,14Z)-octadeca-8,11,14,17-tetraen-1-ol (730 mg, 2.78 mmol, 97% yield) as an oil. 1H NMR (400 MHz, CDCl3) δ 5.84-5.66 (m, 1H), 5.43-5.20 (m, 6H), 5.03-4.82 (m, 2H), 3.57 (t, 2H), 2.84-2.62 (m, 6H), 2.06-1.90 (m, 4H), 1.58-1.42 (m, 3H), 1.33-1.20 (m, 6H). MS (electrospray): 285.1 [M+Na]⁺.

Step 4

A solution of NaOH (2 ml, 37.9 mmol) was slowly added to a vigorously stirred solution of (8Z,11Z,14Z)-octadeca-8,11,14,17-tetraen-1-ol (720 mg, 2.74 mmol), tert-butyl 2-bromobutanoate (918 mg, 4.12 mmol) and tetrabutylammonium hydrogen sulphate (279 mg, 0.823 mmol) in toluene (8 ml) under N2-atmosphere. The mixture was heated at 40° C. overnight. Additional tert-butyl 2-bromobutanoate (306 mg, 1.372 mmol) was added twice after 5 hours and 24 hours. After 48 hours the mixture was cooled to 5-10° C. and saturated NH4Cl (20 ml) was added. The phases were separated, and the aqueous phase was extracted with EtOAc (50 ml). The combined organic phase was dried (Na2SO4), filtered and concentrated in vacuo. Flash chromatography (heptane/EtOAc 99/1) afforded tert-butyl 2-(((8Z,11Z,14Z)- octadeca-8,11,14,17-tetraen-1-yl)oxy)butanoate (675 mg, 1.668 mmol, 60.8% yield) as an oil. 1H NMR (400 MHz, CDCl3) δ 5.86-5.65 (m, 1H), 5.41-5.21 (m, 6H), 5.04-4.83 (m, 2H), 3.57-3.46 (m, 2H), 3.30-3.19 (m, 1H), 2.81-2.68 (m, 6H), 2.02-1.89 (m, 4H), 1.71-1.60 (m, 2H), 1.54-1.50 (m, 2H), 1.41 (s, 12H), 1.32-1.20 (m, 8H), 0.89 (t, 3H).

Step 5

A solution of tert-butyl 2-(((8Z,11Z,14Z)-octadeca-8,11,14,17-tetraen-1-yl)oxy)butanoate (675 mg, 1.668 mmol) in HCOOH (6.75 ml, 179 mmol) was stirred for 21 hrs at 40° C. under N2-atmosphere. The reaction mixture was evaporated under reduced pressure and purified by prep HPLC eluting with CH3CN:H2O-90:10 with 0.02% HCOOH. The prep-fractions containing pure product was evaporated under reduced pressure to remove the CH3CN. The residue was added tert-butyl methyl ether and brine and the phases were separated. The organic phase was dried (Na2SO4), filtered and evaporated under reduced pressure to afford 2-((8Z,11Z,14Z)-octadeca-8,11,14,17-tetraen-1-yloxy)butanoic acid (163 mg, 0.464 mmol, 27.8% yield) as an oil. 1H NMR (400 MHz, CDCl3) δ 5.89-5.70 (m, 1H), 5.51-5.22 (m, 6H), 5.00 (dd, 2H), 3.84 (t, 1H), 3.62-3.38 (m, 2H), 2.79 (m, 6H), 2.12-1.95 (m, 2H), 1.88-1.75 (m, 2H), 1.64-1.58 (m, 2H), 1.31 (s, 8H), 0.96 (t, 3H). HRMS (electrospray) [M–H]⁻: Calculated: 347.2586, found: 347.2589.

Example 66: Preparation of 2-(((5Z,8Z,11Z,14Z)-nonadeca-5,8,11,14-tetraen-1-yl)oxy)butanoic acid

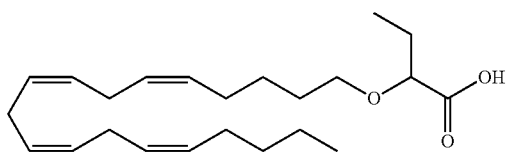 [SMILES: CCCC/C=C\C/C=C\C/C=C\C/C=C\CCCCOC(CC)C(=O)O]

Step 1

A solution of (5Z,8Z,11Z,14Z)-ethyl nonadeca-5,8,11,14-tetraenoate (21 g, 65.9 mmol) in THF (50 ml) was added dropwise over 15 minutes to a cooled (0° C.) suspension of LAH (2.503 g, 65.9 mmol) in dry THF (300 ml) under nitrogen atmosphere. The mixture was stirred for 1 hour at 0° C., and carefully poured into cold saturated NH4Cl (300 mL). The aqueous layer was acidified with HCl (2 M) to pH-2. The phases were separated, and the aqueous phase was extracted with heptane (2×250 mL). The combined organic phase was washed with brine (300 mL), dried (Na2SO4), filtered and concentrated in vacuo to afford (5Z,8Z,11Z,14Z)-nonadeca-5,8,11,14-tetraen-1-ol (17.9 g, 64.7 mmol, 98% yield) as an oil. 1H NMR (300 MHz, CDCl3) δ 5.46-5.11 (m, 8H), 3.68-3.57 (m, 2H), 2.89-2.69 (m, 6H), 2.12-1.98 (m, 4H), 1.62-1.51 (m, 2H), 1.47-1.23 (m, 6H), 0.91-0.85 (m, 3H).

Step 2

To a solution of (5Z,8Z,11Z,14Z)-nonadeca-5,8,11,14-tetraen-1-ol (17.9 g, 64.7 mmol) in THF (350 ml) was added 2-bromobutanoic acid (10.35 ml, 97 mmol). The reaction mixture was cooled to 8-10° C. A solution of sodium-t-butoxide (17.42 g, 181 mmol) (17% in MTBE (120 mL)) was added over 25 minutes while maintaining the temperature between 8-10° C. The reaction was stirred for 30 minutes at 8-10° C. Additional sodium-t-butoxide (2.489 g, 25.9 mmol) (17% in MTBE (25 mL)) was added over 5 minutes. The mixture was stirred for 30 minutes at 8-10° C. followed by addition of 2-bromobutyric acid (6.90 ml, 64.7 mmol) over 5 minutes. The mixture was then stirred at 8-10° C. for 30 minutes. Additional sodium-t-butoxide (4.98 g, 51.8 mmol) (17% in MTBE (40 mL)) was added over 5 minutes. The mixture was stirred for 30 minutes at 8-10° C. Additional sodium-t-butoxide (2.489 g, 25.9 mmol) (17% in MTBE (25 mL)) was added over 5 minutes. The mixture was stirred for 30 minutes at 8-10° C. HCOOH (3 mL) was added followed by 2 M HCl (aq) to give pH~2. The phases were separated, and the aqueous phase was extracted with MTBE (2×300 mL). The combined organic phase was washed with water (300 mL), saturated NaHCO3 (4×200 ml) and brine (300 ml), dried (Na2SO4), filtered and concentrated in vacuo. The residue was purified by flash chromatography (heptane/EtOAc/HCOOH 90/10/0.5) and the appropriate fractions were pooled and concentrated under vacuo. The residue was then purified further by preparative HPLC using 88% MeCN (containing 0.02% HCOOH) in water (containing 10% MeCN and 0.02% HCOOH) as eluent. The solvents were removed to produce 10.16 g of 2-(((5Z,8Z,11Z,14Z)-nonadeca-5,8,11,14-tetraen-1-yl)oxy)butanoic acid (26.8 mmol, 41.5% yield) as an oil. 1H NMR (300 MHz, CDCl3) δ 9.93 (s, 1H), 5.51-5.21 (m, 8H), 3.84-3.80 (m, 1H), 3.62-3.54 (m, 1H), 3.50-3.39 (m, 1H), 2.96-2.61 (m, 6H), 2.12-2.01 (m, 4H), 1.90-1.71 (m, 2H), 1.69-1.57 (m, 2H), 1.49-1.37 (m, 2H), 1.36-1.23 (m, 4H), 0.97 (t, 3H), 0.91-0.84 (m, 3H). MS (electrospray): 361.2 [M–H]–.

Example 67: Preparation of 2-(((8Z,11Z,14Z)-octadeca-8,11,14-trien-1-yl)oxy)butanoic acid

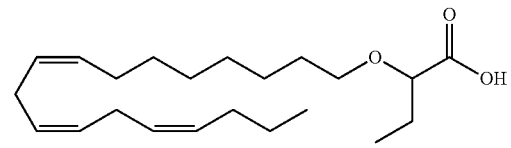 [SMILES: CCC/C=C\C/C=C\C/C=C\CCCCCCCOC(CC)C(=O)O]

Step 1

To a stirred solution of Cs2CO3 (106 g, 326 mmol), sodium iodide (44.8 g, 299 mmol) and copper(I) iodide (56.9 g, 299 mmol) in DMF (750 ml) under nitrogen atmosphere at ambient temperature was added ethyl non-8-ynoate (49.5 g, 272 mmol) followed by 1-bromonona-2,5-diyne (54.1 g, 272 mmol). The mixture was stirred overnight at ambient temperature and poured into saturated NH4Cl (600 mL). The mixture was extracted with MTBE (3×300 mL) and the combined organic phase was washed with brine (400 mL), dried (Na2SO4), filtered and concentrated in vacuo. Flash chromatography (heptane/EtOAc 95/5-92/8-90/10) afforded ethyl octadeca-8,11,14-triynoate (52.8 g, 176 mmol, 64.7% yield) as an oil. 1H NMR (400 MHz, CDCl3) δ 4.09 (q, 2H), 3.15-3.06 (m, 4H), 2.26 (t, 2H), 2.15-2.06 (m, 4H), 1.63-1.56 (m, 2H), 1.53-1.42 (m, 4H), 1.40-1.26 (m, 4H), 1.22 (t, 3H), 0.93 (t, 3H). MS (electrospray): 323.2 [M+Na]⁺.

Step 2

To a stirring solution of Nickelous acetate, 4-hydrate (7.67 ml, 55.4 mmol) in absolute EtOH (150 ml) at room temperature was added solid NaBH4 (2.097 g, 55.4 mmol) under a H2 atmosphere (1 atm). The resulting suspension was stirred for 30 min before ethylenediamine (12.38 ml, 185 mmol) was added. Following complete addition, the suspension was stirred for another 15 min before ethyl octadeca-8,11,14-triynoate (11.1 g, 36.9 mmol) in absolute EtOH (50 ml) was added. The reaction mixture was stirred at room temperature under H2 (1 atm) for 3 nights. Diethyl ether (500 mL) was added to dilute the reaction mixture, and the resulting mixture was then passed through a short silica gel column. The filtrate was concentrated in vacuo. The residue was purified by flash column chromatography (heptane/EtOAc 98/2) to afford ethyl (8Z,11Z,14Z)-octadeca-8,11,14-trienoate (10 g, 32.6 mmol, 88% yield) as an oil. 1H NMR (300 MHz, CDCl3) δ 5.46-5.23 (m, 6H), 4.10 (q, 2H), 2.87-2.67 (m, 3H), 2.26 (t, 2H), 2.07-1.97 (m, 4H), 1.66-1.55 (m, 2H), 1.41-1.18 (m, 11H), 0.91-0.84 (m, 3H).

Step 3

A solution of ethyl (8Z,11Z,14Z)-octadeca-8,11,14-trienoate (24.6 g, 80 mmol) in THF (50 ml) was added drop wise over 15 minutes to a cooled (0° C.) suspension of LAH (3.05 g, 80 mmol) in dry THF (300 ml) under nitrogen. The mixture was stirred for 1 hour at 0° C. The mixture was carefully poured into cold saturated NH4Cl (300 mL). The aqueous layer was acidified with HCl (2 M) to pH-2. The phases were separated, and the aqueous phase was extracted with heptane (2×250 mL). The combined organic phase was washed with brine (300 mL), dried (Na2SO4) and filtered and concentrated in vacuo to afford (8Z,11Z,14Z)-octadeca-8,11,14-trien-1-ol (20.7 g, 78 mmol, 98% yield) as an oil. 1H NMR (300 MHz, CDCl3) δ 5.49-5.23 (m, 6H), 3.61 (t, 2H), 2.86-2.67 (m, 4H), 2.11-1.92 (m, 4H), 1.59-1.49 (m, 2H), 1.43-1.21 (m, 10H), 0.94-0.83 (m, 3H).

Step 4

To a solution of (8Z,11Z,14Z)-octadeca-8,11,14-trien-1-ol (20.7 g, 78 mmol) in THF (350 ml) was added 2-bromobutanoic acid (12.51 ml, 117 mmol). The reaction mixture was cooled to 8-10° C. A solution of sodium-t-butoxide (21.06 g, 219 mmol) (17% in MTBE (130 mL)) was added over 15 minutes, while maintaining the temperature between 8-10° C. The reaction was stirred for 30 minutes at 8-10° C. Additional sodium-t-butoxide (3.01 g, 31.3 mmol) (17% in MTBE (25 mL)) was added over 5 minutes. The mixture was stirred for 30 minutes at 8-10° C. followed by addition of 2-bromobutyric acid (8.34 ml, 78 mmol) over 5 minutes. The mixture was then stirred at 8-10° C. 30 minutes. Additional sodium-t-butoxide (6.02 g, 62.6 mmol) (17% in MTBE (40 mL)) was added over 5 minutes. The mixture was stirred for 30 minutes at 8-10° C. Additional sodium-t-butoxide (3.01 g, 31.3 mmol) (17% in MTBE (25 mL)) was added over 5 minutes. The mixture was stirred for 30 minutes at 8-10° C.

HCOOH (3 mL) was added followed by 2 M HCl (aq) to give pH~2. The phases were separated, and the aqueous phase was extracted with MTBE (2×300 mL). The combined organic phase was washed with water (300 mL), saturated NaHCO$_3$ (4×200 ml) and brine (300 ml), dried (Na2SO4), filtered and concentrated in vacuo. The residue was purified by flash chromatography (heptane/EtOAc/HCOOH 90/10/0.5) and the appropriate fractions were pooled and concentrated under vacuo. The residue was then purified further by preparative HPLC using 88% MeCN (containing 0.02% HCOOH) in water (containing 10% MeCN and 0.02% HCOOH) as eluent. The solvents was removed to produce 10.55 g of 2-(((8Z,11Z,14Z)-octadeca-8,11,14-trien-1-yl)oxy)butanoic acid (28.8 mmol, 36.8% yield) as an oil. 1H NMR (300 MHz, CDCl3) δ 9.70 (s, 1H), 5.47-5.25 (m, 6H), 3.85-3.81 (m, 1H), 3.60-3.52 (m, 1H), 3.49-3.42 (m, 1H), 2.87-2.68 (m, 4H), 2.10-1.94 (m, 4H), 1.89-1.69 (m, 2H), 1.66-1.54 (m, 2H), 1.43-1.24 (m, 10H), 0.96 (t, 3H), 0.89 (t, 3H). MS (electrospray): 349.2 [M−H]−.

Example 68: Preparation of 2-(((9Z,12Z,15Z)-octadeca-9,12,15-trien-1-yl)oxy)butanoic acid

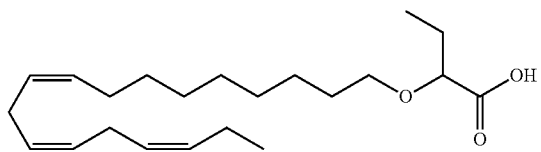 [SMILES: CC/C=C\C/C=C\C/C=C\CCCCCCCCOC(CC)C(=O)O]

To a solution of (9Z,12Z,15Z)-octadeca-9,12,15-trien-1-ol (29.6 g, 112 mmol) in THF (400 ml) was added 2-bromobutanoic acid (17.89 ml, 168 mmol). The reaction mixture was cooled to 8-10° C. A solution of sodium-t-butoxide (30.1 g, 313 mmol) (17% in MTBE (180 mL)) was added over 5 minutes, while maintaining the temperature between 8-10° C. The reaction was stirred for 30 minutes at 8-10° C. Additional sodium-t-butoxide (4.30 g, 44.8 mmol) (17% in MTBE (30 mL)) was added over 5 minutes. The mixture was stirred for 30 minutes at 8-10° C. followed by addition of 2-bromobutyric acid (11.93 ml, 112 mmol) over 5 minutes. The mixture was then stirred at 8-10° C. for 30 minutes. Additional sodium-t-butoxide (8.61 g, 90 mmol) (17% in MTBE (55 mL)) was added over 5 minutes. The mixture was stirred for 30 minutes at 8-10° C. Additional sodium-t-butoxide (4.30 g, 44.8 mmol) (17% in MTBE (30 mL)) was added over 5 minutes. The mixture was stirred for 30 minutes at 8-10° C.

HCOOH (3 mL) was added followed by 2 M HCl (aq) to give pH~2. The phases were separated, and the aqueous phase was extracted with MTBE (2×300 mL). The combined organic phase was washed with water (300 mL), saturated NaHCO$_3$ (4×200 ml) and brine (300 ml), dried (Na2SO4), filtered and concentrated in vacuo. The residue was purified by flash chromatography (heptane/EtOAc/HCOOH 90/10/0.5) on silica gel. The appropriate fractions were pooled and concentrated under vacuo to produce 2-(((9Z,12Z,15Z)-octadeca-9,12,15-trien-1-yl)oxy)butanoic acid (28 g, 78 mmol, 69.9% yield) as an oil. 1H NMR (300 MHz, CDCl3) δ 10.07 (s, 1H), 5.48-5.16 (m, 6H), 3.84-3.80 (m, 1H), 3.60-3.53 (m, 1H), 3.48-3.40 (m, 1H), 2.87-2.70 (m, 4H), 2.12-1.97 (m, 4H), 1.91-1.70 (m, 2H), 1.66-1.53 (m, 2H), 1.38-1.27 (m, 10H), 0.99-0.93 (m, 6H). MS (electrospray): 373.3 [M+Na]+.

Example 69: Preparation of 2-(((6Z,9Z,12Z)-octadeca-6,9,12-trien-1-yl)oxy)butanoic acid

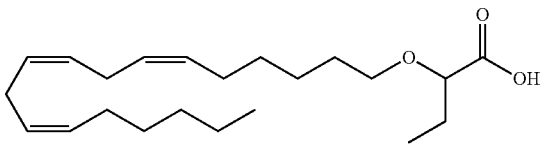 [SMILES: CCCCC/C=C\C/C=C\C/C=C\CCCCCOC(CC)C(=O)O]

To a solution of (6Z,9Z,12Z)-octadeca-6,9,12-trien-1-ol (29.6 g, 112 mmol) in THF (400 ml) was added 2-bromobutanoic acid (17.89 ml, 168 mmol). The reaction mixture was cooled to 8-10° C. A solution of sodium-t-butoxide (30.1 g, 313 mmol) (17% in MTBE (180 mL)) was added over 25 minutes, while maintaining the temperature between 8-10° C. The reaction was stirred for 30 minutes at 8-10° C. Additional sodium-t-butoxide (4.30 g, 44.8 mmol) (17% in MTBE (30 mL)) was added over 5 minutes. The mixture was stirred for 30 minutes at 8-10° C. followed by addition of 2-bromobutyric acid (11.93 ml, 112 mmol) over 5 minutes. The mixture was then stirred at 8-10° C. for 30 minutes. Additional sodium-t-butoxide (8.61 g, 90 mmol) (17% in MTBE (55 mL)) was added over 5 minutes. The mixture was stirred for 30 minutes at 8-10° C. Additional sodium-t-butoxide (4.30 g, 44.8 mmol) (17% in MTBE (30 mL)) was added over 5 minutes. The mixture was stirred for 30 minutes at 8-10° C.

HCOOH (3 mL) was added followed by 2 M HCl (aq) to give pH~2. The phases were separated, and the aqueous phase was extracted with MTBE (2×300 mL). The combined organic phase was washed with water (300 mL), saturated NaHCO$_3$ (4×200 ml) and brine (300 ml), dried (Na2SO4), filtered and concentrated in vacuo. The residue was purified by flash chromatography (heptane/EtOAc/HCOOH 90/10/0.5) on silica gel. The appropriate fractions were pooled and concentrated under vacuo to produce 2-((6Z,9Z,12Z)-octadeca-6,9,12-trien-1-yloxy)butanoic acid (30.2 g, 83 mmol, 74.1% yield) as an oil. 1H NMR (300 MHz, CDCl3) δ 9.56 (s, 1H), 5.46-5.22 (m, 6H), 3.84-3.80 (m, 1H), 3.61-3.54 (m, 1H), 3.47-3.40 (m, 1H), 2.86-2.71 (m, 4H), 2.10-1.99 (m, 4H), 1.91-1.70 (m, 2H), 1.65-1.56 (m, 2H), 1.45-1.18 (m, 10H), 0.97 (t, 3H), 0.87 (t, 3H). MS (electrospray): 373.2 [M+Na]+.

Example 70: Preparation of 2-(((6Z,9Z,12Z,15Z,18Z)-henicosa-6,9,12,15,18-pentaen-1-yl)oxy)butanoic acid

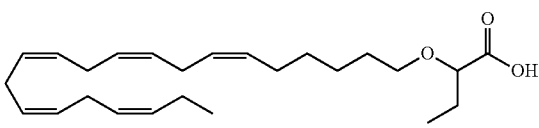 [SMILES: CC/C=C\C/C=C\C/C=C\C/C=C\C/C=C\CCCCCOC(CC)C(=O)O]

To a solution of (6Z,9Z,12Z,15Z,18Z)-henicosa-6,9,12,15,18-pentaen-1-ol (23 g, 76 mmol) in THF (350 ml) was added 2-bromobutanoic acid (12.15 ml, 114 mmol). The reaction mixture was cooled to 8-10° C. A solution of sodium-t-butoxide (20.46 g, 213 mmol) (17% in MTBE (140 mL)) was added over 25 minutes, while maintaining the temperature between 8-10° C. The reaction was stirred for 30 minutes at 8-10° C. Additional sodium-t-butoxide (2.92 g, 30.4 mmol) (17% in MTBE (25 mL)) was added over 5 minutes. The mixture was stirred for 30 minutes at 8-10° C. followed by addition of 2-bromobutyric acid (8.10 ml, 76 mmol) over 5 minutes. The mixture was then stirred at 8-10° C. for 30 minutes. Additional sodium-t-butoxide (5.85 g, 60.8 mmol) (17% in MTBE (45 mL)) was added over 5 minutes. The mixture was stirred for 30 minutes at 8-10° C. Additional sodium-t-butoxide (2.92 g, 30.4 mmol) (17% in MTBE (25 mL)) was added over 5 minutes. The mixture was stirred for 30 minutes at 8-10° C. HCOOH (3 mL) was added followed by 2 M HCl (aq) to give pH~2. The phases were separated, and the aqueous phase was extracted with MTBE (2×300 mL). The combined organic phase was washed with water (300 mL), saturated NaHCO$_3$ (4×200 ml) and brine (300 ml), dried (Na2SO4), filtered and concentrated in vacuo. The residue was purified by flash chromatography (heptane/EtOAc/HCOOH 90/10/0.5) on silica gel. The appropriate fractions were pooled and concentrated under vacuo to produce 2-(((6Z,9Z,12Z,15Z,18Z)-henicosa-6,9,12,15,18-pentaen-1-yl)oxy)butanoic acid (18.9 g, 47.3 mmol, 62.2% yield) as an oil. 1H NMR (300 MHz, CDCl3) δ 9.85 (s, 1H), 5.48-5.21 (m, 10H), 3.84-3.81 (m, 1H), 3.61-3.53 (m, 1H), 3.48-3.41 (m, 1H), 2.93-2.71 (m, 8H), 2.18-1.96 (m, 4H), 1.91-1.70 (m, 2H), 1.66-1.57 (m, 2H), 1.45-1.30 (m, 4H), 0.99-0.93 (m, 6H). MS (electrospray): 411.4 [M+Na]+.

Example 71: Preparation of 2-(((4Z,7Z,10Z,13Z,16Z,19Z)-docosa-4,7,10,13,16,19-hexaen-1-yl)oxy)butanoic acid

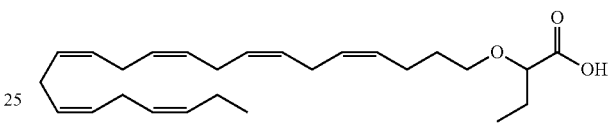

To a solution of (4Z,7Z,10Z,13Z,16Z,19Z)-docosa-4,7,10,13,16,19-hexaen-1-ol (30 g, 95 mmol) in toluene (11 ml) and THF (400 ml) was added 2-bromobutyric acid (17.28 ml, 162 mmol) followed by addition of a solution of sodium-t-butoxide (25.7 g, 267 mmol) in THF (160 ml) during 35 minutes, while maintaining the temperature between 8-10° C. The reaction was stirred for 40 minutes at 8-10° C. Sodium-t-butoxide (4.17 g, 43.4 mmol) in THF (60 ml) was added during 10 minutes. The resulting mixture was stirred at 8-10° C. for 40 minutes, before more 2-bromobutyric acid (10.17 ml, 95 mmol) was added in one portion. The mixture was stirred at 8-10° C. for 1 hour, before more sodium-t-butoxide (7.33 g, 76 mmol) in THF (100 ml) was added during 10 minutes, keeping the temperature below 12° C. The reaction was stirred at 10° C. for 60 minutes. Sodium-t-butoxide (4.17 g, 43.4 mmol) was added in one portion and then stirred for an additional 1 hour. More 2-bromobuttyric acid (8.5 ml, 50 mmol) and sodium-t-butoxide (4.8 g, 50 mmol) were added and the mixture was stirred for 1 hour at 8-10° C. More 2-bromobuttyric acid (8.5 ml, 50 mmol) and sodium-t-butoxide (4.8 g, 50 mmol) were added and the mixture was stirred for 1 hour at 8-10° C. More THF (200 ml) was added and the reaction mixture was stirred at room temperature overnight. More 2-bromobutyric acid (17 ml, 100 mmol) and sodium-t-butoxide (9.6 g, 100 mmol) were added and the reaction mixture was stirred for 1 hour at 8-10° C. To the reaction was then added (1 ml) formic acid and the resulting mixture was stirred at 8-10° C. for 10 minutes, before 6M HCl was added to give pH~2. Water (100 mL) was added and the aqueous phase and the organic phase were separated. The aqueous phase was extracted twice with diethyl ether (2×500 mL). The combined organic phase was washed with water (3×1000 ml), sat. NaHCO$_3$ (3×500 ml) and brine 1×100 ml), dried with Na2SO4, filtered and concentrated in vacuo. The residue was purified by flash chromatography (EtOAc/Heptan/5% HCOOH) (90/10) on silica gel to afford 2-(((4Z,7Z,10Z,13Z,16Z,19Z)-docosa-4,7,10,13,16,19-hexaen-1-yl)oxy)butanoic acid (10.3 g, 25.07 mmol, 26.3% yield) as an oil. 1H NMR (300 MHz, CDCl3) δ 5.49-5.20 (m, 12H), 3.90-3.75

(m, 1H), 3.65-3.52 (m, 1H), 3.51-3.35 (m, 1H), 2.91-2.69 (m, 10H), 2.21-1.98 (m, 4H), 1.91-1.59 (m, 4H), 1.05-0.88 (m, 6H). MS (electrospray): 423.3 [M+Na]+.

Example 72: Preparation of 2-(((8Z,11Z,14Z,17Z)-icosa-8,11,14,17-tetraen-1-yl)oxy)butanoic acid

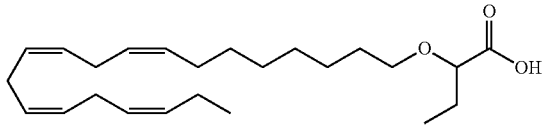 [SMILES: CC/C=C\C/C=C\C/C=C\C/C=C\CCCCCCCOC(CC)C(=O)O]

Step 1

To a heated suspension of magnesium (0.217 g, 8.93 mmol) in THF (3 ml) was added 1,2-dibromoethane (2 drops), followed by drop wise addition of a solution of 2-((5-bromopentyl)oxy)tetrahydro-2H-pyran (2.07 g, 8.24 mmol) in THF (15 ml) under nitrogen atmosphere. The mixture was refluxed for 1 hour and cooled to ambient temperature. A solution of (3Z,6Z,9Z,12Z)-pentadeca-3,6,9,12-tetraenal (1.5 g, 6.87 mmol) in THF (10 ml) was added drop wise and the mixture was stirred for 1 hour at ambient temperature. 1M HCl was added and the mixture was extracted with EtOAc (2×50 mL). The combined organic phase was washed with brine (50 mL), dried (Na2SO4), filtered and concentrated in vacuo. Flash chromatography on silica gel (heptane/EtOAc 80/20-75/25) afforded (8Z,11Z,14Z,17Z)-1-((tetrahydro-2H-pyran-2-yl)oxy)icosa-8,11,14,17-tetraen-6-ol (0.74 g, 1.895 mmol, 27.6% yield) as an oil. 1H NMR (400 MHz, CDCl3) δ 5.59-5.49 (m, 1H), 5.49-5.25 (m, 7H), 4.56-4.53 (m, 1H), 3.88-3.82 (m, 1H), 3.77-3.67 (m, 1H), 3.65-3.59 (m, 1H), 3.52-3.43 (m, 1H), 3.40-3.34 (m, 1H), 2.85-2.77 (m, 6H), 2.23 (t, 2H), 2.13-1.97 (m, 2H), 1.84-1.77 (m, 1H), 1.73-1.67 (m, 1H), 1.63-1.34 (m, 12H), 0.96 (t, 3H). MS (electrospray): 413.3 [M+Na]+.

Step 2

To a solution of (8Z,11Z,14Z,17Z)-1-((tetrahydro-2H-pyran-2-yl)oxy)icosa-8,11,14,17-tetraen-6-ol (0.74 g, 1.895 mmol) in THF (20 ml) was added TEA (0.528 ml, 3.79 mmol) followed by methanesulfonyl chloride (0.192 ml, 2.463 mmol). The mixture was stirred under nitrogen atmosphere for 3 hours at ambient temperature. Citric acid (5%, aq, 50 mL) was added and the mixture was extracted with EtOAc (2×50 mL). The combined organic phase was washed with saturated NaHCO3 (50 mL) and brine (50 mL), dried (Na2SO4), filtered and concentrated in vacuo to afford 0.82 g of the intermediate mesylate. The intermediate mesylate was dissolved in Et2O (10 ml) and added drop wise to a stirred suspension of LAH (0.288 g, 7.58 mmol) in Et2O (25 ml). The mixture was stirred for 1 hour at ambient temperature. 1 M HCl (50 mL) was added carefully. The mixture was extracted with MTBE (2×50 mL). The combined organic phase was washed with saturated NaHCO3 (50 mL) and brine (50 mL), dried (Na2SO4), filtered and concentrated in vacuo. Flash chromatography on silica gel (heptane/EtOAc 97/3) afforded 2-(((8Z,11Z,14Z,17Z)-icosa-8,11,14,17-tetraen-1-yl)oxy)tetrahydro-2H-pyran (0.46 g, 1.228 mmol, 64.8% yield) as an oil. 1H NMR (400 MHz, CDCl3) δ 5.46-5.20 (m, 8H), 4.57-4.54 (m, 1H), 3.88-3.82 (m, 1H), 3.74-3.68 (m, 1H), 3.51-3.44 (m, 1H), 3.39-3.33 (m, 1H), 2.84-2.77 (m, 6H), 2.14-1.96 (m, 4H), 1.85-1.77 (m, 1H), 1.73-1.65 (m, 1H), 1.62-1.46 (m, 6H), 1.37-1.24 (m, 8H), 0.96 (t, 3H). MS (electrospray): 397.3 [M+Na]+.

Step 3

To a solution of 2-(((8Z,11Z,14Z,17Z)-icosa-8,11,14,17-tetraen-1-yl)oxy)tetrahydro-2H-pyran (0.46 g, 1.228 mmol) in EtOH (5 ml) was added pyridinium-p-toluenesufonate (PPTS, 0.309 g, 1.228 mmol) and the mixture was heated at 50° C. for 2 hours. The mixture was cooled to ambient temperature. Saturated NaHCO3 (50 mL) was added and the mixture was extracted with EtOAc (2×50 mL). The combined organic layer was washed with brine (50 mL), dried (Na2SO4), filtered and concentrated in vacuo. Flash chromatography on silica gel (heptane/EtOAc 80/20) afforded (8Z,11Z,14Z,17Z)-icosa-8,11,14,17-tetraen-1-ol (0.26 g, 0.895 mmol, 72.9% yield) as an oil. 1H NMR (400 MHz, CDCl3) δ 5.41-5.17 (m, 8H), 3.57 (t, 2H), 2.84-2.68 (m, 6H), 2.06-1.94 (m, 4H), 1.54-1.46 (m, 2H), 1.34-1.21 (m, 8H), 1.20-1.13 (m, 1H), 0.91 (t, 3H).

Step 4

To a solution of (8Z,11Z,14Z,17Z)-icosa-8,11,14,17-tetraen-1-ol (93 mg, 0.32 mmol) in toluene (3 mL) was added tert-butyl 2-bromobutanoate (143 mg, 0.64 mmol), tetrabutylammonium hydroxide (TBAOH) (5 mg, 0.02 mmol) and NaOH (50 w/w %, 1 mL) and the mixture was heated to 45° C. 71.4 mg (0.32 mmol) tert-butyl 2-bromobutanoate was added to the reaction mixture after 1.5 hours of stirring, 71.4 mg (0.32 mmol) tert-butyl 2-bromobutanoate was added to the reaction mixture after 3 hours and 143 mg (0.64 mmol) tert-butyl 2-bromobutanoate was added to the reaction mixture after 8 hours at 45° C. The mixture was cooled to room temperature after 24 hours and water was added (40 mL). The resulting mixture was extracted twice with Et2O (25+40 mL) and the combined organic extract was washed with water (4×25 mL) and brine (25 mL), dried (MgSO4), filtered and evaporated in vacuo. The residue was purified by flash chromatography on silica gel (heptane→heptatne:acetone-5:1). The appropriate fractions were pooled and concentrated to give 15 mg of tert-butyl 2-(((8Z,11Z,14Z,17Z)-icosa-8,11,14,17-tetraen-1-yl)oxy)butanoate. This intermediate was dissolved in formic acid (5 mL) and the resulting mixture was stirred at RT for 1 hour and 45 min. The solvent was removed under vacuo and to the residue was added EtOAc (30 mL). The solution was washed with water (4×25 mL) and brine (25 mL), dried (MgSO4), filtered and concentrated in vacuo. The residue was purified by preparative HPLC using 85% MeCN in water as eluent. The appropriate fractions were pooled and concentrated to give 15 mg (0.04 mmol, 12% yield) of 2-(((8Z,11Z,14Z,17Z)-icosa-8,11,14,17-tetraen-1-yl)oxy)butanoic acid. 1H NMR (400 MHz, CDCl3) δ 1.00 (td, 6H), 1.49-1.20 (m, 8H), 1.64 (t, 2H), 1.96-1.73 (m, 2H), 2.08 (dt, 4H), 2.84 (q, 6H), 3.55-3.43 (m, 1H), 3.65-3.54 (m, 1H), 3.87 (dd, 1H), 5.49-5.24 (m, 8H). HRMS (electrospray), [M−H]−: Calculated: 375.2899, found: 375.2892.

Example 73: Preparation of 2-(((5Z,8Z,11Z,14Z)-icosa-5,8,11,14-tetraen-1-yl)oxy)butanoic acid

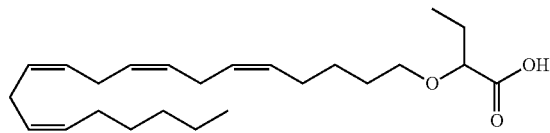 [SMILES: CCCCC/C=C\C/C=C\C/C=C\C/C=C\CCCCOC(CC)C(=O)O]

Step 1

A solution of (5Z,8Z,11Z,14Z)-ethyl icosa-5,8,11,14-tetraenoate (501.9 mg, 1,509 mmol) in dry THF (1 ml) was added drop wise to a cooled (0° C.) suspension of LiAlH4 (64.8 mg, 1.707 mmol) in dry THF (3 ml) under N2-atmosphere. The mixture was stirred for 55 minutes at 0° C. Water (5 ml) was added drop wise and then 1 M HCl (10 ml) was added. The cooling bath was removed, and the reaction mixture was stirred for 5 minutes. The reaction mixture was extracted with tert-butyl methyl ether (2×50 ml), the organic phase was washed with 1 M HCl (20 ml), dried (Na2SO4), filtered and evaporated under reduced pressure to afford (5Z,8Z,11Z,14Z)-icosa-5,8,11,14-tetraen-1-ol (397.7 mg, 1.369 mmol, 91% yield) as a liquid. 1H NMR (400 MHz, CDCl3) δ 5.41-5.29 (m, 8H), 3.63 (t, 2H), 2.83-2.77 (m, 6H), 2.20-1.91 (m, 4H), 1.61-1.54 (m, 2H), 1.46-1.41 (m, 2H), 1.35-1.28 (m, 8H), 0.87 (t, 3H).

Step 2

To a solution of (5Z,8Z,11Z,14Z)-icosa-5,8,11,14-tetraen-1-ol (349 mg, 1.20 mmol) in toluene (5 mL) was added tert-butyl 2-bromobutanoate (535 mg, 2.40 mmol), tetrabutylammonium hydroxide (TBAOH) (156 mg, 0.24 mmol, 40% w/w) and NaOH (50 w/w %, 2 mL) and the mixture was heated to 45° C. The mixture was cooled to room temperature after 12 hours and ice water (25 mL) and Et2O (20 mL) were added. The phases were separated and the aqueous phase was extracted with Et2O (20 mL). The combined organic extract was washed with water (25 mL) and brine (25 mL), dried (MgSO4), filtered and evaporated in vacuo. The residue was dissolved in EtOH (20 mL) and evaporated in vacuo. The residue was purified by flash chromatography on silica gel (heptane:acetone-1:20→heptane:acetone-1:10). The appropriate fractions were pooled and concentrated to give 360 mg (0.83 mmol, 69% yield) of the intermediate tert-butyl 2-(((5Z,8Z,11Z,14Z)-icosa-5,8,11,14-tetraen-1-yl)oxy)butanoate. 342 mg (0.79 mmol) of this intermediate was dissolved in formic acid (7 mL) and the resulting mixture was stirred at RT for 3 hours. The solvent was removed under vacuo and the residue was added to EtOAc (75 mL). The solution was washed with water (3×50 mL), dried (MgSO4), filtered and concentrated in vacuo. The residue was purified by flash chromatography on silica gel (acetone:heptane:HOAc-10:10:1→acetone:heptane:HOAc-30:70:1). The appropriate fractions were pooled and concentrated to give 181 mg (0.48 mmol, 58% yield) of 2-(((5Z,8Z,11Z,14Z)-icosa-5,8,11,14-tetraen-1-yl)oxy)butanoic acid.

Example 74: Preparation of 2-(((7Z,10Z,13Z,16Z,19Z)-docosa-7,10,13,16,19-pentaen-1-yl)oxy)butanoic acid

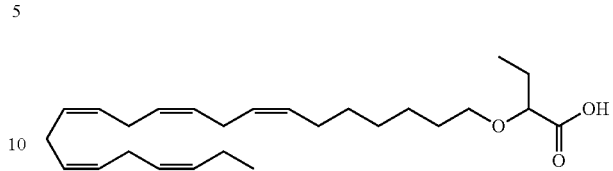

Step 1

A solution of (7Z,10Z,13Z,16Z,19Z)-ethyl docosa-7,10,13,16,19-pentaenoate (1.5 g, 4.18 mmol) in THF (4 ml) was added drop wise to a cooled (0° C.) suspension of LAH (0.159 g, 4.18 mmol) in dry THF (20 ml) under nitrogen. The mixture was stirred for 1 hour at 0° C. The mixture was carefully poured into 1M HCl (100 mL). The phases were separated, and the aqueous phase was extracted with heptane (100 mL). The combined organic phase was washed with brine (30 mL), dried (Na2SO4), filtered and concentrated in vacuo to afford (7Z,10Z,13Z,16Z,19Z)-docosa-7,10,13,16,19-pentaen-1-ol (1.16 g, 3.66 mmol, 88% yield) as an oil. 1H NMR (400 MHz, CDCl3) δ 5.44-5.23 (m, 10H), 3.62 (t, 2H), 2.87-2.73 (m, 8H), 2.10-1.99 (m, 4H), 1.60-1.51 (m, 2H), 1.40-1.29 (m, 6H), 0.95 (t, 3H).

Step 2

To a solution of (7Z,10Z,13Z,16Z,19Z)-docosa-7,10,13,16,19-pentaen-1-ol (1.16 g, 3.66 mmol) in THF (50 ml) was added 2-bromobutanoic acid (0.918 g, 5.50 mmol). The reaction mixture was cooled to 8-10° C. A solution of sodium tert-butoxide (0.986 g, 10.26 mmol) in MTBE (15 mL) was added over 5 minutes. The reaction was stirred for 30 minutes at 8-10° C. Additional sodium tert-butoxide (0.141 g, 1.466 mmol) in MTBE (4 mL) was added. The mixture was stirred for 30 minutes at 8-10° C. followed by addition of 2-bromobutanoic acid (0.612 g, 3.66 mmol) over 5 minutes. The mixture was then stirred at 8-10° C. for 30 minutes. Additional sodium tert-butoxide (0.282 g, 2.93 mmol) in MTBE (8 mL) was added. The mixture was stirred for 30 minutes at 8-10° C. Additional sodium tert-butoxide (0.141 g, 1.466 mmol) in MTBE (4 mL) was added. The mixture was stirred for 30 minutes at 8-10° C. HCOOH (0.5 mL) was added followed by 1 M HCl (aq) to give pH~2. The phases were separated, and the aqueous phase was extracted with MTBE (2×50 mL). The combined organic phase was washed with water (50 mL), saturated NaHCO3 (4×30 ml) and brine (30 ml), dried (Na2SO4), filtered and concentrated in vacuo. Preparative HPLC using 90% MeCN (containing 0.02% HCOOH) in water (containing 10% MeCN and 0.02% HCOOH) as eluent, afforded 2-(((7Z,10Z,13Z,16Z,19Z)-docosa-7,10,13,16,19-pentaen-1-yl)oxy)butanoic acid (1 g, 2.439 mmol, 66.6% yield) as an oil. 1H NMR (400 MHz, CDCl3) δ 5.44-5.24 (m, 10H), 3.84-3.81 (m, 1H), 3.59-3.64 (m, 1H), 3.47-3.41 (m, 1H), 2.90-2.73 (m, 8H), 2.11-1.98 (m, 4H), 1.90-1.71 (m, 2H), 1.64-1.57 (m, 2H), 1.41-1.26 (m, 6H), 0.98-0.93 (m, 6H). HRMS (electrospray), [M]+: Calculated: 402.3134, found: 402.3141.

Example 75: Preparation of (5Z,8Z,11Z,14Z,17Z)-icosa-5,8,11,14,17-pentaen-1-yl 2-(((5Z,8Z,11Z,14Z,17Z)-icosa-5,8,11,14,17-pentaen-1-yl)oxy)butanoate

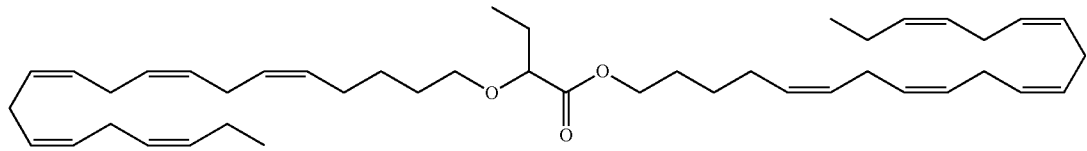 [SMILES: CC/C=C\C/C=C\C/C=C\C/C=C\C/C=C\CCCCOC(=O)C(CC)OCCCC/C=C\C/C=C\C/C=C\C/C=C\C/C=C\CC]

2-((5Z,8Z,11Z,14Z,17Z)-icosa-5,8,11,14,17-pentaen-1-yloxy)butanoic acid (14.28 g, 38.1 mmol) and (5Z,8Z,11Z,14Z,17Z)-icosa-5,8,11,14,17-pentaen-1-ol (10.00 g, 34.7 mmol) was added to a mixture of D(+)-10-camphorsulfonic acid (0.530 g, 2.282 mmol) in cyclohexane (50 mL) and heated to reflux, removing water by Dean-Stark apparatus. The reaction mixture was cooled to room temperature and purified by dry flash chromatography using silica gel (100 g) and eluting with cyclohexane (50 mL), followed by heptane (50 mL), 2% EtOAc in heptane (2×200 mL) and 4% EtOAc in heptane (2×200 mL). The appropriate fractions were pooled and concentrated in vacuo to afford (5Z,8Z,11Z,14Z,17Z)-icosa-5,8,11,14,17-pentaen-1-yl 2-((5Z,8Z,11Z,14Z,17Z)-icosa-5,8,11,14,17-pentaen-1-yloxy)butanoate (20.3 g, 30.5 mmol, 88% yield) as an oil. 1H NMR (300 MHz, Chloroform-d) δ 0.99 (t, 9H), 1.45 (ddd, 4H), 1.56-1.93 (m, 6H), 2.09 (p, 8H), 2.85 (dt, 16H), 3.34 (dt, 1H), 3.60 (dt, 1H), 3.76 (dd, 1H), 4.16 (td, 2H), 5.05-5.76 (m, 20H). MS (electrospray): 645.5 [M+H]+.

Example 76: Preparation of (2R)-2-((2-(((5Z,8Z,11Z,14Z,17Z)-icosa-5,8,11,14,17-pentaen-1-yl)oxy)butanoyl)oxy)butanoic acid

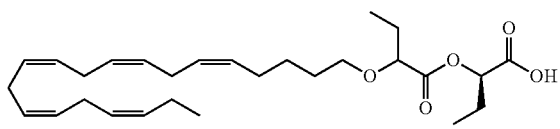 [SMILES: CC/C=C\C/C=C\C/C=C\C/C=C\C/C=C\CCCCOC(CC)C(=O)O[C@H](CC)C(=O)O]

Step 1

To a solution of 2-((5Z,8Z,11Z,14Z,17Z)-icosa-5,8,11,14,17-pentaen-1-yloxy)butanoic acid (400 mg, 1.07 mmol) in CDM (10 mL) was added N-methylmorpholine (235 µL, 2.15 mmol) and TBTU (2-(1H-Benzotriazole-1-yl)-1,1,3,3-tetramethylaminium tetrafluoroborate) (344 mg, 1.07 mmol). The reaction mixture was stirred for 30 min before tert-butyl (R)-2-hydroxybutanoate (250 mg, 2.14 mmol) was added. The resulting mixture was stirred at room temperature for 22 hours and then washed with water (10 mL), 1M HCl (10 mL), saturated NaHCO₃ (10 mL) and brine (10 mL). The organic phase was dried (Na2SO4), filtered and concentrated in vacuo. 161 mg (0.312 mmol, 29.2% yield) of the intermediate (R)-1-(tert-butoxy)-1-oxobutan-2-yl 2-(((5Z,8Z,11Z,14Z,17Z)-icosa-5,8,11,14,17-pentaen-1-yl)oxy)butanoate was isolated as an oil. MS (electrospray): 539.4 [M+Na]+.

Step 2

(R)-1-(tert-butoxy)-1-oxobutan-2-yl 2-(((5Z,8Z,11Z,14Z,17Z)-icosa-5,8,11,14,17-pentaen-1-yl)oxy)butanoate (161 mg, 0.312 mmol) was dissolved in formic acid (4 mL) and the reaction mixture was stirred at room temperature for 17 hours. To the mixture was added EtOAc (10 mL) and the resulting mixture was washed with water (10 mL) and brine (10 mL). The organic phase was dried (Na2SO4), filtered and concentrated in vacuo. 60 mg (0.130 mmol, 41.8% yield) of (2R)-2-((2-(((5Z,8Z,11Z,14Z,17Z)-icosa-5,8,11,14,17-pentaen-1-yl)oxy)butanoyl)oxy)butanoic acid was isolated as an oil. MS (electrospray): 459.3 [M–H]–.

Example 77: Preparation of (2S,3S,4S,5R,6S)-3,4,5-trihydroxy-6-((2-(((5Z,8Z,11Z,14Z,17Z)-icosa-5,8,11,14,17-pentaen-1-yl)oxy)butanoyl)oxy)tetrahydro-2H-pyran-2-carboxylic acid

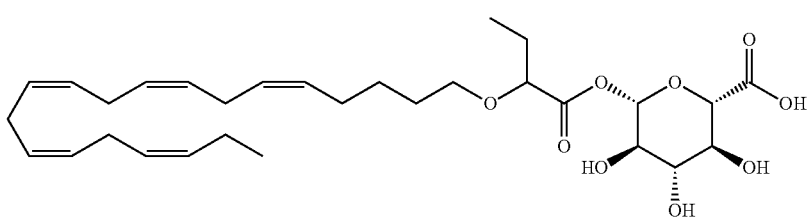 [SMILES: CC/C=C\C/C=C\C/C=C\C/C=C\C/C=C\CCCCOC(CC)C(=O)O[C@@H]1O[C@H](C(=O)O)[C@@H](O)[C@H](O)[C@H]1O]

Step 1

To a mixture of 4-methoxybenzyl (2S,3S,4S,5R,6R)-3,4,5,6-tetrahydroxytetrahydro-2H-pyran-2-carboxylate (2.47 g, 7.86 mmol), 2-(((5Z,8Z,11Z,14Z,17Z)-icosa-5,8,11,14,17-pentaen-1-yl)oxy)butanoic acid (2.94 g, 7.85 mmol) and HATU (1-[Bis(dimethylamino)methylene]-1H-1,2,3-triazolo[4,5-b]pyridinium 3-oxid hexafluorophosphate) (3.00 g, 7.90 mmol) in acetonitrile (85 ml) was added 4-methylmorpholine (1.75 ml, 15.92 mmol). The reaction mixture was stirred for 23.5 hrs under N2-atmosphere at room temperature. Amberlyst-15 (4.7 mEq/g) (3.35 g) was added and the mixture was stirred for approximately 5 minutes. The reaction mixture was filtered and concentrated under reduced pressure and the residue was purified by flash chromatography on silica gel eluting with CH2Cl2-CH2Cl2:EtOH (95:5). The appropriate fractions were pooled and concentrated in vacuo to give 2.64 g of an impure mixture. The residue was purified by flash chromatography on silica gel eluting with CH2Cl2-CH2Cl2:EtOH (95:5) and then CH2Cl2-CH2Cl2:EtOH (97:3). The appropriate fractions were pooled and concentrated in vacuo to give the intermediate (4-methoxycyclohexyl)methyl (2S,3S,4S,5R,6S)-3,4,5-trihydroxy-6-((2-(((5Z,8Z,11Z,14Z,17Z)-icosa-5,8,11,14,17-pentaen-1-yl)oxy)butanoyl)oxy)tetrahydro-2H-pyran-2-carboxylate (1.27 g, 1.78 mmol, 22.4% yield) as an oil. 1H NMR (400 MHz, CDCl3) δ 7.26-7.22 (m, 2H), 6.83-6.81 (m, 2H), 5.60-5.57 (m, 1H), 5.40-5.26 (m, 10H), 5.12-5.10 (m, 2H), 4.60-4.56 (m, 1H), 4.14-4.13 (m, 1H), 3.98 (t, 1H), 3.93-3.67 (m, 3H), 3.74 (s, 3H), 3.61-3.56 (m, 3H), 3.31-3.25 (m, 1H), 2.82-2.77 (m, 8H), 2.07-2.02 (m, 4H), 1.80-1.67 (m, 2H), 1.57-1.54 (s, 2H), 1.43-1.36 (m, 2H), 1.05-0.77 (m, 6H). MS (electrospray): 693.4 [M+Na]+.

Step 2

(4-Methoxycyclohexyl)methyl (2S,3S,4S,5R,6S)-3,4,5-trihydroxy-6-((2-(((5Z,8Z,11Z,14Z,17Z)-icosa-5,8,11,14,17-pentaen-1-yl)oxy)butanoyl)oxy)tetrahydro-2H-pyran-2-carboxylate (1.20 g, 1.79 mmol) was treated with a solution of 10% TFA in DCM (8 mL) at 0° C. under nitrogen atmosphere. After stirring for 3 h at ambient temperature, the solvent was removed in vacuo. Flash chromatography (DCM/MeOH/HCOOH-95/5/0.2) afforded 500 mg of an impure product. The product was further purified by preparative HPLC using 85% MeCN (containing 0.02% HCOOH) in water (containing 10% MeCN and 0.02% HCOOH) as eluent. The appropriate fractions were pooled and concentrated to give (2S,3S,4S,5R,6S)-3,4,5-trihydroxy-6-((2-(((5Z,8Z,11Z,14Z,17Z)icosa-5,8,11,14,17-pentaen-1-yl)oxy)butanoyl)oxy)tetrahydro-2H-pyran-2-carboxylic acid (80 mg, 0.139 mmol, 7.8% yield) as a solid. 1H NMR (400 MHz, MeOD) δ 5.60-5.56 (m, 1H), 5.51 5.27 (m, 10H), 3.99-3.88 (m, 2H), 3.71-3.63 (m, 1H), 3.62-3.54 (m, 1H), 3.53-3.38 (m, 3H), 2.93-2.83 (m, 8H), 2.19-2.07 (m, 4H), 1.93-1.83 (m, 1H), 1.81-1.72 (m, 1H), 1.69-1.60 (m, 2H), 1.53-1.45 (m, 2H), 1.04-0.98 (m, 6H). MS (electrospray): 549.3 [M−H]−.

Example 78: Preparation of 2-(((5Z,8Z,11Z,14Z,17Z)-icosa-5,8,11,14,17-pentaen-1-yl)oxy)butan-1-ol

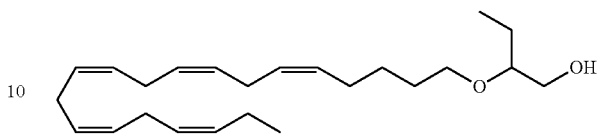

A solution of butyl 2-(((5Z,8Z,11Z,14Z,17Z)-icosa-5,8,11,14,17-pentaen-1-yl)oxy)butanoate (1.008 g, 2.34 mmol) in dry THF (3 ml) was added dropwise to a suspension of LiAlH4 (94.9 mg, 2.50 mmol) in dry THF (10 ml) at 0° C. under N2-atmosphere. The reaction mixture was stirred at 0° C. for 1.5 hrs before the cooling bath was removed and the reaction mixture was stirred at room temperature for 20 hrs. The reaction mixture was cooled in an ice-water bath before dropwise addition of water (2.5 ml) and 1 M HCl (10 ml). The cooling bath was removed, and the mixture was stirred for 10 minutes at room temperature. The resulting mixture was extracted with heptane (2×50 ml), washed with 1 M HCl (10 ml), dried (Na2SO4), filtered and concentrated under reduced pressure. Flash-chromatography on silica gel eluting with heptane-EtOAc (90:10) afforded 0.705 g (83% yield) of the title compound as an oil. 1H NMR (400 MHz, CDCl3) δ 5.71-4.93 (m, 10H), 3.63 (dd, 1H), 3.58-3.34 (m, 3H), 3.29-3.23 (m, 1H), 2.95-2.65 (m, 8H), 2.18-1.98 (m, 4H), 1.88 (bs, 1H), 1.66-1.51 (m, 3H), 1.45 (dt, 3H), 0.95 (t, 3H), 0.89 (t, 3H). MS (ESI, pos) 383 [M+Na]+.

Example 79: Preparation of 2-(((5Z,8Z,11Z,14Z,17Z)-icosa-5,8,11,14,17-pentaen-1-yl)oxy)butyl acetate

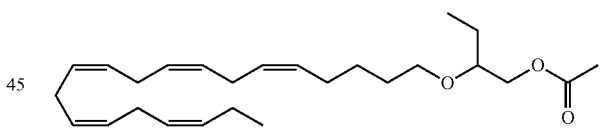

A mixture of 2-(((5Z,8Z,11Z,14Z,17Z)-icosa-5,8,11,14,17-pentaen-1-yl)oxy)butan-1-ol (300.9 mg, 0.834 mmol), triethyl amine (140 ml, 1.00 mmol) and DMAP (4.7 mg, 0.038 mmol) in dry CH2Cl2 (5 ml) was added to acetic anhydride (95 ml, 1.00 mmol). The reaction mixture was stirred under N2-atmosphere at room temperature for 80 minutes. Water (10 ml) was added and the mixture was extracted with heptane (2×50 ml), washed with brine (20 ml), dried (Na2SO4), filtered and concentrated under reduced pressure. Flash-chromatography on silica gel eluting with heptane-EtOAc (100:1) afforded 0.319 g (95%) of the title compound as an oil. 1H NMR (400 MHz, CDCl3) δ 5.59-5.14 (m, 10H), 4.10 (dd, 1H), 4.02 (dd, 1H), 3.54 (dt, 1H), 3.43 (dt, 1H), 3.38-3.29 (m, 1H), 2.92-2.65 (m, 8H), 2.14-1.95 (m, 4H), 2.05 (s, 3H), 1.63-1.47 (m, 4H), 1.45-1.38 (m, 2H), 0.96 (t, 3H), 0.92 (t, 3H). MS (ESI, pos) 425 [M+Na]+.

BIOLOGICAL EXAMPLES

Evaluation of Compound a in a Diet Induced NASH Mouse Model (CDAA/High-Fat Diet)

Mouse models that are deficient in methionine and/choline (MCD and CDAA respectively) are well established for studying the development and treatment of NASH in preclinical drug development. As precursors for the synthesis of phosphatidylcholine, a dietary deficiency of methionine/choline leads to an inability to synthesize hepatic lipoproteins for the export of triglyceride that results in severe hepatic steatosis, inflammation and fibrosis.

Although the widely used methionine-choline deficient (MCD) diet consistently reproduces severe NASH-like hepatic inflammation and fibrosis in mice, it is also associated with severe weight-loss (loss of both skeletal muscle and fat mass). This is associated with an increased risk of death which presents major problems for long-term fibrogenesis experiments. By adding a sub-optimal dose of methionine (0.17%), the CDAA dietary model overcomes these problems and has been demonstrated to mimic human NASH in both mice and rats by sequentially producing steatohepatitis, liver fibrosis and liver cancer with less severe loss of body weight.

In Biological Examples 1-7, studies were performed in male C56BL/6J mice (9 weeks old). Mice were fed either choline-sufficient (CS) or choline deficient high-fat diets (31% total calories; "CDAA/high-fat"). The NASH inducing diet was instigated 6 weeks prior to the commencement of treatment in order to design the study as a treatment/reversal set-up rather than prophylaxis.

In Biological Examples 1-5, mice were divided into 6 experimental groups (n=9 per group) and fed either CS or CDAA/high-fat diets. After 6 weeks of either the CS- or CDAA diet, mice were orally administered Compound A or comparison Compound N, both at 2 doses, 0.15 mmol/kg bw/day (low-dose, LD) and 0.3 mmol/kg bw per day (high-dose, HD). The test substances were administered orally as admix to the high-fat diet. Hepatic fibrosis was assessed by both measurement of hydroxyproline (HYP) content and Sirius Red (SR) morphometry. Fibrosis, inflammation and metabolism related transcripts levels were measured by quantitative real-time polymerase chain reaction (qPCR)

In Biological Examples 6 and 7, mice were fed either CS or CDAA/high-fat diets as described above. In Example 6, after 6 weeks of either the CS or CDAA/high-fat diet, mice were administered 56 mg/kg bw per day of Compound A delivered orally, or the long-acting GLP-1R agonist Bydureon® (exenatide), which is approved for the treatment of type 2 diabetes, injected subcutaneously at 0.4 mg/kg per week for six weeks. The effect on hepatic collagen fiber number, thickness, and length was determined via nonlinear multiphoton optical imaging system in isolated liver samples from vehicle control (n=8), Compound A (n=9) and GLP-1R (n=8) fed groups.

In Biological Example 7, after 6 weeks of either the CS or CDAA/high-fat diet, mice were administered 112 mg/kg bw per day of Compound A, or an equimolar dose of eicosapentaenoic acid (EPA), delivered orally. Hepatic lipidomic analysis was performed in isolated liver samples from CS (n=9), Compound A (n=9) and EPA (n=8) groups.

In Biological Examples 21-24, the effects of Compound A alone and in combination with GLP-1 agonist exenatide were studied. Studies were performed in male C56BL/6J mice (9 weeks old).

Mice were divided into 6 experimental groups (n=9 per group) containing either CS or CDAA/high-fat diets, as described above. The NASH inducing CDAA/high fat diet was instigated 6 weeks prior to the commencement of treatment in order to assess treatment/reversal rather than prophylaxis. Thus, after 6 weeks of either the CS or CDAA/high-fat diet, mice were treated with (A) oral Compound A at 0.3 mmol/kg bw/day alone, (B) a GLP-1 agonist alone, delivered i.p. at 0.4 mg/kg once weekly, or (C) a combination of Compound A at 0.3 mmol/kg bw/day and a GLP-1 agonist delivered i.p. at 0.4 mg/kg once weekly (reduced to 0.1 mg/kg for final 3 weeks due to excessive weight loss). Compound A was administered orally as admix to the high-fat diet whilst GLP-1 agonist was delivered via intraperitoneal injection (i.p.). Fibrosis, inflammation and metabolism related transcripts levels were measured by quantitative real-time polymerase chain reaction (qPCR) in isolated liver tissue.

Evaluation of Compound a in a Streptozotocin Injection/High-Fat Diet Induced NASH Model (STAM Model)

In Biological Example 8, pathogen-free 15-day-pregnant C57BL/6 mice were obtained from Charles River Laboratories in Japan Inc. (Kanagawa, Japan). NASH was established in male mice by a single subcutaneous injection of streptozotocin (STZ) (Sigma, USA) after birth and feeding with a high fat diet (HFD; CLEA) Japan, Japan) ad libitum after 4 weeks of age (day 28±2). Mice were randomised into 3 groups of 8 mice at 6 weeks of age the day before the start of treatment: vehicle (saline), Compound A and telmisartan (positive control). Treatment with Compound A at a dose of 37 mg/kg bw per day via oral gavage in conjunction with a high-fat diet was given for 6 weeks before sacrifice. NAFLD activity score (NAS) was calculated according to standardised criteria and fibrosis area was assessed via Sirius Red staining.

Evaluation of Effects of Compound a in a Diet Induced NASH Mouse Model (APOE*3Leiden.CETP Double Transgenic Mice)

The APOE*3Leiden.CETP double transgenic mouse expresses a variant of the human apolipoprotein E3 (APOE3), the APOE*3Leiden, in addition to the human apolipoprotein C1 (APOC1) and CETP. APOE*3Leiden.CETP double transgenic mice exhibit elevated plasma cholesterol and triglyceride levels, mainly confined to the VLDL/LDL sized lipoprotein fraction. By increasing the cholesterol content of the diet in this model, all the characteristics of human NASH develop.

In Biological Example 9, studies were performed in APOE*3Leiden.CETP mice placed on a high fat diet (24% fat w/w) with varying cholesterol content (0.25-1% cholesterol w/w). In one study (using 1% cholesterol w/w), after a 3 weeks run-in period low-responder mice (20% of total) were removed from the study and the remaining mice were sub-divided into 4 groups of 12 mice each (+5 in the control group), matched for plasma cholesterol, triglycerides, blood glucose, body weight and age (t=0) and treatment was started. The mice received a daily gavage between 07hr00 and 10hr00 with either Compound A at 0.3 mmol/kg bw per day, the comparison compound Compound N (0.3 mmol/kg bw per day), rosiglitazone (13 mg/kg bw per day) or control (corn oil). After 20 weeks of treatment mice were sacrificed by $CO_2$ asphyxiation, the liver was collected and the level of hepatocellular hypertrophy was graded.

In Biological Example 25, the effects of Compound A alone and in combination with omega-3 fattay acid were studied. APOE*3Leiden.CETP mice were placed on a semi-synthetic high fat diet (24% fat w/w) with 0.25 cholesterol w/w. After a 4-week run-in period, low-responder mice were removed from the study and the remaining mice were sub-divided into groups of 8 mice each, matched for plasma cholesterol, triglycerides, blood glucose, body weight and age (t=0) and treatment was started. To facilitate mixing of the compounds, sunflower oil was added to a total oil volume of 10 mL/kg diet. Compound A was administered at 0.3 mmol/kg bw/day whilst the omega-3 fatty acid ethyl-esters (85% w/w EPA/DHA ethyl-esters) were administered at 3.0 mmol/kg bw/day. Both Compound A and the omega-3 ethyl esters were administered orally as admix to the high-fat diet. After 4 weeks of treatment, mice were sacrificed by $CO_2$ asphyxiation, the liver was collected and the hepatic content of free cholesterol, cholesterol ester and triglyceride were measured after extraction and separation by high performance thin layer chromatography.

Evaluation of Effects of Compound a in an Obese Diet-Induced NASH Mouse Model (Ob/Ob AMLN Model)

Obese diet-induced B6.V-Lepob/Jrj mice (ob/ob) are consistently fibrosis (liver) prone when cholesterol (2%), 40% fat (containing 18% trans-fatty acids) and 20% fructose are added to a high-caloric diet (i.e., AMLN high-fat diet). ob/ob mice on AMLN diet (termed 'ob/ob AMLN mice') develop steatohepatitis and fibrosis within a shorter timeframe (5-12 weeks) compared with wild-type C57BL/6 mice (AMLN mice) fed the same diet. ob/ob AMLN mice provide an obese diet-induced model of NASH that also allows the study of effects on glycemic control. Development of NASH in the ob/ob AMLN model is confirmed by biopsy.

In Biological Examples 10-12, 15, and 19, studies were performed in male ob/ob mice (5 weeks old) fed an AMLN high-fat diet for 15 weeks, then randomized into 3 groups (n=10 per group) to receive either 112 mg/kg bw per day of Compound A via diet, 30 mg/kg bw per day pioglitazone via diet or no treatment (vehicle) for a further 4 weeks. An oral glucose tolerance test (OGTT) was performed at week 3. Hepatic fibrosis was assessed via measurements of hepatic fibrogenic/fibrolytic gene expression by RNA sequencing at 4 weeks.

In Biological Examples 10, 13-14, and 16-18, studies were performed in male ob/ob mice (5 weeks old) fed an AMLN high-fat diet for 18 weeks, then randomized into 6 groups (n=10 per group) to receive either Compound A (at 3 different daily doses, 45 mg/kg, 90 mg/kg or 135 mg/kg) via diet, 30 mg/kg bw per day obeticholic acid (OCA) via diet, or no treatment (vehicle) for a further 8 weeks. Assessment of NASH related parameters and fibrosis was made at study end by quantitative immune histochemistry (IHC) measurements.

With respect to clinical translation, the doses of Compound A used here (45 mg/kg, 90 mg/kg, and 135 mg/kg in the 8-week study and 112 mg/kg in the 4-week study) correspond to human doses of approximately 250 mg/day, 500 mg/day, and 750 mg/day (and 600 mg/day in the 4-week study) for a 70 kg human, when corrected for interspecies difference. See Nair, A. B., and Jacob, S., J Basic Clin Pharm, 2016; 7(2): 27-31, for a guide to interspecies dose conversion.

Evaluation of Effects of Compound a on Human Hepatic Stellate Cells In Vitro

Stellate cells are resident liver cells and the major cell type involved in the initiation and progression of liver fibrosis. In Biological Example 20, in vitro studies were performed on cultured human stellate cells (LX-2 cells) to assess direct effects of Compound A on these cells. Cells were treated for 24 hours with Compound A (10 µM, 25 µM, 50 µM, or 75 µM) or oleic acid (OA; 75 µM) and bromodeoxyuridine (BrdU) incorporation was assessed to determine effects on proliferation. A MTS (3-(4,5-dimethylthiazol-2-yl)-5-(3-carboxymethoxyphenyl)-2-(4-sulfophenyl)-2H-tetrazolium) assay was used to determine cell viability.

Biological Example 1. Effects of Compound a and Compound N on Hepatic Fibrosis Content as Measured by Total Hydroxyproline (HYP) Content Per Liver Compound A at both low- (LD) and high- (HD) doses administered to CDAA/high-fat fed mice induced a significant decrease in hepatic fibrosis (HYP content per liver) versus control (p<0.01* and 0.001** respectively). No significant effects were observed for the comparison Compound N. The effects of Compound A on hepatic HYP content are shown in Table 1.

TABLE 1

| Compound | Hydroxyproline (µg) content per liver |
| --- | --- |
| CSAA (high-fat choline sufficient control) | 310 |
| CDAA (choline deficient) | 1250 |
| CDAA + Compound A LD | 800* |
| CDAA + Compound A HD | 750** |
| CDAA + Compound N LD | 1100 |
| CDAA + Compound N HD | 950 |

Biological Example 2. Effects of Compound A and Compound N on Hepatic Fibrosis Content as Measured by Relative Hydroxyproline (HYP) Content (Ug HYP Per 100 mg Liver)

Compound A at both low- (LD) and high- (HD) doses administered to CDAA/high-fat fed mice decreased hepatic fibrosis (HYP content per liver) whereas no effects were observed for Compound N. The effects of Compound A on relative HYP content are shown in Table 2.

TABLE 2

| Hydroxyproline (µg HYP/per 100 mg liver) | |
| --- | --- |
| Compound | Hydroxyproline (µg) content per 100 mg liver |
| CSAA (high-fat choline sufficient control) | 26 |
| CDAA (choline deficient) | 52 |
| CDAA + Compound A LD | 38 |
| CDAA + Compound A HD | 37 |
| CDAA + Compound N LD | 48 |
| CDAA + Compound N HD | 54 |

Biological Example 3. Effects of Compound A and Compound N on Hepatic Inflammatory Gene Expression (TNF-α mRNA Expression)

Compound A at both low- (LD) and high- (HD) doses administered to CDAA/high-fat fed mice induced a significant decrease in hepatic inflammation (TNF-a mRNA) versus control (both p<0.001***). A significant reduction (p<0001) was observed also for Compound N, but not for the high dose (HD). The effects of Compound A on hepatic TNF-α are shown in Table 3.

TABLE 3

Hepatic inflammatory gene expression (TNF-a mRNA)

| Compound | TNF-a (relative mRNA expression) |
| --- | --- |
| CSAA (high-fat choline sufficient control) | 1 |
| CDAA (choline deficient) | 1.7 |
| CDAA + Compound A LD | 0.75*** |
| CDAA + Compound A HD | 0.65*** |
| CDAA + Compound N LD | 1*** |
| CDAA + Compound N HD | 1.2 |

Biological Example 4. Effects of Compound A and Compound N on Fibrosis Related Gene Expression (Col1a1 mRNA Expression)

Compound A at both low- (LD) and high- (HD) doses administered to CDAA/high-fat fed mice induced a significant decrease in hepatic fibrosis related gene expression (Col1a1 mRNA) versus control (both p<0.001*** respectively). No significant effects were observed for Compound N. The effects of Compound A on hepatic Col1a1 are shown in Table 4.

TABLE 4

Hepatic fibrosis related gene expression (Col1 a1 mRNA)

| Compound | Col1a1 (relative mRNA expression) |
| --- | --- |
| CSAA (high-fat choline sufficient control) | 1 |
| CDAA (choline deficient) | 19 |
| CDAA + Compound A LD | 10*** |
| CDAA + Compound A HD | 6*** |
| CDAA + Compound N LD | 15 |
| CDAA + Compound N HD | 16 |

Biological Example 5. Effects of Compound A on Hepatic Fibrosis Content as Measured by Sirius Red Morphometry In order to more accurately quantify the amount location and functional relevance of the hepatic fibrosis, Sirius Red (SR) morphometry was performed. In contrast to examples 1 and 2 where biochemical assessment of hydroxyproline (HYP) content measuring collagen in the large vessels was used, SR morphometry quantifies the more functionally relevant sinusoidal collagen deposits. 10 areas per slide were measured using 100× magnification. Compound A at both low-(LD) and high- (HD) doses administered to CDAA/high-fat fed mice induced a significant decrease in the percentage surface area of hepatic fibrosis versus control (p<0.001*** and 0.05* respectively). The effects of Compound A on hepatic fibrosis as measured by SR morphometry are shown in Table 5.

TABLE 5

Hepatic fibrosis by SR morphometry

| Compound | Fibrosis area (mean %) |
| --- | --- |
| CSAA (high-fat choline sufficient control) | 0.9 |
| CDAA (choline deficient) | 2.46 |
| CDAA + Compound A LD | 0.76*** |
| CDAA + Compound A HD | 1.56* |

Biological Example 6. Effects of Compound a and Bydureon® on Collagen Fibers

Figure 1A:
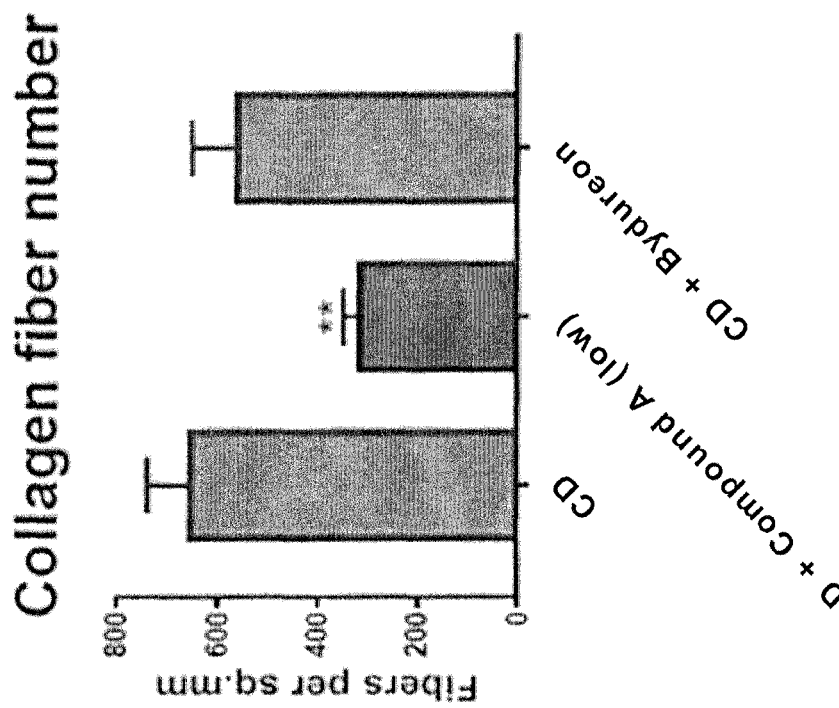
Figure 1C:
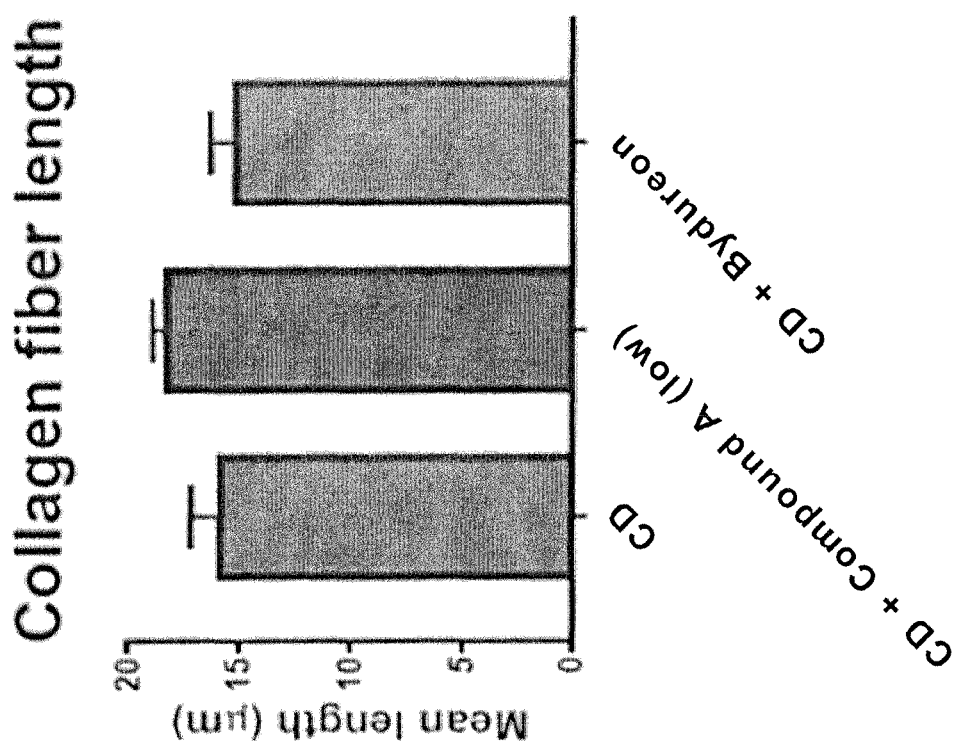

When administered at low doses (56 mg/kg) to CDAA/high-fat fed mice, Compound A significantly reduced the collagen fiber numbers (FIG. 1A) by 51% (p=0.01). This effect was reflected in the almost complete disappearance of short (<8.5 μm) and thin (<3.5 μm) collagen fibers as reflected in the slight increases of fiber thickness and length by Compound A in FIG. 1B and FIG. 1C, respectively. Bydureon® (0.4 mg/kg weekly injected subcutaneously) had no significant effect.

Biological Example 7. Effects of Compound a and EPA on Hepatic Lipid Metabolism

Figure 2A:
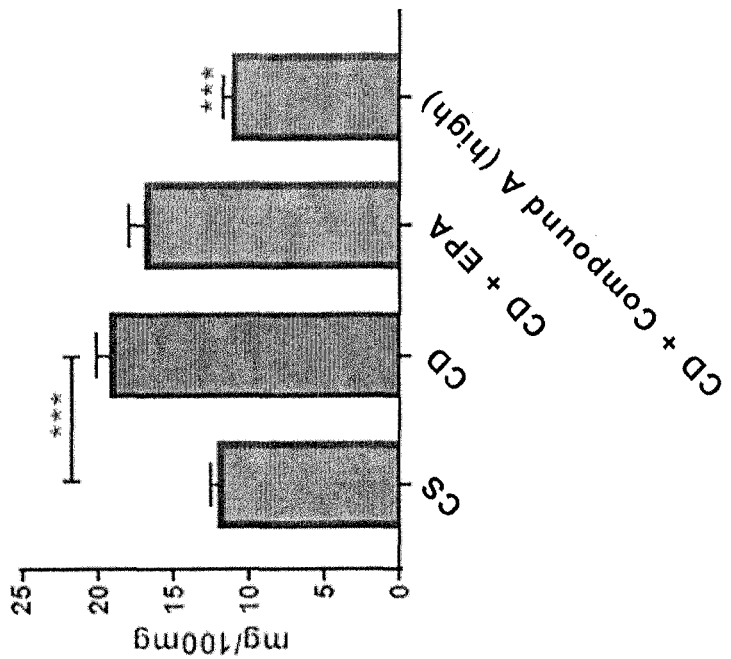
FIGS. 2A-2D depict the effects of Compound A on hepatic lipid content of triglycerides (TG, FIG. 2A), diglycerides (DG, FIG. 2B), free fatty acids (FFA, FIG. 2C), and cholesteryl ester (FIG. 2D) in a CDAA/high-fat diet mouse model.
Figure 2B:
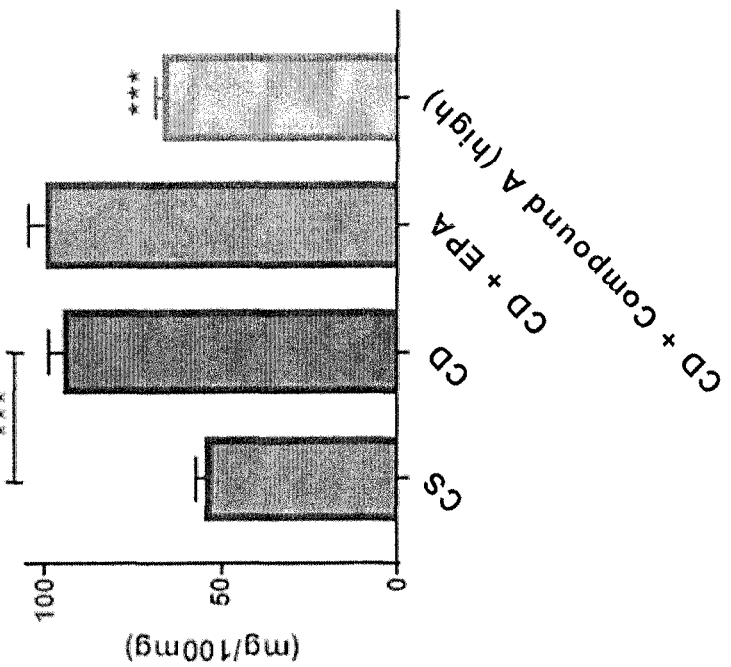
Figure 2D:
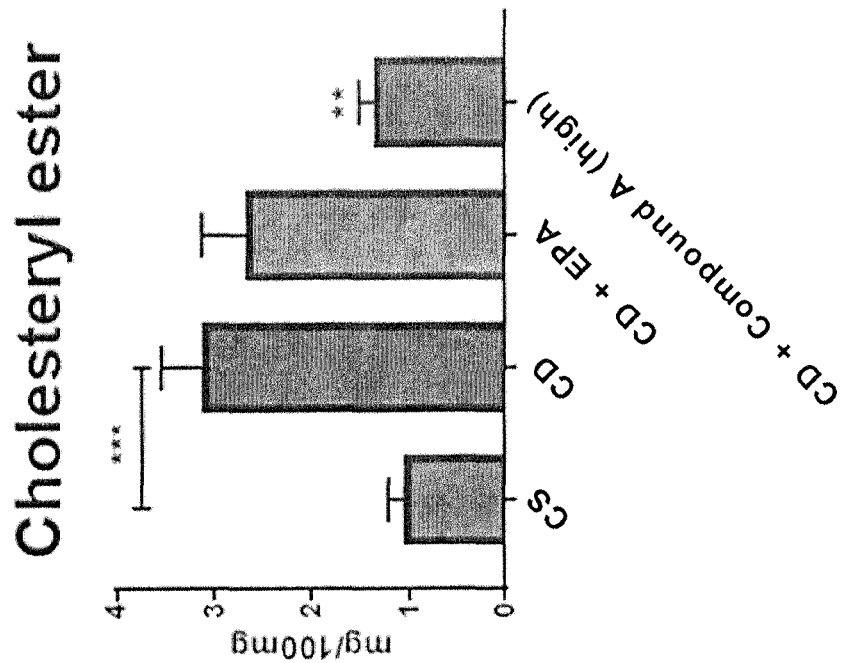
Figure 2C:
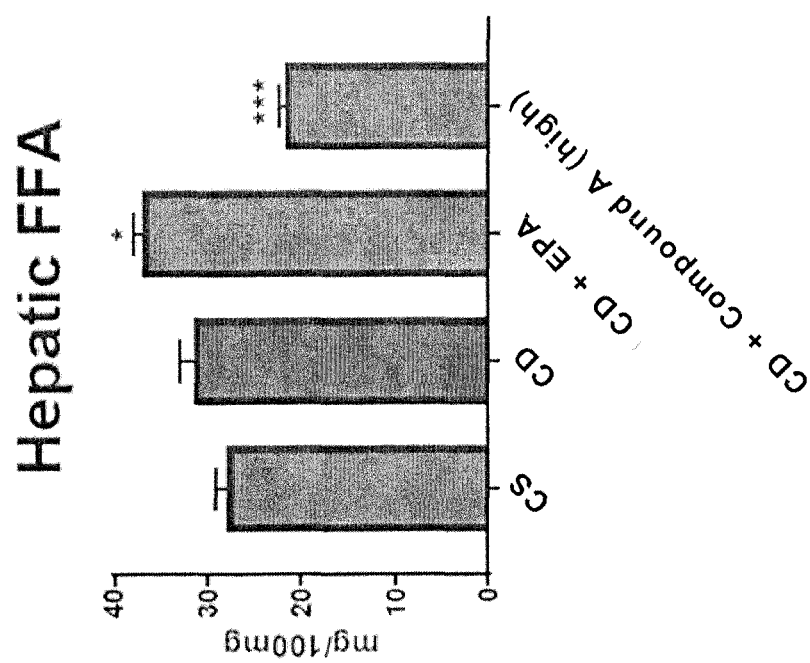

To further understand the effects of Compound A on hepatic lipid metabolism, lipidomic analysis of CS- and CDAA/high-fat fed mice ("CD") was performed in isolated liver tissue. When administered at high dose (112 mg/kg) to CDAA/high-fat fed mice, Compound A significantly reduced the effects of choline deficiency as measured by hepatic triglyceride (TG) (FIG. 2A), hepatic diglycerides (DG) (FIG. 2B), hepatic free fatty acids (FFA) (FIG. 2C) or cholesteryl ester (FIG. 2D). In contrast, treatment with equimolar amount of EPA did not reduce the increase in hepatic TG, DG, FFA or cholesteryl ester associated with a choline deficient diet.

Biological Example 8. Effects of Compound A on Hepatocellular Ballooning, Lobular Inflammation, Steatosis, Composite NAS Score and Fibrosis Area Compound A administered to STAM (model) mice decreased hepatocellular ballooning in addition to steatosis and lobular inflammation. Both composite NAS score (p<0.001*) and fibrosis area (Sirius Red positive area) were decreased by Compound A.

TABLE 6

Hepatocellular ballooning, total NAS score and fibrosis area

| Compound | Steatosis | Lobular inflammation | Hepatocellular ballooning | NAS score (mean ± SD) | Fibrosis area (%) |
| --- | --- | --- | --- | --- | --- |
| Vehicle n = 6 (saline) | 1 | 1.9 | 2 | 5.3 ± 0.8 | 1.01 |
| Compound A n = 8 (37 mg/kg/day) | 0.12 | 0.88 | 1 | 2.3 ± 1.5* | 0.79 |
| Telmisartan n = 6 | 0.7 | 0.45 | 0.8 | 1.8 ± 0.8 | 0.44 |

Biological Example 9. Effects of Compound A and Compound N on Hepatocellular Hypertrophy Compound A administered to ApoE*3L-CETP mice (0.25% cholesterol diet w/w) induced a significant decrease in hepatocellular hypertrophy (p<0.01*), constituting an 83% decrease vs. control (p<0.01). No effect was observed with Compound N.

TABLE 7

Hepatocellular hypertrophy

| Compound | Hepatocellular hypertrophy | Decrease in hypertrophy vs. control (%) |
|---|---|---|
| Control | 46 ± 23.9 | — |
| Compound A | 8.9 ± 5.9* | 83* |
| Compound N | 42.9 ± 29.7 | 7 |

Figure 3B:
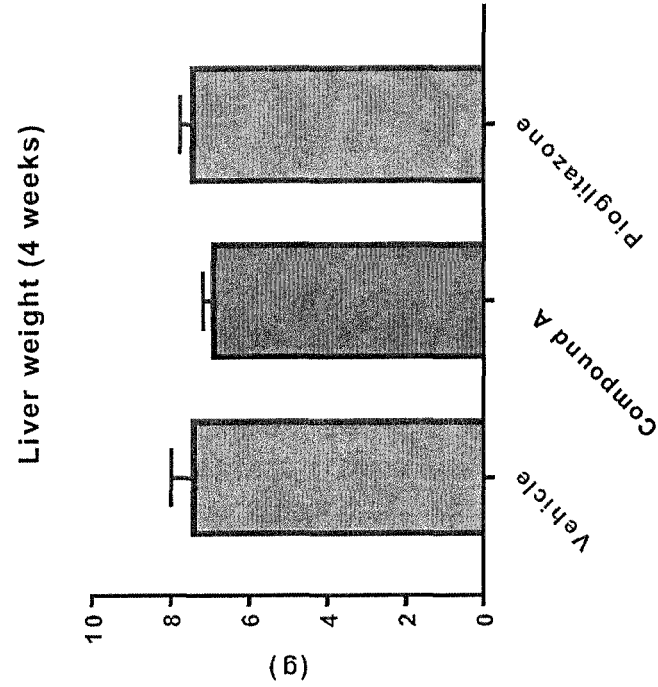
FIGS. 3A-3D show that Compound A does not have a significant effect in ob/ob AMLN-fed mice on body weight (FIG. 3A) or liver weight (FIG. 3B) after 4 weeks of treatment or body weight (FIG. 3C) or liver weight (FIG. 3D) after 8 weeks of treatment.
Figure 3A:
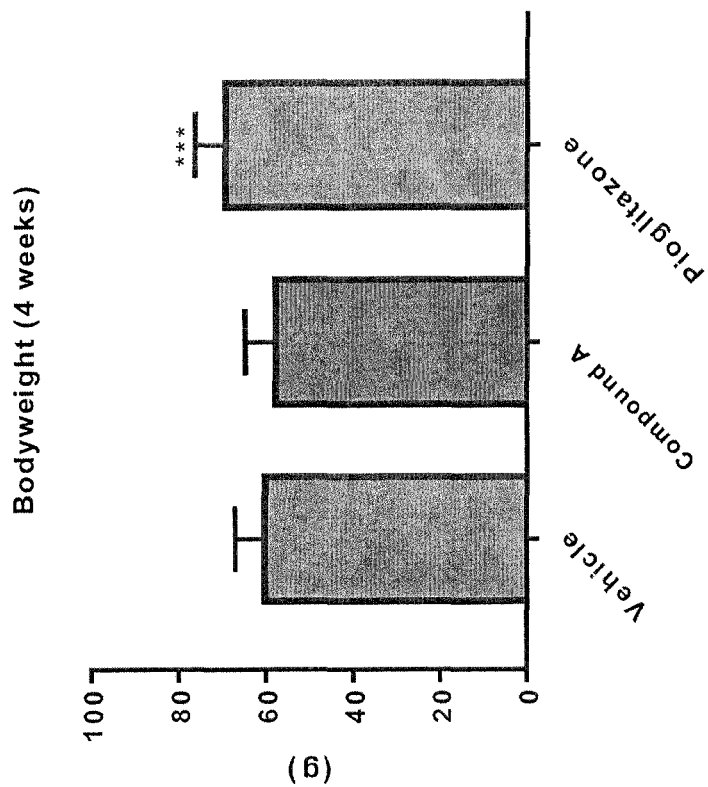
Figure 3D:
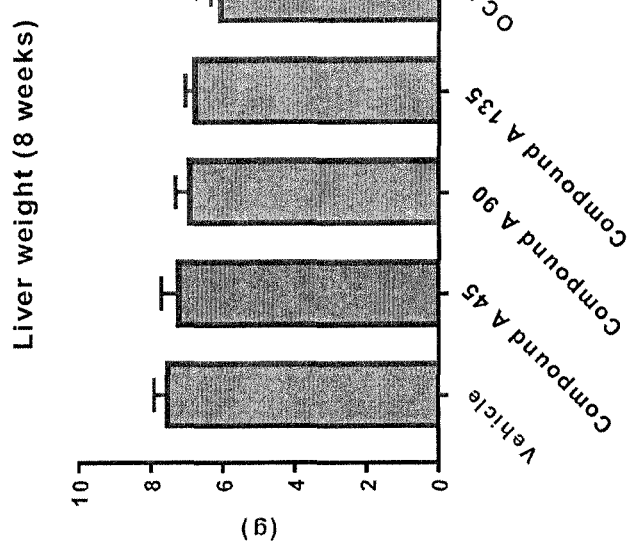
Figure 3C:
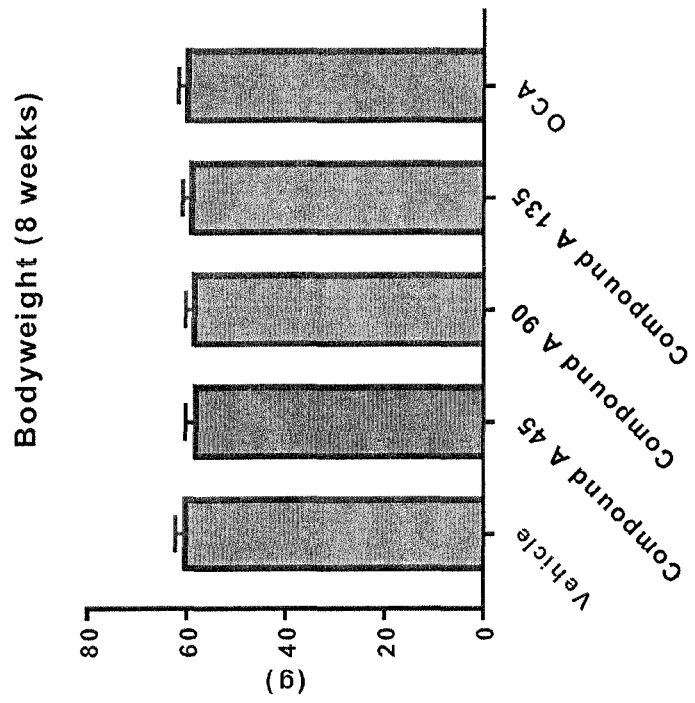

Biological Example 10. Effects of Compound A, Pioglitazone, and OCA on Liver Weight and Body Weight As shown in FIG. 3A, at 4 weeks, Compound A (112 mg/kg) had no effect on body weight of ob/ob AMLN mice whereas pioglitazone induced a significant 15% increase in bodyweight ($p<0.01$). Liver weight was unchanged in all groups at week 4 as shown in FIG. 3B. At 8 weeks, neither Compound A (45 mg/kg, 90 mg/kg, and 135 mg/kg) nor OCA significantly affected body weight, as shown in FIG. 3C, and food intake was not affected in either group. OCA significantly ($p<0.05$) reduced liver weight at 8 weeks whereas Compound A had no significant effects at any dose as compared to vehicle, as shown in FIG. 3D.

Figures 4A, 4B:
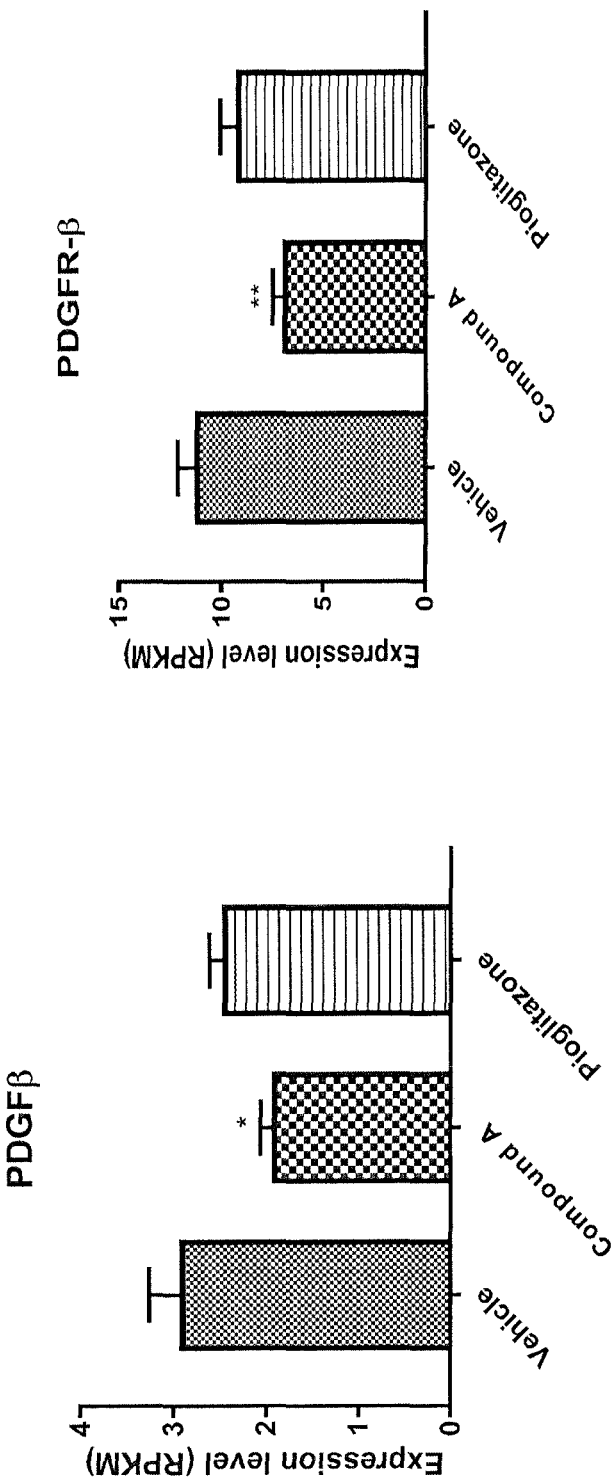
FIGS. 4A-4F depict the effect of 4 weeks of treatment with Compound A on the expression of canonical genes regulating hepatic fibrogenesis in ob/ob AMLN-fed mice.
Figure 4D:
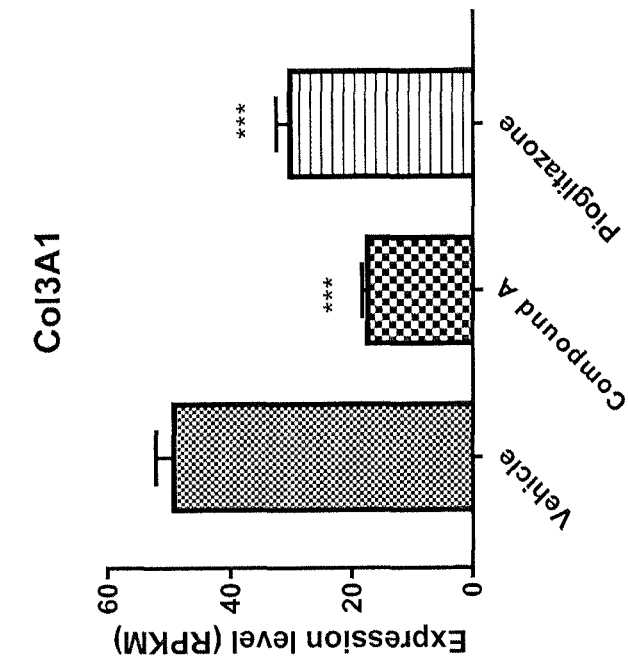
Figure 4C:
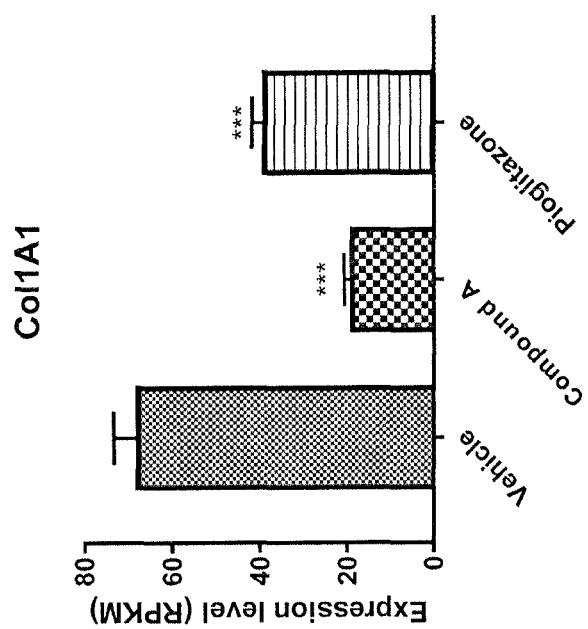
Figure 4F:
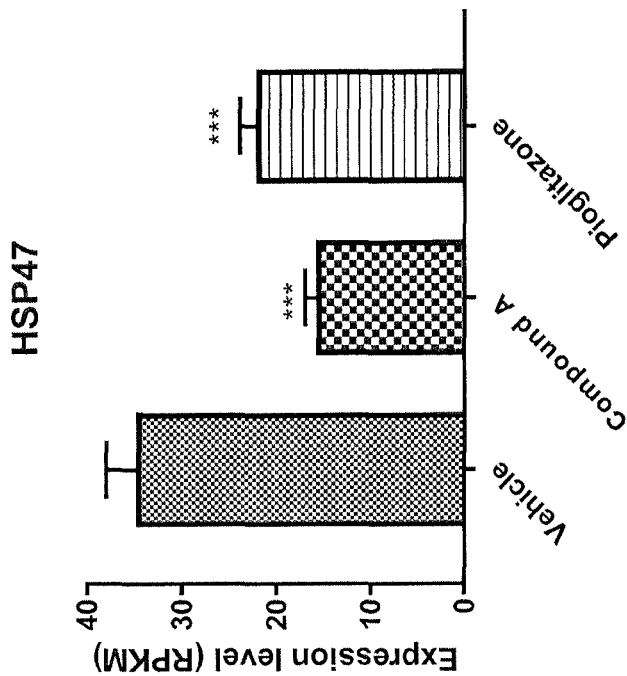
Figure 4E:
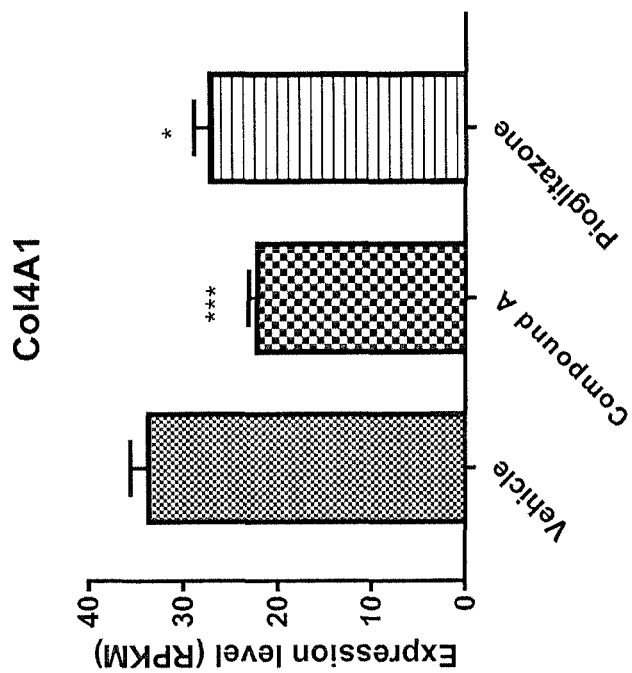
Figure 5B:
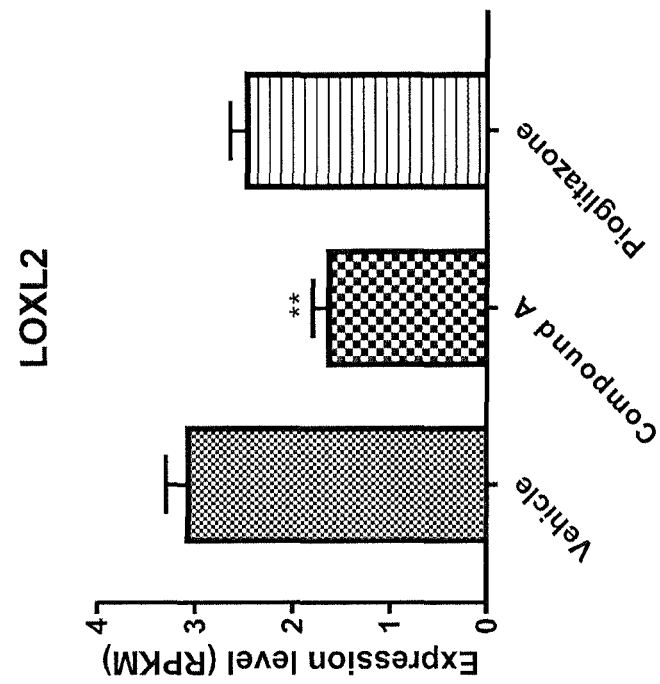
FIGS. 5A-5D depict the effect of 4 weeks of treatment with Compound A on the expression of genes regulating extracellular matrix (ECM) stability or fibrolysis in ob/ob AMLN-fed mice.
Figure 5A:
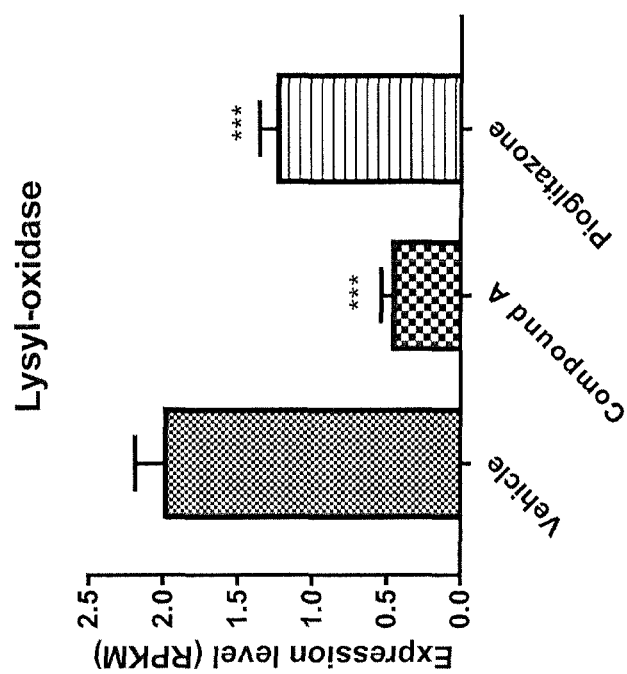
Figure 5D:
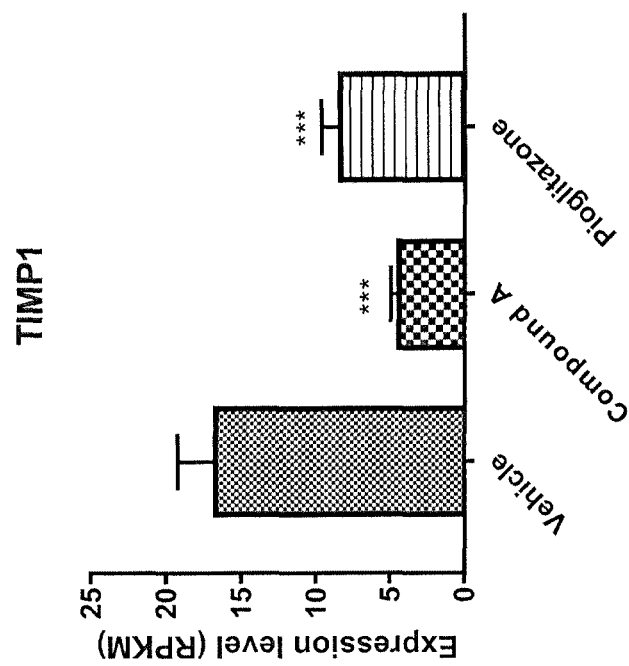
Figure 5C:
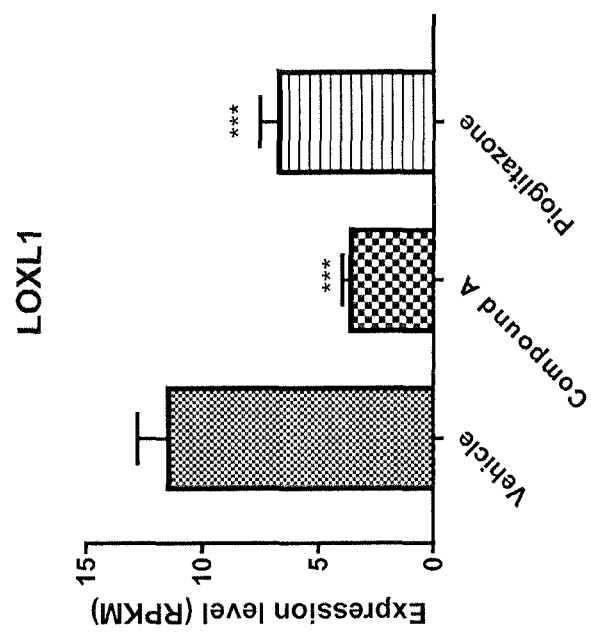

Biological Example 11. Effects of Compound A and Pioglitazone on Hepatic Fibrogenic and Fibrolytic Gene Expression The effects of 4 weeks treatment with either Compound A (112 mg/kg) or pioglitazone (30 mg/kg) on fibrogenic and fibrolytic gene expression in ob/ob AMLN mice isolated liver samples are shown in FIGS. 4A-4F. Compound A significantly reduced the expression of canonical genes regulating hepatic fibrogenesis including platelet-derived growth factor-beta (PDGF-0) (FIG. 4A), platelet-derived growth factor receptor-$\beta$ (PDGFR-$\beta$) (FIG. 4B), collagen-1 $\alpha$1 (col1A1) (FIG. 4C), col3A1 (FIG. 4D), col4A1 (FIG. 4E), and heat-shock protein-47 (HSP47) (FIG. 4F). Pioglitazone significantly reduced the expression of the examined collagen isoforms (col1A1, col3A1, col4A1) and HSP47 but had no effect on PDGF-$\beta$ or PDGFR-$\beta$ expression.

Biological Example 12. Effects of Compound A and Pioglitazone on Hepatic Extracellular Matrix Stability and Fibrolysis Gene Expression As shown in FIGS. 5A-5D, with respect to genes regulating extracellular matrix (ECM) stability or fibrolysis, 4 weeks of treatment with Compound A significantly reduced the hepatic expression of lysyl-oxidase (LOX) (FIG. 5A), LOX-like 2 (LOXL2) (FIG. 5B), and LOXL1 (FIG. 5C), as well as the tissue-inhibitor of metalloproteinase (TIMP1) (FIG. 5D) in ob/ob AMLN mice. Pioglitazone also significantly reduced transcript levels of these transcripts, although the effect was milder than the effect obtained with Compound A.

Figures 6A, 6B:
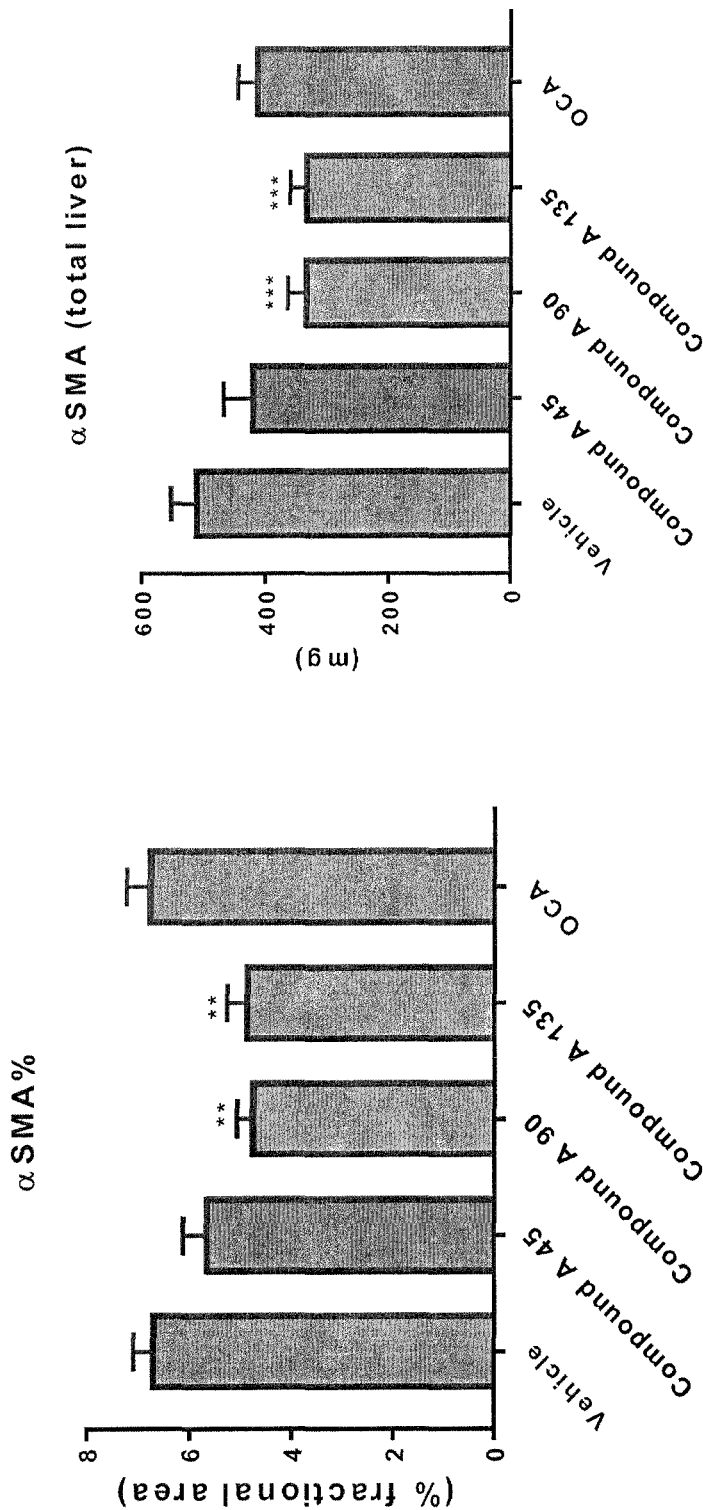
FIGS. 6A-6F shows that 8 weeks of treatment with Compound A reduces hepatic α-SMA (FIGS. 6A-6B), col1a1 (FIGS. 6C-6D), and collagen (FIGS. 6E-6F) content in ob/ob AMLN-fed mice.

Biological Example 13. Effects of Compound A and OCA on Hepatic Fibrosis Progression To assess the effects of 8 weeks of administration of either Compound A (45 mg/kg, 90 mg/kg, or 135 mg/kg) or OCA (30 mg/kg) on hepatic fibrosis progression in ob/ob AMLN mice, quantitative immuno histochemistry (IHC) was performed measuring col1A1 and $\alpha$-smooth muscle actin (SMA) content. As shown in FIG. 6A and FIG. 6B, at the 90 mg/kg and 135 mg/kg doses, Compound A markedly reduced myofibroblast marker $\alpha$-SMA (expressed both as total and a % of fractional area content) whereas OCA did not show any significant effect.

Figure 6D:
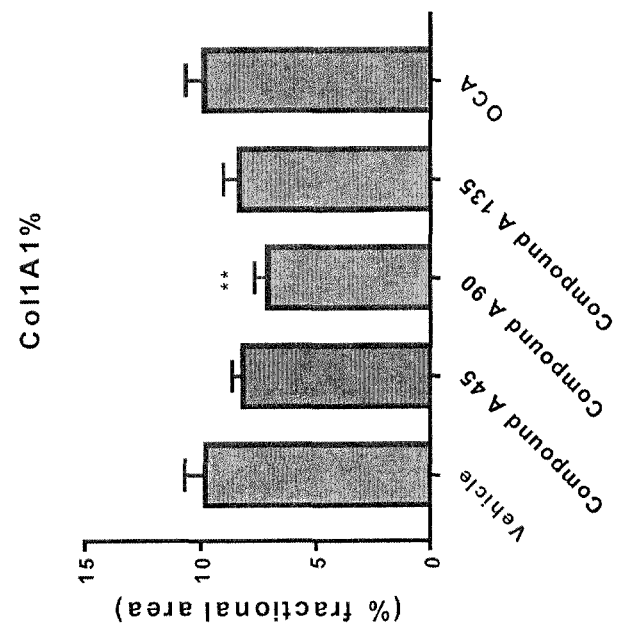
Figure 6C:
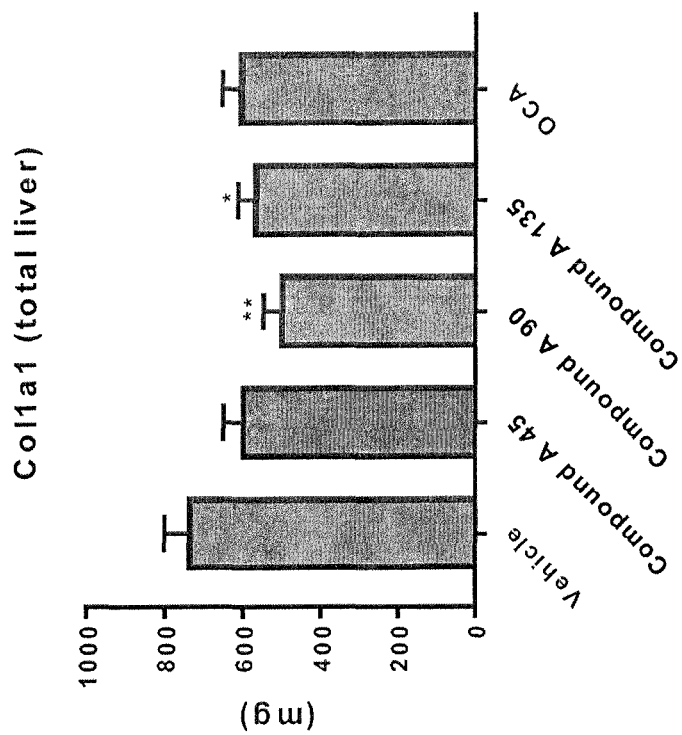
Figure 6F:
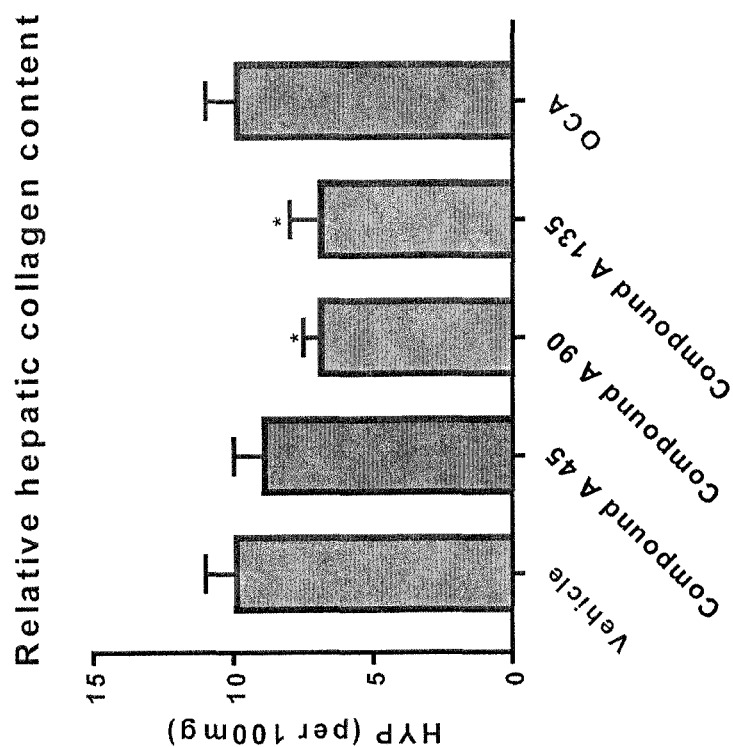
Figure 6E:
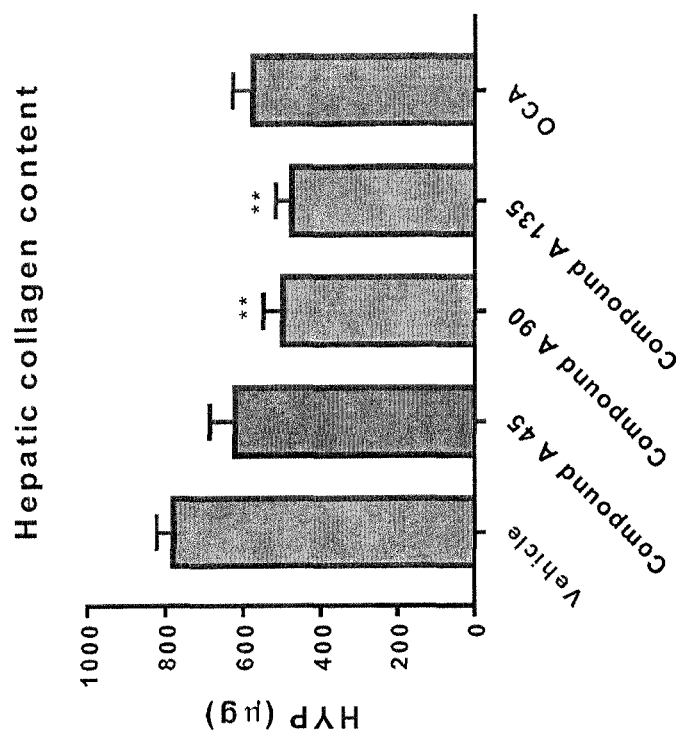

Similarly, Compound A administered at 90 and 135 mg/kg reduced total col1A1 content (FIG. 6C), whereas OCA had no significant effect. When expressed as a percentage of total surface area (FIG. 6D), the 90 mg/kg dose induced a significant reduction on col1A1 levels, whereas the reductions at the 45 and 135 mg/kg doses were not statistically significant. To corroborate the anti-fibrotic effects seen with quantitative IHC, hepatic concentrations of hydroxyproline (HYP) were measured, as shown in FIG. 6E and FIG. 6F. Only Compound A reduced HYP content, expressed either as total ($p<0.01$ for both 90 and 135 mg/kg doses) or relative ($p<0.05$ for both 90 and 135 mg/kg doses) content.

Figure 7B:
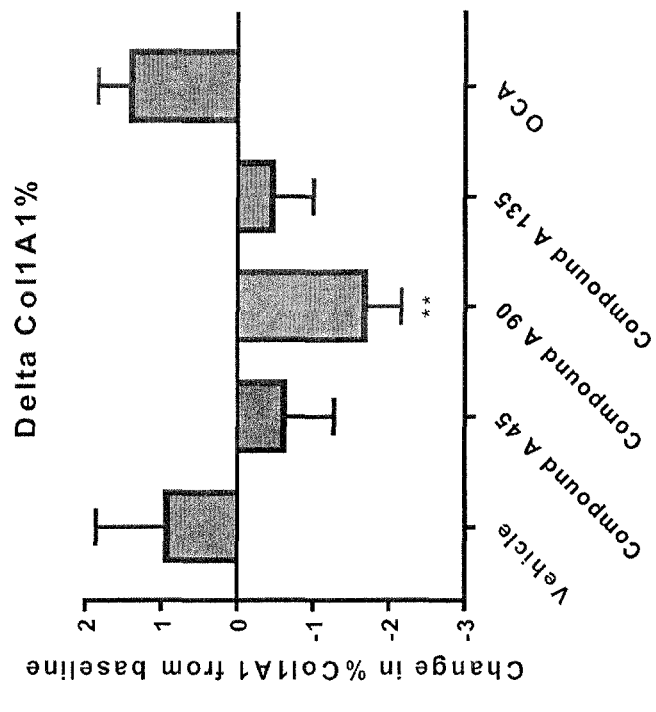
FIGS. 7A-7B shows that 8 weeks of treatment with Compound A in ob/ob AMLN-fed mice decreased the number of activated hepatic stellate cells (myofibroblasts) and induced regression of fibrosis as demonstrated by a decrease in hepatic α-SMA (FIG. 7A) and col1a1 (FIG. 7B) content respectively compared with pre-treatment levels.
Figure 7A:
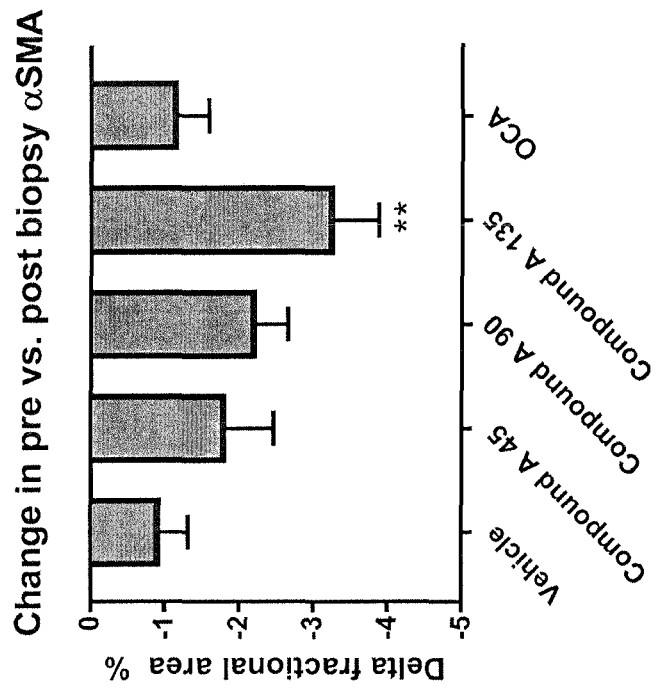

Biological Example 14. Effects of Compound A and OCA on Hepatic Fibrosis Regression As baseline (pre-treatment) biopsies of ob/ob AMLN mice incorporating IHC measurement of both hepatic col1A1 and $\alpha$-SMA were performed, terminal values of col1A1 and $\alpha$-SMA were compared with baseline (pre-treatment biopsy) values in all groups to establish if the significant reductions we observed after Compound A treatment versus vehicle at study end were associated with fibrosis regression. As shown in FIG. 7A, treatment with 135 mg/kg Compound A decreased the area percentage of $\alpha$-SMA content assessed by immunohistochemical stain as compared to $\alpha$-SMA content in the pre-treatment biopsy. The 45 mg/kg and 90 mg/kg doses of Compound A resulted in a non-significant trend. OCA had no significant effect. Similarly, all Compound A doses showed a trend towards decreased col1A1 content compared with pre-biopsy content, although only the 90 mg/kg dose was statistically significant ($p<0.005$) (FIG. 7B). Both vehicle and OCA treatments showed mild increases in hepatic col1A1 content after the 8-week administration period although the increase was only significant for OCA ($p<0.05$).

Figure 8B:
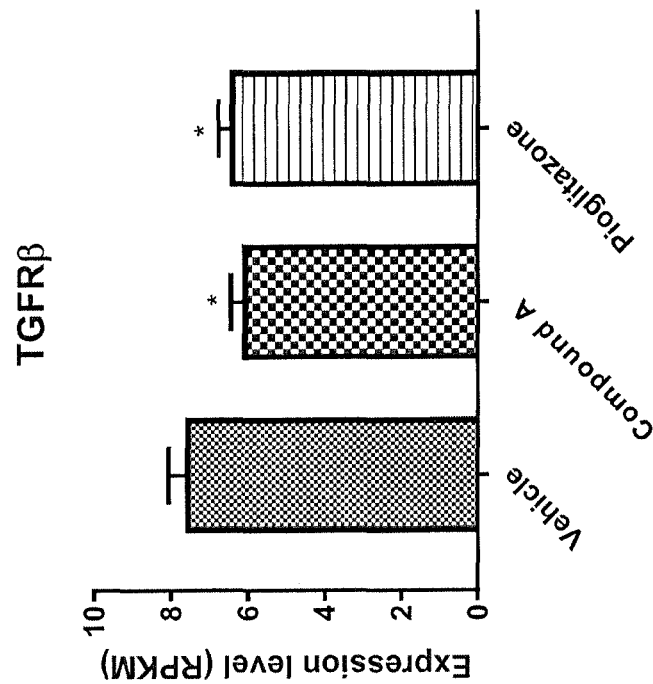
FIGS. 8A-8F show that 4 weeks of treatment with 112 mg/kg of Compound A resulted in lower expression of hepatic genes associated with inflammation in ob/ob AMLN mice.
Figure 8A:
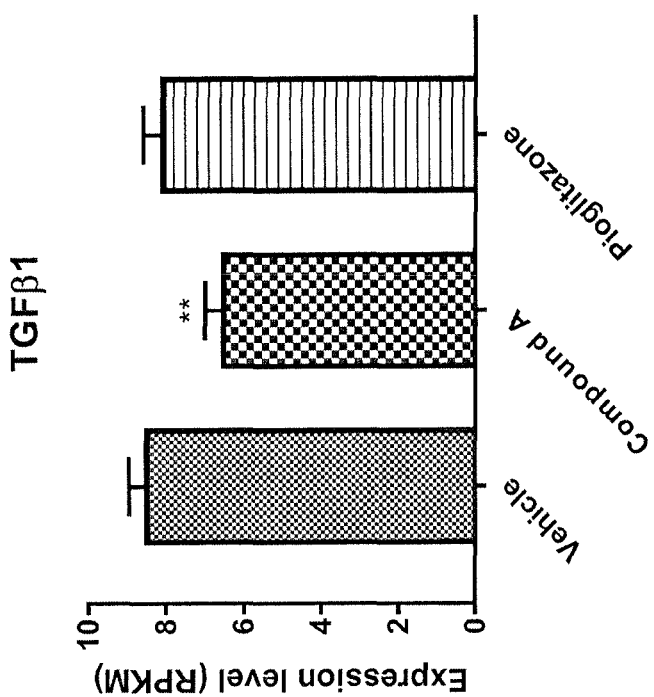
Figure 8C:
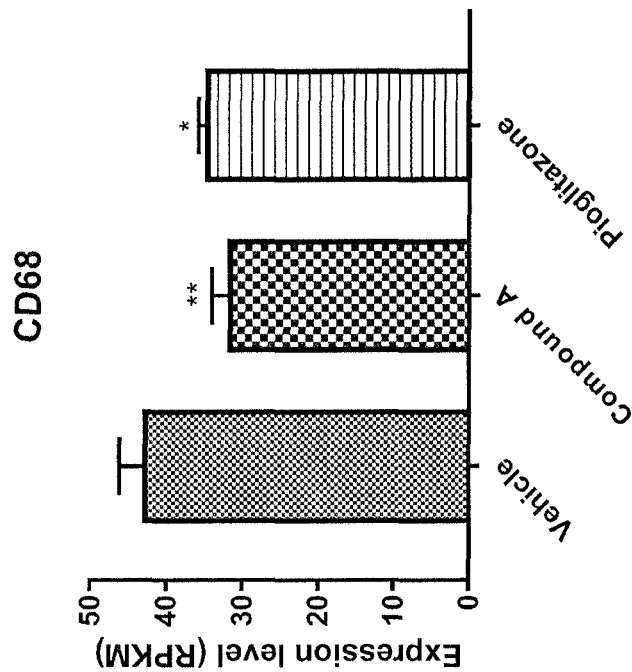
Figure 8D:
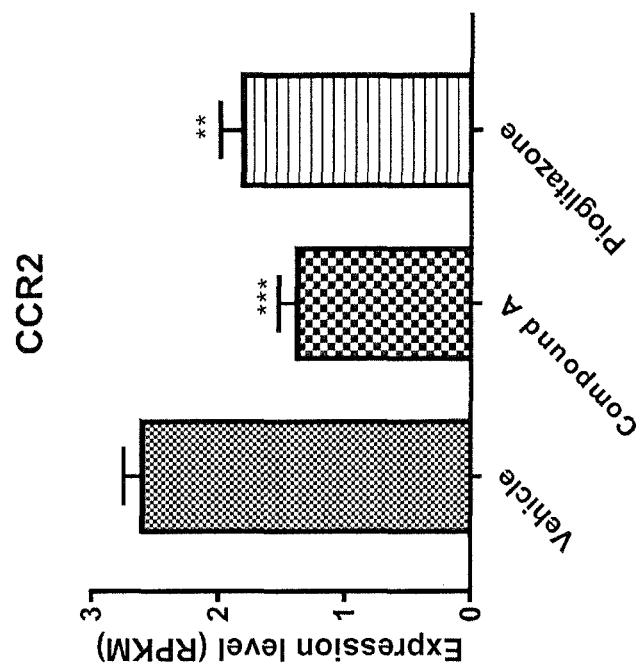
Figure 8F:
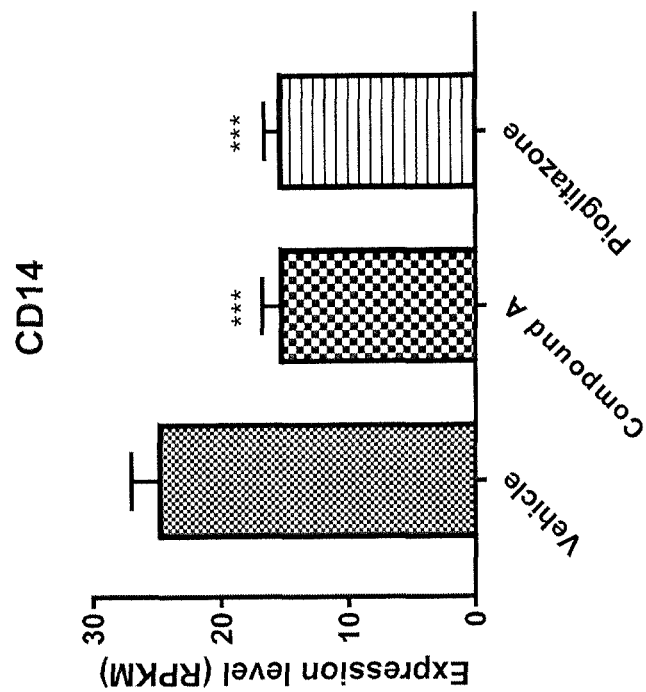
Figure 8E:
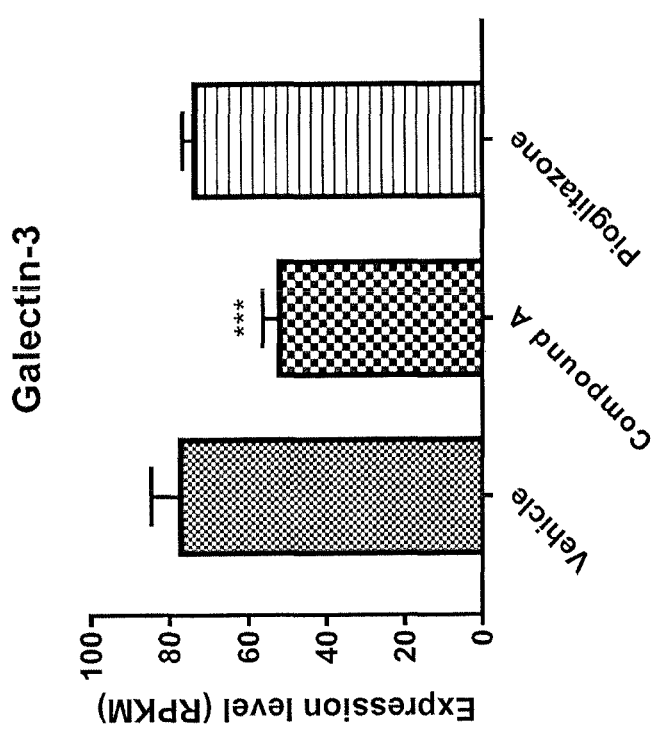

Biological Example 15. Effects of Compound A and Pioglitazone on Inflammatory Gene Expression Of specific relevance to fibrosis progression in ob/ob AMLN mice, 4 weeks of treatment with 112 mg/kg of Compound A significantly reduced expression of inflammatory genes as compared with vehicle-administered control mice. Specifically, Compound A reduced transcript levels of both transforming-growth factor beta 1 (TGF-$\beta$1) ($p<0.05$) and TGF-$\beta$1 receptor (TGFR$\beta$) ($p<0.01$) as shown in FIG. 8A and FIG. 8B, respectively. Pioglitazone reduced expression of TGFR$\beta$ ($p<0.05$), but not TGF-$\beta$1. Significant reductions in CCR2, MAC-2 (data not shown), CD68 and CD14 (all $p<0.001$) were found after Compound A treatment compared to control, as shown in FIGS. 8C, 8D, and 8F. Compound A treatment also significantly reduced Galectin-3 (Gal-3) levels compared with vehicle-administered controls (FIG. 8E). Pioglitazone significantly reduced CCR2 ($p<0.01$) (FIG. 8C), CD68 ($p<0.01$) (FIG. 8D), and CD14 ($p<0.001$) (FIG. 8F). Neither compound significantly reduced interleukin (IL)-1$\beta$ or MCP-1 transcript levels (data not shown).

Biological Example 16. Effects of Compound A and OCA on Hepatic Inflammation as Measured by Hepatic Gal-3

Figure 9B:
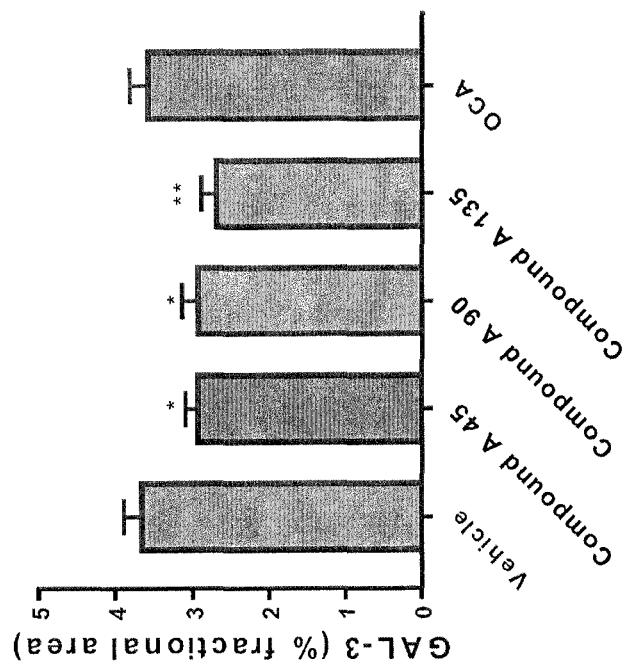
FIGS. 9A-9B depict the effects of 8 weeks of treatment with Compound A on hepatic Galectin-3 (Gal-3) levels in ob/ob AMLN mice.
Figure 9A:
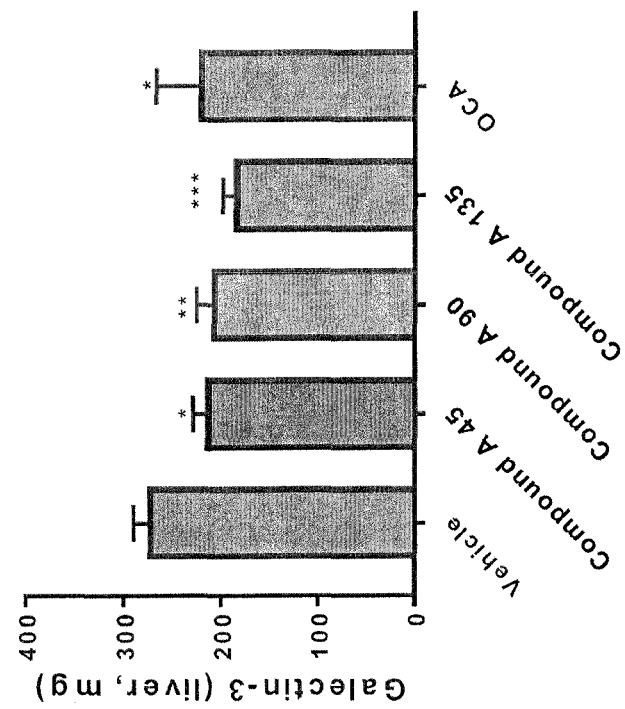

To assess the effects of 8 weeks treatment with either Compound A (45 mg/kg, 90 mg/kg, or 135 mg/kg) or OCA (30 mg/kg) on hepatic inflammation in ob/ob AMLN mice, IHC was performed to assess galectin-3 (Gal-3) levels. As shown in FIG. 9A and FIG. 9B, treatment with Compound A resulted in a dose responsive reduction in Gal-3 expression level when measured either as total content or percentage of area, whereas OCA only reduced Gal-3 expression levels when measured as total content.

Figure 10B:
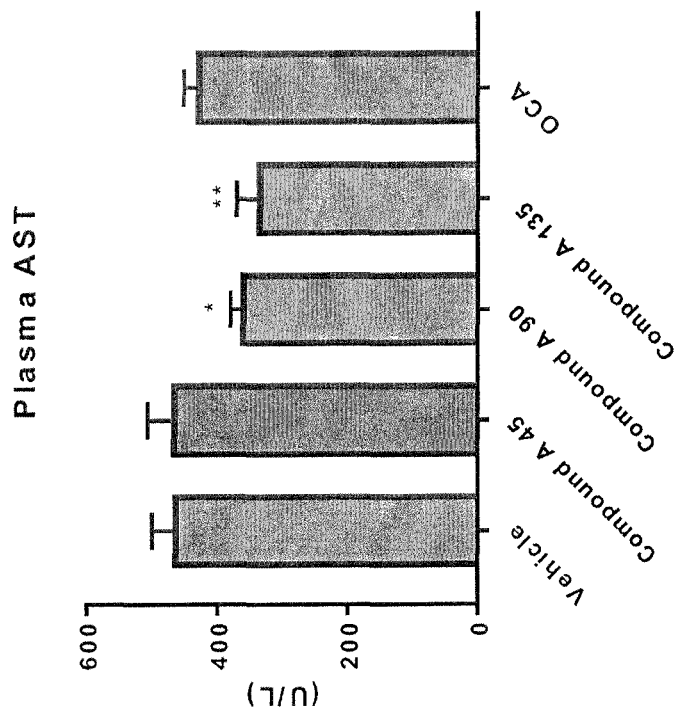
FIGS. 10A-10B depict the effects of 8 weeks of treatment with Compound A on hepatocellular damage in ob/ob AMLN mice as determined by levels of hepatic enzymes aminotransferase (ALT) (FIG. 10A) and aspartate transaminase (AST) (FIG. 10B).
Figure 10A:
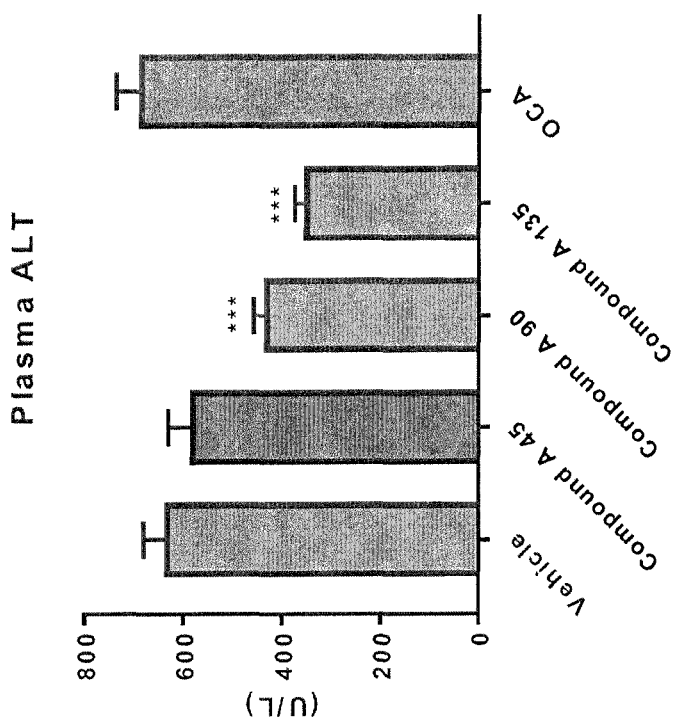

Biological Example 17. Effects of Compound A and OCA on Hepatocellular Damage To assess the effects of Compound A and pioglitazone on hepatocellular injury or damage in ob/ob AMLN mice, plasma alanine aminotransferase (ALT) and aspartate transaminase (AST) were measured after 8 weeks of administration. As shown in FIG. 10A, a marked and significant reduction in ALT was achieved with the 90 mg/kg and 135 mg/kg doses of Compound A ($p<0.01$ and $p<0.001$ respectively) whereas OCA had no effect. At the 90 mg/kg and 135 mg/kg doses Compound A also significantly reduced AST ($p<0.05$ and $p<0.01$ respectively) while OCA showed no effect on AST levels (FIG. 10B).

Figure 11B:
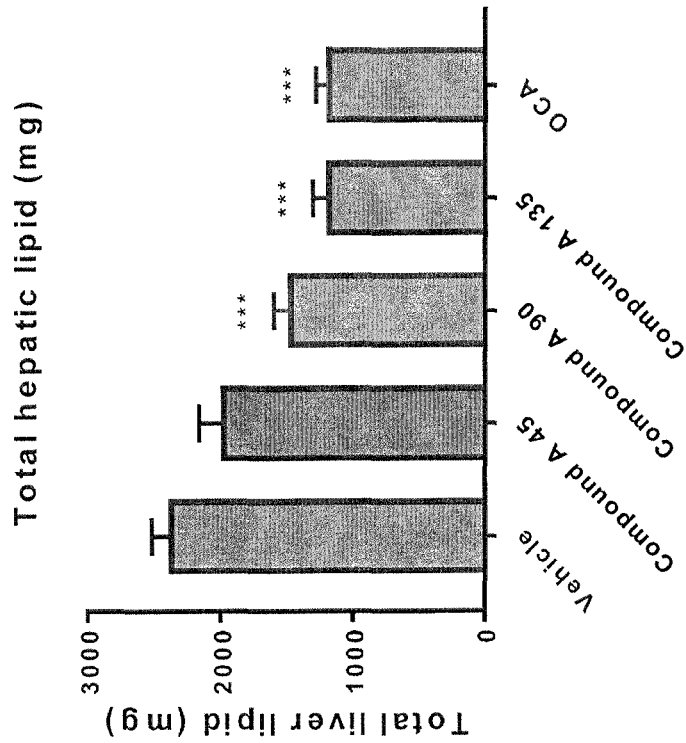
FIGS. 11A-11E depict the effect of 8 weeks of treatment with Compound A on hepatic steatosis determined by percentage of area (FIG. 11A), total hepatic lipid (FIG. 11B), cholesterol content (FIG. 11C), plasma triglyceride (FIG. 11D) and cholesterol (FIG. 11E) levels in ob/ob AMLN mice.
Figure 11A:
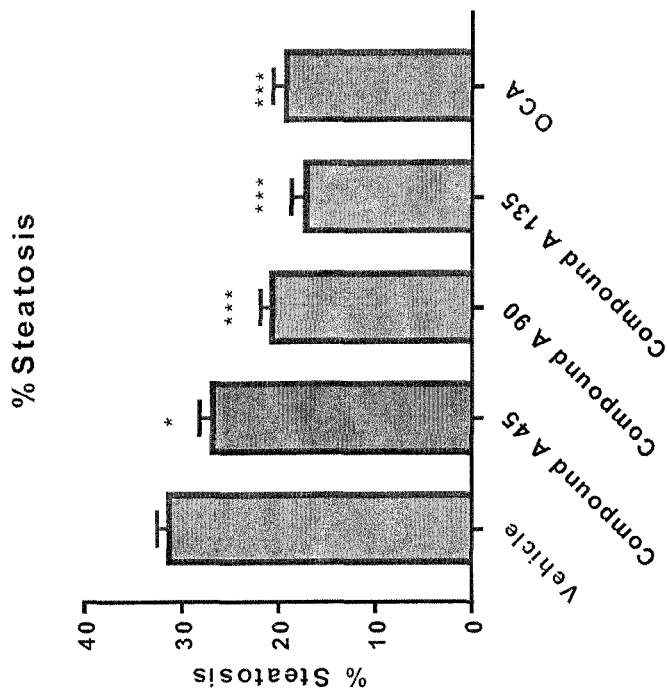
Figure 11C:
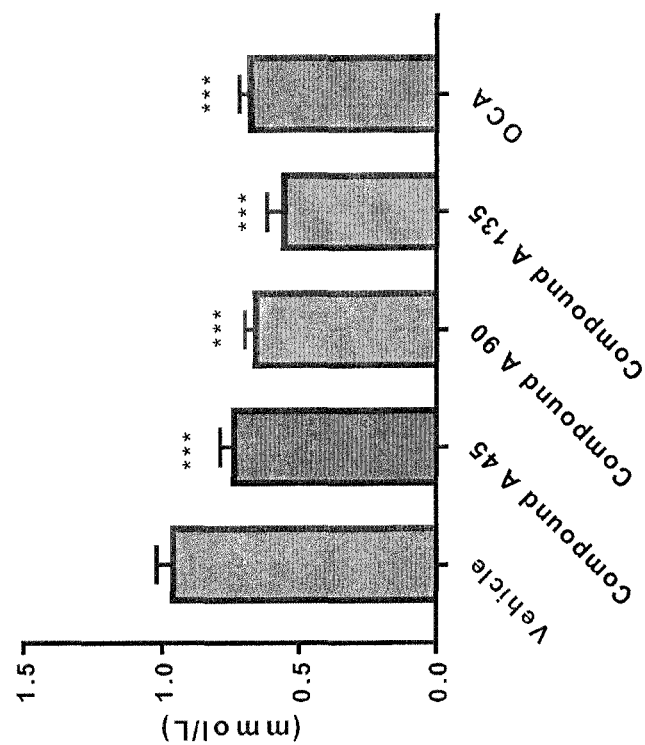
Figure 11D:
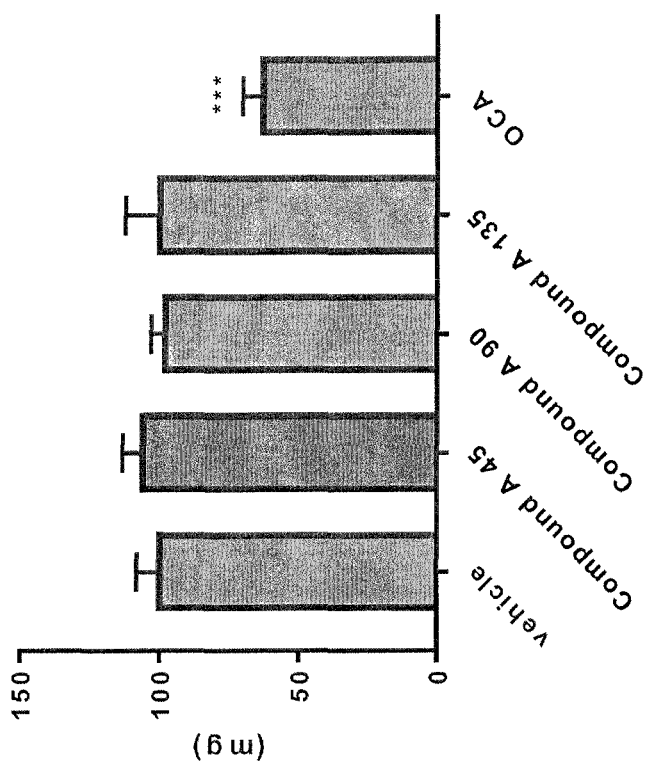
Figure 11E:
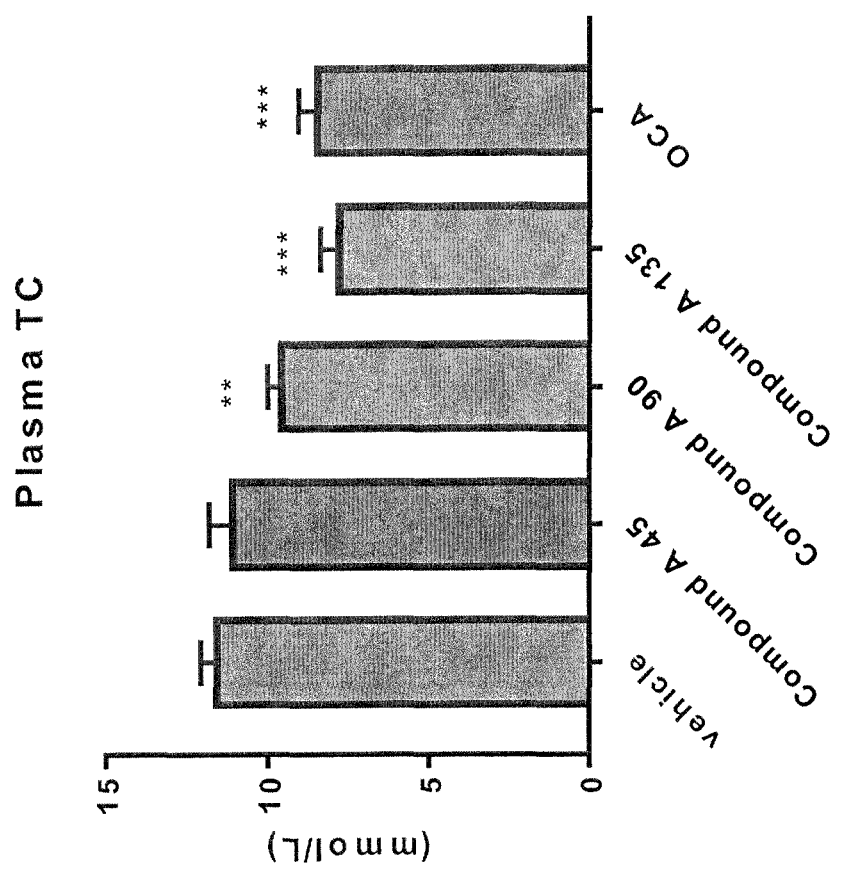

Biological Example 18. Effects of Compound A and OCA on Hepatic Steatosis, Hepatic Lipids Levels, and Plasma Lipid Levels As shown in FIG. 11A and FIG. 11B, both Compound A and OCA significantly reduced steatosis in ob/ob AMLN mice after 8 weeks of administration (expressed either as percent area or total lipid content), with OCA demonstrating comparable efficacy with the highest dose (135 mg/kg) of Compound A (both $p<0.001$). Similarly, both OCA and Compound A (at the 90 mg/kg and 135 mg/kg doses) demonstrated comparable reductions in plasma triglyceride and total cholesterol levels as shown in FIG. 11D and FIG. 11E. OCA treatment, but not Compound A, showed reduced total hepatic cholesterol content ($p<0.01$) (FIG. 11C).

Figure 12B:
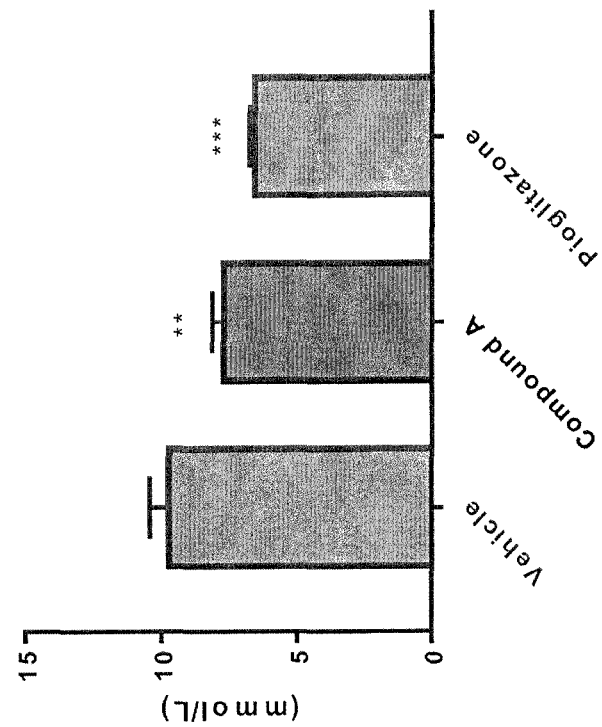
FIGS. 12A-12C depict the effects of 3 weeks of treatment with Compound A on glycemic control in ob/ob AMLN mice.
Figure 12A:
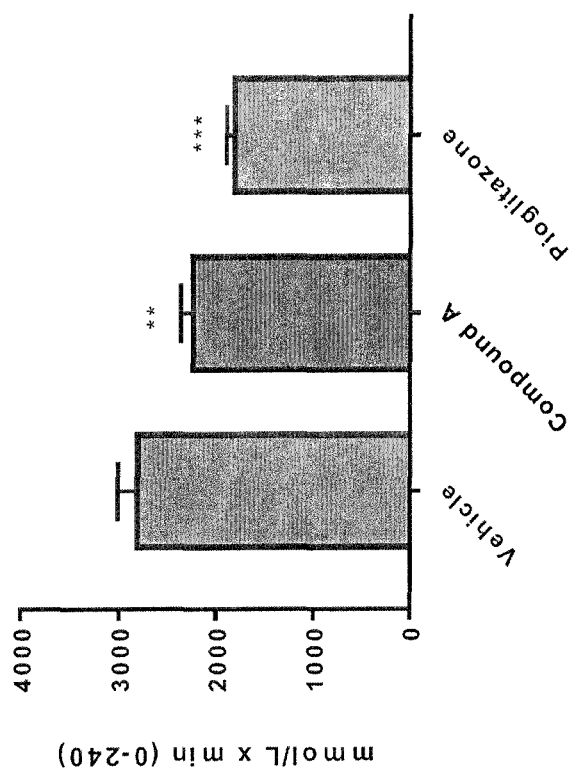
Figure 12C:
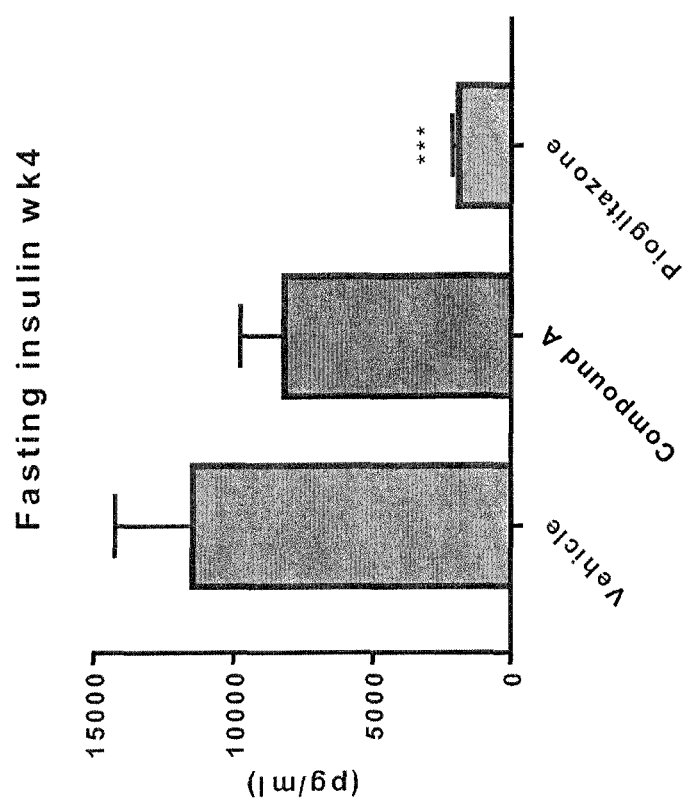

Biological Example 19. Effects of Compound A and Pioglitazone on Glycemic Control After 3 weeks of administration of Compound A (112 mg/kg), pioglitazone, or vehicle control, an oral glucose tolerance test (OGTT) was performed in ob/ob AMLN mice. As shown in FIG. 12A, both Compound A and pioglitazone significantly reduced glucose excursion over the first 240 minutes after glucose load (AUC 0-240 mins), although the effect was more pronounced with pioglitazone. Similarly, significant reductions in fasting plasma glucose levels were achieved with both compounds, although the effect was more pronounced with pioglitazone compared to Compound A (FIG. 12B). Pioglitazone, but not Compound A, reduced fasting insulin ($p<0.001$) (FIG. 12C).

Figure 13A:
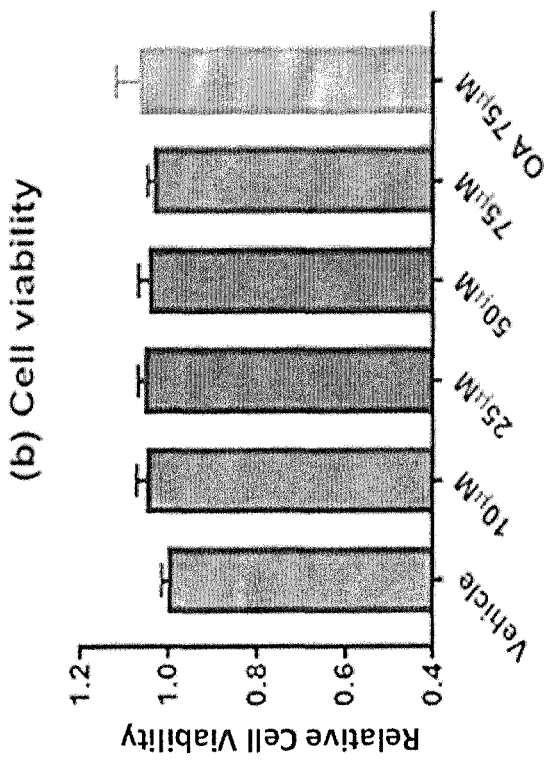
FIGS. 13A-13B depict the effects of Compound A on human hepatic stellate cells (LX-2) in vitro.
Figure 13B:
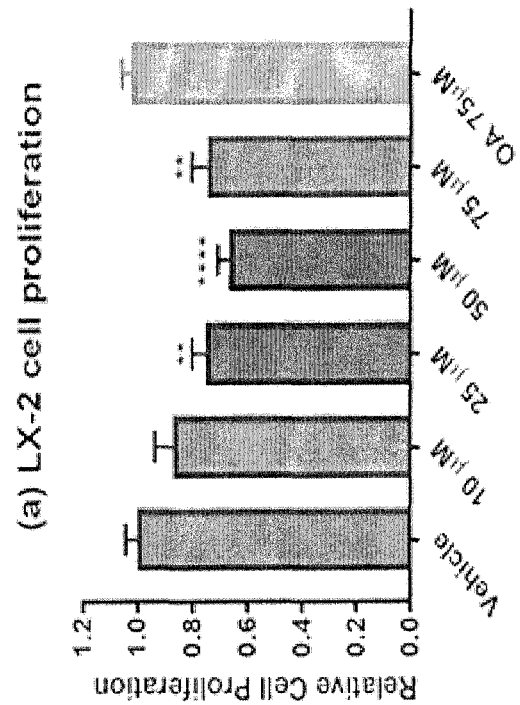

Biological Example 20. Effects of Compound a and Oleic Acid on Stellate Cell Proliferation and Viability In Vitro Cell proliferation of LX-2 human hepatic stellate cells treated for 24 hours with 10-75 µM of Compound A or oleic acid (OA) (75 µM) was assessed by BrdU incorporation. The results are normalised mean values±S.E.M. of 5 independent experiments for icosabutate and 2 independent experiments for OA. As shown in FIG. 13A, LX-2 cells treated with 25 µM ($p<0.005$), 50 µM ($p<0.0001$), and 75 µM ($p<0.005$) of Compound A were less proliferative when compared to OA or vehicle. The reduction in proliferation by Compound A was 25-34% at 24 hours whereas OA had no effect. The comparisons were made by one-way ANOVA with Dunnett's correction for multiple comparisons. As shown in FIG. 13B, neither Compound A nor OA showed a significant effect on cell viability as measured by an MTS assay in 2 independent experiments.

Biological Example 21. Effects of Compound A and a GLP-1 Agonist (GLP-1a, Exenatide), Alone and in Combination, on Hepatic Fibrosis Related Gene Expression (Col1a1 mRNA Expression)

Compound A, GLP-1a, and Compound A+GLP-1a in combination administered to CDAA/high-fat fed mice induced a significant decrease in Col1a1 mRNA expression versus CDAA fed mice (all $p<0.00^{***}$). The effects of Compound A alone and in combination with GLP-1a on hepatic Col1a1 mRNA are shown in Table 8.

TABLE 8

| Hepatic fibrosis related gene expression (Col1 a1 mRNA) | |
|---|---|
| Compound | Corl1a1 (relative mRNA expression) |
| CSAA (high-fat choline sufficient control) | 1 |
| CDAA (choline deficient) | 19 |
| CDAA + Compound A | 6.2*** |
| CDAA + GLP-1a | 10.3*** |
| CDAA + Compound A + GLP-1a | 4.9*** |

Biological Example 22. Effects of Compound A and a GLP-1 Agonist (GLP-La, Exenatide), Alone and in Combination, on Hepatic Fibrosis Related Gene Expression (TIMP (Tissue Inhibitor of Matrix Metalloproteinase)-1a mRNA Expression)

Compound A, GLP-1a, and Compound A+GLP-1a in combination administered to CDAA/high-fat fed mice induced a significant decrease in hepatic TIMP-1a mRNA expression versus CDAA fed mice (all $p<0.001^{***}$). The effects of Compound A alone and in combination with GLP-1a on hepatic hepatic TIMP-1a mRNA are shown in Table 9.

TABLE 9

| Hepatic fibrosis related gene expression (TIMP-1a mRNA) | |
|---|---|
| Compound | TIMP-1a (relative mRNA expression) |
| CSAA (high-fat choline sufficient control) | 1 |
| CDAA (choline deficient) | 6.7 |
| CDAA + Compound A | 2*** |
| CDAA + GLP-1a | 2.4*** |
| CDAA + Compound A + GLP-1a | 0.76*** |

Biological Example 23. Effects of Compound A and GLP-1 Agonist (GLP-1a, Exenatide), Alone and in Combination, on Hepatic Fibrosis Related Gene Expression (MMP (Matrix Metalloproteinase)-13 mRNA Expression)

Compound A, GLP-1a and Compound A+GLP-1a in combination administered to CDAA/high-fat fed mice induced a significant decrease in hepatic MMP-13 mRNA expression versus CDAA fed mice (all p<0.001***). The effects of Compound A alone and in combination with GLP-1a on hepatic hepatic MMP-13 mRNA are shown in Table 10.

TABLE 10

Hepatic fibrosis related gene expression (MMP-13 mRNA)

| Compound | MMP-13 (relative mRNA expression) |
|---|---|
| CSAA (high-fat choline sufficient control) | 1 |
| CDAA (choline deficient) | 3.2 |
| CDAA + Compound A | 1.6*** |
| CDAA + GLP-1a | 2.1*** |
| CDAA + Compound A + GLP-1a | |

Biological Example 24. Effects of Compound A and GLP-1 Agonist (GLP-1a, Exenatide), Alone and in Combination, on Hepatic Inflammation Related Gene Expression (TNF-α mRNA Expression)

Compound A, GLP-1a, and Compound A+GLP-1a in combination administered to CDAA/high-fat fed mice induced a significant decrease in hepatic TNF-α mRNA expression versus CDAA fed mice (p<0.001 for Compound A alone or in combination with GLP-1a, p<0.05 for GLP-1a alone). The effects of Compound A alone and in combination with GLP-1a on hepatic hepatic TNF-a mRNA are shown in Table 11.

TABLE 11

Hepatic fibrosis related gene expression (TNF-α mRNA)

| Compound | TNF-α (relative mRNA expression) |
|---|---|
| CSAA (high-fat choline sufficient control) | 1 |
| CDAA (choline deficient) | 1.7 |
| CDAA + Compound A | 0.65*** |
| CDAA + GLP-1a | 1.05* |
| CDAA + Compound A + GLP-1a | 0.66*** |

Biological Example 25. Effects of Compound A and Concentrated Omega-3 Ethyl Esters, Alone and in Combination, on Hepatic Lipids (Cholesterol Ester-CE, Free Cholesterol-FC, Triglycerides-TG)

Low dose (0.3 mmol/kg bw/day) Compound A (LID) administered to ApoE*3L-CETP transgenic mice fed a Western diet with 0.25% cholesterol in combination with high-dose (3 mmol/kg bw/day) 85% EPA/DHA ethyl-ester omega-3 (HD) induced a significant decrease in FC (p<0.1), CE (p<0.001) and TG (p<0.81). No compound significantly reduced hepatic TG as monotherapy in this model.

TABLE 12

| Compound | Hepatic lipids | | |
|---|---|---|---|
| | Hepatic FC | Hepatic CE | Hepatic TG |
| Control | 12.3 | 22.7* | 95.4 |
| Compound A LD | 9.5 | 17* | 58.8 |
| EPA/DHA HD | 8.9* | 12** | 65.4 |
| Compound A LD + EPA/DHA HD | 8.1 | 8*** | 39.1** |

Biological Example 26: A Multi-Centre, Randomised, Double-Blind, Placebo-Controlled, Parallel Group Study of Compound A in Patients with Non-Alcoholic Steatohepatitis (NASH)

The goals of this clinical trial are to evaluate the efficacy of different doses of Compound A in re-solving NASH in patients without worsening fibrosis and to determine the safety and tolerability of Compound A in patients suffering from NASH.

Number of Patients 600 patients suffering from NASH are screened across approximately 30 sites for suitability; approximately 264 are anticipated to be found compatible with the selection criteria outlined below and approximately 198 are expected to complete the full trial (giving 66 subjects per treatment arm, assuming 25% of patients drop out).

Treatment Assignment

Patients found to be eligible for the study are randomly divided into 3 parallel groups, consisting of 88 patients each. Group 1 is administered placebo Compound A, group 2 is administered 300 mg of Compound A, and group 3 is administered 600 mg of Compound A. Compound A or placebo is administered once daily in one (300 mg) or two (600 mg) capsules for 52 weeks. Stratification for F1 vs F2/F3.

Efficacy of treatment with Compound A is assessed, e.g., by NAS score from liver biopsies, MRI LiverMultiScan assessment PDFF and cT1, liver function tests, HOMA-IR, and biomarkers of inflammation and fibrosis (including hsCRP, Pro-C3, ELF panel, and other suitable biomarkers).

Safety and tolerability are assessed by adverse event reporting, monitoring of vital signs, physical examination, haematology and biochemistry (renal, liver), urinalysis, and resting 12 lead ECGs.

Blood pressure is monitored by three sitting blood pressure readings that are taken at each visit.

Study Design

The study is performed for 58 weeks and 10 clinical visits per patient, including screening, a double-blind treatment period, and post-treatment follow-up. Procedures performed at each visit are described below and summarized in Table 13.

Visit 1 (1 to 42 days before start of administration of treatment): patients are screened for compatibility according the criteria outlined below, and consent is obtained from the patient. Assessment may be performed over more than one visit.

Visit 2: patients are randomised into one of 3 treatment groups. Each of the treatment groups is administered 300 or 600 mg of Compound A, or a placebo daily for 52 weeks. Baseline assessments are performed, including hepatic imaging (MRI-PDFF and cT1), vital signs, safety labs (baseline haematology, biochemistry and urinalysis), resting 12 lead ECGs, and biomarkers (HOMA-IR, hsCRP, Pro-C3 and ELF panel).

Visit 3 (after 4 weeks of treatment): patients are assessed for adverse events, vital signs, safety labs (haematology, biochemistry and urinalysis), resting 12 lead ECGs, and trough PK sample.

Visit 4 (after 10 weeks of treatment): patients are assessed for adverse events, vital signs, safety labs (haematology, biochemistry and urinalysis), resting 12 lead ECGs, and trough PK sample.

Visit 5 (after 16 weeks of treatment): patients are assessed for adverse events, hepatic imaging (MRI-PDFF and cT1), vital signs, safety labs (haematology, biochemistry and urinalysis), resting 12 lead ECGs, biomarkers (HOMA-IR, hsCRP, Pro-C3 and ELF panel), and trough PK sample.

Visits 6, 7, and 8 (after 24, 32, and 40 weeks of treatment): patients are assessed for adverse events, vital signs, safety labs (haematology, biochemistry and urinalysis), resting 12 lead ECGs, biomarkers (hsCRP), and trough PK sample.

Visit 9 (after 52 weeks of treatment): patients are assessed by liver biopsy, hepatic imaging (MRI-PDFF and cT1), vital signs, safety labs (haematology, biochemistry and urinalysis), resting 12 lead ECGs, biomarkers (HOMA-IR, hsCRP, Pro-C3 and ELF panel) and trough PK sample.

Visit 10 (14-21 days after discontinuing trial medication): patients undergo a safety follow-up and are assessed for adverse events, vital signs, safety labs (haematology, biochemistry and urinalysis), resting 12 lead ECGs, and trough PK sample.

Patients that drop out of the study before completion are assessed for adverse events, vital signs, safety labs (haematology, biochemistry and urinalysis), resting 12 lead ECGs, trough PK sample, and biomarkers (HOMA-IR, hsCRP, Pro-C3 and ELF panel).

Patient Inclusion Criteria:

Patients meet the below criteria to be included in the trial.

Between 18 and 75 years of age.

Women are of non-child bearing potential or use acceptable means of contraception.

If female partners of male patients are of childbearing potential, male patients are willing to use contraception (e.g. condoms). In addition, their female partner uses contraception (e.g. hormonal, intra-uterine device etc). Double contraception is used from the first dose of compound drug until 90 days after the last dose of study drug.

Written informed consent.

Optional fibroscan criteria prior to biopsy.

A histological diagnosis of NASH on screening or within 6 months of screening.

NAS score ≥4.

Fibrosis score 1-3 inclusive (F1 capped at 30%).

Optional PDFF >10% on MRI

Prepared to undergo a liver biopsy after 52 weeks treatment.

Compensated liver disease with the following hematologic and biochemical criteria on entry into protocol:
ALT<5×ULN
AST >30
Hemoglobin >11 g/dL for females and >12 g/dL for males
White blood cell (WBC) >2.5 K/μL
Neutrophil count >1.5 K/μL
Platelets >100 K/μL Total bilirubin <35 μmol/L. Patients with bilirubin >35 μmol/L can be included if non-conjugated bilirubin in the setting of a Gilbert syndrome.

Albumin >36 g/L

International Normalized Ratio (INR)<1.4

Serum creatinine <1.3 mg/dL (men) or <1.1 (women) or estimated glomerular filtration rate 60 mL/min/1.73 m2

No other cause of chronic liver disease (autoimmune, primary biliary cholangitis, HBV, HCV, Wilson's, α-1-antitrypsin deficiency, hemochromatosis etc. . . . )

If applicable, stable type 2 diabetes (defined as HgbA1c<9.5% and fasting glycemia <10 mmol/L, no changes in medication in the previous 6 months, and no new symptoms associated with decompensated diabetes in the previous 3 months).

Have a stable weight since the liver biopsy was performed, where stable is defined as being no more than a 5% loss of initial body weight.

Patient Exclusion Criteria

Patients do not meet any of the following exclusion criteria:

A history of sustained excess alcohol ingestion as assessed by an alcohol intake questionnaire.

An unstable metabolic condition as defined by: a gain or loss in weight of greater than 5 kg in the last three months, diabetes with poor glycaemic control (HgbA1c>9.5%), or introduction of an antidiabetic or of an anti-obesity drug/malabsorptive or restrictive bariatric (weight loss) surgery in the past 6 months prior to screening.

A history of gastrointestinal malabsorptive bariatric surgery within less than 5 years or ingestion of drugs known to produce hepatic steatosis including corticosteroids, high-dose oestrogens, methotrexate, tetracycline or amiodarone in the previous 6 months.

Significant systemic or major illnesses other than liver disease, including congestive heart failure (class C and D of the AHA), unstable coronary artery disease, cerebrovascular disease, pulmonary disease, renal failure, organ transplantation, serious psychiatric disease, or malignancy that, in the opinion of the investigator, would preclude treatment with Compound A.

HB antigen >0, HCV PCR >0 (patients with a history of HCV infection can be included if HCV PCR is negative for more than 3 years), or HIV infection.

Any other condition which, in the opinion of the investigator would impede competence or compliance or possibly hinder completion of the study.

Body mass index (BMI) >45 kg/m$^2$.

Type 1 diabetes or a type 2 diabetes treated with insulin.

Diabetic ketoacidosis.

Fasting Triglycerides >300 mg/dL.

Haemostasis disorders or current treatment with anticoagulants.

A contra-indication to liver biopsy.

A history of, or current cardiac dysrhythmias and/or a history of cardiovascular disease, including myocardial infarction, except in patients with well controlled hypertension, and any clinically significant ECG abnormality Participation in any other investigational drug study within the previous 3 months or 5 half-lives of said drug.

A known hypersensitivity to any of the ingredients or excipients of the IMP.

Taking antidiabetics that are known to have activity against NASH, e.g pioglitazone, and GLP-1 receptor agonists.

Endpoint Criteria

The primary endpoint for efficacy of Compound A is the percentage of patients with resolution of NASH as defined by the disappearance of ballooning (score=0) with lobular inflammation score 0 or 1, and with no worsening of fibrosis.

Secondary endpoints for efficacy of Compound A are change from baseline in NAS score, changes in individual histological scores for steatosis, ballooning, inflammation and fibrosis, changes in liver enzymes, changes in imaging parameters, and changes in biomarkers (including hsCRP, Pro-C3, ELF panel, and cytokines.

Secondary endpoints for safety/tolerability include reported adverse events, laboratory values (haematology, biochemistry, and urinalysis), vital signs (blood pressure, pulse rate and temperature), and hsCRP.

Secondary endpoints for pharmacokinetics include comparison of mean trough plasma concentrations at steady state for the 3 doses of Compound A taken at visits 4, 5, 6, 7 and 8.

Statistical Methods

A sample size of 88 patients per group provides 80% power to detect a 40% responder rate for active vs placebo assuming a placebo response rate of 18% and a dropout rate of 25%. Following a 16-week interim analysis, a sample size re-estimation may be made. Efficacy analysis is performed on a modified intention to treat population consisting of those with a baseline and at least one post baseline efficacy measurement. Comparisons are made between each individual dose and placebo.

TABLE 13

Schedule of assessments

| Assessments | Visit 1 Screening* Day −42--1 | Visit 2 Randomisation and baseline Day 0 | Visit 3 After 4 weeks Rx Day 28 | Visit 4 After 10 weeks Rx Day 70 | Visit 5 After 16 weeks Rx Day 112 | Visit 6 After 24 weeks Rx Day 168 | Visit 7 After 32 weeks Rx Day 224 | Visit 8 After 40 weeks Rx Day 280 | Visit 9 After 52 weeks Rx Day 364 | Visit 10 Safety follow-up Day 378 | ET Early termination |
|---|---|---|---|---|---|---|---|---|---|---|---|
| Informed consent | X | | | | | | | | | | |
| Demographics + PMH | X | | | | | | | | | | |
| Con meds | X | X | X | X | X | X | X | X | X | X | X |
| Physical Examination[1] | X | X | X | X | X | X | X | X | X | X | X |
| 12 lead ECG | X | | | X | X | X | X | X | X | X | X |
| Safety labs[2] | X | X | X | X | X | X | X | X | X | X | X |
| Liver Biopsy | X | | | | | | | | X | | |
| Confirm eligibility | | X | | | | | | | | | |
| MRI - PDFF and cT1 | | X | | | X | | | | X | | |
| Biomarkers[3] | | X | | | X | X | X | X | X | | X |
| PK sample | | | X | X | X | X | X | X | X | X | X |
| AE monitoring | | X | X | X | X | X | X | X | X | X | X |
| Drug dispensing and accountability | | X | X | X | X | X | X | X | X | | X |

[1]Full examination at visits 1, 2, 9 and 10 abbreviated examination at all other visits

[2]Haematology, Biochemistry, coagulation, urinalysis, lipids

[3]hsCRP, Pro-c3, ELF panel, HOMA-IR, cytokines

*screening period of up to 6 weeks may include more than one actual visit if going ahead to biopsy

The invention claimed is:

1. A method of reducing fibrosis in a subject in need thereof, comprising administering to the subject a pharmaceutically effective amount of a compound of formula (II):

$$R_1—O—\underset{R_3}{\overset{R_2}{C}}—X \quad (II)$$

wherein $R_1$ is selected from a $C_{10}$-$C_{22}$ alkenyl having 3-6 double bonds;

$R_2$ and $R_3$ are the same or different and are selected from the group of a hydrogen atom, a hydroxy group, an alkyl group, a halogen atom, an alkoxy group, an acyloxy group, an acyl group, an alkenyl group, an alkynyl group, an aryl group, an alkylthio group, an alkoxycarbonyl group, a carboxy group, an alkylsulfinyl group, an alkylsulfonyl group, an amino group, and an alkylamino group; wherein $R_2$ and $R_3$ can be connected in order to form a cycloalkane like cyclopropane, cyclobutane, cyclopentane or cyclohexane;

X is a carboxylic acid or a derivative thereof; wherein the derivative is a carboxylate, a carboxylic ester, a glyceride, an anhydride, a carboxamide, a phospholipid, or a hydroxymethyl;

or a pharmaceutically acceptable salt, solvate, or solvate of such a salt, thereof;

wherein the subject has non-alcoholic steatohepatitis or alcoholic steatohepatitis; and wherein the subject has hepatic fibrosis.

2. The method according to claim 1, wherein the compound is of Formula (I):

[Structure of Formula (I)]

3. The method according to claim 1, wherein $R_2$ and $R_3$ are independently chosen from a hydrogen atom, a methyl group, an ethyl group, an n-propyl group, and an isopropyl group.

4. The method according to claim 1, wherein $R_2$ and $R_3$ are both independently $C_1$-$C_6$ alkyl groups.

5. The method according to claim 1, wherein one of $R_2$ and $R_3$ is a hydrogen atom and the other is an ethyl group.

6. The method according to claim 1, wherein X is a carboxylic acid.

7. The method according to claim 1, wherein X is a $C_1$-$C_6$ alkyl ester.

8. The method according to claim 7, wherein X is chosen from a methyl ester, an ethyl ester, an isopropyl ester, a n-butyl ester, and a tert-butyl ester.

9. The method according to claim 7, wherein X is chosen from a methyl ester and an ethyl ester.

10. The method according to claim 1, wherein the compound is present in the form of an enantiomer, diastereomer, or mixture thereof.

11. The method according to claim 1, wherein the compound is present in its R form, in its S form, or in racemic form.

12. The method according to claim 1, wherein the compound is 2-(((5Z,8Z,11Z,14Z,17Z)-icosa-5,8,11,14,17-pentaen-1-yl)oxy)butanoic acid (Compound A), or a pharmaceutically acceptable salt or ester thereof, and the formula is

[Structure of Compound A]

13. The method according to claim 1, wherein said compound is administered in a dose ranging from about 5 mg to about 4 g per dose.

14. The method according to claim 1, wherein the compound is administered once daily.

15. The method according to claim 1, wherein the method treats or reverses non-alcoholic steatohepatitis and/or alcoholic steatohepatitis.

16. The method according to claim 1, wherein the method provides a reduction of hepatic inflammation, hepatocellular ballooning, steatohepatitis, fibrosis, and/or an improvement in a NAS score from a liver biopsy, a liver function test, an MRI LiverMultiScan assessment PDFF and cT1, and/or HOMA-IR.

17. The method of according to claim 16, wherein the reduction of hepatic inflammation is a reduction in lobular inflammation.

18. The method according to claim 1, wherein the compound is formulated as a pharmaceutical composition, wherein the pharmaceutical composition further comprises at least one binder, excipient, diluent, or antioxidant, or a combination thereof.

19. The method according to claim 18, wherein the pharmaceutical composition is formulated for oral administration.

20. The method according to claim 1, wherein the compound is administered at a dosage of 300 mg daily or 600 mg daily.

21. The method according to claim 1, wherein plasma alanine aminotransferase levels are reduced by 30-40% and/or the plasma aspartate transaminase levels are reduced by 10-20%.

22. The method according to claim 1, wherein hepatic steatosis is reduced by 70-90%.

23. The method according to claim 1, wherein the NAS score is reduced by 50-70%.

24. The method according to claim 1, wherein the hepatic fibrotic area is decreased by 40-60%.

25. The method according to claim 1, wherein the compound is administered as a monotherapy.

26. The method according to claim 1, further comprising co-administering at least one additional active agent.

27. The method according to claim 26, wherein the one or more additional active agents are independently chosen from allosteric acetyl-CoA carboxylase (ACC) inhibitors, angiotensin II receptor antagonists, angiotensin converting enzyme (ACE) inhibitors, apoptosis signal-regulating kinase-1 (ASK1) inhibitors, caspase inhibitors, cathepsin B inhibitors, CCR2 chemokine antagonists, CCR5 chemokine antagonists, chloride channel stimulators, cholesterol solubilizers, diacyl glycerol O-acyltransferase 1 (DGAT1) inhibitors, dipeptidyl peptidase IV (DPP IV) inhibitors, fibroblast-growth factor (FGF)-21 agonists, farnesoid X receptor (FXR) agonists, anti-CD3 mAb, galectin-3 inhibitors, glucagon-like peptide 1 (GLP1) receptor agonists, glutathione precursors, hepatitis C virus NS3 protease inhibitors, HMG CoA reductase inhibitors, 1 Iβ-hydroxysteroid dehydrogenase (I Iβ-HSDI) inhibitors, heat shock protein (Hsp)47 inhibitors, IL-1β antagonists, IL-6 antagonists, IL-10 agonists, IL-17 antagonists, ileal sodium bile acid co-transporter inhibitors, leptin analogs, 5-lipoxygenase inhibitors, LPL gene stimulators, lysyl oxidase homolog 2 (LOXL2) inhibitors, lysophosphatidic acid 1 (LPA1) receptor antagonists, omega-3 fatty acids, PDE3 inhibitors, PDE4 inhibitors, phospholipase C (PLC) inhibitors, PPARα agonists, PPARγ agonists, PPARβ/δ agonists, recombinant human pentraxin-2 protein (PRF-1), Rho associated protein kinase 2 (ROCK2) inhibitors, semicarbazide-sensitive amine oxidase (SSAO) inhibitors, sodium glucose transporter-2 (SGLT2) inhibitors, stearoyl CoA desaturase-1 inhibitors, thyroid hormone receptor β agonists, tumor necrosis factor a (TNFα) ligand inhibitors, transglutaminase inhibitors, transglutaminase inhibitor precursors, and small activating RNA (saRNA).

28. The method according to claim 26, wherein the one or more additional active agents are independently chosen from a Glucagon-like peptide 1 (GLP-1) receptor agonist; a dipeptidyl peptidase (DPP IV) inhibitor; and omega-3 fatty acids (n-3 PUFA).

29. The method according to claim 26, wherein the one or more additional active agents are independently chosen from acetylsalicylic acid, alipogene tiparvovec, aramchol, atorvastatin, BI 1467335, BLX-1002, BMS-986036, BMS-986020, cenicriviroc, cobiprostone, colesevelam, emricasan, enalapril, foramulab, GFT-505, GR-MD-02, GS-0976, GS-9674, hydrochlorothiazide, icosapent ethyl ester (ethyl eicosapentaenoic acid), IMM-124E, IVA337, K-877, KD-025, linagliptin, liraglutide, mercaptamine, MGL-3196, ND-L02-s0201, obeticholic acid, olesoxime, peg-ilodecakin, pioglitazone, PRM-151, PX-102, remogliflozin etabonate, selonsertib, simtuzumab, SHP-626, solithromycin, tipelukast, TRX-318, ursodeoxycholic acid, and VBY-376.

30. The method according to claim 26, wherein the co-administration is by simultaneous administration, sequential administration, overlapping administration, interval administration, continuous administration, or a combination thereof.

\* \* \* \* \*

UNITED STATES PATENT AND TRADEMARK OFFICE
CERTIFICATE OF CORRECTION

PATENT NO. : 11,925,614 B2
APPLICATION NO. : 16/769659
DATED : March 12, 2024
INVENTOR(S) : Hilde Hermansen Steineger, David Alan Fraser and Tore Skjaeret It is certified that error appears in the above-identified patent and that said Letters Patent is hereby corrected as shown below:

On the Title Page

Item (57) Abstract, Line 9, "RI," should read as --R1--.

In the Claims

Claim 27, Column 109, Lines 3-4, "1 Iβ-hydroxysteroid dehydrogenase" should read as --1 1β-hydroxysteroid dehydrogenase--.

Claim 27, Column 109, Line 4, "(I Iβ-HSDI)" should read as --(1 1β-HSDI)--.

Signed and Sealed this
Twentieth Day of August, 2024

Katherine Kelly Vidal
*Director of the United States Patent and Trademark Office*